(12) United States Patent
Brockunier et al.

(10) Patent No.: US 9,840,512 B2
(45) Date of Patent: Dec. 12, 2017

(54) ANTIDIABETIC BICYCLIC COMPOUNDS

(71) Applicant: Merck Sharp & Dohme Corp., Rahway, NJ (US)

(72) Inventors: Linda L. Brockunier, Orange, NJ (US); Helen Chen, Marlboro, NJ (US); Harry R. Chobanian, Aberdeen, NJ (US); Matthew J. H. Clements, Old Bridge, NJ (US); Alejandro Crespo, Edison, NJ (US); Duane E. DeMong, Somerset, NJ (US); Yan Guo, Westfield, NJ (US); William K. Hagmann, Westfield, NJ (US); Karen M. Marcantonio, New York, NY (US); Michael Miller, Scotch Plains, NJ (US); Barbara Pio, West Orange, NJ (US); Christopher W. Plummer, Hoboken, NJ (US); Dong Xiao, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/767,815

(22) PCT Filed: Feb. 20, 2014

(86) PCT No.: PCT/US2014/017264
§ 371 (c)(1),
(2) Date: Aug. 13, 2015

(87) PCT Pub. No.: WO2014/130608
PCT Pub. Date: Aug. 28, 2014

(65) Prior Publication Data
US 2016/0002255 A1   Jan. 7, 2016

Related U.S. Application Data

(60) Provisional application No. 61/768,065, filed on Feb. 22, 2013.

(51) Int. Cl.
*C07D 311/04* (2006.01)
*C07D 311/28* (2006.01)
(Continued)

(52) U.S. Cl.
CPC ......... *C07D 493/04* (2013.01); *A61K 31/352* (2013.01); *A61K 31/416* (2013.01); *A61K 31/422* (2013.01); *A61K 31/427* (2013.01); *A61K 31/436* (2013.01); *A61K 31/444* (2013.01); *A61K 31/4433* (2013.01); *A61K 31/497* (2013.01); *A61K 31/538* (2013.01); *A61K 45/06* (2013.01); *C07D 201/00* (2013.01); *C07D 311/04* (2013.01); *C07D 311/28* (2013.01); *C07D 319/20* (2013.01); *C07D 405/04* (2013.01); *C07D 405/06* (2013.01); *C07D 405/10* (2013.01); *C07D 405/14* (2013.01); *C07D 413/10* (2013.01); *C07D 417/04* (2013.01); *C07D 491/048* (2013.01); *C07D 491/052* (2013.01)

(58) Field of Classification Search
None
See application file for complete search history.

(56) References Cited

U.S. PATENT DOCUMENTS 4,057,641 A * 11/1977 Appleton ............. C07D 311/22
514/456
4,151,179 A    4/1979 Appleton et al.
(Continued)

FOREIGN PATENT DOCUMENTS

EP    1630152 A1    3/2006
EP    1698624 B1    6/2012
(Continued)

OTHER PUBLICATIONS

Bagnoli, L., Vinyl selenones: annulation agents for the synthesis of six-membered benzo- 1,4-heterocyclic compounds, Tetrahedron, 2013, p. 481-486, vol. 69.

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.

Brown, S. P. et al., Discovery of AM-1638: A Potent and Orally Bioavailable GPR40/FFA1 Full Agonist, American Chemical Society, 2012, p. 726-730, vol. 3.

Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.

(Continued)

*Primary Examiner* — Deepak Rao
*Assistant Examiner* — Laura Daniel
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

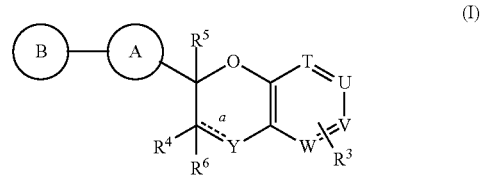

23 Claims, No Drawings

(51) Int. Cl.

| | | |
|---|---|---|
| C07D 491/052 | (2006.01) |
| C07D 493/04 | (2006.01) |
| C07D 201/00 | (2006.01) |
| C07D 405/14 | (2006.01) |
| C07D 319/20 | (2006.01) |
| C07D 405/04 | (2006.01) |
| C07D 405/06 | (2006.01) |
| C07D 405/10 | (2006.01) |
| C07D 413/10 | (2006.01) |
| C07D 417/04 | (2006.01) |
| C07D 491/048 | (2006.01) |
| A61K 31/352 | (2006.01) |
| A61K 31/416 | (2006.01) |
| A61K 31/422 | (2006.01) |
| A61K 31/427 | (2006.01) |
| A61K 31/436 | (2006.01) |
| A61K 31/4433 | (2006.01) |
| A61K 31/444 | (2006.01) |
| A61K 31/497 | (2006.01) |
| A61K 31/538 | (2006.01) |
| A61K 45/06 | (2006.01) |

(56) References Cited

U.S. PATENT DOCUMENTS

| | | | | |
|---|---|---|---|---|
| 4,310,589 A | * | 1/1982 | Doria | A61K 31/35 514/337 |
| 4,824,833 A | * | 4/1989 | Iijima | C07D 417/14 514/230.5 |
| 2003/0158259 A1 | | 8/2003 | Archimbault et al. | |
| 2005/0020684 A1 | | 1/2005 | Brooks et al. | |
| 2005/0234245 A1 | | 10/2005 | DiNinno et al. | |
| 2007/0213364 A1 | | 9/2007 | Yasuma et al. | |
| 2012/0004187 A1 | | 1/2012 | Keil et al. | |

FOREIGN PATENT DOCUMENTS

| | | |
|---|---|---|
| GB | 2498976 A | 7/2013 |
| WO | WO2004022551 A1 | 3/2004 |
| WO | WO2004041266 A1 | 5/2004 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009111056 A1 | 9/2009 |
| WO | 2010004347 A1 | 1/2010 |
| WO | WO2010045258 A2 | 4/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2012072691 A1 | 6/2012 |
| WO | WO2013122028 A1 | 8/2013 |
| WO | WO2013122029 A1 | 8/2013 |
| WO | WO2014130608 A1 | 8/2014 |

OTHER PUBLICATIONS

Houze, J. B. et al., AMG 837: A potent, orally bioavailable GPR40 agonist, Bioorganic & Medicinal Chemistry Letters, 2012, p. 1267-1270, vol. 22.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

Lin, D. C. H. et al., Identification and Pharmacological Characterization of Multiple Allosteric Binding Sites on the Free Fatty Acid 1 Receptor, Molecular Pharmacology, 2012, p. 843-859, vol. 82, No. 5.

Lin, D. D. H. et al., AMG 837: A Novel GPR40/FFA1 Agonist that Enhances Insulin Secretion and Lowers Glucose Levels in Rodents, PLoS One, 2011, p. 1-10, vol. 6, No. 11.

Lou, Y. et al., Epidemiological Impact of a Genital Herpes Type 2 Vaccine for Young Females, PLOS ONE, 2012, p. 1-9, vol. 7, No. 10.

Naidu, A. B., Copper(I)-Catalyzed Intramolecular Caryl-O Bond-Forming Cyclization for the Synthesis of 1,4-Benzodioxines and Its Application in the Total Synthesis of Sweetening Isovanillins, Synthesis, 2010, p. 3509-3519, vol. 20.

PCT, PCT—International Search Report and Written Opinion, International Searching Authority, Jul. 18, 2014, p. 1-11.

Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.

Walker, et al., Development of a Scalable Synthesis of a GPR40 Receptor Agonist, Organic Process Research & Development, 2011, p. 570-580, vol. 15.

Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.

Wang, Y. et al., Discovery and Optimization of Potent GPR40 Full Agonists Containing Tricyclic Spirocycles, ACS Medicinal Chemistry Letters, 2013, p. 551-555, vol. 4.

Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.

Zhou, C. et al., Discovery of 5-aryloxy-2,4-thiazolidinediones as potent GPR40 agonists, Bioorganic & Medicinal Chemistry Letters, 2010, p. 1298-1301, vol. 20.

De Lartigue, L., TAK-875, Drugs of the Future, 2011, p. 813-818, vol. 36. No. 11.

Lu, H. et al., Discovery of novel orally bioavailable GPR40 agonists, Bioorganic & Medicinal Chemistry Letters, 2013, p. 2920-2924, vol. 23.

Naik, H. et al., Safety, Tolerability, Pharmacokinetics, and Pharmacodynamic Properties of the GPR40 Agonist TAK-875: Results From a Double-Blind, Placebo-Controlled Single Oral Dose Rising Study in Healthy Volunteers, J. Clin.Pharmacol, 2012, p. 1007-1016, vol. 52.

XP-002759082—Retrieved from Caplus 1959:29075, (1957).

XP-002759083—Retrieved from STN CAS Rigistry No. 1000543-24-7, (2008).

* cited by examiner

ANTIDIABETIC BICYCLIC COMPOUNDS

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The biguanides are a class of drugs that are widely used to treat Type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogue, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e., 5-benzylthiazolidine-2,4-diones) are a newer class of compounds that can ameliorate hyperglycemia and other symptoms of Type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of Type 2 diabetes, resulting in partial or complete correction of elevated plasma glucose levels without the occurrence of hypoglycemia. PPAR-gamma agonism is believed to be responsible for the improved insulin sensitization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) have been made and tested, but so far none have been approved by the regulatory authorities. The currently marketed PPAR gamma agonists are modestly effective in reducing plasma glucose and HemoglobinA1C. The currently marketed compounds do not greatly improve lipid metabolism and may actually have a negative effect on the lipid profile. Selective PPAR Gamma Partial Agonists (SPPARM's) are currently being developed and may be equally effective, with fewer side effects, such as weight gain and edema. Thus, the PPAR compounds represent an important advance in diabetic therapy.

Another widely used drug treatment involves the administration of insulin secretagogues, such as the sulfonylureas (e.g. tolbutamide, glipizide, and glimepiride). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

Dipeptidyl peptidase IV (DPP-4) inhibitors (e.g., sitagliptin, alogliptin, vildagliptin, linagliptin, denagliptin and saxagliptin) provide a new route for increasing insulin secretion in response to food consumption. DPP-4 is a cell surface protein with broad tissue distribution that has been implicated in a wide range of biological functions. DPP-4 is identical to the T-cell activation marker CD26 and can cleave a number of immunoregulatory, endocrine, and neurological peptides in vitro. It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Studies with DPP-4(−/−)-deficient mice and clinical trials with DPP-4 inhibitors indicate that DPP-4 inhibition increases the steady state concentrations of GLP-1 and GIP, resulting in improved glucose tolerance. Inactivation of these peptides by DPP-4 may also play a role in glucose homeostasis. DPP-4 inhibitors therefore have utility in the treatment of Type 2 diabetes and in the treatment and prevention of the numerous conditions that often accompany Type 2 diabetes, including Metabolic Syndrome, reactive hypoglycemia, and diabetic dyslipidemia. GLP-1 has other effects that help to lower blood glucose and contribute to glucose homeostasis. GLP-1 inhibits glucagon secretion from the liver. Glucagon is a hormone that increases blood glucose levels by stimulating glucose production from glycogen stores in the liver. GLP-1 also delays stomach emptying, which helps to spread glucose absorption out over time, and thus limit hyperglycemia. Also, studies in animals have shown that GLP-1 can increase the number of beta cells, either through promoting growth or by inhibiting apoptosis. Thus, potentiation of GLP-1 action by preventing its degradation offers several mechanisms to attenuate hyperglycemia associated with Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/072691, WO 2013/122028, WO2013/122029, and GB 2498976.

GPR40 agonists are also disclosed in Walsh et al., Bioorganic & Medicinal Chemistry Letters (2011), 21(11), 3390-3394; Zhou et al., Bioorganic & Medicinal Chemistry Letters (2010), 20(3), 1298-1301; Tan et al., Diabetes (2008), 57(8), 2211-2219; Houze et al., Bioorganic & Medicinal Chemistry Letters (2012), 22(2), 1267-1270;

Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; and Houze et al., Abstracts of Papers, 243rd ACS National Meeting & Exposition, San Diego, Calif., USA Mar. 25-29, 2012, MEDI-265.

SUMMARY OF THE INVENTION

The present invention relates to novel substituted compounds of structural formula I:

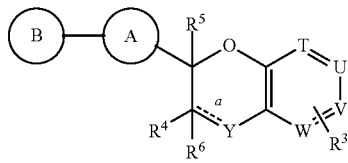

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

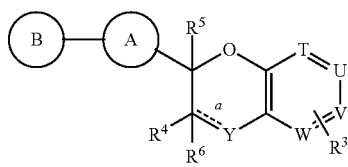

or a pharmaceutically acceptable salt thereof; wherein "a" is a single bond or a double bond, provided that if "a" is a double bond, then $R^6$ is absent and Y is selected from the group consisting of: $C-R^g$, $-C-OC_{1-6}alkyl$, CF and N;
T is selected from the group consisting of:
  (1) CH,
  (2) N, and
  (3) N-oxide;
U is selected from the group consisting of:
  (1) $CR^1$,
  (2) N, and
  (3) N-oxide;
V is selected from the group consisting of:
  (1) $CR^2$,
  (2) N, and
  (3) N-oxide;
W is selected from the group consisting of:
  (1) CH,
  (2) N, and
  (3) N-oxide,
provided that no more than two of T, U, V and W are selected from N and N-oxide, further provided that if both T and W are N or N-oxide, then $R^3$ is absent, and further provided that both U and V are not N or N-oxide;
Y is selected from the group consisting of:
  (1) oxygen,
  (2) sulfur,
  (3) $-CR^gR^g$,
  (4) C=O,
  (5) $-C(R^g)OC_{1-6}alkyl$,
  (6) $-CF_2$, and
  (7) $-NR^c$;
A is selected from the group consisting of:
  (1) aryl,
  (2) heteroaryl,
  (3) $C_{3-6}$cycloalkyl, and
  (4) $C_{2-5}$cycloheteroalkyl,
wherein A is unsubstituted or substituted with one to five substituents selected from $R^a$;
B is selected from the group consisting of:
  (1) hydrogen,
  (2) aryl,
  (3) aryl-O—,
  (4) aryl-$C_{1-10}$ alkyl-,
  (5) aryl-$C_{1-10}$ alkyl-O—,
  (6) $C_{3-6}$cycloalkyl,
  (7) $C_{3-6}$cycloalkyl-$C_{1-10}$alkyl-,
  (8) $C_{3-6}$cycloalkyl-$C_{1-10}$alkyl-O—,
  (9) $C_{3-6}$cycloalkenyl,
  (10) $C_{3-6}$cycloalkenyl-$C_{1-10}$alkyl-,
  (11) $C_{3-6}$cycloalkenyl-$C_{1-10}$alkyl-O—,
  (12) $C_{2-5}$cycloheteroalkyl,
  (13) $C_{3-6}$cycloheteroalkyl-$C_{1-10}$alkyl-,
  (14) $C_{3-6}$cycloheteroalkyl-$C_{1-10}$alkyl-O—,
  (15) heteroaryl,
  (16) heteroaryl-O—,
  (17) heteroaryl-$C_{1-10}$ alkyl-, and
  (18) heteroaryl-$C_{1-10}$ alkyl-O—,
wherein B is unsubstituted or substituted with one to five substituents selected from $R^b$;
$R^1$ and $R^2$ are each independently selected from:
  (1) a bond,
  (2) hydrogen,
  (3) halogen,
  (4) $-OR^k$,
  (5) $-CN$,
  (6) $-C_{1-6}alkyl$, (7) —C$_{3-6}$cycloalkyl,
(8) —C$_{3-6}$cycloalkyl-C$_{1-3}$alkyl-,
(9) —C$_{2-6}$cycloheteroalkyl, and
(10) —C$_{2-6}$cycloheteroalkyl-C$_{1-3}$alkyl-,
wherein each alkyl, cycloalkyl and cycloheteroalkyl is unsubstituted or substituted with one to three substituents selected from R$^L$, and wherein one of R$^1$ and R$^2$ is substituted with a substituent selected from R$^7$,
or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with a substituent selected from R$^7$;
R$^3$ is selected from the group consisting of:
 (1) hydrogen,
 (2) halogen,
 (3) —OR$^e$,
 (4) —CN,
 (5) —C$_{1-6}$alkyl,
 (6) —C$_{3-6}$cycloalkyl, and
 (7) —C$_{3-6}$cycloalkyl-C$_{1-3}$alkyl-,
wherein each alkyl and cycloalkyl is unsubstituted or substituted with one to three substituents selected from R$^i$;
R$^4$ is selected from the group consisting of:
 (1) hydrogen,
 (2) halogen,
 (3) OR$^e$,
 (4) C$_{1-6}$alkyl,
 (5) C$_{1-6}$alkyl-O—,
 (6) C$_{3-6}$cycloalkyl,
 (7) C$_{3-6}$cycloalkyl-O—,
 (8) C$_{3-6}$cycloalkyl-C$_{1-10}$alkyl-,
 (9) C$_{3-6}$cycloalkyl-C$_{1-10}$alkyl-O—,
 (10) C$_{2-5}$cycloheteroalkyl,
 (11) C$_{2-5}$cycloheteroalkyl-O—,
 (12) C$_{2-5}$cycloheteroalkyl-C$_{1-10}$alkyl-,
 (13) C$_{2-5}$cycloheteroalkyl-C$_{1-10}$alkyl-O—,
 (14) aryl,
 (15) aryl-O—,
 (16) aryl-C$_{1-10}$alkyl-,
 (17) heteroaryl,
 (18) heteroaryl-O—, and
 (19) heteroaryl-C$_{1-10}$alkyl-,
wherein each alkyl, cycloalkyl, cycloheteroalkyl, aryl and heteroaryl is unsubstituted or substituted with one to three substituents selected from R$^j$,
provided that when R$^4$ is selected from the group consisting of:
 (1) OR$^e$,
 (2) C$_{1-6}$alkyl-O—,
 (3) C$_{3-6}$cycloalkyl-O—,
 (4) C$_{3-6}$cycloalkyl-C$_{1-10}$alkyl-O—,
 (5) C$_{2-5}$cycloheteroalkyl-O—,
 (6) C$_{2-5}$cycloheteroalkyl-C$_{1-10}$alkyl-O—,
 (7) aryl-O—, and
 (8) heteroaryl-O—,
then Y is selected from the group consisting of:
 (1) —CR$^g$R$^g$,
 (2) C=O,
 (3) —C(R$^g$)OC$_{1-6}$alkyl, and
 (4) —CF$_2$;
R$^5$ is selected from the group consisting of:
 (1) hydrogen,
 (2) —C$_{1-6}$alkyl, and
 (3) —C$_{3-6}$cycloalkyl, wherein each alkyl and cycloalkyl is unsubstituted or substituted with one to three substituents selected from R$^j$;
R$^6$ is selected from the group consisting of:
 (1) hydrogen,
 (2) —C$_{1-6}$alkyl, and
 (3) —C$_{3-6}$cycloalkyl,
wherein each alkyl and cycloalkyl is unsubstituted or substituted with one to three substituents selected from R$^j$;
R$^7$ is selected from the group consisting of:
 (1) —CO$_2$R$^8$,
 (2) —C$_{1-6}$alkyl-CO$_2$R$^8$,
 (3) —C$_{1-6}$alkyl-CONHSO$_2$R$^m$,
 (4) —C$_{1-6}$alkyl-SO$_2$NHCOR$^m$,
 (5) —C$_{1-6}$alkyl-tetrazolyl, and
 (6) a cycloheteroalkyl selected from the group consisting of:

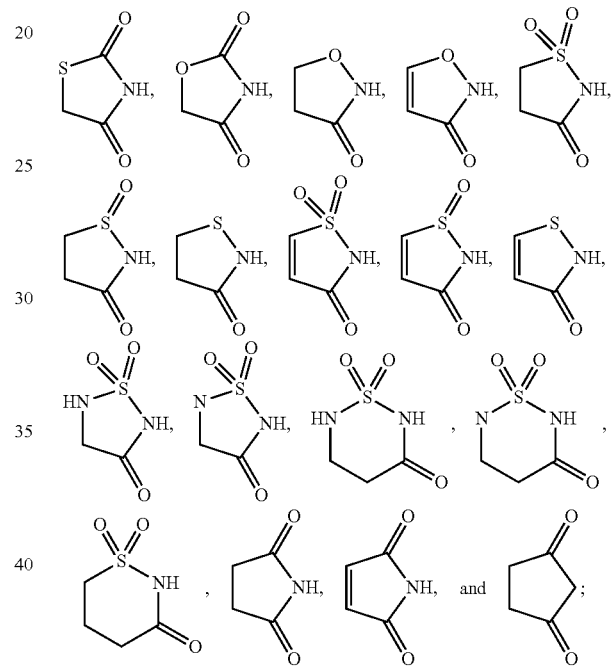

R$^8$ is selected from the group consisting of:
 (1) hydrogen,
 (2) —C$_{1-6}$alkyl,
 (3) —C$_{3-6}$cycloalkyl, and
 (4) aryl-C$_{1-6}$alkyl,
wherein each alkyl, cycloalkyl and aryl is unsubstituted or substituted with one to three substituents selected from R$^j$;
R$^a$ is selected from the group consisting of:
 (1) —C$_{1-6}$alkyl,
 (2) halogen,
 (3) —OR$^e$,
 (4) —NR$^c$S(O)$_n$R$^e$,
 (5) —S(O)$_n$R$^e$,
 (6) —S(O)$_n$NR$^c$R$^d$,
 (7) —NR$^c$R$^d$,
 (8) —C(O)R$^e$,
 (9) —OC(O)R$^e$,
 (10) —CO$_2$R$^e$,
 (11) —CN,
 (12) —C(O)NR$^c$R$^d$,
 (13) —NR$^c$C(O)R$^e$,
 (14) —NR$^c$C(O)OR$^e$,

(15) —NR$^c$C(O)NR$^c$R$^d$,
(16) —CF$_3$,
(17) —OCF$_3$,
(18) —OCHF$_2$,
(19) aryl,
(20) heteroaryl,
(21) —C$_{3-6}$cycloalkyl,
(22) —C$_{3-6}$cycloalkenyl, and
(23) —C$_{2-5}$cycloheteroalkyl,
wherein each alkyl, cycloalkyl, cycloalkenyl, cycloheteroalkyl, aryl and heteroaryl is unsubstituted or substituted with —C$_{1-6}$alkyl, halogen, —O—C$_{1-6}$alkyl and —CF$_3$;
R$^b$ is independently selected from the group consisting of:
(1) —C$_{1-10}$alkyl,
(2) —C$_{2-10}$alkenyl,
(3) —CF$_3$,
(4) halogen,
(5) —CN,
(6) —OH,
(7) —OC$_{1-10}$alkyl,
(8) —OC$_{2-10}$alkenyl,
(9) —O(CH$_2$)$_p$OC$_{1-10}$alkyl,
(10) —O(CH$_2$)$_p$C$_{3-6}$cycloalkyl,
(11) —O(CH$_2$)$_p$C$_{3-6}$cycloalkyl-C$_{1-10}$alkyl-,
(12) —O(CH$_2$)$_p$C$_{2-5}$cycloheteroalkyl,
(13) —O(CH$_2$)$_p$C$_{2-5}$cycloheteroalkyl-C$_{1-10}$alkyl-,
(14) —O-aryl,
(15) —O-heteroaryl,
(16) —O-aryl-C$_{1-10}$alkyl-,
(17) —O-heteroaryl-C$_{1-10}$alkyl-,
(18) —O(CH$_2$)$_p$NR$^c$S(C)$_m$R$^e$,
(19) —O(CH$_2$)$_p$S(O)$_m$R$^e$,
(20) —O(CH$_2$)$_p$S(O)$_m$NR$^c$R$^d$,
(21) —O(CH$_2$)$_p$NR$^c$R$^d$,
(22) —C(O)R$^e$,
(23) —OC(O)R$^e$,
(24) —CO$_2$R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH$_2$)$_p$O—C$_{3-6}$cycloalkyl,
(30) —O(CH$_2$)$_p$O—C$_{2-5}$cycloheteroalkyl,
(31) —OCF$_3$,
(32) —OCHF$_2$,
(33) —(CH$_2$)$_p$C$_{3-6}$cycloalkyl,
(34) —(CH$_2$)$_p$C$_{2-5}$cycloheteroalkyl,
(35) aryl,
(36) heteroaryl,
(37) aryl-C$_{1-10}$alkyl-, and
(38) heteroaryl-C$_{1-10}$alkyl-,
wherein each CH, CH$_2$, alkyl, alkenyl, cycloalkyl, cycloheteroalkyl, aryl and heteroaryl is unsubstituted or substituted with —C$_{1-6}$alkyl, halogen, —O—C$_{1-6}$alkyl and —CF$_3$;
R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$cycloheteroalkyl,
(7) C$_{2-5}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^f$, or R$^c$ and R$^d$ together with the atom(s) to which they are attached form a C$_{2-5}$ cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$;
each R$^e$ is independently selected from the group consisting of:
(1) hydrogen,
(2) —C$_{1-10}$alkyl,
(3) —C$_{2-10}$alkenyl,
(4) —C$_{3-6}$ cycloalkyl,
(5) —C$_{3-6}$ cycloalkyl-C$_{1-10}$alkyl-,
(6) —C$_{2-5}$cycloheteroalkyl,
(7) —C$_{2-5}$cycloheteroalkyl-C$_{1-10}$alkyl-,
(8) aryl,
(9) aryl-C$_{1-10}$alkyl-,
(10) heteroaryl, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents selected from R$^h$;
each R$^f$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
each R$^g$ is selected from the group consisting of:
(1) hydrogen,
(2) —C(O)R$^e$, and
(3) —C$_{1-10}$alkyl,
wherein each alkyl is unsubstituted or substituted with one to five halogens;
each R$^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
R$^i$ is independently selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$, (9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

R$^j$ is independently selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;

each R$^k$ is independently selected from the group consisting of:
(1) hydrogen,
(2) —C$_{1-6}$alkyl,
(3) —C$_{1-6}$alkyl-SO$_2$C$_{1-6}$alkyl,
(4) —CF$_3$, and
(5) —CHF$_2$,
wherein each alkyl is unsubstituted or substituted with one to three substituents independently selected from: —OH, —OC$_{1-6}$alkyl, halogen, cyano, and —S(O)$_2$C$_{1-6}$alkyl;

each R$^L$ is independently selected from the group consisting of:
(1) —CO$_2$C$_{1-6}$alkyl,
(2) —C$_{1-10}$alkyl,
(3) —C$_{2-10}$alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with 1-4 substituents selected from C$_{1-6}$alkyl, halogen, and —OC$_{1-6}$alkyl;

each R$^m$ is independently selected from the group consisting of:
(1) —C$_{1-10}$alkyl,
(2) —C$_{2-10}$alkenyl,
(3) —C$_{3-6}$ cycloalkyl,
(4) —C$_{3-6}$ cycloalkyl-C$_{1-10}$alkyl-,
(5) —C$_{2-5}$cycloheteroalkyl,
(6) —C$_{2-5}$cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;

each n is independently selected from: 0, 1 or 2;
each m is independently selected from: 0, 1 or 2; and
each p is independently selected from: 0, 1, 2, 3, 4, 5 or 6.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, "a" is a single bond.

In another embodiment of the present invention, "a" is a single bond, and Y is selected from the group consisting of: oxygen, sulfur, —CR$^g$R$^g$, C═O, —C(R$^g$)OC$_{1-6}$alkyl, —CF$_2$, and —NR$^c$.

In another embodiment of the present invention, "a" is a single bond and R$^6$ is present.

In another embodiment of the present invention, "a" is a double bond and R$^6$ is absent.

In another embodiment of the present invention, "a" is a double bond, R$^6$ is absent and Y is selected from the group consisting of: C—R$^g$, CF, and N. In a class of this embodiment, Y is selected from the group consisting of: —CH, —CF, and —N. In another class of this embodiment, Y is selected from the group consisting of: —C—R$^g$. In a subclass of this class, Y is —CH.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: CR$^1$, N and N-oxide. In a class of this embodiment, U is selected from the group consisting of: CR$^1$ and N. In another class of this embodiment, U is CR$^1$. In another class of this embodiment, U is N or N-oxide. In another class of this embodiment, U is N. In another class of this embodiment, U is N-oxide.

In another embodiment of the present invention, V is selected from the group consisting of: CR$^2$, N and N-oxide. In a class of this embodiment, V is selected from the group consisting of: CR$^2$ and N.

In another class of this embodiment, V is CR$^2$. In another class of this embodiment, V is N or N-oxide. In another class of this embodiment, V is N. In another class of this embodiment, V is N-oxide.

In another embodiment of the present invention, W is selected from the group consisting of: CH, N and N-oxide, provided that no more than two of T, U, V and W are selected from N and N-oxide, further provided that if both T and W are N or N-oxide, then R$^3$ is absent, and further provided that both U and V are not N or N-oxide. In a class of this embodiment, W is selected from the group consisting of: CH and N, provided that no more than two of T, U, V and W are selected from N and N-oxide, further provided that if both T and W are N or N-oxide, then R$^3$ is absent, and further provided that both U and V are not N or N-oxide. In another class of this embodiment, W is CH, provided that no more than two of T, U, V and W are selected from N and N-oxide, further provided that if both T and W are N or N-oxide, then R$^3$ is absent, and further provided that both U and V are not N or N-oxide. In another class of this embodiment, W is N or N-oxide, provided that no more than two of T, U, V and W are selected from N and N-oxide, further provided that if both T and W are N or N-oxide, then $R^3$ is absent, and further provided that both U and V are not N or N-oxide. In another class of this embodiment, W is N, provided that no more than two of T, U, V and W are selected from N and N-oxide, further provided that if both T and W are N or N-oxide, then $R^3$ is absent, and further provided that both U and V are not N or N-oxide.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T is CH, U is $CR^1$, V is $CR^2$, and W is CH. In a class of this embodiment, T is CH, U is $CR^1$, V is CH, and W is CH. In another class of this embodiment, T is CH, U is CH, V is $CR^2$, and W is CH.

In another embodiment of the present invention, T is N or N-oxide, U is $CR^1$, V is $CR^2$, and W is CH. In a class of this embodiment, T is N, U is $CR^1$, V is $CR^2$, and W is CH.

In another embodiment of the present invention, T is CH, U is N or N-oxide, and V is $CR^2$, and W is CH. In a class of this embodiment, T is CH, U is N, V is $CR^2$, and W is CH.

In another embodiment of the present invention, T is CH, U is $CR^1$, V is N or N-oxide, and W is CH. In a class of this embodiment, T is CH, U is $CR^1$, and V is N or N-oxide, and W is CH.

In another embodiment of the present invention, T is CH, U is $CR^1$, V is $CR^2$, and W is CH, N or N-oxide.

In another embodiment of the present invention, T is CH, U is $CR^1$, V is $CR^2$, and W is N or N-oxide. In a class of this embodiment, T is CH, U is $CR^1$, V is $CR^2$, and W is N.

In another embodiment of the present invention, T is N or N-oxide, U is N or N-oxide, V is $CR^2$, and W is CH. In a class of this embodiment, T is N, U is N, V is $CR^2$, and W is CH.

In another embodiment of the present invention, T is N or N-oxide, U is $CR^1$, V is N or N-oxide, and W is CH. In a class of this embodiment, T is N, U is $CR^1$, V is N, and W is CH.

In another embodiment of the present invention, T is N or N-oxide, U is $CR^1$, V is $CR^2$, and W is N or N-oxide. In a class of this embodiment, T is N, U is $CR^1$, V is $CR^2$, and W is N.

In another embodiment of the present invention, T is N or N-oxide, U is $CR^1$, V is $CR^2$, and W is N or N-oxide; and $R^3$ is absent. In a class of this embodiment, T is N, U is $CR^1$, V is $CR^2$, and W is N; and $R^3$ is absent.

In another embodiment of the present invention, T is CH, U is N or N-oxide, V is $CR^2$, and W is N or N-oxide. In a class of this embodiment, T is CH, U is N, V is $CR^2$, and W is N.

In another embodiment of the present invention, T is CH, U is $CR^1$, V is N or N-oxide, and W is N or N-oxide. In a class of this embodiment, T is CH, U is $CR^1$, V is N, and W is N.

In another embodiment of the present invention, T is CH; U is $CR^1$; V is $CR^2$; and W is CH, N or N-oxide.

In another embodiment of the present invention, Y is selected from the group consisting of: oxygen and sulfur.

In another embodiment of the present invention, Y is selected from the group consisting of: $—CR^gR^g$, C=O, $—CF_2$, and $—NR^c$. In a class of this embodiment, Y is selected from the group consisting of: $—CH_2$, C=O, $—CF_2$, and $—NH$. In another embodiment of the present invention, Y is selected from the group consisting of: $—CR^gR^g$, C=O, and $—CF_2$. In a class of this embodiment, Y is selected from the group consisting of: $—CH_2$, C=O, and $—CF_2$. In another embodiment of the present invention, Y is selected from the group consisting of: $—CR^gR^g$. In a class of this embodiment, Y is $—CH_2$.

In another embodiment of the present invention, A is selected from the group consisting of: aryl and heteroaryl, wherein each aryl and heteroaryl is unsubstituted or substituted with one to five substituents selected from $R^a$. In a class of this embodiment, A is selected from the group consisting of: phenyl, pyridine, and thiazole, wherein each phenyl and pyridine and thiazole is unsubstituted or substituted with one to five substituents selected from $R^a$.

In another embodiment of the present invention, B is selected from the group consisting of: hydrogen, aryl, aryl-O—, aryl-C1-10 alkyl-O—, C3-6cycloalkenyl, and heteroaryl, wherein B is unsubstituted or substituted with one to five substituents selected from $R^b$. In a class of this embodiment, B is selected from the group consisting of: hydrogen, phenyl, phenyl-O—, phenyl-CH2-O—, cyclopentenyl, pyridine, isoxazole and indazole, wherein B is unsubstituted or substituted with one to five substituents selected from $R^b$.

In another embodiment of the present invention, B is selected from the group consisting of: aryl, aryl-O—, aryl-$C_{1-10}$ alkyl-O—, $C_{3-6}$cycloalkenyl and heteroaryl, wherein B is unsubstituted or substituted with one to five substituents selected from $R^b$. In a class of this embodiment, B is selected from the group consisting of: phenyl, phenyl-O—, phenyl-$CH_2$—O—, cyclopentenyl, pyridine, isoxazole and indazole, wherein B is unsubstituted or substituted with one to five substituents selected from $R^b$.

In another embodiment of the present invention, B is selected from the group consisting of: aryl, and heteroaryl, wherein each aryl and heteroaryl is unsubstituted or substituted with one to five substituents selected from $R^b$. In a class of this embodiment, B is selected from the group consisting of: phenyl, pyridine, isoxazole and indazole wherein phenyl, pyridine, isoxazole and indazole is unsubstituted or substituted with one to five substituents selected from $R^b$. In another class of this embodiment, B is selected from the group consisting of: phenyl and pyridine, wherein each phenyl and pyridine is unsubstituted or substituted with one to five substituents selected from $R^b$.

In another embodiment of the present invention, $R^1$ and $R^2$ are each independently selected from: a bond, hydrogen, $—OR^k$, and $—C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^1$ and $R^2$ are each independently selected from: a bond, hydrogen, $—OR^k$ and $—C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: a bond, hydrogen, —$OR^k$ and —$C_{1-6}$alkyl, wherein each alkyl is unsubstituted or substituted with one to three substituents selected from $R^L$, and wherein one of $R^1$ and $R^2$ is substituted with a substituent selected from $R^7$.

In another embodiment of the present invention, $R^1$ and $R^2$ are each independently selected from: a bond, hydrogen, —$OR^k$, and —$C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$.

In another embodiment of the present invention, $R^1$ and $R^2$ are each independently selected from: a bond, hydrogen, —OH, —$OC_{1-6}$alkyl and $C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^1$ and $R^2$ are each independently selected from: a bond, hydrogen, —OH, —$OC_{1-6}$alkyl, and $C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: a bond, hydrogen, —OH, —$OC_{1-6}$alkyl, and $C_{1-6}$alkyl, wherein each alkyl is unsubstituted or substituted with one to three substituents selected from $R^L$, and wherein one of $R^1$ and $R^2$ is substituted with a substituent selected from $R^7$.

In another embodiment of the present invention, $R^1$ and $R^2$ are each independently selected from: a bond, hydrogen, and —$C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^1$ and $R^2$ are each independently selected from: a bond, hydrogen and —$C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: a bond, hydrogen and —$C_{1-6}$alkyl, wherein each alkyl is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: a bond, hydrogen and —$C_2$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: a bond, hydrogen and —$C_2$alkyl, wherein each alkyl is unsubstituted or substituted with one to three substituents selected from $R^L$, and wherein one of $R^1$ and $R^2$ is substituted with a substituent selected from $R^7$.

In another embodiment of the present invention, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: hydrogen and —$C_{1-6}$alkyl, wherein each alkyl is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: hydrogen and —$C_2$alkyl-, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ and $R^2$ are each independently selected from: hydrogen and —C$_2$alkyl-, wherein each alkyl is unsubstituted or substituted with one to three substituents selected from R$^L$, and wherein one of R$^1$ and R$^2$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring, wherein each R$^1$ and R$^2$ is unsubstituted or substituted with one to three substituents selected from R$^L$, and wherein one of R$^1$ and R$^2$ is substituted with a substituent selected from R$^7$. In another class of this embodiment, R$^1$ and R$^2$ are each independently selected from: hydrogen and —C$_2$alkyl-, wherein each alkyl is unsubstituted or substituted with one to three substituents selected from R$^L$, and wherein one of R$^1$ and R$^2$ is substituted with a substituent selected from R$^7$.

In another embodiment, R$^1$ is independently selected from: a bond, hydrogen, halogen, —OR$^k$, —CN, —C$_{1-6}$alkyl, —C$_{3-6}$cycloalkyl, —C$_{3-6}$cycloalkyl-C$_{1-3}$alkyl-, —C$_{2-6}$cycloheteroalkyl, and —C$_{2-6}$cycloheteroalkyl-C$_{1-3}$alkyl-, wherein each alkyl, cycloalkyl and cycloheteroalkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with a substituent selected from R$^7$.

In a class of this embodiment, R$^1$ is independently selected from: a bond, hydrogen, halogen, —OR$^k$, —CN, —C$_{1-6}$alkyl, —C$_{3-6}$cycloalkyl, —C$_{3-6}$cycloalkyl-C$_{1-3}$alkyl-, —C$_{2-6}$cycloheteroalkyl, and —C$_{2-6}$cycloheteroalkyl-C$_{1-3}$alkyl-, wherein each alkyl, cycloalkyl and cycloheteroalkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring, wherein each R$^1$ and R$^2$ is unsubstituted or substituted with one to three substituents selected from R$^L$, and wherein one of R$^1$ and R$^2$ is substituted with a substituent selected from R$^7$.

In another class of this embodiment, R$^1$ is independently selected from: a bond, hydrogen, halogen, —OR$^k$, —CN, —C$_{1-6}$alkyl, —C$_{3-6}$cycloalkyl, —C$_{3-6}$cycloalkyl-C$_{1-3}$alkyl-, —C$_{2-6}$cycloheteroalkyl, and —C$_{2-6}$cycloheteroalkyl-C$_{1-3}$alkyl-, wherein each alkyl, cycloalkyl and cycloheteroalkyl is unsubstituted or substituted with one to three substituents selected from R$^L$, and wherein R$^1$ is substituted with a substituent selected from R$^7$.

In another embodiment of the present invention, R$^1$ is independently selected from: a bond, hydrogen, —OR$^k$ and —C$_{1-6}$alkyl, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with a substituent selected from R$^7$. In a class of this embodiment, R$^1$ is independently selected from: a bond, hydrogen, —OR$^k$ and —C$_{1-6}$alkyl, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring, wherein each R$^1$ and R$^2$ is unsubstituted or substituted with one to three substituents selected from R$^L$, and wherein one of R$^1$ and R$^2$ is substituted with a substituent selected from R$^7$.

In another class of this embodiment, R$^1$ is selected from: a bond, hydrogen, —OR$^k$ and —C$_{1-6}$alkyl, wherein each alkyl is unsubstituted or substituted with one to three substituents selected from R$^L$, and wherein R$^1$ is substituted with a substituent selected from R$^7$.

In another embodiment of the present invention, R$^1$ is selected from: a bond, hydrogen, —OH, —OC$_{1-6}$alkyl and —C$_{1-6}$alkyl, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with a substituent selected from R$^7$.

In a class of this embodiment, R$^1$ is selected from: a bond, hydrogen, —OH, —OC$_{1-6}$alkyl, and —C$_{1-6}$alkyl-, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring, wherein each R$^1$ and R$^2$ is unsubstituted or substituted with one to three substituents selected from R$^L$, and wherein one of R$^1$ and R$^2$ is substituted with a substituent selected from R$^7$. In another class of this embodiment, R$^1$ is selected from: a bond, hydrogen, —OH, —OC$_{1-6}$alkyl, and —C$_{1-6}$alkyl-, wherein each alkyl is unsubstituted or substituted with one to three substituents selected from R$^L$, and wherein R$^1$ is substituted with a substituent selected from R$^7$.

In another embodiment of the present invention, R$^1$ is selected from: a bond, hydrogen, and —C$_{1-6}$alkyl, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents selected from R$^L$, and wherein one of R$^1$ and R$^2$ is substituted with a substituent selected from R$^7$. In a class of this embodiment, R$^1$ is selected from: a bond, hydrogen, and —C$_{1-6}$alkyl, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a C$_{3-6}$cycloalkyl ring or a C$_{2-5}$cycloheteroalkyl ring, wherein each R$^1$ and R$^2$ is unsubstituted or substituted with one to three substituents selected from R$^L$, and wherein one of R$^1$ and R$^2$ is substituted with a substituent selected from R$^7$. In a class of this embodiment, R$^1$ is selected from: a bond, hydrogen, and —C$_{1-6}$alkyl, wherein each alkyl is unsubstituted or substituted with one to three substituents selected from R$^L$, and wherein R$^1$ is substituted with a substituent selected from R$^7$. In another class of this embodiment, R$^1$ is selected from: a bond, hydrogen and —C$_2$alkyl-, wherein each alkyl is unsubstituted or substituted with one to three substituents selected from R$^L$, and wherein R$^1$ is substituted with a substituent selected from R$^7$, or R$^1$ and R$^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ is selected from: a bond, hydrogen and —$C_2$alkyl-, wherein each alkyl is unsubstituted or substituted with one to three substituents selected from $R^L$, and wherein $R^1$ is substituted with a substituent selected from $R^7$.

In another embodiment of the present invention, $R^1$ is selected from: hydrogen and —$C_{1-6}$alkyl, wherein each alkyl is unsubstituted or substituted with one to three substituents selected from $R^L$, and wherein $R^1$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^1$ is selected from: hydrogen and —$C_{1-6}$alkyl-, wherein each alkyl is unsubstituted or substituted with one to three substituents selected from $R^L$, and wherein $R^1$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ is selected from: hydrogen and —$C_{1-6}$alkyl-, wherein each alkyl is unsubstituted or substituted with one to three substituents selected from $R^L$, and wherein $R^1$ is substituted with a substituent selected from $R^7$. In another class of this embodiment, $R^1$ is selected from: hydrogen and —$C_2$alkyl-, wherein each alkyl is unsubstituted or substituted with one to three substituents selected from $R^L$, and wherein $R^1$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ is selected from: hydrogen and —$C_2$alkyl-, wherein each alkyl is unsubstituted or substituted with one to three substituents selected from $R^L$, and wherein $R^1$ is substituted with a substituent selected from $R^7$.

In another embodiment of the present invention, $R^1$ is selected from: —$C_{1-6}$alkyl, wherein each alkyl is unsubstituted or substituted with one to three substituents selected from $R^L$, and wherein $R^1$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^1$ is selected from: —$C_{1-6}$alkyl-, wherein each alkyl is unsubstituted or substituted with one to three substituents selected from $R^L$, and wherein $R^1$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ is selected from: —$C_{1-6}$alkyl-, wherein each alkyl is unsubstituted or substituted with one to three substituents selected from $R^L$, and wherein $R^1$ is substituted with a substituent selected from $R^7$. In another class of this embodiment, $R^1$ is —$C_2$alkyl, wherein each alkyl is unsubstituted or substituted with one to three substituents selected from $R^L$, and wherein $R^1$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^1$ is —$C_2$alkyl-, wherein each alkyl is unsubstituted or substituted with one to three substituents selected from $R^L$, and wherein $R^1$ is substituted with a substituent selected from $R^7$.

In another embodiment of the present invention, $R^1$ is hydrogen. In another embodiment, $R^1$ is independently selected from: a bond, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with a substituent selected from $R^7$; and $R^2$ is hydrogen.

In another embodiment of the present invention, $R^1$ is selected from: a bond, —$OR^k$ and —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen. In a class of this embodiment, $R^1$ is selected from: a bond, —OH, —$OC_{1-6}$alkyl, and —$C_{1-6}$alkyl-, wherein each alkyl is unsubstituted or substituted with one to three substituents selected from $R^L$, and wherein $R^1$ is substituted with a substituent selected from $R^7$; and $R^2$ is hydrogen.

In another embodiment of the present invention, $R^1$ is selected from: a bond and —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen. In a class of this embodiment, $R^1$ is selected from: a bond and —$C_2$alkyl-, wherein each alkyl is unsubstituted or substituted with one to three substituents selected from $R^L$, and wherein $R^1$ is substituted with a substituent selected from $R^7$; and $R^2$ is hydrogen.

In another embodiment of the present invention, $R^1$ is selected from: —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen. In a class of this embodiment, $R^1$ is selected from: —$C_2$alkyl-, wherein each alkyl is unsubstituted or substituted with one to three substituents selected from $R^L$, and wherein $R^1$ is substituted with a substituent selected from $R^7$; and $R^2$ is hydrogen.

In another embodiment, $R^2$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring, wherein each $R^1$ and $R^2$ is unsubstituted or substituted with one to three substituents selected from $R^L$, and wherein one of $R^1$ and $R^2$ is substituted with a substituent selected from $R^7$.

In another class of this embodiment, $R^2$ is independently selected from: a bond, hydrogen, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with a substituent selected from $R^7$.

In another embodiment of the present invention, $R^2$ is independently selected from: a bond, hydrogen, —$OR^k$ and —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is independently selected from: a bond, hydrogen, —$OR^k$ and —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is selected from: a bond, hydrogen, —$OR^k$ and —$C_{1-6}$alkyl, wherein each alkyl is unsubstituted or substituted with one to three substituents selected from $R^L$, and wherein $R^2$ is substituted with a substituent selected from $R^7$.

In another embodiment of the present invention, $R^2$ is selected from: a bond, hydrogen, —OH, —$OC_{1-6}$alkyl and —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is selected from: a bond, hydrogen, —OH, —$OC_{1-6}$alkyl, and —$C_{1-6}$alkyl-, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is selected from: a bond, hydrogen, —OH, —$OC_{1-6}$alkyl, and —$C_{1-6}$alkyl-, wherein each alkyl is unsubstituted or substituted with one to three substituents selected from $R^L$, and wherein $R^2$ is substituted with a substituent selected from $R^7$.

In another embodiment of the present invention, $R^2$ is selected from: a bond, hydrogen, and —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is selected from: a bond, hydrogen, and —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is selected from: a bond, hydrogen, and —$C_{1-6}$alkyl, wherein each alkyl is unsubstituted or substituted with one to three substituents selected from $R^L$, and wherein $R^2$ is substituted with a substituent selected from $R^7$. In another class of this embodiment, $R^2$ is selected from: a bond, hydrogen and —$C_2$alkyl-, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is selected from: a bond, hydrogen and —$C_2$alkyl-, wherein each alkyl is unsubstituted or substituted with one to three substituents selected from $R^L$, and wherein $R^2$ is substituted with a substituent selected from $R^7$.

In another embodiment of the present invention, $R^2$ is selected from: hydrogen and —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is selected from: hydrogen and —$C_{1-6}$alkyl-, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is selected from: hydrogen and —$C_{1-6}$alkyl-, wherein each alkyl is unsubstituted or substituted with one to three substituents selected from $R^L$, and wherein $R^2$ is substituted with a substituent selected from $R^7$. In another class of this embodiment, $R^2$ is selected from: hydrogen and —$C_2$alkyl-, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is selected from: hydrogen and —$C_2$alkyl-, wherein each alkyl is unsubstituted or substituted with one to three substituents selected from $R^L$, and wherein $R^2$ is substituted with a substituent selected from $R^7$.

In another embodiment of the present invention, $R^2$ is selected from: —$C_{1-6}$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$. In a class of this embodiment, $R^2$ is selected from: —$C_{1-6}$alkyl-, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is selected from: —$C_{1-6}$alkyl-, wherein each alkyl is unsubstituted or substituted with one to three substituents selected from $R^L$, and wherein $R^2$ is substituted with a substituent selected from $R^7$. In another class of this embodiment, $R^2$ is —$C_2$alkyl, wherein each alkyl is unsubstituted or substituted with one to three substituents selected from $R^L$, and wherein $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring, wherein each $R^1$ and $R^2$ is unsubstituted or substituted with one to three substituents selected from $R^L$, and wherein one of $R^1$ and $R^2$ is substituted with a substituent selected from $R^7$. In another class of this embodiment, $R^2$ is —$C_2$alkyl-, wherein each alkyl is unsubstituted or substituted with one to three substituents selected from $R^L$, and wherein $R^2$ is substituted with a substituent selected from $R^7$.

In another embodiment of the present invention, $R^2$ is hydrogen.

In another embodiment, $R^2$ is independently selected from: a bond, halogen, —$OR^k$, —CN, —$C_{1-6}$alkyl, —$C_{3-6}$cycloalkyl, —$C_{3-6}$cycloalkyl-$C_{1-3}$alkyl-, —$C_{2-6}$cycloheteroalkyl, and —$C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with a substituent selected from $R^7$; and $R^1$ is hydrogen.

In another embodiment of the present invention, $R^2$ is selected from: a bond, —$OR^k$ and —$C_{1-6}$alkyl, wherein each alkyl is unsubstituted or substituted with one to three substituents selected from $R^L$, and wherein $R^2$ is substituted with a substituent selected from $R^7$; and $R^1$ is hydrogen. In a class of this embodiment, $R^2$ is selected from: a bond, —OH, —$OC_{1-6}$alkyl, and —$C_{1-6}$alkyl-, wherein each alkyl is unsubstituted or substituted with one to three substituents selected from $R^L$, and wherein $R^2$ is substituted with a substituent selected from $R^7$; and $R^1$ is hydrogen.

In another embodiment of the present invention, $R^2$ is selected from: a bond and —$C_{1-6}$alkyl, wherein each alkyl is unsubstituted or substituted with one to three substituents selected from $R^L$, and wherein $R^2$ is substituted with a substituent selected from $R^7$; and $R^1$ is hydrogen. In a class of this embodiment, $R^2$ is selected from: a bond and —$C_2$alkyl-, wherein each alkyl is unsubstituted or substituted with one to three substituents selected from $R^L$, and wherein $R^2$ is substituted with a substituent selected from $R^7$; and $R^1$ is hydrogen.

In another embodiment of the present invention, $R^2$ is selected from: —$C_{1-6}$alkyl, wherein each alkyl is unsubstituted or substituted with one to three substituents selected from $R^L$, and wherein $R^2$ is substituted with a substituent selected from $R^7$; and $R^1$ is hydrogen. In a class of this embodiment, $R^2$ is selected from: —$C_2$alkyl-, wherein each alkyl is unsubstituted or substituted with one to three substituents selected from $R^L$, and wherein $R^2$ is substituted with a substituent selected from $R^7$; and $R^1$ is hydrogen.

In another embodiment, $R^3$ is absent or when present is selected from the group consisting of: hydrogen, halogen, —$OR^e$, —CN, —$C_{1-6}$alkyl, —$C_{3-6}$cycloalkyl, and —$C_{3-6}$cycloalkyl-$C_{1-3}$alkyl-, wherein each alkyl and cycloalkyl is unsubstituted or substituted with one to three substituents selected from $R^i$.

In another embodiment of the present invention, when present, $R^3$ is selected from the group consisting of: hydrogen, halogen, —$OR^e$, —CN and —$C_{1-6}$alkyl, wherein each alkyl is unsubstituted or substituted with one to three substituents selected from $R^i$.

In another embodiment of the present invention, when present, $R^3$ is selected from the group consisting of: hydrogen, halogen and —$C_{1-6}$alkyl, wherein each alkyl is unsubstituted or substituted with one to three substituents selected from $R^i$. In a class of this embodiment, when present, $R^3$ is selected from the group consisting of: hydrogen and —$C_{1-6}$alkyl, wherein each alkyl is unsubstituted or substituted with one to three substituents selected from $R^i$. In another class of this embodiment, when present, $R^3$ is selected from the group consisting of: —$C_{1-6}$alkyl, wherein each alkyl is unsubstituted or substituted with one to three substituents selected from $R^i$. In another class of this embodiment, when present $R^3$ is hydrogen.

In another embodiment of the present invention, $R^3$ is selected from the group consisting of: hydrogen, halogen, —$OR^e$, —CN, —$C_{1-6}$alkyl, —$C_{3-6}$cycloalkyl and —$C_{3-6}$cycloalkyl-$C_{1-3}$alkyl-, wherein each alkyl and cycloalkyl is unsubstituted or substituted with one to three substituents selected from $R^i$.

In another embodiment of the present invention, $R^3$ is selected from the group consisting of: hydrogen, halogen, —OR$^e$, —CN and —C$_{1-6}$alkyl, wherein each alkyl is unsubstituted or substituted with one to three substituents selected from R$^i$.

In another embodiment of the present invention, R$^3$ is selected from the group consisting of: hydrogen, halogen and —C$_{1-6}$alkyl, wherein each alkyl is unsubstituted or substituted with one to three substituents selected from R$^i$. In a class of this embodiment, R$^3$ is selected from the group consisting of: hydrogen and —C$_{1-6}$alkyl, wherein each alkyl is unsubstituted or substituted with one to three substituents selected from R$^i$. In another class of this embodiment, R$^3$ is selected from the group consisting of: —C$_{1-6}$alkyl, wherein each alkyl is unsubstituted or substituted with one to three substituents selected from R$^i$. In another class of this embodiment, R$^3$ is hydrogen.

In another embodiment of the present invention, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-O—, C$_{3-6}$cycloalkyl-C$_{1-10}$alkyl-, C$_{3-6}$cycloalkyl-C$_{1-10}$alkyl-O—, C$_{2-5}$cycloheteroalkyl, C$_{2-5}$cycloheteroalkyl-O—, C$_{2-5}$cycloheteroalkyl-C$_{1-10}$alkyl-, C$_{2-5}$cycloheteroalkyl-C$_{1-10}$alkyl-O—, aryl, aryl-O—, aryl-C$_{1-10}$alkyl-, heteroaryl, heteroaryl-O—, and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: —OR$^e$, C$_{1-6}$alkyl-O—, C$_{3-6}$cycloalkyl-O—, C$_{3-6}$cycloalkyl-C$_{1-10}$alkyl-O—, C$_{2-5}$cycloheteroalkyl-O—, C$_{2-5}$cycloheteroalkyl-C$_{1-10}$alkyl-O—, aryl-O—, and heteroaryl-O—; then Y is selected from the group consisting of: —CR$^g$R$^g$, C═O, and —CF$_2$. In a class of this embodiment, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-O—, C$_{3-6}$cycloalkyl-C$_{1-10}$alkyl-, C$_{3-6}$cycloalkyl-C$_{1-10}$alkyl-O—, C$_{2-5}$cycloheteroalkyl, C$_{2-5}$cycloheteroalkyl-O—, C$_{2-5}$cycloheteroalkyl-C$_{1-10}$alkyl-, C$_{2-5}$cycloheteroalkyl-C$_{1-10}$alkyl-O—, aryl, aryl-O—, aryl-C$_{1-10}$alkyl-, heteroaryl, heteroaryl-O—, and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: —OR$^e$, C$_{1-6}$alkyl-O—, C$_{3-6}$cycloalkyl-O—, C$_{3-6}$cycloalkyl-C$_{1-10}$alkyl-O—, C$_{2-5}$cycloheteroalkyl-O—, C$_{2-5}$cycloheteroalkyl-C$_{1-10}$alkyl-O—, aryl-O—, and heteroaryl-O—; then Y is selected from the group consisting of: —CR$^g$R$^g$. In a subclass of this class, Y is —CH$_2$.

In another embodiment of the present invention, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-C$_{1-10}$alkyl-, C$_{2-5}$cycloheteroalkyl, C$_{2-5}$cycloheteroalkyl-C$_{1-10}$alkyl-, aryl, aryl-C$_{1-10}$alkyl-, heteroaryl and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CR$^g$R$^g$, C═O, —C(R$^g$)OC$_{1-6}$alkyl, and —CF$_2$. In a class of this embodiment, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-C$_{1-10}$alkyl-, C$_{2-5}$cycloheteroalkyl, C$_{2-5}$cycloheteroalkyl-C$_{1-10}$alkyl-, aryl, aryl-C$_{1-10}$alkyl-, heteroaryl and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CR$^g$R$^g$, C═O, and —CF$_2$. In another class of this embodiment, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-C$_{1-10}$alkyl-, C$_{2-5}$cycloheteroalkyl, C$_{2-5}$cycloheteroalkyl-C$_{1-10}$alkyl-, aryl, aryl-C$_{1-10}$alkyl-, heteroaryl and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CH$_2$, C═O, and —CF$_2$. In another class of this embodiment, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-C$_{1-10}$alkyl-, C$_{2-5}$cycloheteroalkyl, C$_{2-5}$cycloheteroalkyl-C$_{1-10}$alkyl-, aryl, aryl-C$_{1-10}$alkyl-, heteroaryl and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CR$^g$R$^g$. In another class of this embodiment, R$^4$ is selected from the group consisting of: hydrogen, halogen, OR$^e$, C$_{1-6}$alkyl, C$_{1-6}$alkyl-O—, C$_{3-6}$cycloalkyl, C$_{3-6}$cycloalkyl-C$_{1-10}$alkyl-, C$_{2-5}$cycloheteroalkyl, C$_{2-5}$cycloheteroalkyl-C$_{1-10}$alkyl-, aryl, aryl-C$_{1-10}$alkyl-, heteroaryl and heteroaryl-C$_{1-10}$alkyl-, wherein each alkyl, cycloalkyl, cycloheteroalkyl, aryl and heteroaryl is unsubstituted or substituted with one to three substituents selected from R$^j$, provided that when R$^4$ is selected from the group consisting of: OR$^e$ and —C$_{1-6}$alkyl-O—, then Y is —CH$_2$.

In another embodiment of the present invention, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$, and —C$_{1-6}$alkyl-O—, then Y is selected from the group consisting of: —CR$^g$R$^g$, C═O, —C(R$^g$)OC$_{1-6}$alkyl, and —CF$_2$. In a class of this embodiment, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$, and —C$_{1-6}$alkyl-O—, then Y is selected from the group consisting of: —CR$^g$R$^g$, C═O and —CF$_2$. In another class of this embodiment, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CH$_2$, C=O, and —CF$_2$.

In another embodiment of the present invention, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$ and —C$_{1-6}$alkyl-O—, then Y is selected from the group consisting of: —CR$^g$R$^g$. In another class of this embodiment, R$^4$ is selected from the group consisting of: hydrogen, halogen, OR$^e$, C$_{1-6}$alkyl, and C$_{1-6}$alkyl-O—, wherein each alkyl is unsubstituted or substituted with one to three substituents selected from R$^j$, provided that when R$^4$ is selected from the group consisting of: OR$^e$ and —C$_{1-6}$alkyl-O—, then Y is —CH$_2$.

In another embodiment of the present invention, R$^4$ is selected from the group consisting of: hydrogen, halogen and C$_{1-6}$alkyl, wherein each alkyl is unsubstituted or substituted with one to three substituents selected from R$^j$.

In another embodiment of the present invention, R$^4$ is selected from the group consisting of: hydrogen and C$_{1-6}$alkyl, wherein each alkyl is unsubstituted or substituted with one to three substituents selected from R$^j$.

In another embodiment of the present invention, R$^4$ is selected from the group consisting of: —C$_{1-6}$alkyl, wherein each alkyl is unsubstituted or substituted with one to three substituents selected from R$^j$.

In another embodiment of the present invention, R$^4$ is hydrogen.

In another embodiment of the present invention, R$^5$ is selected from the group consisting of: hydrogen, —C$_{1-6}$alkyl and —C$_{3-6}$cycloalkyl, wherein each alkyl and cycloalkyl is unsubstituted or substituted with one to three substituents selected from R$^j$.

In another embodiment of the present invention, R$^5$ is selected from the group consisting of: hydrogen and —C$_{1-6}$alkyl, wherein each alkyl is unsubstituted or substituted with one to three substituents selected from R$^j$. In another embodiment of the present invention, R$^5$ is selected from the group consisting of: —C$_{1-6}$alkyl, wherein each alkyl is unsubstituted or substituted with one to three substituents selected from R$^j$. In another embodiment of the present invention, R$^5$ is hydrogen.

In another embodiment of the present invention, R$^6$ is absent, or when present R$^6$ is selected from the group consisting of: hydrogen, —C$_{1-6}$alkyl, and —C$_{3-6}$cycloalkyl, wherein each alkyl and cycloalkyl is unsubstituted or substituted with one to three substituents selected from R$^j$.

In another embodiment of the present invention, R$^6$ is absent, or when present R$^6$ is selected from the group consisting of: hydrogen and —C$_{1-6}$alkyl, wherein each alkyl is unsubstituted or substituted with one to three substituents selected from R$^j$. In a class of this embodiment, R$^6$ is absent, or when present R$^6$ is selected from the group consisting of: —C$_{1-6}$alkyl, wherein each alkyl is unsubstituted or substituted with one to three substituents selected from R$^j$. In another class of this embodiment, R$^6$ is absent, or when present R$^6$ is hydrogen.

In another embodiment of the present invention, R$^6$ is selected from the group consisting of: hydrogen, —C$_{1-6}$alkyl, and —C$_{3-6}$cycloalkyl, wherein each alkyl and cycloalkyl is unsubstituted or substituted with one to three substituents selected from R$^j$.

In another embodiment of the present invention, R$^6$ is selected from the group consisting of: hydrogen and —C$_{1-6}$alkyl, wherein each alkyl is unsubstituted or substituted with one to three substituents selected from R$^j$. In a class of this embodiment, R$^6$ is selected from the group consisting of: —C$_{1-6}$alkyl, wherein each alkyl is unsubstituted or substituted with one to three substituents selected from R$^j$. In another class of this embodiment, R$^6$ is hydrogen.

In another embodiment of the present invention, R$^7$ is selected from the group consisting of: —CO$_2$R$^8$, —C$_{1-6}$alkyl-CO$_2$R$^8$, and a cycloheteroalkyl selected from the group consisting of:

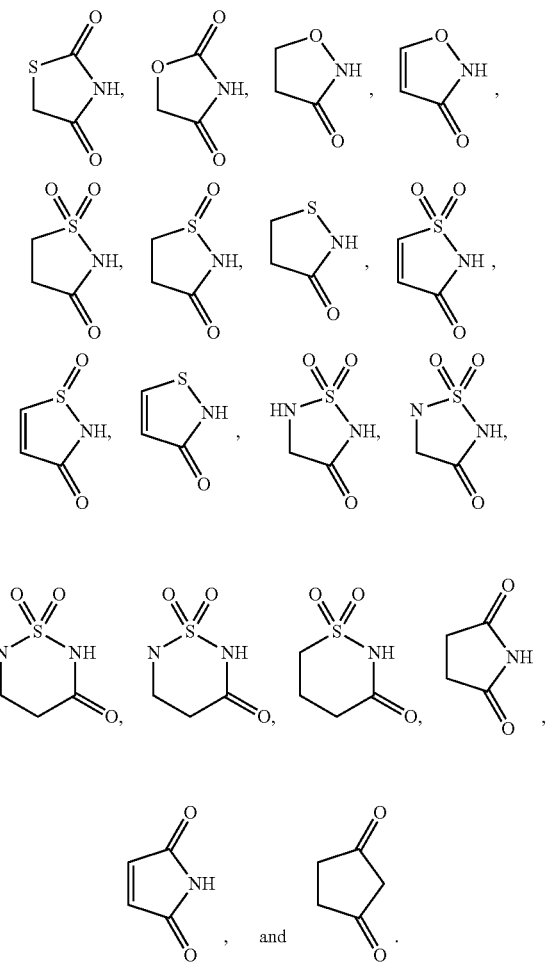

In a class of this embodiment, R$^7$ is selected from the group consisting of: —CO$_2$R$^8$, —C$_{1-6}$alkyl-CO$_2$R$^8$, and a cycloheteroalkyl selected from:

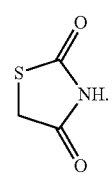

In another class of this embodiment, R$^7$ is selected from the group consisting of: —CO$_2$H, —CH$_2$CO$_2$H, —(CH$_2$)$_2$CO$_2$H, and a cycloheteroalkyl selected from:

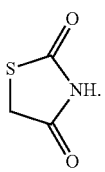

In another class of this embodiment, $R^7$ is selected from the group consisting of: —$CO_2H$, —$CH_2CO_2H$, and a cycloheteroalkyl selected from:

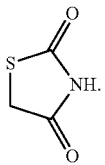

In another embodiment of the present invention, $R^7$ is —$CO_2R^8$. In a class of this embodiment, $R^7$ is —$CO_2H$.

In another embodiment of the present invention, $R^8$ is selected from the group consisting of: hydrogen, —$C_{1-6}$alkyl and —$C_{3-6}$cycloalkyl, wherein each alkyl and cycloalkyl is unsubstituted or substituted with one to three substituents selected from $R^j$. In a class of this embodiment, $R^8$ is selected from the group consisting of: hydrogen and —$C_{1-6}$alkyl, wherein each alkyl is unsubstituted or substituted with one to three substituents selected from $R^j$. In another class of this embodiment, $R^8$ is —$C_{1-6}$alkyl, wherein each alkyl is unsubstituted or substituted with one to three substituents selected from $R^j$. In another class of this embodiment, $R^8$ is hydrogen.

In another embodiment of the present invention, $R^a$ is selected from the group consisting of: —$C_{1-6}$alkyl, halogen, —$OR^e$, —$CF_3$, aryl, and —$C_{3-6}$cycloalkenyl, wherein each alkyl, cycloalkenyl and aryl is unsubstituted or substituted with —$C_{1-6}$alkyl, halogen, —O—$C_{1-6}$alkyl and —$CF_3$. In a class of this embodiment, each alkyl, cycloalkenyl and aryl is unsubstituted or substituted with —$C_{1-6}$alkyl. In a subclass of this class, each alkyl, cycloalkenyl and aryl is unsubstituted or substituted with —$CH_3$. In another class of this embodiment, $R^a$ is selected from the group consisting of: —$CH_3$, Br, F, Cl, —O—$CH_2$-phenyl, —$CF_3$, phenyl, and cyclopentenyl, wherein each alkyl, cycloalkenyl and aryl is unsubstituted or substituted with —$C_{1-6}$alkyl, halogen, —O—$C_{1-6}$alkyl and —$CF_3$. In a subclass of this class, each alkyl, cycloalkenyl and aryl is unsubstituted or substituted with —$C_{1-6}$alkyl. In another subclass of this class, each alkyl, cycloalkenyl and aryl is unsubstituted or substituted with —$CH_3$.

In another embodiment of the present invention, $R^a$ is selected from the group consisting of: —$C_{1-6}$alkyl, halogen, and —$C_{3-6}$cycloalkenyl, wherein each alkyl and cycloalkenyl is unsubstituted or substituted with —$C_{1-6}$alkyl, halogen, —O—$C_{1-6}$alkyl and —$CF_3$. In a class of this embodiment, each alkyl and cycloalkenyl is unsubstituted or substituted with —$C_{1-6}$alkyl. In a subclass of this class, each alkyl and cycloalkenyl is unsubstituted or substituted with —$CH_3$. In another class of this embodiment, $R^a$ is selected from the group consisting of: —$C_{1-6}$alkyl, halogen and —$C_{3-6}$cycloalkenyl. In another class of this embodiment, $R^a$ is selected from the group consisting of: —$CH_3$, Br, F, Cl, and cyclopentenyl, wherein each alkyl and cycloalkenyl is unsubstituted or substituted with —$C_{1-6}$alkyl, halogen, —O—$C_{1-6}$alkyl and —$CF_3$. In a subclass of this class, each alkyl and cycloalkenyl is unsubstituted or substituted with —$C_{1-6}$alkyl. In another subclass of this class, each alkyl and cycloalkenyl is unsubstituted or substituted with —$CH_3$. In another subclass of this class, $R^a$ is selected from the group consisting of: —$CH_3$, Br, F, Cl, and cyclopentenyl. In another class of this embodiment, $R^a$ is selected from the group consisting of: —$CH_3$, F, and cyclopentenyl, wherein each alkyl and cycloalkenyl is unsubstituted or substituted with —$C_{1-6}$alkyl, halogen, —O—$C_{1-6}$alkyl and —$CF_3$. In a subclass of this class, each alkyl and cycloalkenyl is unsubstituted or substituted with —$C_{1-6}$alkyl. In another subclass of this class, each alkyl and cycloalkenyl is unsubstituted or substituted with —$CH_3$. In another subclass of this class, $R^a$ is selected from the group consisting of: —$CH_3$, F and cyclopentenyl.

In another embodiment of the present invention, $R^b$ is independently selected from the group consisting of: —$C_{1-10}$alkyl, —$CF_3$, halogen, —CN, —$OC_{1-10}$alkyl, and —$O(CH_2)_pS(O)_mR^e$, wherein each $CH_2$ and alkyl is unsubstituted or substituted with —$C_{1-6}$alkyl, halogen, —O—$C_{1-6}$alkyl and —$CF_3$. In a class of this embodiment, each $CH_2$ and alkyl is unsubstituted or substituted with —$C_{1-6}$alkyl. In a subclass of this class, each $CH_2$ and alkyl is unsubstituted or substituted with —$CH_3$. In another class of this embodiment, $R^b$ is independently selected from the group consisting of: —$C_{1-10}$alkyl, —$CF_3$, halogen, —CN, —$OC_{1-10}$alkyl and —$O(CH_2)_2S(O)_2C_{1-10}$alkyl, wherein each $CH_2$ and alkyl is unsubstituted or substituted with —$C_{1-6}$alkyl, halogen, —O—$C_{1-6}$alkyl and —$CF_3$. In a subclass of this class, each $CH_2$ and alkyl is unsubstituted or substituted with —$C_{1-6}$alkyl. In another subclass of this class, each $CH_2$ and alkyl is unsubstituted or substituted with —$CH_3$. In another class of this embodiment, $R^b$ is independently selected from the group consisting of: —$CH_3$, —$CF_3$, F, —CN, —$OCH_3$ and —$O(CH_2)_2S(O)_2CH_3$, wherein each $CH_2$ and alkyl is unsubstituted or substituted with —$C_{1-6}$alkyl, halogen, —O—$C_{1-6}$alkyl and —$CF_3$. In a subclass of this class, each $CH_2$ and alkyl is unsubstituted or substituted with —$C_{1-6}$alkyl. In another subclass of this class, each $CH_2$ and alkyl is unsubstituted or substituted with —$CH_3$.

In another embodiment of the present invention, $R^b$ is independently selected from the group consisting of: —$C_{1-10}$alkyl, —$CF_3$, halogen and —$OC_{1-10}$alkyl, wherein each alkyl is unsubstituted or substituted with —$C_{1-6}$alkyl, halogen, —O—$C_{1-6}$alkyl and —$CF_3$. In a class of this embodiment, each alkyl is unsubstituted or substituted with —$C_{1-6}$alkyl. In a subclass of this class, each alkyl is unsubstituted or substituted with —$CH_3$.

In another embodiment of the present invention, $R^b$ is independently selected from the group consisting of: —$CH_3$, —$CF_3$, F and —$OCH_3$.

In another embodiment of the present invention, $R^c$ and $R^d$ are each independently selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are each independently selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^c$ and $R^d$ are each independently selected from the group consisting of: hydrogen, $C_{1-10}$alkyl and $C_{2-10}$alkenyl, wherein each alkyl and alkenyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are each independently selected from the group consisting of: hydrogen, $C_{1-10}$alkyl and $C_{2-10}$alkenyl, wherein each alkyl and alkenyl is unsubstituted or substituted with one to three substituents independently selected from $R^f$.

In another embodiment of the present invention, $R^c$ and $R^d$ are each independently selected from the group consisting of: hydrogen and $C_{1-10}$alkyl, wherein each alkyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are each independently selected from the group consisting of: hydrogen and $C_{1-10}$alkyl, wherein each alkyl is unsubstituted or substituted with one to three substituents independently selected from $R^f$.

In another embodiment of the present invention, $R^c$ and $R^d$ are each independently selected from the group consisting of: $C_{1-10}$alkyl, wherein each alkyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ and $R^d$ are each independently selected from the group consisting of: $C_{1-10}$alkyl, wherein each alkyl is unsubstituted or substituted with one to three substituents independently selected from $R^f$.

In another embodiment of the present invention, $R^c$ and $R^d$ are each hydrogen.

In another embodiment of the present invention, $R^c$ is independently selected from the group consisting of: hydrogen, $C_{1-10}$alkyl, $C_{2-10}$alkenyl, $C_{3-6}$cycloalkyl, $C_{3-6}$cycloalkyl-$C_{1-10}$alkyl-, $C_{2-5}$cycloheteroalkyl, $C_{2-5}$ cycloheteroalkyl-$C_{1-10}$alkyl-, aryl, heteroaryl, aryl-$C_{1-10}$alkyl-, and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-5}$cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is independently selected from the group consisting of: hydrogen, $C_{1-10}$alkyl, $C_{2-10}$alkenyl, $C_{3-6}$cycloalkyl, $C_{3-6}$cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^c$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-5}$cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^c$ is selected from the group consisting of: hydrogen, $C_{1-10}$alkyl and $C_{2-10}$alkenyl, wherein each alkyl and alkenyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is selected from the group consisting of: hydrogen, $C_{1-10}$alkyl and $C_{2-10}$alkenyl, wherein each alkyl and alkenyl is unsubstituted or substituted with one to three substituents independently selected from $R^f$.

In another embodiment of the present invention, $R^c$ is selected from the group consisting of: hydrogen and $C_{1-10}$alkyl, wherein each alkyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is selected from the group consisting of: hydrogen and $C_{1-10}$alkyl, wherein each alkyl is unsubstituted or substituted with one to three substituents independently selected from $R^f$.

In another embodiment of the present invention, $R^c$ is selected from the group consisting of: $C_{1-10}$alkyl, wherein each alkyl is unsubstituted or substituted with one to three substituents independently selected from $R^f$, or $R^c$ and $R^d$ together with the atom(s) to which they are attached form a $C_{2-5}$cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^c$ is selected from the group consisting of: $C_{1-10}$alkyl, wherein each alkyl is unsubstituted or substituted with one to three substituents independently selected from $R^f$.

In another embodiment of the present invention, $R^c$ is hydrogen.

In another embodiment of the present invention, $R^d$ is independently selected from the group consisting of: hydrogen, $C_{1-10}$alkyl, $C_{2-10}$alkenyl, $C_{3-6}$cycloalkyl, $C_{3-6}$cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$.

In another embodiment of the present invention, $R^d$ is independently selected from the group consisting of: hydrogen, $C_{1-10}$alkyl, $C_{2-10}$alkenyl, $C_{3-6}$cycloalkyl, $C_{3-6}$cycloalkyl-$C_{1-10}$alkyl-, $C_{2-5}$cycloheteroalkyl, $C_{2-5}$cycloheteroalkyl-$C_{1-10}$alkyl-, aryl, heteroaryl, aryl-$C_{1-10}$alkyl- and heteroaryl-$C_{1-10}$alkyl-, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^d$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$, or $R^c$ and $R^d$ together with the atom(s) to which they are attached form a $C_{2-5}$cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is selected from the group consisting of: hydrogen, $C_{1-10}$alkyl, $C_{2-10}$alkenyl, $C_{3-6}$cycloalkyl, $C_{2-5}$cycloheteroalkyl, aryl and heteroaryl, wherein each alkyl, alkenyl, cycloalkyl, cycloheteroalkyl, aryl and heteroaryl is unsubstituted or substituted with one to three substituents independently selected from $R^f$.

In another embodiment of the present invention, $R^d$ is selected from the group consisting of: hydrogen, $C_{1-10}$alkyl and $C_{2-10}$alkenyl, wherein each alkyl and alkenyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is selected from the group consisting of: hydrogen, $C_{1-10}$alkyl and $C_{2-10}$alkenyl, wherein each alkyl and alkenyl is unsubstituted or substituted with one to three substituents independently selected from $R^f$.

In another embodiment of the present invention, $R^d$ is selected from the group consisting of: hydrogen and $C_{1-10}$alkyl, wherein each alkyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is selected from the group consisting of: hydrogen and $C_{1-10}$alkyl, wherein each alkyl is unsubstituted or substituted with one to three substituents independently selected from $R^f$.

In another class of this embodiment, $R^d$ is selected from the group consisting of: $C_{1-10}$alkyl, wherein each alkyl is unsubstituted or substituted with one to three substituents independently selected from $R^f$, or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In a class of this embodiment, $R^d$ is selected from the group consisting of: $C_{1-10}$alkyl, wherein each alkyl is unsubstituted or substituted with one to three substituents independently selected from $R^f$.

In another embodiment of the present invention, $R^d$ is hydrogen.

In another embodiment of the present invention, each $R^e$ is independently selected from the group consisting of: hydrogen, —$C_{1-10}$alkyl, —$C_{2-10}$alkenyl, aryl, aryl-$C_{1-10}$alkyl-, heteroaryl and heteroaryl-$C_{1-10}$alkyl-, wherein each alkyl, alkenyl, aryl and heteroaryl is unsubstituted or substituted with one to three substituents selected from $R^h$.

In another embodiment of the present invention, each $R^e$ is independently selected from the group consisting of: hydrogen, —$C_{1-10}$alkyl and aryl-$C_{1-10}$alkyl-, wherein each alkyl and aryl is unsubstituted or substituted with one to three substituents selected from $R^h$. In a class of this embodiment, each $R^e$ is independently selected from the group consisting of: hydrogen, —$C_{1-10}$alkyl and phenyl-$C_{1-10}$alkyl-, wherein each alkyl and phenyl is unsubstituted or substituted with one to three substituents selected from $R^h$. In another class of this embodiment, each $R^e$ is independently selected from the group consisting of: hydrogen, —$CH_3$ and —$CH_2$-phenyl wherein each alkyl and phenyl is unsubstituted or substituted with one to three substituents selected from $R^h$.

In another embodiment, each $R^e$ is —$C_{1-10}$alkyl-, wherein each alkyl is unsubstituted or substituted with one to three substituents selected from $R^h$. In a class of this embodiment, each $R^e$ is —$CH_3$.

In another embodiment of the present invention, each $R^e$ is independently selected from the group consisting of: aryl-$C_{1-10}$alkyl-, wherein each alkyl and aryl is unsubstituted or substituted with one to three substituents selected from $R^h$. In a class of this embodiment, each $R^e$ is —$CH_2$-phenyl, wherein each $CH_2$ and phenyl is unsubstituted or substituted with one to three substituents selected from $R^h$.

In another embodiment of the present invention, each $R^e$ is hydrogen.

In another embodiment of the present invention, each $R^f$ is selected from the group consisting of: halogen, $C_{1-10}$alkyl, —OH, —O—$C_{1-4}$alkyl, —CN, —$CF_3$, —$OCHF_2$ and —$OCF_3$, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen, $C_{1-10}$alkyl and —OH, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^f$ is selected from the group consisting of: halogen and $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^f$ is selected from the group consisting of: $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a subclass of this class, each $R^f$ is selected from the group consisting of: $C_{1-10}$alkyl. In another class of this embodiment, each $R^f$ is halogen.

In another embodiment of the present invention, each $R^g$ is selected from the group consisting of: hydrogen and —$C_{1-10}$alkyl, wherein each alkyl is unsubstituted or substituted with one to five halogens. In another embodiment of the present invention, each $R^g$ is selected from the group consisting of: —$C_{1-10}$alkyl, wherein each alkyl is unsubstituted or substituted with one to five halogens. In another embodiment of the present invention, each $R^g$ is hydrogen.

In another embodiment of the present invention, each $R^h$ is selected from the group consisting of: halogen, $C_{1-10}$alkyl, —OH, —O—$C_{1-4}$alkyl, —CN, —$CF_3$, —$OCHF_2$ and —$OCF_3$, wherein each alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is selected from the group consisting of: halogen, $C_{1-10}$alkyl and —OH, wherein each alkyl is unsubstituted or substituted with one to three substituents independently selected from: —OH, halogen, $C_{1-6}$alkyl, cyano and $S(O)_2C_{1-6}$alkyl.

In another embodiment of the present invention, each $R^h$ is selected from the group consisting of: halogen and $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In a class of this embodiment, each $R^h$ is selected from the group consisting of: $C_{1-10}$alkyl, wherein each alkyl is unsubstituted or substituted with one to three substituents independently selected from: —OH, halogen, $C_{1-6}$alkyl, cyano and $S(O)_2C_{1-6}$alkyl. In another class of this embodiment, each $R^h$ is halogen.

In another embodiment of the present invention, $R^i$ is independently selected from the group consisting of: —$C_{1-6}$alkyl, —$OR^e$, —$NR^cS(O)_mR^e$, halogen, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$ and —$OCHF_2$. In another embodiment of the present invention, $R^i$ is independently selected from the group consisting of: —$C_{1-6}$alkyl, —$OR^e$, —$NR^cS(O)_mR^e$, halogen, —$NR^cR^d$, —$C(O)R^e$, —$OC(O)R^e$, —$CO_2R^e$, —CN, —$CF_3$, —$OCF_3$ and —$OCHF_2$. In another embodiment of the present invention, $R^i$ is independently selected from the group consisting of: —$C_{1-6}$alkyl, —$OR^e$, and halogen. In another embodiment of the present invention, $R^i$ is independently selected from the group consisting of: —$C_{1-6}$alkyl and halogen. In another embodiment of the present invention, $R^i$ is independently selected from the group consisting of: —$C_{1-6}$alkyl.

In another embodiment of the present invention, $R^j$ is independently selected from the group consisting of: —$C_{1-6}$alkyl, —$OR^e$, —$NR^cS(O)_mR^e$, halogen, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$ and —$OCHF_2$. In another embodiment of the present invention, $R^j$ is independently selected from the group consisting of: —$C_{1-6}$alkyl, —$OR^e$, halogen, —$NR^cR^d$, —$C(O)R^e$, —$OC(O)R^e$, —$CO_2R^e$, —CN, —$CF_3$, —$OCF_3$, and —$OCHF_2$. In another embodiment of the present invention, $R^j$ is independently selected from the group consisting of: —$C_{1-6}$alkyl, —$OR^e$, and halogen. In another embodiment of the present invention, $R^j$ is independently selected from the group consisting of: —$C_{1-6}$alkyl and halogen. In another embodiment of the present invention, $R^j$ is independently selected from the group consisting of: —$C_{1-6}$alkyl.

In another embodiment of the present invention, each $R^k$ is independently selected from the group consisting of: hydrogen, —$C_{1-6}$alkyl, —$CF_3$ and —$CHF_2$, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is independently selected from the group consisting of: hydrogen and —$C_{1-6}$alkyl, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is independently selected from the group consisting of: —$C_{1-6}$alkyl, wherein each alkyl is unsubstituted or substituted with one to three substituents independently selected from: —OH, —$OC_{1-6}$alkyl, halogen, cyano, and —$S(O)_2C_{1-6}$alkyl.

In another embodiment of the present invention, each $R^k$ is hydrogen.

In another embodiment of the present invention, each $R^L$ is independently selected from the group consisting of: —$C_{1-10}$alkyl, —$C_{2-10}$alkenyl, —$C_{2-10}$alkynyl, —$C_{3-6}$cycloalkyl, aryl, and heteroaryl, wherein alkyl, alkenyl, alkynyl, cycloalkyl, aryl and heteroaryl are unsubstituted or substituted with 1-4 substituents selected from $C_{1-6}$alkyl, halogen, and —$OC_{1-6}$alkyl. In a class of this embodiment, each $R^L$ is independently selected from the group consisting of: —$C_{1-10}$alkyl, —$C_{2-10}$alkenyl, —$C_{2-10}$alkynyl, —$C_{3-6}$cycloalkyl, phenyl and heteroaryl, wherein alkyl, alkenyl, alkynyl, cycloalkyl, cycloheteroalkyl, phenyl and heteroaryl are unsubstituted or substituted with 1-4 substituents selected from $C_{1-6}$alkyl, halogen, and —$OC_{1-6}$alkyl. In another class of this embodiment, each $R^L$ is independently selected from the group consisting of: —$C_{1-10}$alkyl, —$C_{2-10}$alkenyl, —$C_{2-10}$alkynyl, —$C_{3-6}$cycloalkyl, phenyl, and pyridine, wherein alkyl, alkenyl, alkynyl, cycloalkyl, phenyl and pyridine are unsubstituted or substituted with 1-4 substituents selected from $C_{1-6}$alkyl, halogen, and —$OC_{1-6}$alkyl. In another class of this embodiment, each $R^L$ is independently selected from the group consisting of: —$CH_3$, —$CH=C(CH_3)_2$, —$C_2$alkynyl-$CH_3$, cyclopropyl, phenyl —$OCH_3$ and pyridine, wherein alkyl, alkenyl, alkynyl, cyclopropyl, phenyl and pyridine are unsubstituted or substituted with 1-4 substituents selected from $C_{1-6}$alkyl, halogen and —$OC_{1-6}$alkyl. In another class of this embodiment, each $R^L$ is independently selected from the group consisting of: —$CH_3$, —$CH=C(CH_3)_2$, —$C_2$alkynyl-$CH_3$, cyclopropyl, phenyl —$OCH_3$ and pyridine.

In another embodiment of the present invention, each $R^L$ is independently selected from the group consisting of: —$C_{2-10}$alkynyl, wherein alkynyl is unsubstituted or substituted with 1-4 substituents selected from $C_{1-6}$alkyl, halogen, and —$OC_{1-6}$alkyl. In a class of this embodiment, each $R^L$ is independently selected from the group consisting of: —$C_{2-6}$alkynyl, wherein alkynyl is unsubstituted or substituted with 1-4 substituents selected from $C_{1-6}$alkyl, halogen, and —$OC_{1-6}$alkyl. In another class of this embodiment, each $R^L$ is independently selected from the group consisting of: —$C_{2-10}$alkynyl, wherein alkynyl is unsubstituted or substituted with 1-4 substituents selected from —$CH_3$. In another class of this embodiment, each $R^L$ is —$C_2$alkynyl-$CH_3$.

In another embodiment of the present invention, each $R^m$ is independently selected from the group consisting of: —$C_{1-10}$alkyl, —$C_{2-10}$alkenyl, —$C_{3-6}$cycloalkyl, —$C_{2-5}$cyloheteroalkyl, aryl and heteroaryl.

In another embodiment of the present invention, each $R^m$ is independently selected from the group consisting of: —$C_{1-10}$alkyl and —$C_{2-1010}$ alkenyl.

In another embodiment of the present invention, each $R^m$ is independently selected from the group consisting of: —$C_{1-10}$alkyl.

In another embodiment of the present invention, n is 0, 1 or 2. In a class of this embodiment, n is 0 or 1. In another class of this embodiment, n is 1 or 2. In another class of this embodiment, n is 0. In another class of this embodiment, n is 1. In another class of this embodiment, n is 2.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, each p is independently selected from: 0, 1, 2, 3, 4, 5 or 6. In another embodiment of the present invention, p is 0, 1, 2, 3 or 4. In a class of this embodiment, p is 0, 1, 2 or 3. In a class of this embodiment, p is 0, 1 or 2. In another embodiment of the present invention, p is 1, 2, 3 or 4. In a class of this embodiment, p is 1, 2 or 3. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6.

In another embodiment of the present invention, the invention relates to compounds of structural formula Ia:

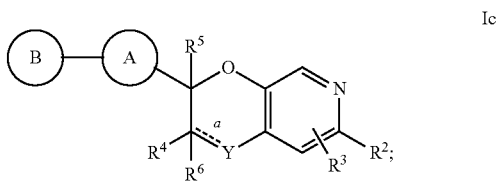

Ia or a pharmaceutically acceptable salt thereof

In another embodiment of the present invention, the invention relates to compounds of structural formula Ib:

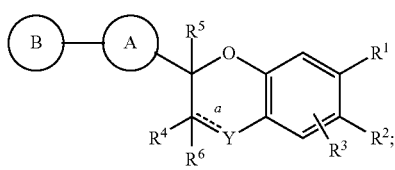

Ib or a pharmaceutically acceptable salt thereof.

In another embodiment of the present invention, the invention relates to compounds of structural formula Ic:

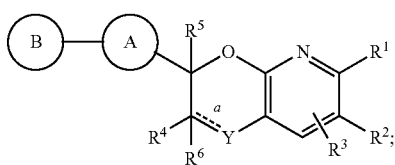

Ic or a pharmaceutically acceptable salt thereof.

In another embodiment of the present invention, the invention relates to compounds of structural formula Id:

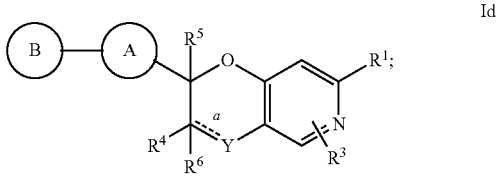

Id or a pharmaceutically acceptable salt thereof.

In another embodiment of the present invention, the invention relates to compounds of structural formula Ie:

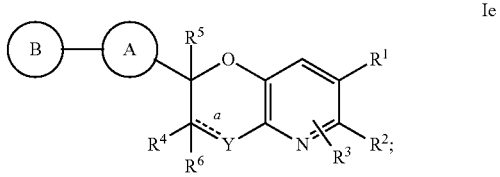

Ie or a pharmaceutically acceptable salt thereof

In another embodiment of the present invention, the invention relates to compounds of structural formula If:

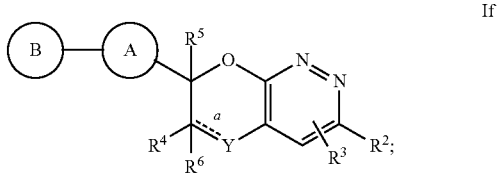

If or a pharmaceutically acceptable salt thereof

In another embodiment of the present invention, the invention relates to compounds of structural formula Ig:

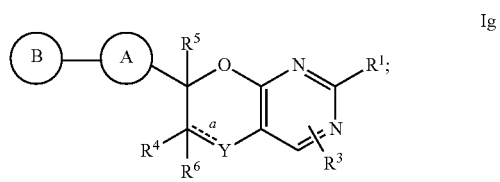

Ig or a pharmaceutically acceptable salt thereof.

In another embodiment of the present invention, the invention relates to compounds of structural formula Ih:

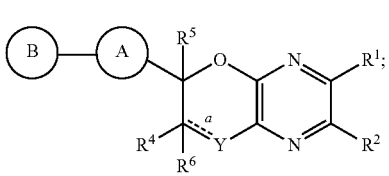

or a pharmaceutically acceptable salt thereof.

In another embodiment of the present invention, the invention relates to compounds of structural formula Ii:

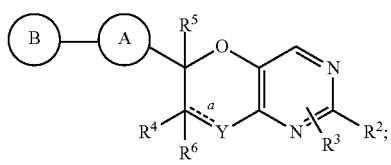

or a pharmaceutically acceptable salt thereof.

In another embodiment of the present invention, the invention relates to compounds of structural formula Ij:

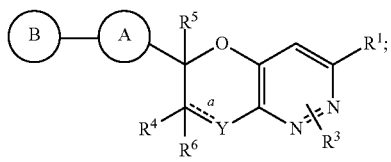

or a pharmaceutically acceptable salt thereof.

In another embodiment of the present invention, the invention relates to compounds of structural formula Ik:

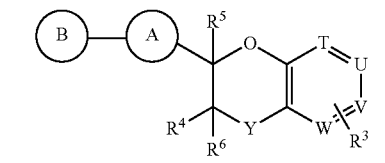

or a pharmaceutically acceptable salt thereof.

In another embodiment of the present invention, the invention relates to compounds of structural formula Il:

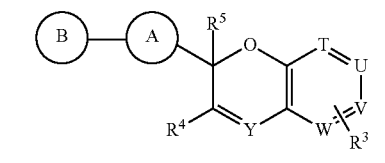

or a pharmaceutically acceptable salt thereof

The compound of structural formula I includes the compounds of structural formulas Ia, Ib, Ic, Id, Ie, If, Ig, Ih, Ii, Ij, Ik, and Il, and pharmaceutically acceptable salts, hydrates and solvates thereof.

Another embodiment of the present invention relates to compounds of structural formula Ik:

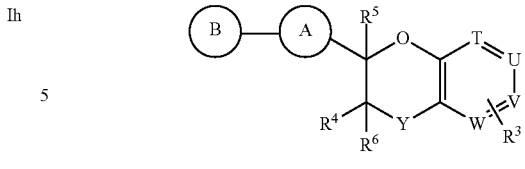

wherein
T is selected from the group consisting of:
 (1) CH, and
 (2) N;
U is selected from the group consisting of:
 (1) $CR^1$, and
 (2) N;
V is selected from the group consisting of:
 (1) $CR^2$, and
 (2) N;
W is selected from the group consisting of:
 (1) CH, and
 (2) N,
provided that no more than two of T, U, V and W are selected from N, further provided that if both T and W are N, then $R^3$ is absent, and further provided that both U and V are not N;
Y is selected from the group consisting of:
 (1) —$CR^gR^g$,
 (2) C=O,
 (3) —$C(R^g)OC_{1-6}$alkyl, and
 (4) —$CF_2$;
A is selected from the group consisting of:
 (1) aryl,
 (2) heteroaryl,
 (3) $C_{3-6}$cycloalkyl, and
 (4) $C_{2-5}$cycloheteroalkyl,
wherein A is unsubstituted or substituted with one to five substituents selected from $R^a$;
B is selected from the group consisting of:
 (1) hydrogen,
 (2) aryl,
 (3) aryl-$C_{1-10}$ alkyl-,
 (4) aryl-O—,
 (5) aryl-$C_{1-10}$alkyl-O—,
 (6) $C_{3-6}$cycloalkyl,
 (7) $C_{3-6}$cycloalkyl-$C_{1-10}$alkyl-,
 (8) $C_{3-6}$cycloalkyl-$C_{1-10}$alkyl-O—,
 (9) $C_{3-66}$cycloalkenyl,
 (10) $C_{2-5}$cycloheteroalkyl,
 (11) $C_{3-6}$cycloheteroalkyl-$C_{1-10}$alkyl-,
 (12) $C_{3-6}$cycloheteroalkyl-$C_{1-10}$alkyl-O—,
 (13) heteroaryl, and
 (14) heteroaryl-$C_{1-10}$ alkyl-,
wherein B is unsubstituted or substituted with one to five substituents selected from $R^b$;
$R^1$ and $R^2$ are each independently selected from:
 (1) a bond,
 (2) hydrogen,
 (3) halogen,
 (4) —$OR^k$, and
 (5) —$C_{1-6}$alkyl,
wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$;
$R^3$ is selected from the group consisting of:
(1) hydrogen,
(2) halogen, and
(3) —$C_{1-6}$alkyl,
wherein each alkyl is unsubstituted or substituted with one to three substituents selected from $R^i$;
$R^4$ is selected from the group consisting of:
(1) hydrogen, and
(2) $C_{1-6}$alkyl,
wherein each alkyl is unsubstituted or substituted with one to three substituents selected from $R^j$;
$R^5$ is selected from the group consisting of:
(1) hydrogen, and
(2) —$C_{1-6}$alkyl,
wherein each alkyl is unsubstituted or substituted with one to three substituents selected from $R^j$;
$R^6$ is selected from the group consisting of:
(1) hydrogen, and
(2) —$C_{1-6}$alkyl,
wherein each alkyl is unsubstituted or substituted with one to three substituents selected from $R^j$;
$R^7$ is selected from the group consisting of:
(1) —$CO_2R^8$,
(2) —$C_{1-6}$alkyl-$CO_2R^8$, and
(3) a cycloheteroalkyl selected from:

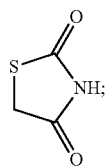

and
$R^8$ is selected from the group consisting of:
(1) hydrogen, and
(2) —$C_{1-6}$alkyl,
wherein each alkyl is unsubstituted or substituted with one to three substituents selected from $R^j$; and
$R^a$, $R^b$, $R^c$, $R^d$, $R^e$, $R^f$, $R^g$, $R^h$, $R^i$, $R^j$, $R^k$, $R^L$, $R^m$, n, m, and p are as defined above;
or a pharmaceutically acceptable salt thereof.

In a class of this embodiment, $R^8$ is hydrogen.

In another class of this embodiment, each $R^g$ is selected from the group consisting of: hydrogen, —C(O)$R^e$, and —$C_{1-10}$alkyl, wherein each alkyl is unsubstituted or substituted with one to five halogens.

In another class of this embodiment, $R^j$ is independently selected from the group consisting of: —$C_{1-6}$alkyl, halogen, —$C_{3-6}$cycloalkyl, and —$C_{2-5}$cycloheteroalkyl.

In another class of this embodiment, each $R^L$ is independently selected from the group consisting of: —$C_{1-10}$alkyl, —$C_{2-10}$alkynyl, —$C_{3-6}$cycloalkyl, and —$C_{2-6}$cycloheteroalkyl, wherein each alkyl, alkynyl, cycloalkyl, cycloheteroalkyl is unsubstituted or substituted with 1-4 substituents selected from $C_{1-6}$alkyl, halogen, and —$OC_{1-6}$alkyl.

Another embodiment of the present invention relates to compounds of structural Formula Ik:

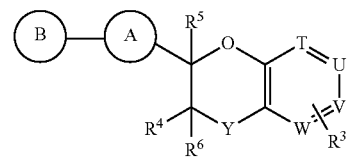

wherein
T is CH or N;
U is $CR^1$;
V is $CR^2$;
W is CH or N,
provided that T and W are both CH or one of T and W is N;
Y is selected from the group consisting of:
(1) —$CR^gR^g$,
(2) C=O, and
(3) —$CF_2$;
A is selected from the group consisting of:
(1) aryl,
(2) heteroaryl,
(3) $C_{3-6}$cycloalkyl, and
(4) $C_{2-5}$cycloheteroalkyl,
wherein each aryl, heteroaryl, cycloalkyl and cycloheteroalkyl is unsubstituted or substituted with one to five substituents selected from $R^a$;
B is selected from the group consisting of:
(1) hydrogen,
(2) aryl,
(3) aryl-$C_{1-10}$ alkyl-,
(4) aryl-O—,
(5) aryl-$C_{1-10}$alkyl-O—,
(6) $C_{3-6}$cycloalkenyl, and
(7) heteroaryl,
wherein each alkyl, cycloalkenyl, aryl and heteroaryl is unsubstituted or substituted with one to five substituents selected from $R^b$;
$R^1$ and $R^2$ are each independently selected from:
(1) a bond,
(2) hydrogen,
(3) —$OR^k$, and
(4) —$C_{1-6}$alkyl,
wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$;
$R^3$ is selected from the group consisting of:
(1) hydrogen,
(2) halogen, and
(3) —$C_{1-6}$alkyl,
wherein each alkyl is unsubstituted or substituted with one to three substituents selected from $R^i$;
$R^4$ is selected from the group consisting of:
(1) hydrogen, and
(2) $C_{1-6}$alkyl,
wherein each alkyl is unsubstituted or substituted with one to three substituents selected from $R^j$;
$R^5$ is selected from the group consisting of:
(1) hydrogen, and
(2) —$C_{1-6}$alkyl, wherein each alkyl is unsubstituted or substituted with one to three substituents selected from $R^j$;

$R^6$ is selected from the group consisting of:
(1) hydrogen, and
(2) —$C_{1-6}$alkyl, wherein each alkyl is unsubstituted or substituted with one to three substituents selected from $R^j$;

$R^7$ is selected from the group consisting of:
(1) —$CO_2R^8$,
(2) —$C_{1-6}$alkyl-$CO_2R^8$, and
(3) a cycloheteroalkyl selected from:

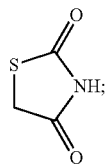

$R^8$ is hydrogen; and $R^a$, $R^b$, $R^e$, $R^d$, $R^e$, $R^f$, $R^g$, $R^h$, $R^i$, $R^j$, $R^k$, $R^L$, $R^m$, n, m, and p are as defined above; or a pharmaceutically acceptable salt thereof.

In a class of this embodiment, T is CH or N. In another class of this embodiment, T is CH. In another class of this embodiment, T is N.

In another class of this embodiment, W is CH or N. In another class of this embodiment, W is CH. In another class of this embodiment, W is N.

In another class of this embodiment, T is CH, U is $CR^1$, V is $CR^2$, W is CH or N. In another class of this embodiment, W is CH. In another class of this embodiment, W is N.

In another class of this embodiment, T is CH or N; U is $CR^1$, V is $CR^2$, W is CH. In another class of this embodiment, T is CH. In another class of this embodiment, T is N.

In another class of this embodiment, Y is —$CR^gR^g$. In a subclass of this class Y is $CH_2$.

In another class of this embodiment, A is selected from the group consisting of: aryl, and heteroaryl, wherein each aryl and heteroaryl is unsubstituted or substituted with one to five substituents selected from $R^a$. In a subclass of this class, A is selected from the group consisting of: phenyl, pyridine, pyrazine, pyrimidine, thiazole, and thiophene, wherein A is unsubstituted or substituted with one to five substituents selected from $R^a$. In another subclass of this class, A is selected from the group consisting of: phenyl, and pyridine, wherein A is unsubstituted or substituted with one to five substituents selected from $R^a$.

In another class of this embodiment, B is selected from the group consisting of: hydrogen, phenyl, benzomorpholine, tetrahydroquinoline, —$CH_2$-phenyl, phenyl-O—, phenyl-$CH_2$-O—, cyclopentenyl, pyridine, oxazole, pyrazine, furopyridine, and indazole, wherein each B is unsubstituted or substituted with one to five substituents selected from $R^b$.

In another class of this embodiment, B is selected from the group consisting of: aryl, and heteroaryl, wherein each aryl and heteroaryl is unsubstituted or substituted with one to five substituents selected from $R^b$. In a subclass of this class, B is selected from the group consisting of: phenyl, and pyridine, wherein each phenyl and pyridine is unsubstituted or substituted with one to five substituents selected from $R^b$.

In another class of this embodiment, $R^1$ and $R^2$ are each independently selected from: hydrogen, and —$C_{1-6}$alkyl, wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$; or a pharmaceutically acceptable salt thereof.

In another class of the present invention, $R^1$ is hydrogen; and $R^2$ is selected from: a bond, —$OR^k$, and —$C_{1-6}$alkyl, wherein each alkyl is unsubstituted or substituted with one to three substituents selected from $R^L$, and wherein $R^2$ is substituted with a substituent selected from $R^7$; or a pharmaceutically acceptable salt thereof.

In another class of this embodiment, $R^1$ is hydrogen; and $R^2$ is selected from: a bond, and —$C_{1-6}$alkyl, wherein each alkyl is unsubstituted or substituted with one to three substituents selected from $R^L$, and wherein $R^2$ is substituted with a substituent selected from $R^7$; or a pharmaceutically acceptable salt thereof.

In another class of this embodiment, $R^1$ is selected from: a bond, —$OR^k$, and —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen; or a pharmaceutically acceptable salt thereof.

In another class of this embodiment, $R^1$ is selected from: a bond, and —$C_{1-6}$alkyl, wherein each alkyl is unsubstituted or substituted with one to three substituents selected from $R^L$, and wherein $R^1$ is substituted with a substituent selected from $R^7$; and $R^2$ is hydrogen.

In another class of this embodiment, $R^1$ and $R^2$ are selected from: —$C_{1-6}$alkyl and hydrogen, wherein each alkyl is unsubstituted or substituted with one to three substituents selected from $R^L$, and wherein each alkyl is substituted with a substituent selected from $R^7$, provided that one of $R^1$ and $R^2$ is —$C_{1-6}$alkyl and the other of $R^1$ and $R^2$ is hydrogen.

In another class of this embodiment, $R^1$ is —$C_{1-6}$alkyl, wherein each alkyl is unsubstituted or substituted with one to three substituents selected from $R^L$, and wherein $R^1$ is substituted with a substituent selected from $R^7$.

In another class of this embodiment, $R^2$ is hydrogen.

In another class of this embodiment, $R^2$ is —$C_{1-6}$alkyl, wherein each alkyl is unsubstituted or substituted with one to three substituents selected from $R^L$, and wherein $R^1$ is substituted with a substituent selected from $R^7$.

In another class of this embodiment, $R^1$ is hydrogen.

In another class of this embodiment, $R^3$ is selected from the group consisting of: hydrogen and halogen. In another class of this embodiment, $R^3$ is halogen. In another class of this embodiment, $R^3$ is hydrogen.

In another class of this embodiment, $R^4$ is hydrogen.

In another class of this embodiment, $R^5$ is hydrogen.

In another class of this embodiment, $R^6$ is hydrogen.

In another class of this embodiment, $R^7$ is —$CO_2R^8$.

In another class of this embodiment, $R^a$ is selected from the group consisting of: —$C_{1-6}$alkyl, halogen, —$OR^e$, —$CF_3$, —$OCF_3$, —$C_{3-6}$cycloalkyl, —$C_{3-6}$cycloalkenyl and —$C_{2-5}$cycloheteroalkyl, wherein each alkyl, cycloalkyl, cycloalkenyl and cycloheteroalkyl is unsubstituted or substituted with one to three substituents selected from: —$C_{1-6}$alkyl, halogen, —O—$C_{1-6}$alkyl and —$CF_3$. In a subclass of this class, $R^a$ is selected from the group consisting of: —$CH_3$, —$CH(CH_3)_2$, —$CH(OH)C(CH_3)_3$, —$CH(OCH_3)C(CH_3)_3$, —$CH(OCH_3)$cyclopropyl, —$CH(OCH_3)$ $CF_3$, F, —$OCH_3$, —$CF_3$, —$OCF_3$, cyclopentane, cyclopentene and azetidine, wherein each alkyl, cycloalkyl, cycloalkenyl and cyclohetereoalkyl is unsubstituted or substituted with one to three substituents selected from: —$C_{1-6}$alkyl, halogen, —O—$C_{1-6}$alkyl and —$CF_3$.

In another class of this embodiment, $R^a$ is halogen. In a subclass of this class, $R^a$ is F.

In another class of this embodiment, $R^b$ is independently selected from the group consisting of: —$C_{1-10}$alkyl, —$CF_3$, halogen, —CN, —OH, —$OC_{1-10}$alkyl, —$O(CH_2)_pS(O)_mR^e$, and —$OCF_3$, wherein each $CH_2$, and alkyl is unsubstituted or substituted with —$C_{1-6}$alkyl, halogen, —O—$C_{1-6}$alkyl and —$CF_3$. In a subclass of this class, $R^b$ is independently selected from the group consisting of: —$CH_3$, —$CF_3$, F, Cl, —CN, —OH, —$OCH_3$, —$OCH_2CF_3$, —$O(CH_2)_2S(O)_2CH_3$, and —$OCF_3$.

In another class of this embodiment, $R^b$ is independently selected from the group consisting of: halogen, and —$OC_{1-10}$alkyl, wherein each $CH_2$, and alkyl is unsubstituted or substituted with —$C_{1-6}$alkyl, halogen, —O—$C_{1-6}$alkyl and —$CF_3$. In a subclass of this class, $R^b$ is independently selected from the group consisting of: F and —$OCH_3$.

In another class of this embodiment, each $R^e$ is —$C_{1-10}$alkyl. In a subclass of this class, $R^e$ is $CH_3$.

In another class of this embodiment, each $R^g$ is hydrogen.

In another class of this embodiment, each $R^L$ is independently selected from the group consisting of: —$C_{1-10}$alkyl, —$C_{2-10}$alkynyl, —$C_{3-6}$cycloalkyl and —$C_{2-6}$cycloheteroalkyl, wherein each alkyl, alkynyl, cycloalkyl, and cycloheteroalkyl is unsubstituted or substituted with 1-4 substituents selected from $C_{1-6}$alkyl, halogen, and —$OC_{1-6}$alkyl.

In another class of this embodiment, each $R^L$ is independently selected from the group consisting of: —$C_{1-10}$alkyl, —$C_{2-10}$alkynyl, and —$C_{3-6}$cycloalkyl, wherein each alkyl, alkynyl, and cycloalkyl is unsubstituted or substituted with 1-4 substituents selected from $C_{1-6}$alkyl, halogen, and —$OC_{1-6}$alkyl. In a subclass of this class, each $R^L$ is independently selected from the group consisting of: —$CH_3$, —C≡C—$CH_3$, cyclopropyl, and cyclobutyl, wherein each alkyl, alkynyl, and cycloalkyl is unsubstituted or substituted with 1-4 substituents selected from $C_{1-6}$alkyl, halogen, and —$OC_{1-6}$alkyl;

In another class of this embodiment, each $R^L$ is independently selected from the group consisting of: —$C_{1-10}$alkyl, and —$C_{3-6}$cycloalkyl, wherein each alkyl and cycloalkyl is unsubstituted or substituted with 1-4 substituents selected from $C_{1-6}$alkyl, halogen, and —$OC_{1-6}$alkyl. In a subclass of this class, each $R^L$ is independently selected from the group consisting of: —$CH_3$, cyclopropyl and cyclobutyl, wherein each: —$CH_3$, cyclopropyl and cyclobutyl, is unsubstituted or substituted with 1-4 substituents selected from $C_{1-6}$alkyl, halogen, and —$OC_{1-6}$alkyl.

In another class of this embodiment, $R^L$ is —$C_{2-10}$alkynyl, wherein each alkynyl is unsubstituted or substituted with 1-4 substituents selected from $C_{1-6}$alkyl. In a subclass of this class, $R^L$ is —C≡C—$CH_3$.

Another embodiment of the present invention relates to compounds of structural formula Ik wherein:
T is CH;
U is $CR^1$;
V is $CR^2$;
W is CH, N or N-oxide;
Y is selected from the group consisting of:
  (1) —$CR^gR^g$,
  (2) C=O,
  (3) —$C(R^g)OC_{1-6}$alkyl,
  (4) —$CF_2$, and
  (5) —$NR^e$;
A is selected from the group consisting of:
  (1) aryl, and
  (2) heteroaryl,
wherein each aryl and heteroaryl is unsubstituted or substituted with one to five substituents selected from $R^a$;
B is selected from the group consisting of:
  (1) hydrogen,
  (2) aryl,
  (3) aryl-O—,
  (4) aryl-$C_{1-10}$ alkyl-O—
  (5) $C_{3-6}$cycloalkenyl, and
  (6) heteroaryl,
wherein each alkyl, cycloalkenyl, aryl and heteroaryl is unsubstituted or substituted with one to five substituents selected from $R^b$;
$R^1$ and $R^2$ are each independently selected from:
  (1) a bond,
  (2) hydrogen,
  (3) —$OR^k$, and
  (4) —$C_{1-6}$alkyl,
wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$;
$R^3$ is hydrogen;
$R^4$ is hydrogen;
$R^5$ is hydrogen;
$R^6$ is hydrogen;
$R^7$ is selected from the group consisting of:
  (1) —$CO_2R^8$,
  (2) —$C_{1-6}$alkyl-$CO_2R^8$, and
  (3) a cycloheteroalkyl selected from:

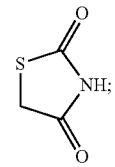

and $R^8$ is hydrogen;
or a pharmaceutically acceptable salt thereof

In a class of this embodiment, W is CH or N. In another class of this embodiment, W is CH. In another class of this embodiment, W is N.

Another embodiment of the present invention relates to compounds of structural formula Ik wherein:
T is CH;
U is $CR^1$;
V is $CR^2$;
W is CH;
Y is selected from the group consisting of: —$CR^gR^g$;
A is selected from the group consisting of:
  (1) aryl, and
  (2) heteroaryl,
wherein each aryl and heteroaryl is unsubstituted or substituted with one to five substituents selected from $R^a$;

B is selected from the group consisting of:
(1) aryl, and
(2) heteroaryl,
wherein each aryl and heteroaryl is unsubstituted or substituted with one to five substituents selected from $R^b$;
$R^1$ and $R^2$ are each independently selected from:
(1) hydrogen, and
(2) —$C_{1-6}$alkyl,
wherein each alkyl is unsubstituted or substituted with one to three substituents selected from $R^L$, and wherein one of $R^1$ and $R^2$ is substituted with a substituent selected from $R^7$;
$R^3$ is hydrogen;
$R^4$ is hydrogen;
$R^5$ is hydrogen;
$R^6$ is hydrogen;
$R^7$ is —$CO_2R^8$; and
$R^8$ is hydrogen;
or a pharmaceutically acceptable salt thereof.

Another embodiment of the present invention relates to compounds of structural Formula Ik:

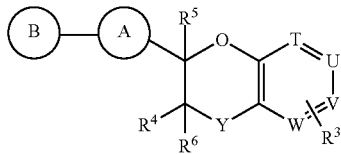

wherein
T is selected from the group consisting of:
(1) CH, and
(2) N;
U is selected from the group consisting of:
(1) $CR^1$, and
(2) N;
V is selected from the group consisting of:
(1) $CR^2$, and
(2) N;
W is selected from the group consisting of:
(1) CH, and
(2) N,
provided that no more than two of T, U, V and W are selected from N, further provided that if both T and W are N, then $R^3$ is absent, and further provided that both U and V are not N;
Y is oxygen;
A is selected from the group consisting of:
(1) aryl,
(2) heteroaryl,
(3) $C_{3-6}$cycloalkyl, and
(4) $C_{2-5}$cycloheteroalkyl,
wherein A is unsubstituted or substituted with one to five substituents selected from $R^a$;
B is selected from the group consisting of:
(1) aryl,
(2) aryl-$C_{1-10}$ alkyl-,
(3) $C_{3-6}$cycloalkyl,
(4) $C_{3-6}$cycloalkyl-$C_{1-10}$alkyl-,
(5) $C_{3-6}$cycloalkyl-$C_{1-10}$alkyl-O—,
(6) $C_{2-5}$cycloheteroalkyl,
(7) $C_{3-6}$cycloheteroalkyl-$C_{1-10}$alkyl-,
(8) $C_{3-6}$cycloheteroalkyl-$C_{1-10}$alkyl-O—,
(9) heteroaryl, and
(10) heteroaryl-$C_{1-10}$ alkyl-;
wherein B is unsubstituted or substituted with one to five substituents selected from $R^b$;
$R^1$ and $R^2$ are each independently selected from:
(1) a bond,
(2) hydrogen,
(3) halogen, and
(4) —$C_{1-6}$alkyl,
wherein each alkyl is unsubstituted or substituted with one to three substituents selected from $R^L$, and wherein one of $R^1$ and $R^2$ is substituted with a substituent selected from $R^7$;
$R^3$ is absent or selected from the group consisting of:
(1) hydrogen,
(2) halogen, and
(3) —$C_{1-6}$alkyl,
wherein each alkyl is unsubstituted or substituted with one to three substituents selected from $R^i$;
$R^4$ is selected from the group consisting of:
(1) hydrogen, and
(2) —$C_{1-6}$alkyl,
wherein each alkyl is unsubstituted or substituted with one to three substituents selected from $R^j$,
$R^5$ is selected from the group consisting of:
(1) hydrogen, and
(2) —$C_{1-6}$alkyl,
wherein each alkyl is unsubstituted or substituted with one to three substituents selected from $R^j$;
$R^6$ is selected from the group consisting of:
(1) hydrogen, and
(2) —$C_{1-6}$alkyl,
wherein each alkyl is unsubstituted or substituted with one to three substituents selected from $R^j$;
$R^7$ is —$CO_2R^8$;
$R^8$ is selected from the group consisting of:
(1) hydrogen, and
(2) —$C_{1-6}$alkyl,
wherein each alkyl is unsubstituted or substituted with one to three substituents selected from $R^j$;
$R^a$, $R^b$, $R^c$, $R^d$, $R^e$, $R^f$, $R^g$, $R^h$, $R^i$, $R^j$, $R^k$, $R^L$, $R^m$, n, m, and p are as defined above;
or a pharmaceutically acceptable salt thereof.

In a class of this embodiment, $R^1$ is —$C_{1-6}$alkyl, wherein each alkyl is unsubstituted or substituted with one to three substituents selected from $R^L$, and wherein $R^1$ is substituted with $R^7$.

In another class of this embodiment, $R^2$ is independently selected from: hydrogen, halogen, and —$C_{1-6}$alkyl.

In another class of this embodiment, $R^2$. In another class of this embodiment, $R^4$, $R^5$ and $R^6$ are hydrogen. In another class of this embodiment, $R^8$ is hydrogen.

In another class of this embodiment, $R^4$, $R^5$, $R^6$ and $R^8$ are hydrogen.

In another class of this embodiment, $R^3$ is absent or selected from the group consisting of: hydrogen, and halogen. In another class of this embodiment, $R^3$ is selected from the group consisting of: hydrogen, and halogen.

In another class of this embodiment, each $R^a$ is independently selected from the group consisting of: —$C_{1-6}$alkyl, halogen, —$CF_3$, —$OCF_3$ and heteroaryl, wherein each alkyl and heteroaryl is unsubstituted or substituted with —$C_{1-6}$alkyl, halogen, —O—$C_{1-6}$alkyl and —$CF_3$. In a subclass of this class, each $R^a$ is independently selected from the group consisting of: —$CH(OCH_3)C(CH_3)_3$, Cl, —$CF_3$, —$OCF_3$, and indole, wherein indole is unsubstituted or substituted with —$C_{1-6}$alkyl.

In another class of this embodiment, each $R^b$ is independently selected from the group consisting of: —$C_{1-10}$alkyl, —$CF_3$, halogen, —CN, —OH, and —$OC_{1-10}$alkyl, wherein each alkyl is unsubstituted or substituted with —$C_{1-6}$alkyl, halogen, —O—$C_{1-6}$alkyl and —$CF_3$. In another class of this embodiment, each $R^b$ is independently selected from the group consisting of: —$C_{1-10}$alkyl, —$CF_3$, halogen, and —$OC_{1-10}$alkyl, wherein each alkyl is unsubstituted or substituted with —$C_{1-6}$alkyl, halogen, —O—$C_{1-6}$alkyl and —$CF_3$. In a subclass of this class, each $R^b$ is independently selected from the group consisting of: —$CH_3$, —$CF_3$, F, and —$OCH_3$.

In another class of this embodiment, each $R^j$ is independently selected from the group consisting of: —$C_{1-6}$alkyl, halogen, —$C_{3-6}$cycloalkyl and —$C_{2-5}$cycloheteroalkyl.

In another class of this embodiment, each $R^L$ is independently selected from the group consisting of: —$C_{1-10}$alkyl, —$C_{2-10}$alkynyl, —$C_{3-6}$cycloalkyl, and —$C_{2-6}$cycloheteroalkyl, wherein each alkyl, alkynyl, cycloalkyl, and cycloheteroalkyl is unsubstituted or substituted with 1-4 substituents selected from $C_{1-6}$alkyl, halogen, and —$OC_{1-6}$alkyl.

In another class of this embodiment, each $R^L$ is independently selected from the group consisting of: —$C_{1-10}$alkyl, —$C_{2-10}$alkynyl, —$C_{3-6}$cycloalkyl, and —$C_{2-6}$cycloheteroalkyl, wherein each alkyl, alkynyl, cycloalkyl, and cycloheteroalkyl is unsubstituted or substituted with 1-4 substituents selected from $C_{1-6}$alkyl, halogen, and —$OC_{1-6}$alkyl.

In another class of this embodiment, each $R^L$ is independently selected from the group consisting of: —$C_{1-10}$alkyl, —$C_{2-10}$alkynyl, and —$C_{3-6}$cycloalkyl, wherein each alkyl, alkynyl, and cycloalkyl is unsubstituted or substituted with 1-4 substituents selected from: $C_{1-6}$alkyl, halogen, and —$OC_{1-6}$alkyl. In a subclass of this class, each $R^L$ is independently selected from the group consisting of: —$CH_3$, —C≡C—$CH_3$, and cyclopropyl.

Another embodiment of the present invention relates to compounds of structural Formula Ik:

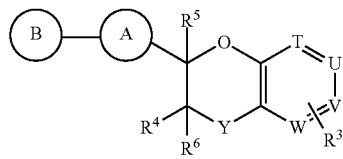

wherein
T is CH;
U is $CR^1$;
V is $CR^2$;
W is CH;
Y is oxygen;
A is selected from the group consisting of:
 (1) aryl,
 (2) heteroaryl, and
 (3) $C_{2-5}$cycloheteroalkyl,
wherein A is unsubstituted or substituted with one to five substituents selected from $R^a$;
B is selected from the group consisting of:
 (1) aryl, and
 (2) aryl-$C_{1-10}$ alkyl-,
wherein B is unsubstituted or substituted with one to five substituents selected from $R^b$;
$R^1$ and $R^2$ are selected from:
 (1) —$C_{1-6}$alkyl, and
 (2) hydrogen,
wherein each alkyl is unsubstituted or substituted with one to three substituents selected from $R^L$, and wherein each alkyl is substituted with a substituent selected from $R^7$, provided that one of $R^1$ and $R^2$ is —$C_{1-6}$alkyl and the other of $R^1$ and $R^2$ is hydrogen;

$R^3$ is selected from the group consisting of:
 (1) hydrogen, and
 (2) halogen;
$R^7$ is —$CO_2R^8$;
$R^4$, $R^5$, $R^6$ and $R^8$ are hydrogen;
each $R^a$ is independently selected from the group consisting of: —$C_{1-6}$alkyl, halogen, —$CF_3$, —$OCF_3$ and heteroaryl, wherein each alkyl and heteroaryl is unsubstituted or substituted with —$C_{1-6}$alkyl, halogen, —O—$C_{1-6}$alkyl and —$CF_3$;
each $R^b$ is independently selected from the group consisting of:
 (1) —$C_{1-10}$alkyl,
 (2) —$CF_3$,
 (3) halogen, and
 (4) —$OC_{1-10}$alkyl,
wherein each alkyl is unsubstituted or substituted with —$C_{1-6}$alkyl, halogen, —O—$C_{1-6}$alkyl and —$CF_3$; and
each $R^L$ is independently selected from the group consisting of:
 (1) —$C_{1-10}$alkyl,
 (2) —$C_{2-10}$alkynyl, and
 (3) —$C_{3-6}$cycloalkyl,
wherein each alkyl, alkynyl, and cycloalkyl is unsubstituted or substituted with 1-4 substituents selected from $C_{1-6}$alkyl, halogen, and —$OC_{1-6}$alkyl;
or a pharmaceutically acceptable salt thereof.

In a class of this embodiment, $R^1$ is —$C_{1-6}$alkyl, wherein each alkyl is unsubstituted or substituted with one to three substituents selected from $R^L$, and wherein $R^1$ is substituted with $R^7$.

In another class of this embodiment, $R^2$ is hydrogen.

Another embodiment of the present invention relates to compounds of structural Formula Ik:

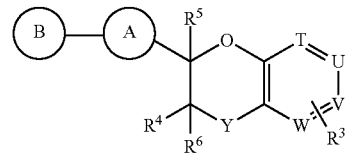

wherein
T is CH;
U is $CR^1$;
V is $CR^2$;
W is CH;
Y is oxygen;
A is selected from the group consisting of:
 (1) aryl,
 (2) heteroaryl, and
 (3) $C_{2-5}$cycloheteroalkyl,
wherein A is unsubstituted or substituted with one to five substituents selected from $R^a$;
B is selected from the group consisting of:
 (1) aryl, and
 (2) aryl-$C_{1-10}$ alkyl-,
wherein B is unsubstituted or substituted with one to five substituents selected from $R^b$;
$R^1$ is —$C_{1-6}$alkyl, wherein each alkyl is unsubstituted or substituted with one to three substituents selected from $R^L$, and wherein $R^1$ is substituted with $R^7$;
$R^3$ is selected from the group consisting of:
 (1) hydrogen, and
 (2) halogen;

$R^7$ is $-CO_2R^8$;
$R^2$, $R^4$, $R^5$, $R^6$ and $R^8$ are hydrogen;
each $R^a$ is independently selected from the group consisting of: $-C_{1-6}$alkyl, halogen, $-CF_3$, $-OCF_3$ and heteroaryl, wherein each alkyl and heteroaryl is unsubstituted or substituted with $-C_{1-6}$alkyl, halogen, $-O-C_{1-6}$alkyl and $-CF_3$;
each $R^b$ is independently selected from the group consisting of:
(1) $-C_{1-10}$alkyl,
(2) $-CF_3$,
(3) halogen, and
(4) $-OC_{1-10}$alkyl,
wherein each alkyl is unsubstituted or substituted with $-C_{1-6}$alkyl, halogen, $-O-C_{1-6}$alkyl and $-CF_3$; and
each $R^L$ is independently selected from the group consisting of:
(1) $-C_{1-10}$alkyl,
(2) $-C_{2-10}$alkynyl, and
(3) $-C_{3-6}$cycloalkyl,
wherein each alkyl, alkynyl, and cycloalkyl is unsubstituted or substituted with 1-4 substituents selected from $C_{1-6}$alkyl, halogen, and $-OC_{1-6}$alkyl;
or a pharmaceutically acceptable salt thereof.

In a class of this embodiment, A is selected from the group consisting of: phenyl, pyridine, and azetidine, wherein each phenyl, pyridine, and azetidine is unsubstituted or substituted with one to five substituents selected from $R^a$.

In another class of this embodiment, B is selected from the group consisting of: phenyl, and $-CH_2$-phenyl, wherein $CH_2$ and phenyl are unsubstituted or substituted with one to five substituents selected from $R^b$.

In another class of this embodiment, $R^1$ is $-C_2$alkyl, wherein each alkyl is unsubstituted or substituted with one to three substituents selected from $R^L$, and wherein $R^1$ is substituted with $R^7$.

In another class of this embodiment, $R^3$ is selected from the group consisting of: hydrogen, and F. In a subclass of this class, $R^3$ is F. In another subclass of this class, $R^3$ is hydrogen.

In another class of this embodiment, each $R^a$ is independently selected from the group consisting of: $-CH(OCH_3)C(CH_3)_3$, Cl, $-CF_3$, $-OCF_3$, and indole, wherein indole is unsubstituted or substituted with $-C_{1-6}$alkyl.

In another class of this embodiment, each $R^b$ is independently selected from the group consisting of: $-CH_3$, $-CF_3$, F, and $-OCH_3$.

In another class of this embodiment, each $R^L$ is independently selected from the group consisting of: $-CH_3$, $-C\equiv C-CH_3$, and cyclopropyl.

Illustrative, but non-limiting, examples of the compounds of the present invention that are useful as agonists of G-protein-coupled receptor 40 (GPR40) are the following compounds:

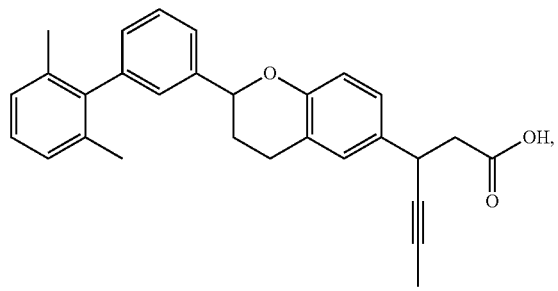

-continued

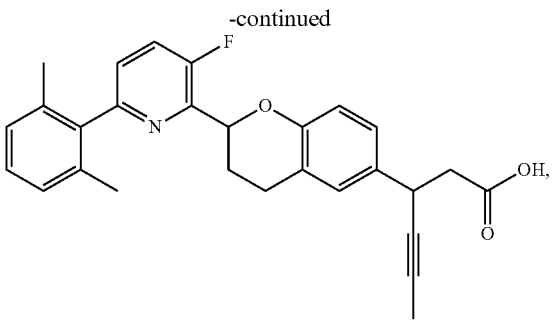

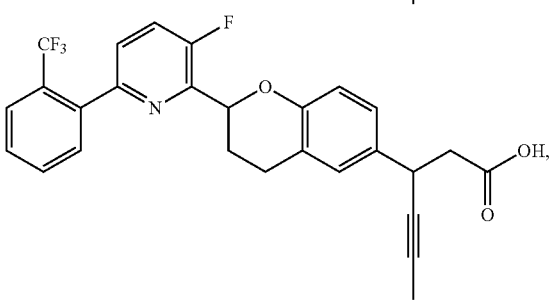

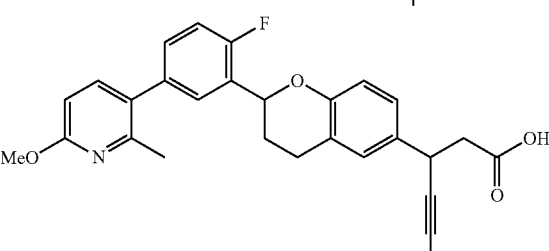

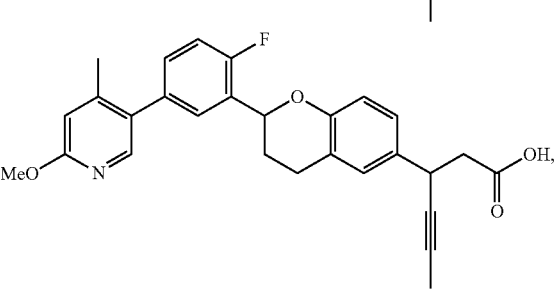

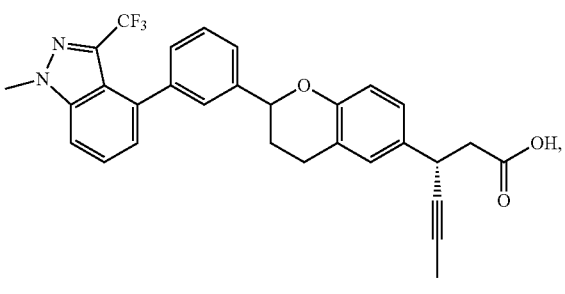

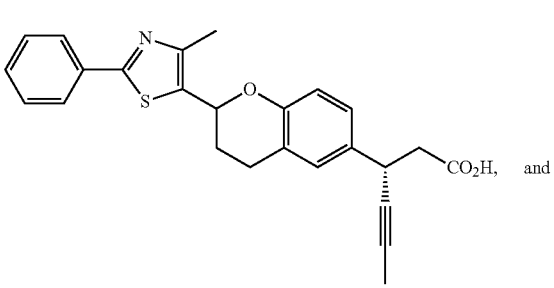

-continued

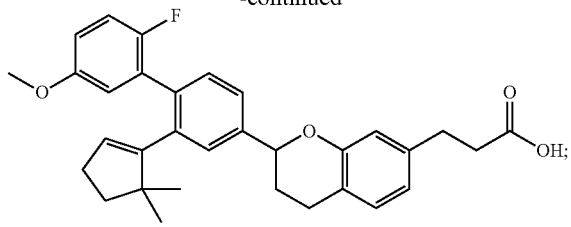

and pharmaceutically acceptable salts thereof.

Although the specific stereochemistries described herein are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is 2-methyl-1-propenyl.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like. In one embodiment, alkynyl is $-C_2$alkyne-$CH_3$.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclopropane, cyclobutane and cyclohexane. In another embodiment of the present invention, cycloalkyl is selected from: cyclopropane.

"Cycloalkenyl" means a nonaromatic monocyclic or bicyclic carbocylic ring containing at least one double bond. Examples of cycloalkenyl include cyclopropenyl, cyclobutenyl, cyclopentenyl, cyclohexenyl, cycloheptenyl, cyclooxtenyl and the like. In one embodiment of the present invention, cycloalkenyl is cycloalkenyl.

"Cycloheteroalkyl" means a saturated or partly unsaturated non-aromatic monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1, 4:3, 6-dianhydromannitol, 1, 4:3, 6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is selected from: hexose, pentose, isosorbide and isomannide. In another embodiment of the present invention, cycloheteroalkyl is selected from: isosorbide and isomannide. In another embodiment of the present invention, cycloheteroalkyl is selected from: oxetane, tetrahydropyran, azetidine, tetrahydrothiopyran and pyrrolidine. In another embodiment of the present invention cycloheteroalkyl is selected from: oxetane, -piperazine, azetidine, pyrrolidine, morpholine and spiro(indene-1,4-piperidine).

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl. In another embodiment of the present invention, aryl-O— is phenyl-O—. In another embodiment of the present invention, aryl-$C_{1-10}$alkyl-O— is phenyl-$CH_2$—O—.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is selected from: pyridine, isoxazole, pyrimidine, thiazole, benzimidazole, benzthiazole, benzoxazole, and benzisoxazole. In another embodiment of the present invention, heteroaryl is selected from: pyridine, isoxazole and benzpyrazole. In another embodiment of the present invention, heteroaryl is pyridine or thiazole. In another embodiment of the present invention, heteroaryl is pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is =O.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

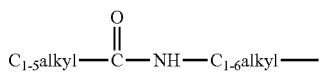

For example, —$NR^cC(O)R^e$ is equivalent to —$N(R^c)C(O)R^e$.

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:

(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapo-B liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The chroman compounds of the present invention have the unexpected benefit of increased potency in the FLIPR Assay (see Biological Assays) compared to the corresponding compounds in which the chroman core is replaced with a 2,3,4,5-tetrahydrobenzo[b]oxepine core or a 2,3-dihydrobenzofuran core.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geq$140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated ($\geq$140 mmHg/$\geq$90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e., cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, inulin degludec, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), aleglitazar, farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H- indene-1-yl]oxy]phenyl]isothiazole-3-ol 1-oxide, 5-(4-((3-(2,6-dimethyl-4-(3-(methylsulfonyl)propoxy)phenyl)phenyl)-methoxy)phenyl)iso, 5-(4-((3-(2-methyl-6-(3-hydroxypropoxyl)pyridine-3-yl)-2-methylphenyl)methoxy)phenyl)-isothiazole-3-ol 1-oxide, and 5-[4-[[3-[4-(3-aminopropoxy)-2,6-dimethylphenyl]phenyl]-methoxy] phenyl]isothiazole-3-ol 1-oxide), and those disclosed in WO 11/078371; 42) SGLT-2 inhibitors such as canagliflozin, dapagliflozin, tofogliflozin, empagliflozin, ipragliflozin, luseogliflozin (TS-071), ertugliflozin (PF-04971729), and remogliflozin; and 43) SGLT-1/SGLT-2 inhibitors, such as LX4211.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimime (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7806, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-Al Milano/ETC216 (Pfizer), ETC-642 (Pfizer), ISIS301012, D4F (Bruin Pharma), synthetic trimeric ApoAl, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/ Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as LY-2523199, BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), omarigliptin, saxagliptin, alogliptin, linagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55)C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, canagliflozin, dapagliflozin, ipraglifozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-diabetic compounds, anti-obesity compounds and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

LIST OF ABBREVIATIONS

Ac is acetyl; AcCN is acetonitrile; AcO is acetoxy; Alk is alkyl; anh. is anhydrous; APCI is atmospheric pressure chemical ionization; aq or aq. is aqueous; Ar is aryl; atm is atmosphere; Boc is tert-butoxycarbonyl; Bn-O is phenyl-$CH_2$—O or benzyloxy; Br is broad; BrettPhos palladacycle precatalyst is Brettphos Pd G1 precatalyst (Aldrich); n-BuLi is n-butyl lithium; $Bu_3P$ is tributylphosphine; t-BuOK is potassium tert-butoxide; C—C refers to a carbon-carbon bond cross coupling reaction; C—N refers to a carbon-nitrogen bond cross coupling reaction; ° C. is degrees celsius; Cataxium precatalyst or Cataxium Pd precat or precatalyst is cataCXium A Pd G3 (Aldrich); Cbz is benzyloxycarbonyl; $CH_2Cl_2$ is dichloromethane; conc or conc. is concentrated; CV is column volumes; d is doublet; DAST is (diethylamino)sulfur trifluoride; DIBAL-H ix diisobutylaluminum hydride; DIAD is diisopropyl azodicarboxylate; DCM is dichloromethane; DEA is diethyl amine; DIPEA is N,N-diisopropylethylamine; DIPA is diisopropyl amine; DMAP is 4-dimethylaminopyridine; DMF is N,N-dimethylformamide; DMS is dimethyl sulfide; DMSO is dimethylsulfoxide; dppf is 1,1'-Bis(diphenyl-phosphino)ferrocene; ESI is electrospray ionization; EA or EtOAc is ethyl acetate; Et is ethyl; $Et_2O$ is diethyl ether; EtMgBr is ethyl magnesium bromide; EtOH is ethanol; g is gram(s); h or hr or hrs is hour(s); hex is hexanes; HPLC is high pressure liquid chromatography; HOAc or AcOH is acetic acid; kg is kilogram(s); IPA is isopropanol; KOH is potassium hydroxide; KOAc is potassium acetate; KOtBu is potassium tert-butoxide; L is liter; LAH is lithium aluminum hydride; LC-M is molar; MS is liquid chromatography-mass spectroscopy; LDA is lithium diisopropyl amide; LiOH is lithium hydroxide; m is multiplet; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeMgBr is methyl magnesium bromide; MeOH is methyl alcohol or methanol; $MgSO_4$ is magnesium sulfate; MPLC is medium pressure liquid chromatography; MS is mass spectroscopy; MsCl or Ms-Cl is methane sulfonyl chloride; MeCN is acetonitrile; MeI is methyl iodide; MsCl is methane sulfonyl chloride; MTBE is methyl tert-butyl ether; N is normal; $Na(AcO)_3BH$ is sodium triacetoxy borohydride; NaHMDS is sodium hexamethyl disilazide; NaOH is sodium hydroxide; $Na_2SO_4$ is sodium sulfate; $NH_4OAc$ is ammonium acetate; NBS is N-bromo succinamide; $NEt_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; paraform is paraformaldehyde; PE is petroleum ether; PG is protecting group; i-PrOH is isopropanol; $P(Cy)_3$ is tricyclohexyl phosphine; $Pd_2(dba)_3$ is tris(dibenzylidene-acetone)-dipalladium(0); $Pd(OAc)_2$ is palladium acetate; $Pd[P(t-Bu)_3]_2$ is bis(tri-tert-butylphosphine)palladium (0); $Pd(dppf)Cl_2$ is [1,1'-bis(diphenylphosphino)-ferrocene]dichloro-palladium (II); $PdCl_2(dppf)_2CH_2Cl_2$ is [1,1'-Bis(diphenylphosphino)-ferrocene] dichloropalladium(II), complex with dichloromethane (Aldrich); $Pd(PPh_3)_4$ is tetrakis or tetrakis(triphenylphosphine) palladium (0); $PPh_3$ is triphenyl phosphine; $Pd(t-Bu_2P)_2FerrCl_2$ is bis-tri-tert-butylphosphino ferrocene dichloro palladium (II); PMB is para-methoxybenzyl; PMBCl is para-methoxybenzyl chloride; precat is precatalyst; prep is preparative; prep. TLC or prep-TLC, or prep TCL is preparative thin layer chromatography; rbf or RBF is round bottom flask; RCM is ring closing metathesis reaction; rt or r.t. or RT is room temperature; RuCl[(R,R)-TSDPEN](mesitylene) is [N-[1R,2R)-2-(Amino-κN)-1,2-diphenylethyl]-4-methylbenzenesulfonamidato-κN]chloro[(1,2,3,4,5,6-η)-1,3,5-trimethylbenzene]-ruthenium; Ru-Josiphos is generated using (Me-allyl)2Ru(COD) (Aldrich) and Josiphos SL-J502-2 (Aldrich); $R_f$ is retention factor; s is singlet; sat or sat. is saturated; SEM is trimethylsilyl ethoxy methyl, SEMCl is trimethylsilyl ethoxy methyl chloride; SFC is supercritical fluid chromatography; S-Phos is 2-dicyclohexylphosphino-2',6'-dimethoxy-biphenyl; S-Phos(Pd) is chloro(2-dicyclohexylphosphino-2',6'-dimethoxy-1,1'-biphenyl)[2-(2-aminoethylphenyl)]palladium (II) [CAS-No. 1028206-58-7]; S-Phos precatalyst is S-Phos Pd G2 precatalyst—Aldrich; S-Phos second generation precatalyst is Chloro(2-dicyclohexyl-phosphino-2',6'-dimethoxy-1,1'-biphenyl)[2-(2'-amino-1,1'-biphenyl)]palladium-(II), SPhos-Pd-G2) [CAS-No. 1375325-64-6]; t is triplet; TBAF is tetrabutylammonium fluoride; TBSCl is tert-butyl dimethylsilyl chloride; TBTU is N,N,NR'-Tetramethyl-O-(benzotriazol-1-yl)uronium tetrafluoroborate; TEA is triethyl amine; Tf is trifluoromethane sulfonyl; THF is tetrahydrofuran; $Ti(OiPr)_4$ is titanium isopropoxide; TFA is trifluoroacetic acid; TLC is thin-layer chromatography; Trixiephos is racemic-2-di-I-butylphosphino-1,1'-binaphthyl; TosCl and TsCl is p-toluene sulfonyl chloride; pTSA, pTsOH and TsOH is p-toluenesulfonic acid, $Ts_2O$ is tosic anhydride or p-toluene sulfonic anhydride; and xphos is 2-dicyclohexylphosphino-2',4',6'-triisopropyl-biphenyl.

Several methods for preparing the compounds of this invention are illustrated in the following Schemes, Intermediates and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided for the purpose of illustration only and are not to be construed as limitations on the disclosed invention. All temperatures are degrees Celsius unless otherwise noted.

Scheme 1

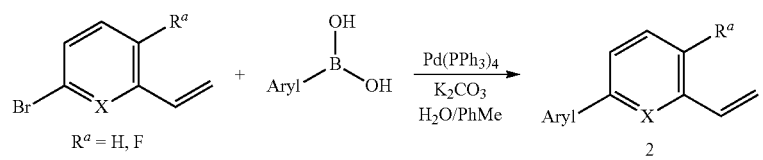

-continued

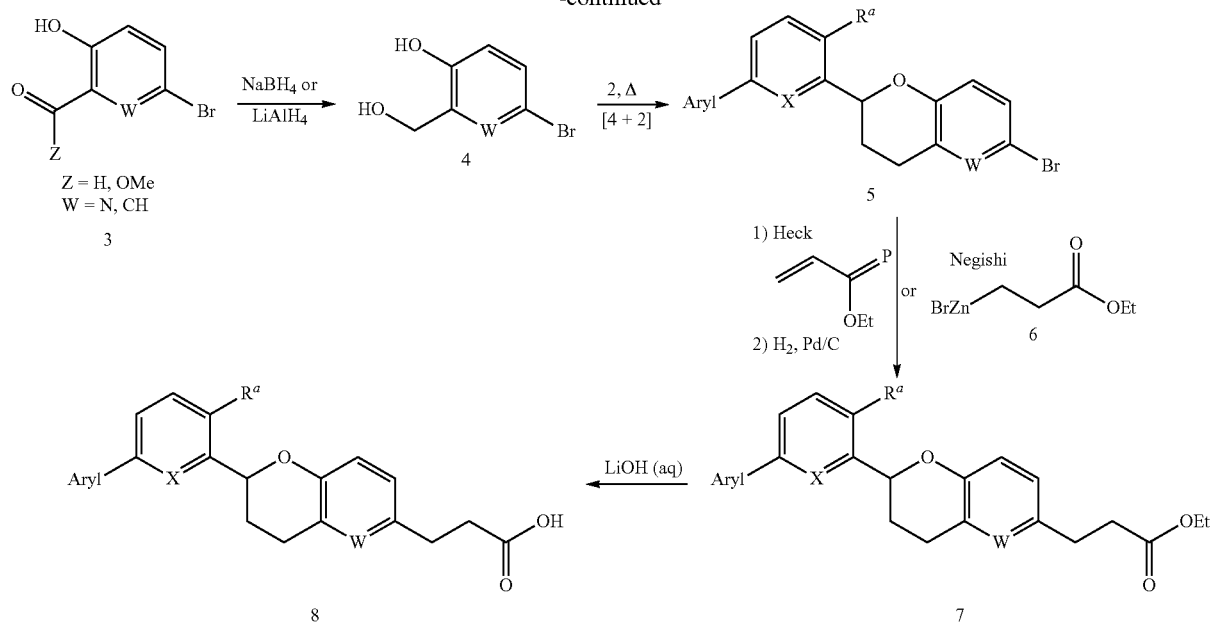

As outlined in Scheme 1, a bromo-styryl derivative 1 is reacted under cross coupling conditions with a boron acid derivative to afford substituted styryl 2. The aldehyde or ester 3 is reduced to hydroxymethyl phenol 4 which is reacted with styrene 2 through a hetero-Diels Alder reaction to give chroman derivative 5. Reaction of 5 with an acrylate under Heck coupling conditions followed by reduction of the double bond or reaction of 5 with a bromo-zinc reagent 6 under Negishi reaction conditions yields ester 7. Hydrolysis of the ester in 7 gives compound 8.

Scheme 2

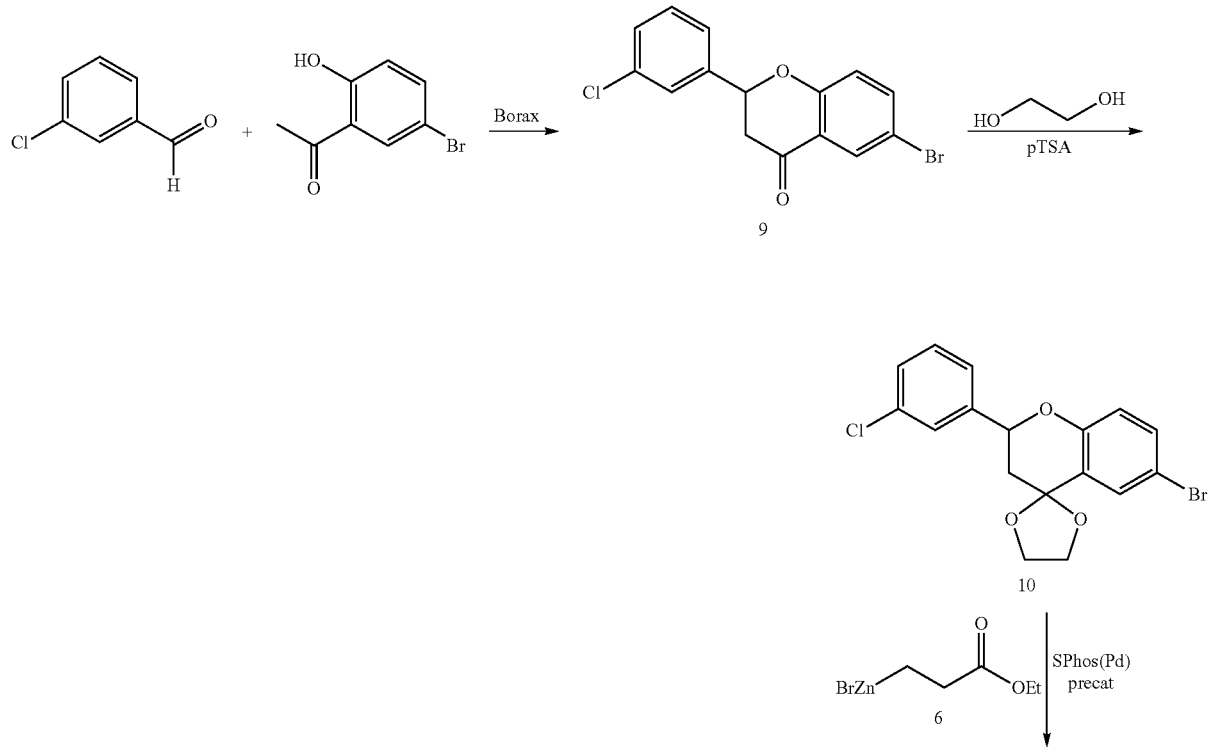

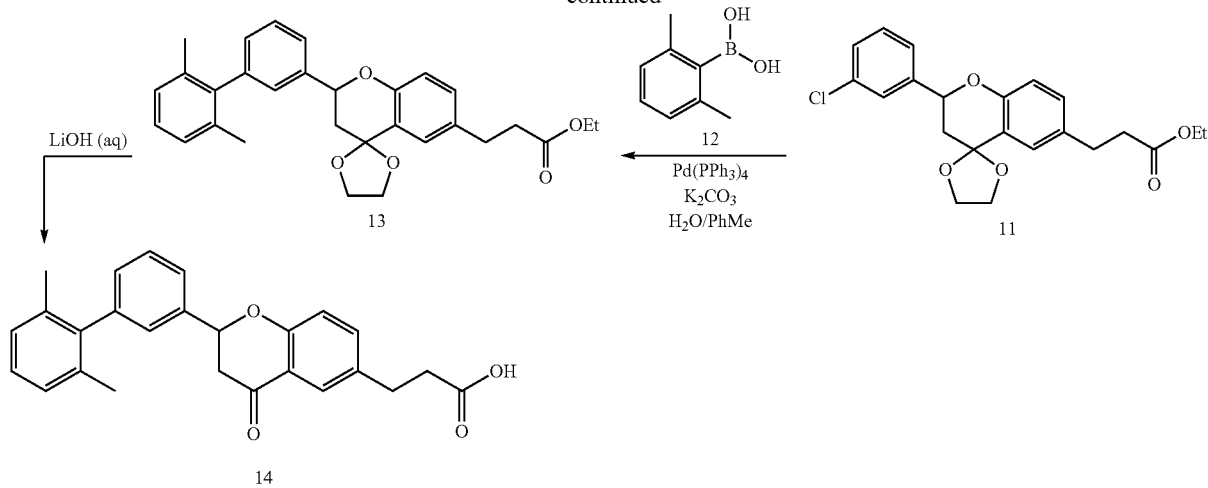

An alternative method for preparing compounds of Formula I is illustrated in Scheme 2. Reaction of 3-chlorobenzaldehyde with 5-bromo-2-hydroxy-acetophenone in the presence of Borax yields chroman 9. The ketone in 9 is then protected as the ketal with ethylene glycol in the presence of acid to afford 10. Reaction of 10 with zinc reagent 6 yields ester 11. C—C coupling of boronate 12 with chloride 11 in the presence of a palladium catalyst gives biaryl derivative 13. Hydrolysis of the ester and ketal in 13 under aqueous conditions gives compound 14.

Scheme 3

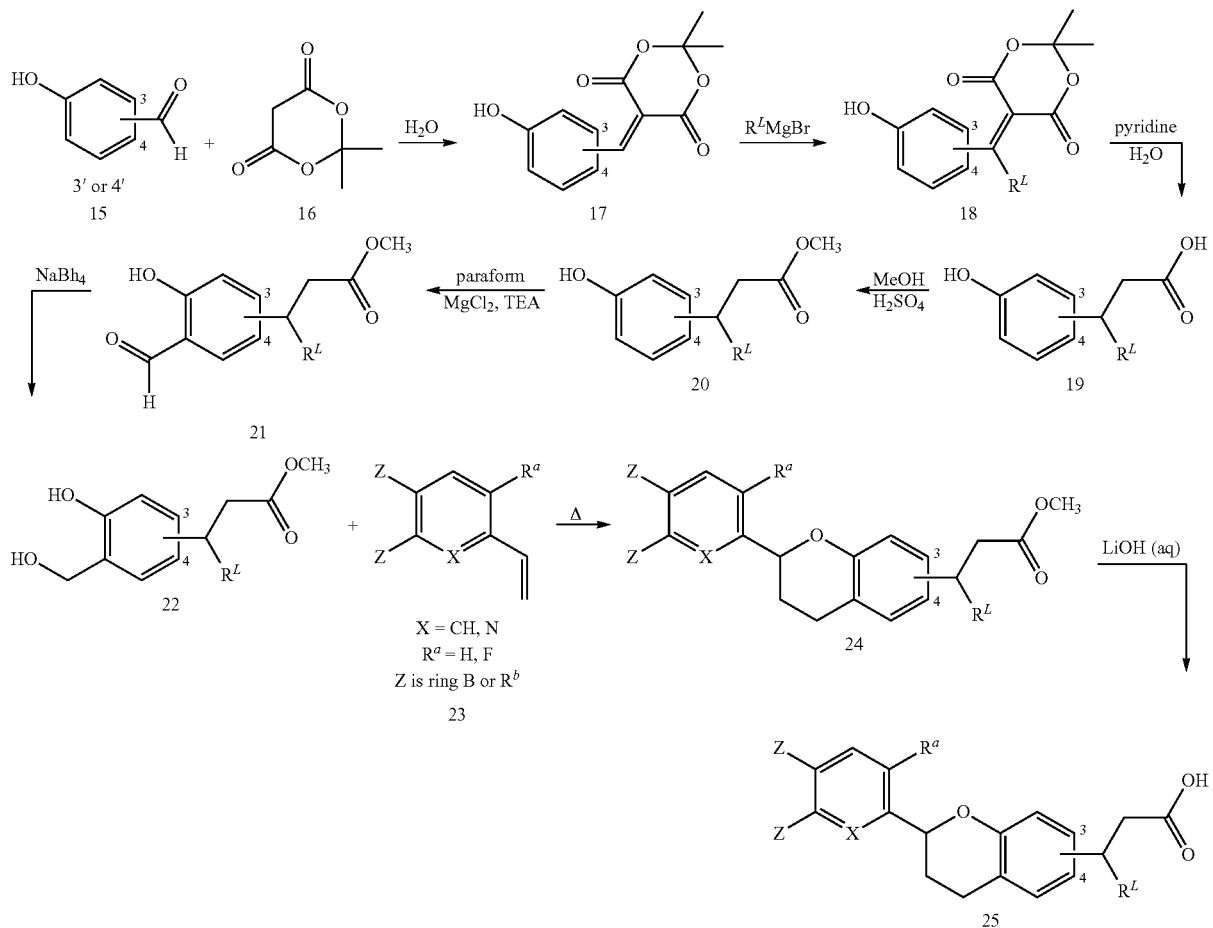

Another method for preparing compounds of Formula I is outlined in Scheme 3. Hydroxy-acetophenone 15 is reacted with Meldrum's acid 16 to yield 17. A Grignard reagent is then added to the double bond in 17 to afford 18, which is hydrolyzed in the presence of pyridine to give hydroxy-phenyl propionic acid 19. Esterification in acid methanol gives ester 20. Reaction of 20 with paraformaldehyde affords hydroxy-aldehyde derivative 21, which is reduced to hydroxymethyl phenol 22. Reaction of 22 with a styryl derivative 23 under oxy-Diels Alder thermal conditions yields chroman 24. Hydrolysis of the ester in 24 gives compound 25.

Step A: 2,6-dimethyl-3'-vinyl-1,1'-biphenyl

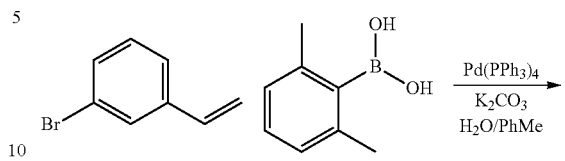

Scheme 4

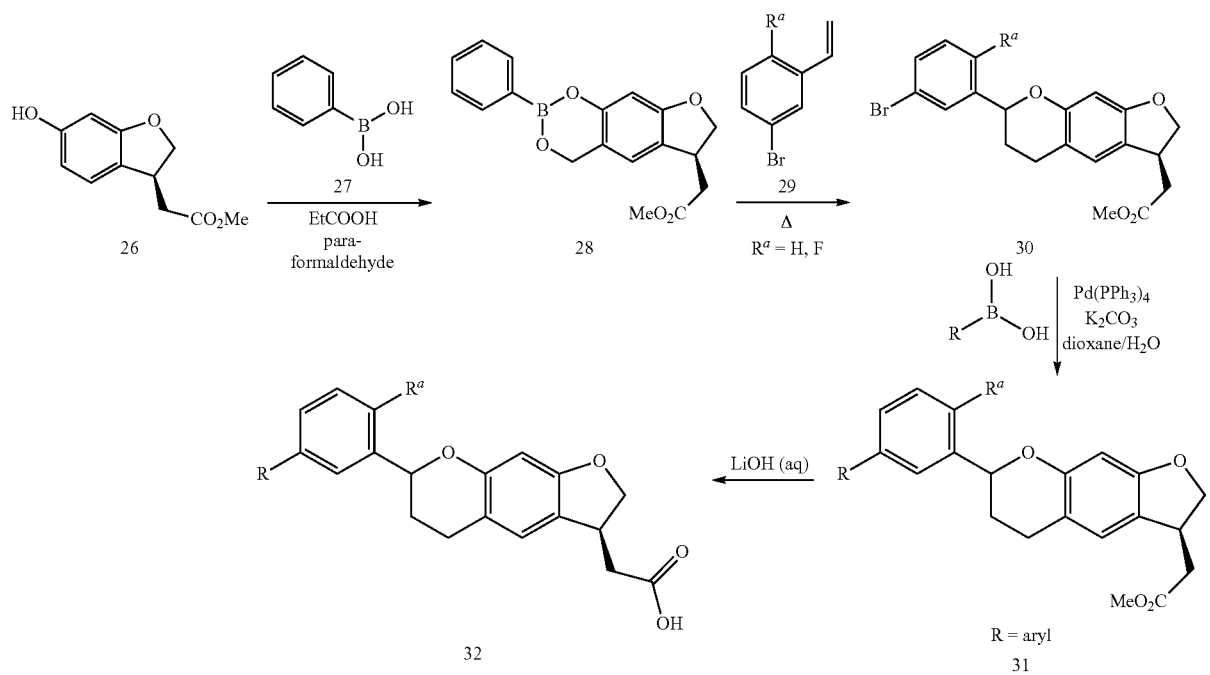

Finally, a fourth method for the preparation of compounds of Formula I is outlined in Scheme 4. Hydroxy-benzofuran acetic acid 26 is reacted with boronic acid 27 and formaldehyde to yield boronate ester 28. Heating of 28 with bromo-styryl 29 gives chroman 30. C—C coupling of 30 with an aryl boronic acid derivative in the presence of a palladium catalyst yields ester 31 which is hydrolyzed to give compound 32.

Intermediate 1

6-Bromo-2-(2',6'-dimethyl-[1,1'-biphenyl]-3-yl)chroman

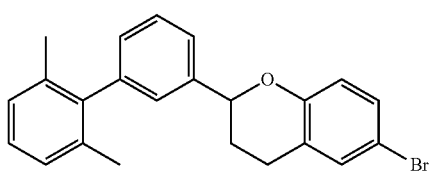 [SMILES: Cc1cccc(C)c1-c1cccc(C2CCc3cc(Br)ccc3O2)c1]

-continued

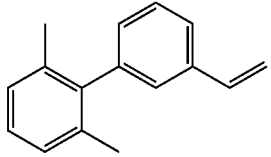

To a nitrogen-purged toluene (25 mL) solution of (2,6-dimethylphenyl)boronic acid (1.97 g, 13.1 mmol), 3-bromo-styrene (2 g, 10.9 mmol), and tetrakis(triphenylphosphine)palladium(0) (379 mg, 0.328 mmol) was added $K_2CO_3$ solution (2 N in water, 10.9 mL, 21.9 mmol). The resulting mixture was heated to 100° C. on a heating block. After 12 h, the reaction was cooled to room temp and then poured into $NH_4Cl$ (sat, aq, 50 mL) and extracted with EA (2×50 mL). The combined organic layers were dried ($MgSO_4$) and concentrated. The resulting residue was purified by HPLC (ISCO 0 to 50% EA/Hex) to the product. 1H NMR (500 MHz, $CDCl_3$) δ7.42 (s, 2H), 7.29-7.10 (m, 5H), 6.80 (dd, 1H), 5.81 (d, 1H), 5.30 (d, 1H).

Step B: 4-bromo-2-(hydroxymethyl)phenol

To a cooled (0° C.) ethanol (50 mL) solution of 4-bromosalicaldehyde (5.00 g, 24.9 mmol) was added NaBH$_4$ (941 mg, 24.9 mmol) in a single portion. After 2 h, the mixture was quenched with 1 N HCl (50 mL) and poured into a reparatory funnel. The mixture was partitioned between brine (100 mL) and EtOAc (2×100 mL). The combined organic layers were dried (MgSO$_4$), concentrated, and purified by HPLC (ISCO, 0 to 50% EA/Hex) to give the product. $^1$H NMR (500 MHz, MeOD) δ 7.41 (s, 1H), 7.19 (d, 1H), 6.68 (d, 1H), 4.60 (s, 2H).

Step C: 6-bromo-2-(2',6'-dimethyl-[1,1'-biphenyl]-3-yl)chroman

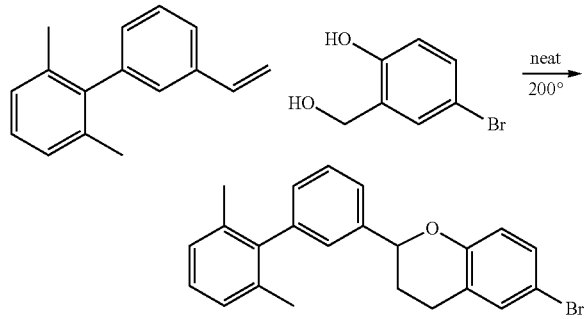

2,6-dimethyl-3'-vinyl-1,1'-biphenyl (1.00 g, 4.80 mmol) and 4-bromo-2-(hydroxymethyl)phenol (200 mg, 0.985 mmol) were combined and then heated neat to 200° C. on a heating block in a sealed tube. After 2 h, the mixture was cooled to room temperature to give a plastic-like semi-solid (styrene had mostly polymerized). The product-containing polymer was then taken up in DCM (2 mL) and diluted with hexanes (50 mL). The insoluble polystyrenes were filtered and the volatiles removed in vacuo. The resulting residue was purified by HPLC (ISCO, 0 to 20% EA/Hex) to give the product. $^1$H NMR (500 MHz, CDCl3) δ 7.51-7.41 (m, 3H), 7.29-7.15 (m, 5H), 6.82 (d, 1H), 5.18 (d, 1H) 3.01 (m, 1H), 2.80 (m, 1H), 2.27 (m, 1H), 2.10 (m, 1H), 2.08 (d, 6H).

Intermediate 2

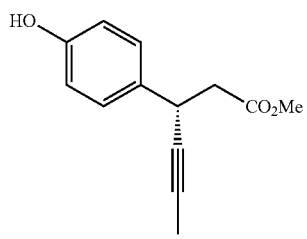 [SMILES: CC#C[C@@H](CC(=O)OC)c1ccc(O)cc1]

(3S)-Methyl 3-(4-hydroxyphenyl)hex-4-ynoate

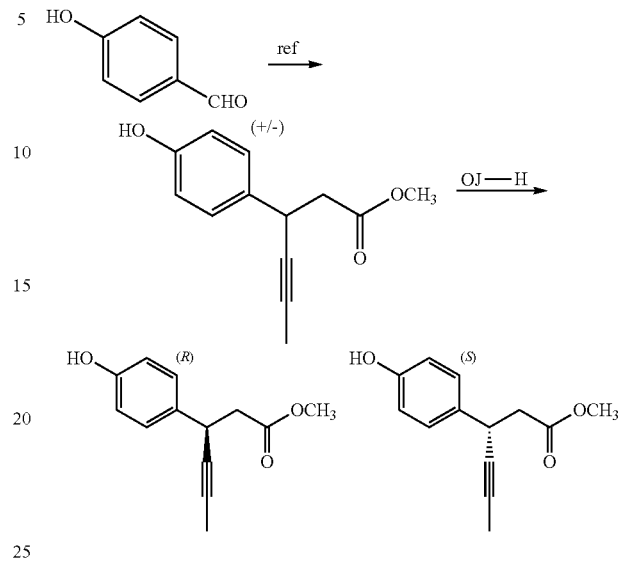

Preparation of racemic methyl 3-(4-hydroxyphenyl)hex-4-ynoate was performed as described in the procedure in *Bioorganic & Medicinal Chemistry Letters* 21(11) 3390, 2011. Separation of the enantiomers was performed by SFC (OJ-H column, 6% IPA/CO$_2$) to give the (R) (faster peak) and (S) (slower peak) enantiomers. $^1$H NMR (500 MHz, acetone-d$_6$) δ8.2 (br, 1H), 7.20 (d, 2H), 6.77 (d, 2H), 3.98 (m, 1H), 3.60 (s, 3H), 2.65 (m, 2H), 1.78 (s, 3H).

(S)-3-(4-hydroxyphenyl)hex-4-ynoic acid (proof of configuration)

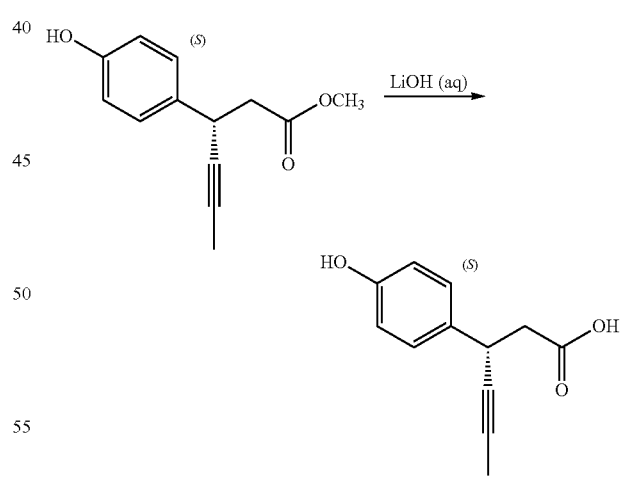

To a solution of (S)-methyl 3-(4-hydroxyphenyl)hex-4-ynoate (slower peak OJ column, 250 mg, 1.145 mmol) in THF/H$_2$O/MeOH in a vial was added LiOH (274 mg, 11.45 mmol). The mixture was heated to 50° C. on a heating block. After 12 h, the reaction was poured into 1 N HCl (25 mL) and extracted with EtOAc (2×25 mL). The combined organic layers were dried (MgSO$_4$) and concentrated. The resulting residue was purified by HPLC (ISCO 40 g, 0 to 50% MeOH/DCM) to give the product. $^1$H NMR (500 MHz, DMSO-$d_6$) δ 12.2 (s, 1H), 9.27 (s, 1H), 7.12 (d, 2H), 6.67 (d, 2H), 3.87 (m, 1H), 2.54 (m, 2H), 1.82 (s, 3H). $[α]^{23}_D$=+16.36° (c 2.2, CDCl$_3$) (literature $[α]^{23}_D$=+10.09, *Organic Process Research & Development* 2011, v15(3), 570-580).

Intermediate 3

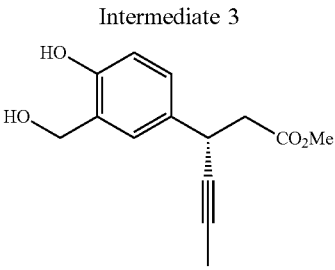

Step A: 3-(3-formyl-4-hydroxyphenyl)hex-4-ynoic acid

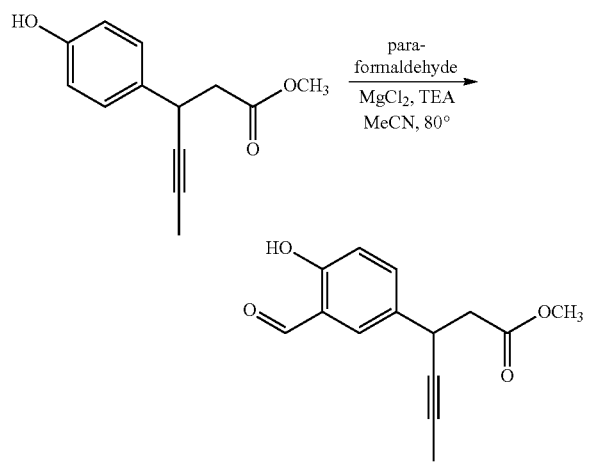

To a solution of acetonitrile (305 ml) and methyl 3-(4-hydroxyphenyl)hex-4-ynoate (2.00 g, 9.16 mmol), magnesium chloride (1.31 g, 13.8 mmol), and paraformaldehyde (1.38 g, 45.8 mmol) was added TEA (4.79 mL, 34.4 mmol). The resulting slurry was heated to reflux. After 3 h, the homogenous yellow solution was cooled to room temperature and poured into 5% HCl (200 mL). The mixture was then extracted with ethyl acetate (2×250 mL). The combined organic layers were dried (MgSO$_4$) and concentrated. The resulting residue was purified by HPLC (ISCO 120 g, 0 to 50% EA/Hex) to give the title compound. $^1$H NMR (500 MHz, CDCl$_3$) δ10.98 (s, 1H), 9.90 (s, 1H), 7.60 (s, 1H), 7.59 (d, 1H), 6.99 (d, 1H), 4.15 (m, 1H), 3.68 (s, 3H), 2.68 (ddd, 2H), 1.85 (s, 3H).

Step B: Methyl 3-(4-hydroxy-3-(hydroxymethyl)phenyl)hex-4-ynoate

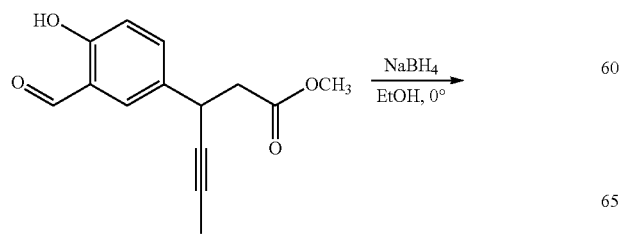

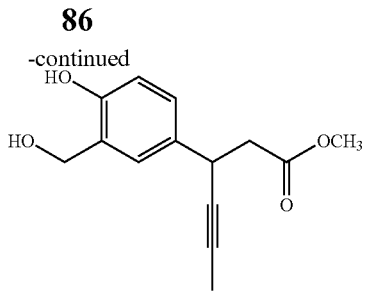

To a cooled (0° C.) ethanol (24 mL) solution of methyl 3-(3-formyl-4-hydroxyphenyl)hex-4-ynoate (1.175 g, 4.77 mmol) was added sodium borohydride (0.181 g, 4.77 mmol) in a single portion. After 30 minutes, the reaction was quenched by the dropwise addition of 1N HCl (20 mL) at 0° C. The mixture was then poured into saturated ammonium chloride (50 mL) and extracted with EtOAc (2×50 mL). The combined organics were dried (MgSO$_4$) and concentrated. The resulting residue was purified by HPLC (ISCO 80 gram, 0 to 80% EA/Hex) to give the title compound. $^1$H NMR (500 MHz, CDCl$_3$) δ7.38 (s, 1H), 7.20 (d, 1H), 7.05 (s, 1H), 6.82 (d, 1H), 4.83 (br, 2H), 4.02 (m, 1H), 3.66 (s, 3H), 2.71 (ddd, 2H), 2.42 (br, 1H), 1.81 (s, 3H).

Intermediate 4

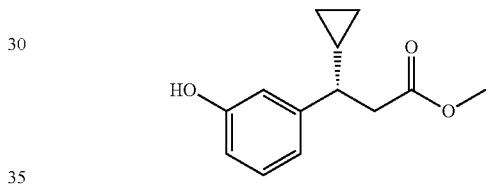

(S)-Methyl 3-cyclopropyl-3-(3-hydroxyphenyl)propanoate

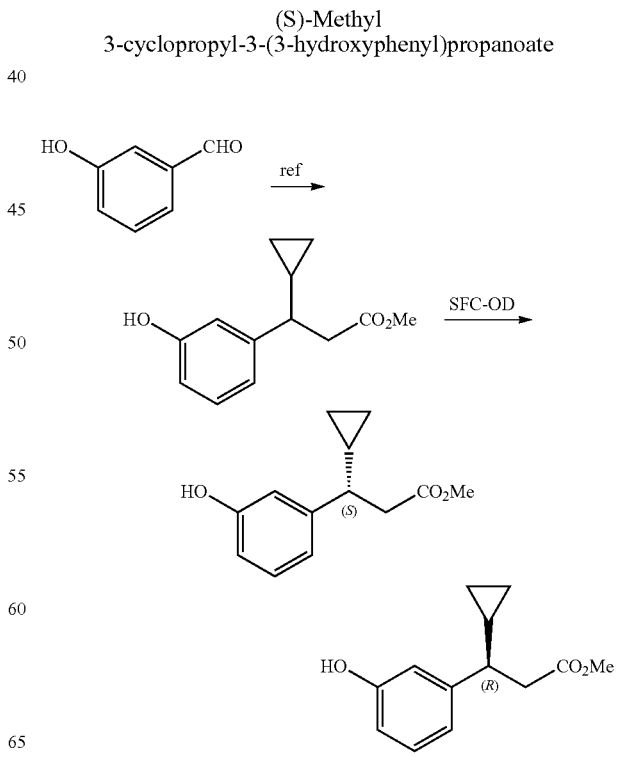

The title compound was prepared according to the procedure disclosed in *ACS Med. Chem. Lett.* 2012, 3, 726-730. Separation of the enantiomers was performed by SFC (OD column, 8% (2:1 IPA/MeCN)/$CO_2$) to give the (S) (faster peak) and (R) (slower peak) enantiomers. $^1$H NMR (500 MHz, $CDCl_3$) δ 7.18 (t, 1H), 6.79 (d, 1H), 6.69 (m, 1H), 3.60 (s, 3H), 2.75 (m, 2H), 2.28 (q, 1H), 0.99 (m, 1H), 0.58 (m, 1H), 0.40 (m, 1H), 0.21 (m, 1H), 0.11 (m, 1H).

Intermediates 5 and 6

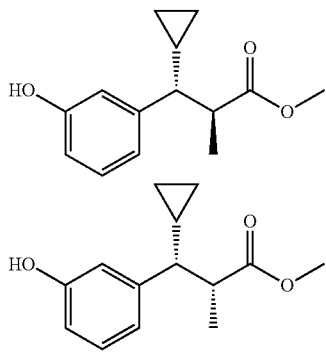

(2R,3R)-Methyl 3-cyclopropyl-3-(3-hydroxyphenyl)-2-methylpropanoate and (2S,3R)-Methyl 3-cyclopropyl-3-(3-hydroxyphenyl)-2-methylpropanoate Step A: To a solution of (S)-methyl 3-cyclopropyl-3-(3-hydroxyphenyl)propanoate (23.6 g, 101 mmol) in DMF (200 mL) was added TBSCl (15.9 g, 106 mmol), followed by imidazole (13.7 g, 201 mmol). The mixture was stirred at rt for 1 h, then diluted with saturated brine solution and extracted with hexanes (2×200 mL). The combined organic layers were dried over $MgSO_4$, filtered and concentrated to give the title compound, which was used immediately in the next step.

Step B: A solution of (S)-methyl 3-(3-((tert-butyldimethylsilyl)oxy)phenyl)-3-cyclopropylpropanoate (2 g, 6.0 mmol) in THF (30 mL) was cooled to −78° C. Then LDA (4.5 mL, 9 mmol, 2.0 M) was added. After 30 minutes, MeI (0.9 mL, 15 mmol) was added dropwise to the reaction mixture. Then the reaction was warmed to rt and poured into saturated aqueous $Na_2S_2O_3$ (50 mL). The aqueous layer was extracted with EtOAc (2×50 mL). The combined organic layers were dried over $MgSO_4$, filtered and concentrated to give an oil. The oil was purified using an ISCO 120 g cartridge (0-30% EtOAc:hexanes) to give a (1:2) mixture of (2R,3R)-methyl 3-(3-((tert-butyldimethyl-silyl)oxy)phenyl)-3-cyclopropyl-2-methylpropanoate and (2S,3R)-methyl 3-(3-((tert-butyl-dimethylsilyl)oxy)phenyl)-3-cyclopropyl-2-methylpropanoate.

Step C: A solution of the (1:2) mixture of (2R,3R)-methyl 3-(3-((tert-butyldimethyl-silyl)oxy)phenyl)-3-cyclopropyl-2-methylpropanoate and (2S,3R)-methyl 3-(3-((tert-butyldimethylsilyl)oxy)phenyl)-3-cyclopropyl-2-methylpropanoate (7.8 g, 22.2 mmol) in THF (80 mL) was cooled to 0° C. Then KOtBu solution (44 mL, 44.6 mmol, 1.0M in THF) was added to effect epimerization. After 20 minutes, the reaction was quenched with 1N HCl (200 mL), and the resulting aqueous layer was extracted with EtOAc (250 mL). The organic layer was removed, dried, filtered and concentrated to give an oil. The resulting crude oil was diluted with THF (40 mL) and treated with TBAF (33 mL, 33 mmol, 1.0 M THF) and stirred at rt until the reaction was complete. Then the reaction was diluted with brine and extracted with EtOAc (200 mL). The organic layer was removed, dried, filtered and concentrated to give a crude oil. The crude oil was purified an ISCO 330 g cartridge (0-40% EtOAc:Hexanes) to give a 3:1 mixture of (2R,3R)-methyl 3-(3-((tert-butyldimethylsilyl)oxy)phenyl)-3-cyclopropyl-2-methylpropanoate and (2S,3R)-methyl 3-(3-((tert-butyldimethylsilyl)oxy)phenyl)-3-cyclopropyl-2-methylpropanoate.

Step D: Separation of the diastereomers in the 3:1 mixture of (2R,3R)-methyl 3-(3-((tert-butyldimethylsilyl)oxy)phenyl)-3-cyclopropyl-2-methylpropanoate and (2S,3R)-methyl 3-(3-((tert-butyldimethylsilyl)oxy)phenyl)-3-cyclopropyl-2-methylpropanoate was performed by SFC (IC, 50×250 mm, 10% IPA/$CO_2$, 200 mL/min, 35° C., 100 bar, 220 nm, 100 mg/mL in 15:1 IPA:DCM) to give Intermediate 5 and Intermediate 6.

Intermediate 5: $^1$H NMR (500 MHz, $CDCl_3$) δ 7.2 (m, 1H), 6.70 (m, 3H), 3.76 (s, 3H), 2.82 (m, 1H), 1.90 (m, 1H), 1.05 (m, 1H), 0.96 (d, 3H), 0.56 (m, 1H), 0.30 (m, 2H), 0.01 (m, 1H).

Intermediate 6: $^1$H NMR (500 MHz, $CD_3OD$) δ 7.24 (m, 1H), 6.70 (m, 3H), 3.40 (s, 3H), 2.98 (m, 1H), 2.15 (m, 1H), 1.35 (d, 3H), 1.25 (m, 1H), 0.75 (m, 1H), 0.45 (m, 2H), 0.1 (m, 1H).

Scheme 5

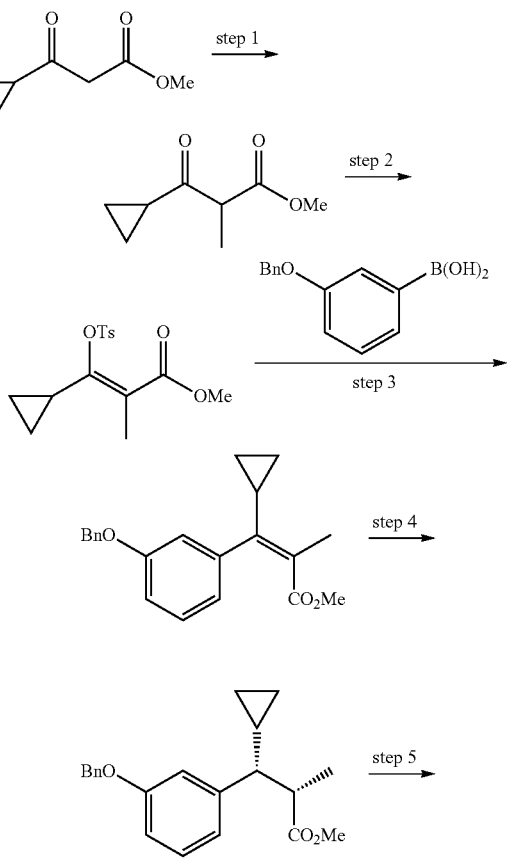

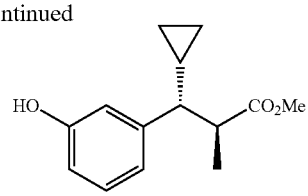

Step 1: MeI, K₂CO₃, THF; Step 2: NaHDMS, Ts₂O, MTBE; Step 3: Cataxium-Pd precat, K₃PO₄, MeCN; Step 4: Ru-Josiphos, BF₄H—Et₂O, H₂ gas, MeOH; Step 5: Pd/Pt/C, H₂ gas, MeOH Scheme 5 provides an alternate route to Intermediate 5. The cyclopropyl β-ketoester is methylated and then trapped at the vinyl tosylate. Suzuki cross-coupling with m-benzyloxy phenylboronic acid delivers the "Z" enoate. Asymmetric reduction of the double bond is followed by debenzylation via hydrogenation.

Alternate Route to Intermediate 5

Step 1: methyl 3-cyclopropyl-2-methyl-3-oxopropanoate

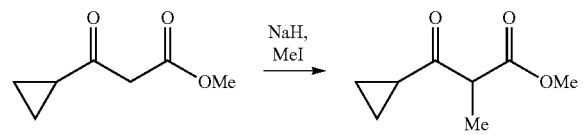

To a slurry of NaH (0.563 g, 60% in mineral oil) in THF (20 mL) was cooled to 10° C., then methyl 3-cyclopropyl-3-oxopropanoate (2 g) was added in portions at room temperature over 30 min. Then MeI (0.88 mL) was added over 5 min at room temperature and stirred at room temperature overnight. The reaction was reverse quenched into a half saturated sodium bicarbonate solution (100 mL) and EtOAc (100 mL). The aqueous layer was separated and extracted once with 50 mL EtOAc. The combined organic layers were washed with water and brine, and concentrated to give the title compound, which was taken on to next the step without further purification.

Step 2: (Z)-methyl 3-cyclopropyl-2-methyl-3-(tosyloxy)acrylate

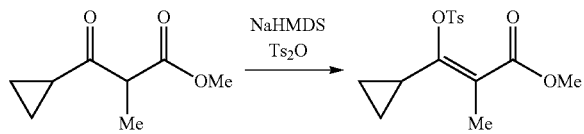 [SMILES: COC(=O)C(C)C(=O)C1CC1 ; COC(=O)/C(C)=C(\OS(=O)(=O)c1ccc(C)cc1)C1CC1]

To a solution of methyl 3-cyclopropyl-2-methyl-3-oxopropanoate (5 g) in MTBE (50 mL) was added a 1M solution of NaHMDS in hexane (41 mL) keeping the internal temperature between 18-23° C. The reaction was stirred at room temperature for 30 min. Then tosic anhydride (10 g) was slurried in MTBE (200 mL), followed by the addition of the reaction mixture to the tosic anhydride slurry, while keeping the internal temperature between 19° C. and 24° C. After 30 min, additional toslic anhydride (3.3 g, 0.3 eq) was added, and the reaction was stirred for x time. On completion, water (500 mL) and EtOAc (400 mL) were added to the reaction mixture. Aqueous layer was separated and extracted once with EtOAc. (100 mL) The combined organic layers were washed with water (200 mL) and brine (100 mL), then concentrated to give the crude product, which was recrystallized from MTBE/heptanes (1:1, 50 mL) to give the title compound.

Step 3: (Z)-methyl 3-(3-(benzyloxy)phenyl)-3-cyclopropyl-2-methylacrylate

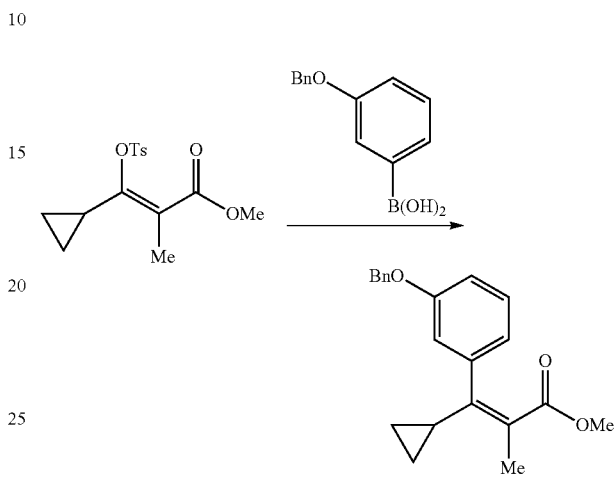

(Z)-methyl 3-cyclopropyl-2-methyl-3-(tosyloxy)acrylate (1.03 g) dissolved in MeCN (10 mL), then aq potassium phosphate (1 M, 10 mL) was added, followed by (3-(benzyloxy)phenyl)boronic acid (1 g). The resulting slurry was degassed with a nitrogen stream for 30 min, then Cataxium Precatalyst (100 mg) was added and the reaction was heated to 35° C. for 14 h. Then the slurry was filtered through Celite™, and the Celite™ was washed with EtOAc (20 mL), then EtOAc (40 mL) and water (50 mL) were added to the filtrate. The aqueous layer was separated, and extracted once with EtOAc (20 mL). The combined organic layers were washed with water (50 mL) and brine (20 mL), then concentrated to give the crude product, which was purified via ISCO silica column (40 g, diluted with 0-30% Hexanes/EtOA) to give the title product.

Step 4: (2S,3R)-methyl 3-(3-(benzyloxy)phenyl)-3-cyclopropyl-2-methylpropanoate

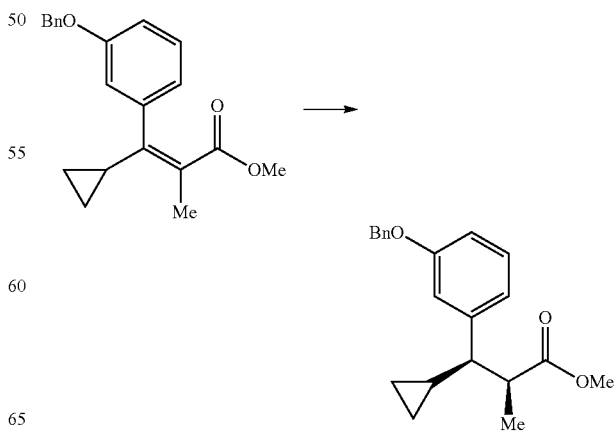

Bis(2-methylallyl)(1,5-cyclooctadiene)Ruthenium (II) (1.0 g) and Josiphos (1.86 g) were added to DCM (12 mL) and agitated for 20 min at rt. Then tetrafluoroboric acid-diethyl ether complex (1.0 g) was added slowly and stirred for 20 min at rt. The reaction mixture was diluted with DCM (100 mL) and added to a catalyst bomb with a MeOH rinse. Then (Z)-methyl 3-(3-(benzyloxy)phenyl)-3-cyclopropyl-2-methylacrylate (2.57 g, 7.97 mmol) was added to the catalyst bomb with MeOH (200 mL) and agitated to dissolve, The catalyst bomb was pressurized to 500 psi with hydrogen, then heated to 80° C. and shaken for 20 h. Then the reaction was cooled, filtered through Celite™ and washed with MeOH The filtrate was concentrated to give the crude product.

Step 5: (2S,3R)-methyl 3-cyclopropyl-3-(3-hydroxyphenyl)-2-methylpropanoate

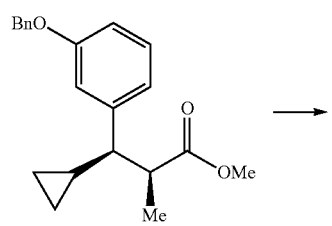

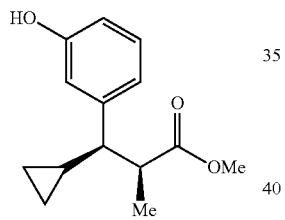

Charged (2S,3S)-methyl 3-(3-(benzyloxy)phenyl)-3-cyclopropyl-2-methylpropanoate (4.81 g, 13 mmol) and methanol (67 ml) to 25 ml glass shaker vessel, followed by the addition of 8% Pd-2% Pt/C—(1.5 g, 35 wt % loading, 50 w/w, Johnson Matthey lot# F27N23). Then the vessel was purged with nitrogen and vacuum three times, and charged with 50 psig of hydrogen gas. The reaction was heated to 25° C. for 6 h, then filtered through Celite™, which was washed with MeOH (50 mL). The filtrate is concentrated to give the title compound.

Intermediate 7

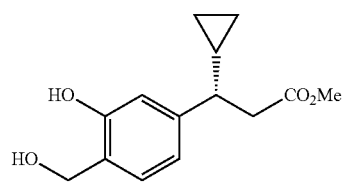 [SMILES: COC(=O)C[C@H](c1ccc(CO)c(O)c1)C1CC1]

(S)-methyl 3-cyclopropyl-3-(3-hydroxy-4-(hydroxymethyl)phenyl)propanoate

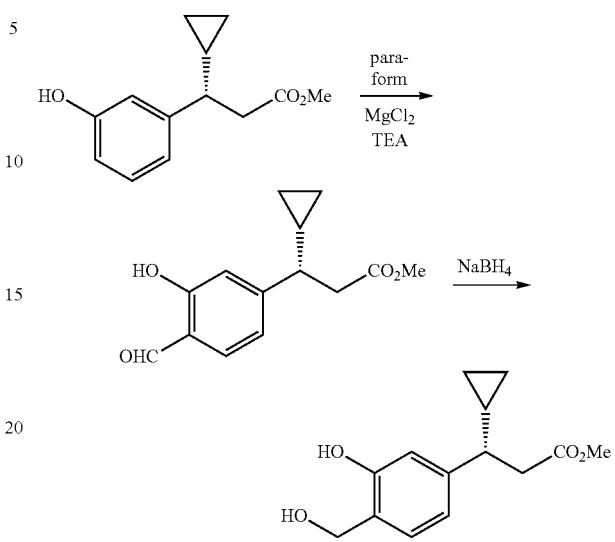

(S)-methyl 3-cyclopropyl-3-(3-hydroxy-4-(hydroxymethyl)phenyl)propanoate was prepared in the same manner as in INTERMEDIATE 6, starting from an appropriate starting material. $^1$H NMR (500 MHz, CDCl$_3$) δ6.94 (d, 1H), 6.72 (s, 1H), 6.69 (d, 1H), 4.80 (s, 2H), 3.60 (s, 3H), 2.74 (m, 2H), 2.24 (q, 1H), 0.97 (m, 1H), 0.58 (m, 1H), 0.40 (m, 1H), 0.21 (m, 1H), 0.11 (m, 1H).

Intermediate 8

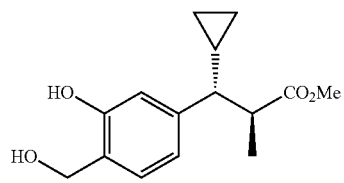 [SMILES: COC(=O)[C@@H](C)[C@H](c1ccc(CO)c(O)c1)C1CC1]

(2S,3R)-methyl 3-cyclopropyl-3-(3-hydroxy-4-(hydroxymethyl)phenyl)-2-methylpropanoate The title compound was prepared in the same manner as INTERMEDIATE 6, starting from an appropriate starting material. $^1$H NMR (500 MHz, CDCl$_3$) δ7.00 (d, 1H), 6.74 (s, 1H), 6.65 (d, 1H), 4.88 (s, 2H), 3.75 (s, 3H), 2.80 (m, 1H), 1.80 (t, 1H), 1.05 (m, 1H), 0.95 (d, 3H), 0.57 (m, 1H), 0.35 (m, 1H), 0.25 (m, 1H), 0.01 (m, 1H).

Intermediate 9

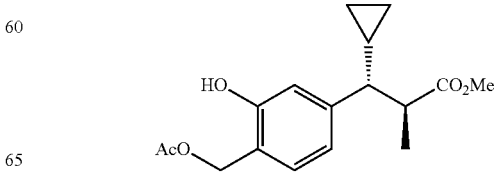

(2S,3R)-methyl 3-(4-(acetoxymethyl)-3-hydroxyphenyl)-3-cyclopropyl-2-methylpropanoate

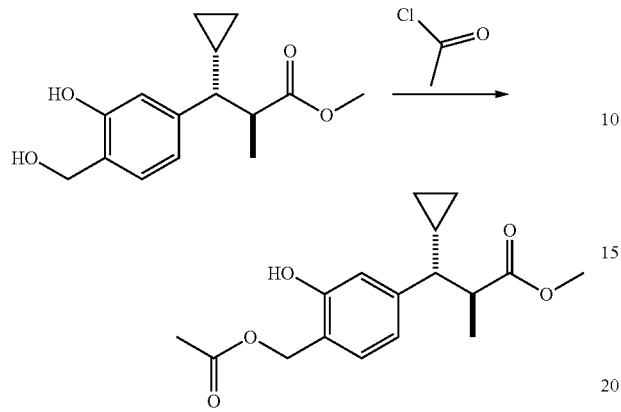

Pyridine (4.0 ml, 49.5 mmol) was added dropwise to a stirred, cooled (0° C.) mixture of (2S,3R)-methyl 3-cyclopropyl-3-(3-hydroxy-4-(hydroxymethyl)phenyl)-2-methylpropanoate (10.94 g, 41.4 mmol) in $CH_2Cl_2$ (200 ml) at 0° C. Then a solution of acetyl chloride (2.94 ml, 41.4 mmol) in $CH_2Cl_2$ (7 mL) was added dropwise to the reaction mixture, and the reaction was stirred at 0° C. for 10 min. The reaction was then partitioned between DCM and saturated $NH_4Cl$. The layers were separated and the organic layer was washed with brine, dried over $MgSO_4$, filtered and concentrated in vacuo. The resulting residue was purified via MPLC (ISCO 220 g; product eluted at 28% EtOAc/hexane) with gradient elution 0-100% EtOAc/hexane to give the title compound. $^1$H NMR (500 MHz, $CHCl_3$-d): 0.01 (m, 1H), 0.23 (dq, 1H), 0.35-0.29 (m, 1H), 0.57-0.52 (m, 1H), 0.93 (d, 3H), 1.02 (m, 1H), 1.87 (t, 1H), 2.12 (s, 3H), 2.82-2.76 (m, 1H), 3.72 (s, 3H), 5.09 (s, 2H), 6.70 (d, 1H), 6.76 (s, 1H), 7.18 (d, 1H), 7.91 (s, 1H).

Scheme 6

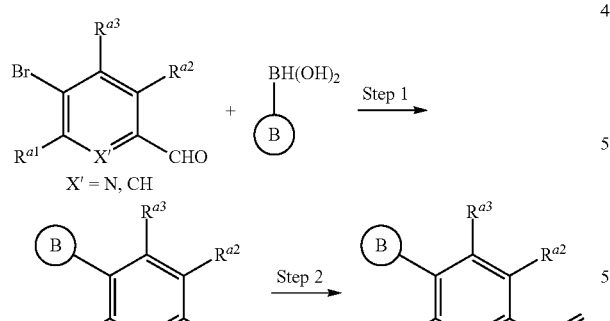

Step 1: Method A: Pd(PPh)$_4$, 3M K$_2$CO$_3$, dioxane; 100° C.; Method B: PdCl$_2$(PPh$_3$)$_2$, AcCN, 1M Na$_2$CO$_3$, 65° C; Method C: Sphos precatalyst, 3M K$_3$PO$_4$, THF, 80° C.
Step 2: KOtBu, THF, MePPh$_3$Br.

The styrene intermediates may be prepared as shown in Scheme 6. In Step 1, the bromide is converted to an aryl group using Suzuki cross-coupling conditions Method A, B or C. The aldehyde is then converted to a vinyl group through a Wittig reaction in Step 2.

Intermediate 10

5'-fluoro-2'-methoxy-6-vinyl-3,4'-bipyridine

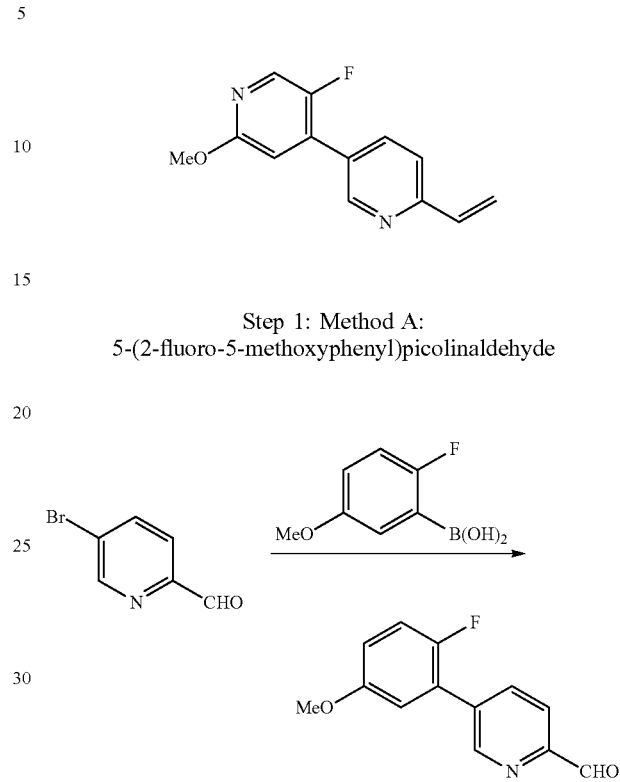

Step 1: Method A:
5-(2-fluoro-5-methoxyphenyl)picolinaldehyde

To a microwave vial charged with 5-bromopicolinaldehyde (1.2 g, 6.45 mmol), Pd(PPh$_3$)$_4$ (0.373 g, 0.323 mmol), and (2-fluoro-5-methoxyphenyl)boronic acid (1.645 g, 9.68 mmol) was added 1,4-Dioxane (12 ml). The resulting mixture was evacuated and filled with N$_2$ (3×). A 3 M aqueous solution of K$_2$CO$_3$ (4.30 ml, 12.90 mmol) was added to the reaction mixture, and the reaction was evacuated and filled with N$_2$ (3×), then sealed and heated to 100° C. for 2 h. Then the reaction was cooled to ambient temperature and partitioned between EtOAc and saturated NH$_4$Cl. The aqueous layer was separated and back-extracted with EtOAc. The combined organic layers were washed with brine, dried over Na$_2$SO$_4$, and concentrated in vacuo. The resulting residue was purified via MPLC (ISCO 40 g; product eluted at 15% EtOAc/hexane) with gradient elution 0-30% EtOAc/hexane to give the title compound. $^1$H NMR (500 MHz, Acetone-d$_6$): 7.09-7.05 (m, 1H), 7.28-7.18 (2H, m), 8.04 (dd, 1H), 8.24-8.22 (m, 1H), 9.01-9.00 (m, 1H), 10.06 (s, 1H).

Step 1: Method B: 2-fluoro-4-(5-fluoro-2-methoxypyridin-4-yl)benzaldehyde

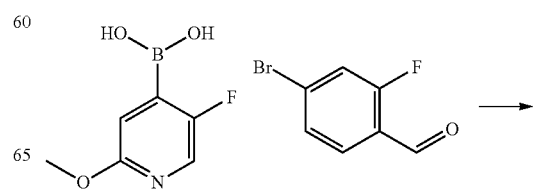

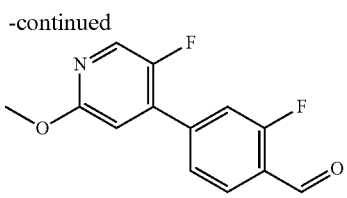

A microwave vial equipped with a stirrer bar was charged with 4-bromo-2-fluoro-benzaldehyde (0.426 g, 2.1 mmol), 5-fluoro-2-methoxypyridine-4-boronic acid (0.4307 g, 2.52 mmol), and Bis(triphenylphosphine)palladium (II) dichloride (0.147 g, 0.210 mmol). The reaction was evacuated and filled with $N_2$ (3×). Then acetonitrile (10.50 ml) was added, followed by the addition of a 1 M aqueous solution of sodium carbonate (5.25 ml, 5.25 mmol), which had been sparged with $N_2$ for 5 min. The reaction was evacuated and filled with $N_2$ (3 s), then sealed, and heated to 65° C. for 17 h. Then the reaction was partitioned between EtOAc and water. The organic layer was separated and washed with brine, dried over $MgSO_2$, and concentrated in vacuo. The resulting residue was purified via MPLC (ISCO 24 g; product eluted at 14% EtOAc/hexane) with gradient elution 0-30% EtOAc/hexane to give the title compound. $^1$H NMR (500 MHz, CHCl$_3$-d): 3.95 (s, 3H), 6.81 (d, 1H), 7.47-7.38 (m, 2H), 7.97 (t, 1H), 8.11 (d, 1H), 10.41 (s, 1H).

Step 1: Method C: 5'-fluoro-2'-methoxy-[3,4'-bipyridine]-6-carbaldehyde

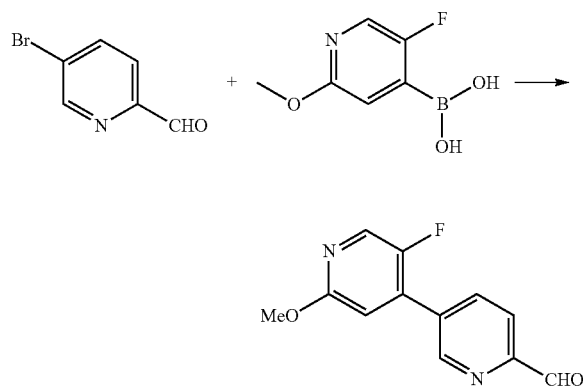 [SMILES: O=Cc1ccc(Br)cn1 ; COc1cc(B(O)O)c(F)cn1 ; COc1cc(-c2ccc(C=O)nc2)c(F)cn1]

To a microwave vial containing a mixture of 5-bromopicolinaldehyde (1.5 g, 8.06 mmol), (5-fluoro-2-methoxypyridin-4-yl)boronic acid (1.68 g, 9.83 mmol), and S-Phos Second Generation Precatalyst (0.291 g, 0.403 mmol), which had been evacuated and filled with $N_2$ (3×), was added a $N_2$-sparged mixture of THF (40.3 mL)/3M aqueous solution of potassium phosphate tribasic (8.06 mL, 24.19 mmol). The reaction vessel was evacuated and filled with $N_2$ (3×), then heated in a heating block to 80° C. for 2 h. The reaction was then cooled to ambient temperature and partitioned between EtOAc and saturated $NH_4Cl$. The organic layer was separated and washed with brine, dried over $MgSO_4$, and concentrated in vacuo. The resulting crude residue was purified via MPLC (ISCO 80 g; product eluted at 24% EtOAc/hexane) with gradient elution 0-50% EtOAc/hexane to give the title compound. $^1$H NMR (500 MHz, CHCl$_3$-d): 3.96 (s, 3H), 6.85 (d, 1H), 8.10-8.06 (m, 2H), 8.15 (d, 1H), 8.98 (s, 1H), 10.13 (s, 1H).

Step 2: 5'-fluoro-2'-methoxy-6-vinyl-3,4'-bipyridine

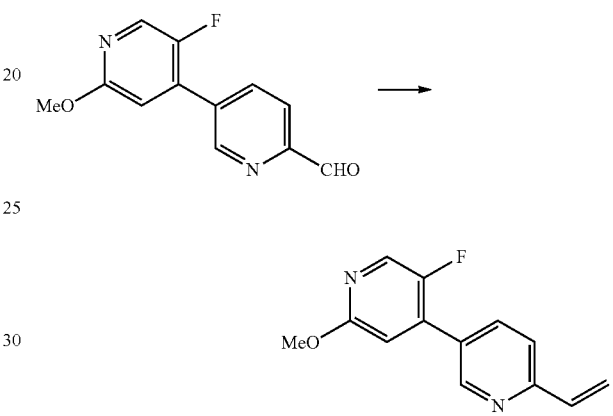

To a cooled mixture of methyltriphenylphosphonium bromide (2.214 g, 6.20 mmol) in THF (20 mL) at 0° C. in/$N_2$ was added dropwise a 1 M solution of potassium tert-butoxide in THF (6.20 ml, 6.20 mmol). The resulting mixture was stirred at 0° C. for 30 min. before adding a solution of 5'-fluoro-2'-methoxy-[3,4'-bipyridine]-6-carbaldehyde (1.1072 g, 4.77 mmol) in THF (10 mL) dropwise. The ice bath was removed, and the reaction mixture was warmed to r.t. and stirred for 10 min. Then the reaction mixture was partitioned between EtOAc and saturated $NH_4Cl$. The aqueous layer was separated and back-extracted with EtOAc. The combined organic layers were washed with brine, dried over $MgSO_4$, and concentrated in vacuo. The resulting residue was purified via MPLC (ISCO 40 g; product eluted at 20% EtOAc/hexane) with gradient elution 0-40% EtOAc/hexane to give the title compound. $^1$H NMR (500 MHz, CHCl$_3$-d): 3.95 (s, 3H), 5.57 (dd, 1H, J=10.79, 1.12 Hz), 6.30 (dd, 1H, J=17.46, 1.13 Hz), 6.89-6.81 (m, 2H), 7.44 (d, 1H), 7.88 (dt, 1H, J=8.17, 1.97 Hz), 8.09 (d, 1H), 8.78 (s, 1H).

Scheme 7

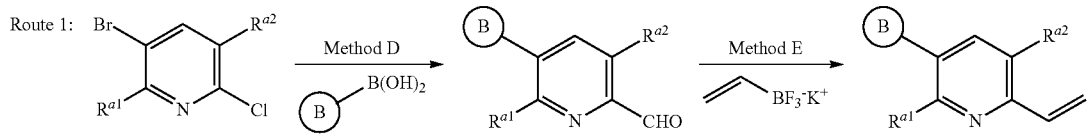

Route 2: 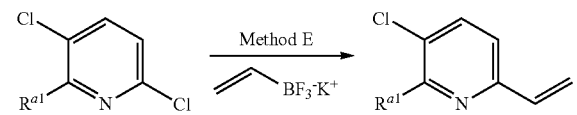

Route 3: 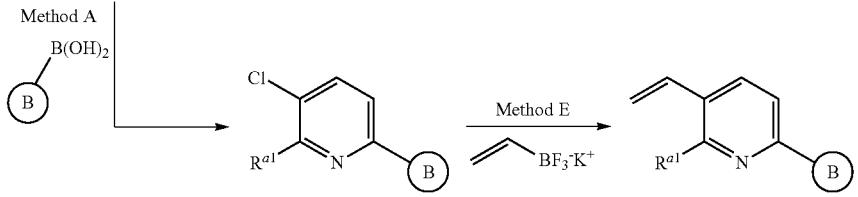

Method A: Pd(PPh₃)₄, 3M K₂CO₃, dioxane; Method C: S-Phos precat., 3M K₃PO₄, THF; Method D: Pd(tBu₂P)₂FerrCl₂, K₂CO₃, THF; Method E: PdCl₂(dppf)₂CH₂Cl₂, NEt₃, 1-propanol.

Vinylpyridine intermediates may be prepared as shown in Scheme 7. In Route 1, site-selective Suzuki cross-coupling of a 2-chloro-3-bromopyridine with an arylboronic acid delivers the biaryl intermediate. Suzuki vinylation of this chloropyridine then delivers the vinylpyridine. In Route 2, vinylation of a 2,5-dichloropyidine preceeds the Suzuki cross-coupling with an arylboronic acid to give the vinylpyridine intermediate. Finally, in Route 3, arylation at the "2" position of the pyridyl ring was followed by vinylation at the "5" position to give regioisomeric vinylpyridines.

Intermediate 11

3-fluoro-5-(2-fluoro-5-methoxyphenyl)-6-methyl-2-vinylpyridine

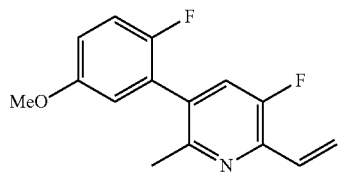 [SMILES: C=Cc1nc(C)c(-c2cc(OC)ccc2F)cc1F]

Method D: 2-chloro-3-fluoro-5-(2-fluoro-5-methoxyphenyl)-6-methylpyridine

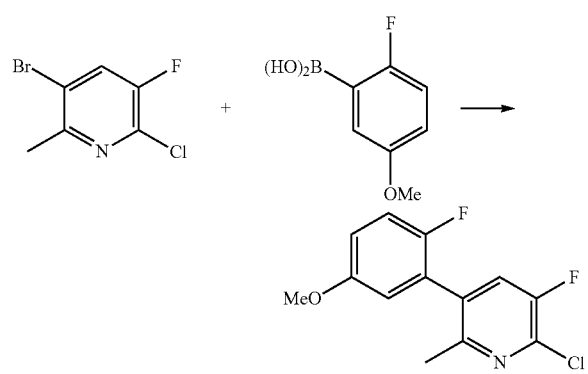

$Pd(t-Bu_2P)_2FerrCl_2$ (0.050 g, 0.073 mmol) was added to a stirred, degassed mixture of 3-bromo-6-chloro-5-fluoro-2-methylpyridine (0.329 g, 1.466 mmol), (2-fluoro-5-methoxyphenyl)boronic acid (0.249 g, 1.466 mmol) and $K_2CO_3$ (0.810 g, 5.86 mmol) in THF (7.5 ml). The reaction was sealed and stirred at room temperature for 14 h. Then water was added to the reaction and the mixture was extracted with EtOAc (2×). The combined organic layers were washed with brine, dried over $MgSO_4$, filtered and evaporated under reduced pressure. The resulting residue was purified via MPLC (ISCO 40 g, product eluted at 16% EtOAc/hexane) with gradient elution 0-40% EtOAc/hexane to give the title compound. $^1$H NMR (500 MHz, $CHCl_3$-d: 2.40 (s, 3H), 3.81 (s, 3H), 6.72 (dd, 1H), 6.94-6.87 (m, 1H), 7.10 (t, 1H), 7.35 (d, 1H); LC/MS (m/z): 270.2 (M+H)⁺.

Method E: 3-fluoro-5-(2-fluoro-5-methoxyphenyl)-6-methyl-2-vinylpyridine

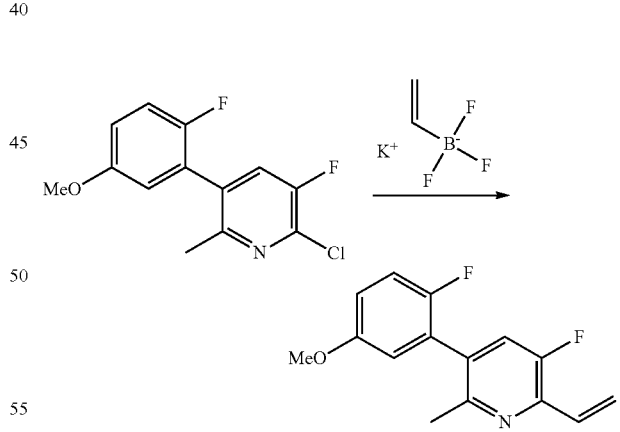

A microwave vial equipped with a stirrer bar was charged with 2-chloro-3-fluoro-5-(2-fluoro-5-methoxyphenyl)-6-methylpyridine (0.2289 g, 0.849 mmol), potassium vinyl-fluoroborate (0.119 g, 0.891 mmol), 1,1'-bis(diphenylphosphino)ferrocene palladium (II) dichloride dichloromethane complex (0.035 g, 0.042 mmol), 1-Propanol (4.24 ml), and TEA (0.118 ml, 0.849 mmol). The reaction mixture was purged with $N_2$ for 5 min, then the vial was sealed, and the reaction was heated to 100° C. in a heating block for 5 h. Then the reaction mixture was partitioned between EtOAc and brine. The organic layer was separated, dried over MgSO$_4$, and concentrated in vacuo The resulting product was purified via MPLC (ISCO 24 g, product eluted at 14% EtOAc/hexane) with gradient elution 0-40% EtOAc/hexane to give the title compound. $^1$H NMR (500 MHz, CHCl$_3$-d): 2.43 (s, 3H), 3.82 (s, 3H), 5.62 (dd, 1H, J=11.02, 1.84 Hz), 6.47 (dd, 1H, J=17.44, 1.83 Hz), 6.74 (dd, 1H, J=5.88, 3.15 Hz), 6.93-6.89 (m, 1H), 7.09-6.98 (m, 2H), 7.25 (d, 1H); LC/MS (m/z): 262.4 (M+H)$^+$.

(23 ml, 23.00 mmol). The reaction was allowed to warm to ambient temperature and stirred for 20 h. Then the reaction was quenched with MeOH and the mixture was heated to 80° C. for 1 h. The reaction mixture was concentrated in vacuo. The resulting residue was preabsorbed onto Celite™ with MeOH for solid phase loading and purified via MPLC (ISCO 40 g, product eluted at 47% EtOAc/hexane) with gradient elution 0-100% EtOAc/hexane to give the title Scheme 8

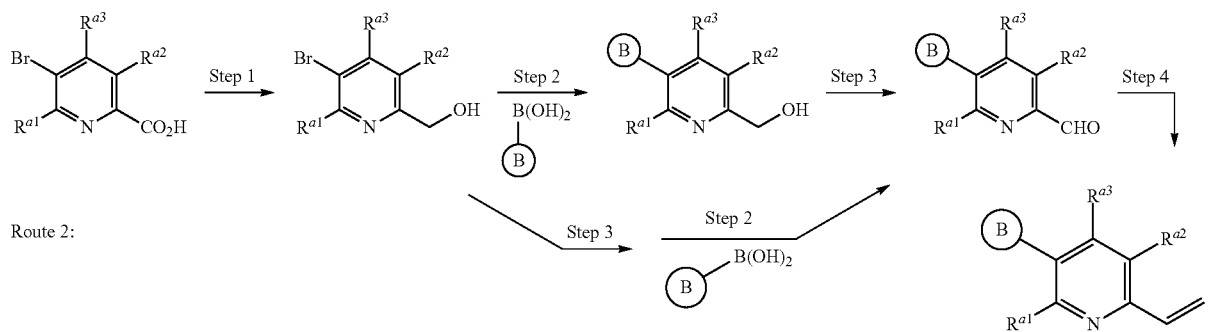

Step 1: BH$_3$—THF; Step 2: Pd(PPh$_3$)$_4$, 3M K$_2$CO$_3$, dioxane, Step 3: Dess-Martin Periodinane, DCM; Step 4: KOtBu, THF, MePPh$_3$Br Scheme 8 provides two additional synthetic routes (Route 1 and Route 2) for the preparation of vinylpyridine intermediates. Reduction of the carboxylic acid to the methyl alcohol is followed by cross-coupling at the bromo position to give the biaryl intermediate. Oxidation of the methyl alcohol then gives the aldehyde. Wittig olefination of the aldehyde provides the vinylpyridine.

Intermediate 12

3-fluoro-5-(2-fluoro-5-methoxyphenyl)-2-vinylpyridine

Step 1: (5-bromo-3-fluoropyridin-2-yl)methanol

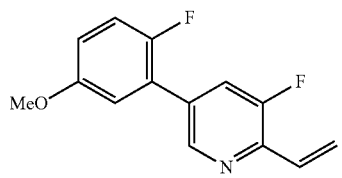

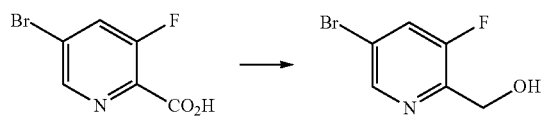 [SMILES: O=C(O)c1ncc(Br)cc1F ; OCc1ncc(Br)cc1F]

To a solution of 5-bromo-3-fluoropyridine-2-carboxylic acid (2.02 g, 9.18 mmol) in THF (20 ml) was added dropwise at 0° C. under N$_2$, borane tetrahydrofuran complex compound. $^1$H NMR (500 MHz, CHCl$_3$-d): 4.78 (s, 2H), 7.59 (dt, 1H, J=8.51, 1.94 Hz), 8.47 (s, 1H); LC/MS (m/z): 206.1 (M+H)$^+$.

Step 2: (3-fluoro-5-(2-fluoro-5-methoxyphenyl)pyridin-2-yl)methanol

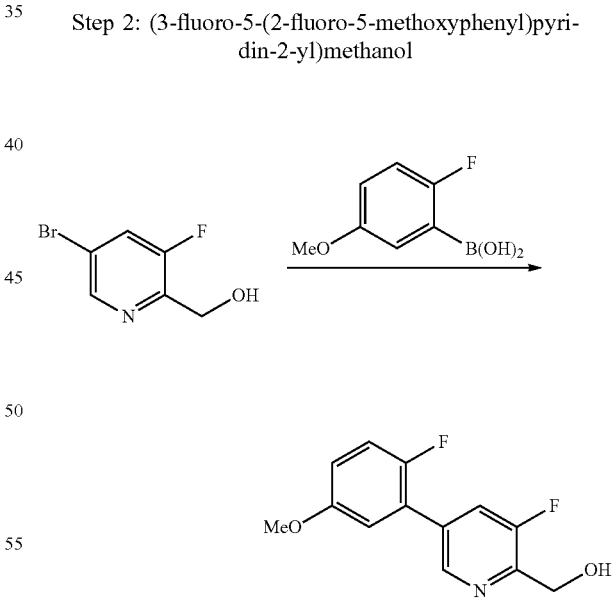

Utilizing the procedure of Intermediate 10 Step 1 Method A, (5-bromo-3-fluoropyridin-2-yl)methanol (0.8288 g, 4.02 mmol) was coupled with (2-fluoro-5-methoxyphenyl)boronic acid (1.013 g, 5.96 mmol) to give the title compound. $^1$H NMR (500 MHz, Acetone-d$_6$): 3.86 (s, 3H), 4.36 (t, 1H), 4.79 (dd, 2H, J=5.85, 1.93 Hz), 7.02 (ddd, 1H, J=9.03, 3.88, 3.18 Hz), 7.24-7.14 (m, 2H), 7.80 (dt, 1H, J=10.74, 1.54 Hz), 8.60 (q, 1H, J=1.64).

101

Step 3: 3-fluoro-5-(2-fluoro-5-methoxyphenyl)pico-
linaldehyde

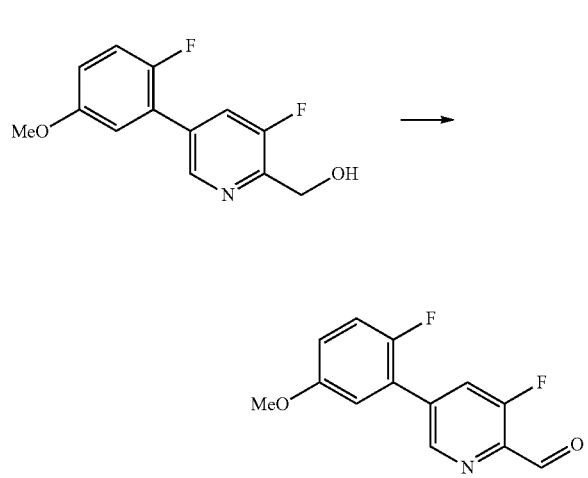

To a solution of (3-fluoro-5-(2-fluoro-5-methoxyphenyl) pyridin-2-yl)methanol (0.6413 g, 2.55 mmol) in DCM (17 ml) was added Dess-Martin Periodinane (2.165 g, 5.11 mmol) in a single portion. After 2 h, the reaction was diluted with Et$_2$O, and quenched with 5% Na$_2$SO$_3$/saturated NaHCO$_3$ (1:1). The layers were separated and the aqueous layer was back-extracted with Et$_2$O (2×). The combined organic layers were washed with brine, dried over MgSO$_4$, and concentrated in vacuo. The resulting residue was purified via MPLC (ISCO 40 g, product eluted at 33% EtOAc/hexane) with gradient elution 0-100% EtOAc/hexane to give the title compound. $^1$H NMR (500 MHz, Acetone-d$_6$): 3.90 (s, 3H), 7.12 (dt, 1H, J=9.03, 3.55 Hz), 7.31-7.26 (2H, m), 8.07 (d, 1H, J=11.62 Hz), 8.89 (s, 1H), 10.15 (s, 1H).

Step 4: 3-fluoro-5-(2-fluoro-5-methoxyphenyl)-2-
vinylpyridine

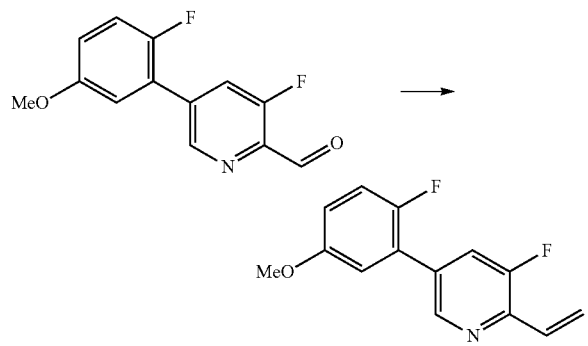

Utilizing the procedure from INTERMEDIATE 10 Step 2, 3-fluoro-5-(2-fluoro-5-methoxyphenyl)-2-vinylpyridine was prepared starting from 3-fluoro-5-(2-fluoro-5-methoxyphenyl)picolinaldehyde. $^1$H NMR (500 MHz, Acetone-d$_6$): 3.23 (s, 3H), 5.62 (dd, 1H, J=10.87, 2.03 Hz), 6.48 (dd, 1H, J=17.32, 2.00 Hz), 7.06-6.99 (m, 2H), 7.22-7.14 (m, 2H), 7.80 (d, 1H, J=11.54), 8.63 (s, 1H).

102

Intermediate 13

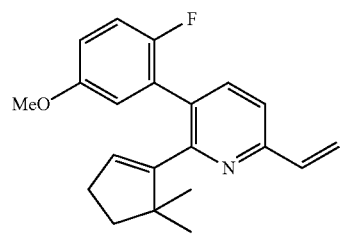 [SMILES: C=Cc1ccc(-c2cc(OC)ccc2F)c(C2=CCCC2(C)C)n1]

Step 1: Methyl 5-chloro-6-(5,5-dimethylcyclopent-
1-en-1-yl)picolinate

A microwave vial was charged with methyl 6-bromo-5-chloropicolinate (0.674 g, 2.69 mmol), 2-(5,5-dimethylcyclopent-1-en-1-yl)-4,4,5,5-tetramethyl-1,3,2-dioxaborolane (0.5 g, 2.25 mmol, prepared according to procedure in ACS Medicinal Chemistry Letters, 3(9), 726-730, 2012), and 1,1'-bis(di-tert-butylphosphino)ferrocene palladium dichloride (0.147 g, 0.225 mmol). The reaction was evacuated and filled with N$_2$ (3×). Then NMP (16 ml) was added and the reaction sparged with N$_2$ for 5 min. Subsequently, a 1 M aqueous solution of potassium phosphate tribasic (4.50 ml, 4.50 mmol) was added, and the reaction was sealed and heated at 85° C. for 2 h. Then the reaction was partitioned between Et$_2$O and water. The aqueous phase was separated and back-extracted with Et$_2$O (2×). The combined organic layers were washed with brine, dried over MgSO$_4$, and concentrated in vacuo. The resulting crude product was purified via MPLC (ISCO 24 g, product eluted at 10% EtOAc/hexane) with gradient elution 0-40% EtOAc/hexane to give the title compound. $^1$H NMR (500 MHz, CHCl$_3$-d): 1.25 (s, 6H), 1.89 (m, 2H), 2.51 (m, 2H), 3.96 (s, 3H), 6.07 (s, 1H), 7.82 (d, 1H), 7.90 (d, 1H). LC/MS (m/z): 266.3 (M+H)$^+$.

Step 2: 5-chloro-6-(5,5-dimethylcyclopent-1-en-1-
yl)picolinaldehyde

To a solution of methyl 5-chloro-6-(5,5-dimethylcyclopent-1-en-1-yl)picolinate (0.508 g, 1.912 mmol) in CH$_2$Cl$_2$ (10 ml) at −78° C. was added dropwise a 1M solution of DIBAL-H in CH$_2$Cl$_2$ (1.912 ml, 1.912 mmol). After 5 min., additional DIBAL-H solution (1.0 mL). Then the reaction was quenched with MeOH (2.5 mL), followed by the addition of 25% aqueous potassium sodium tartrate solution (7.5 mL). Then the cooling bath was removed and replaced with an ice/water bath. The reaction was stirred at 0° C. for 1 h, then filtered through Celite™ and the Celite™ pad was washed with EtOAc. The filtrate was partitioned between EtOAc and brine. The organic layer was separated, dried over MgSO$_4$, and concentrated in vacuo. The resulting crude product was purified via MPLC (ISCO 24 g, product eluted at 16% EtOAc/hexane) with gradient elution 0-60% EtOAc/hexane to give the title compound. $^1$H NMR (500 MHz, CHCl$_3$-d): 1.26 (s, 6H), 1.91 (t, 2H, J=2.49, 7.05 Hz), 2.54 (td, 2H, J=7.06, 2.57 Hz), 6.15 (t, 1H, J=2.56), 7.75 (d, 1H, J=8.20), 7.87 (dd, 1H, J=8.20, 0.88 Hz), 10.01 (d, 1H, J=0.88).

Step 3: 6-(5,5-dimethylcyclopent-1-en-1-yl)-5-(2-
fluoro-5-methoxyphenyl)-picolinaldehyde Utilizing the procedure described in Scheme 6, Step 1, Method C, 5-chloro-6-(5,5-dimethylcyclopent-1-en-1-yl)picolinaldehyde (0.1371 g, 0.582 mmol) was coupled with (2-fluoro-5-methoxyphenyl)boronic acid (0.148 g, 0.872 mmol) to give the title compound. ¹H NMR (500 MHz, CHCl₃-d): 1.33 (s, 6H), 1.76 (t, 2H, J=6.97), 2.21 (td, 2H, J=6.97, 2.62 Hz), 3.79 (s, 3H), 5.46 (t, 1H, J=2.60), 6.75 (dd, 1H, J=5.83, 3.14 Hz), 6.87-6.82 (m, 1H), 7.00 (t, 1H), 7.72 (d, 1H), 7.84 (d, 1H), 10.09 (s, 1H).

Step 4: 2-(5,5-dimethylcyclopent-1-en-1-yl)-3-(2-fluoro-5-methoxyphenyl)-6-vinylpyridine Utilizing the procedure described in Scheme 6, Step 2, 2-(5,5-dimethylcyclopent-1-en-1-yl)-3-(2-fluoro-5-methoxyphenyl)-6-vinylpyridine was prepared starting from 6-(5,5-dimethylcyclopent-1-en-1-yl)-5-(2-fluoro-5-methoxyphenyl)picolinaldehyde. ¹H NMR (500 MHz, CHCl₃-d): 1.33 (s, 6H), 1.72 (t, 3H), 2.17 (td, 2H), 3.78 (s, 3H), 5.37 (t, 1H), 5.46 (dd, 1H), 6.31 (dd, 1H), 6.74 (dd, 1H), 6.85-6.78 (m, 2H), 6.97 (t, 1H), 7.17 (d, 1H), 7.50 (d, 1H).

Scheme 9

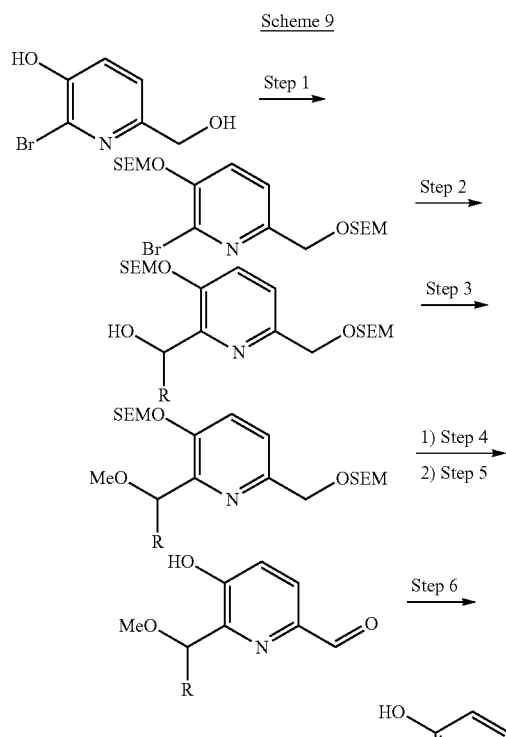

Step 1: SEMCl, NaH, THF; Step 2: 1) nBuLi, THF, -78° C., 2) RCHO; Step 3: NaH, MeI, DMF; Step 4: 4M HCl/dioxane, 65° C.; Step 5: MnO₂ iPrOH, reflux; Step 6: KOtBu, THF, MePPh₃Br.

Scheme 9 provides a general synthetic procedure for making 3-hydroxyl-2-vinylpyridines, such as Intermediate 14. Bis-protection of the starting diol is followed by metal-halide exchange and subsequent reaction with an aldehyde to give the secondary alcohol. Methylation of the alcohol is followed by deprotection. The resulting diol is selectively oxidized to give the hydroxy aldehyde. Wittig olefination of this intermediate provides the 3-hydroxyl-2-vinylpyridines.

Intermediate 14

2-(1-methoxy-2,2-dimethylpropyl)-6-vinylpyridin-3-ol

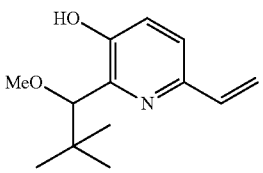 [SMILES: C=Cc1ccc(O)c(C(OC)C(C)(C)C)n1]

Step 1: 2-bromo-3-((2-(trimethylsilyl)ethoxy)methoxy)-6-((2-(trimethylsilyl)-ethoxy)methoxy)methyl)pyridine

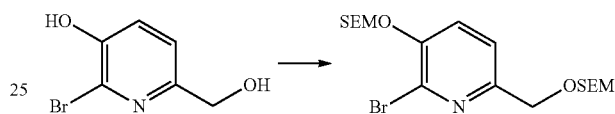

To a solution of 2-bromo-6-(hydroxymethyl)pyridin-3-ol (0.97 g, 4.75 mmol) in THF (24 ml) at 0° C. was added NaH (0.666 g, 16.64 mmol) in several portions. After gas evolution ceased, SEM-Cl (1.855 ml, 10.46 mmol) was added dropwise under N₂. Then the ice bath was removed and the reaction was stirred at ambient temperature for 19 h. The reaction was then quenched with the slow addition of ice-cold water. The reaction mixture was extracted with EtOAc (2×). The combined organic layers were washed with brine, dried over MgSO₄, and concentrated in vacuo. The resulting residue was purified via MPLC (ISCO 80 g, product eluted at 10% EtOAc/hexane) with gradient elution 0-30% EtOAc/hexane to give the title compound. ¹H NMR (500 MHz, CHCl₃-d): 0.01 (2s, 18H), 0.97-0.93 (m, 4H), 3.66 (t, 2H), 3.80 (t, 2H), 4.65 (s, 2H), 4.80 (s, 2H), 5.31 (s, 2H), 7.33 (d, 1H), 7.45 (d, 1H).

Step 2: 2,2-dimethyl-1-(3-((2-(trimethylsilyl)ethoxy)methoxy)-6-((2-(trimethylsilyl)-ethoxy)methoxy)methyl)pyridin-2-yl)propan-1-ol

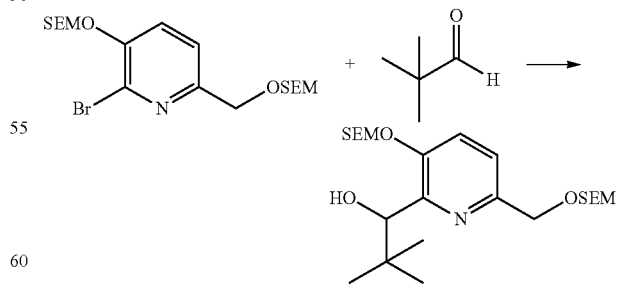

To a solution of 2-bromo-3-((2-(trimethylsilyl)ethoxy)methoxy)-6-(((2-(trimethyl-silyl)ethoxy)methoxy)methyl)pyridine (1.0489 g, 2.258 mmol, azeotroped with toluene before use) in THF (15 ml) at −78° C. was added dropwise n-BuLi in hexanes (1.355 ml, 3.39 mmol) under N₂. After 1 h, trimethylacetaldehyde (0.556 ml, 4.97 mmol) was added, and the reaction was warmed to 0° C. After 25 min., the reaction was warmed to ambient temperature and stirred for 30 min, then cooled to 0° C. and quenched by the a slow addition of saturated NH$_4$Cl. The reaction mixture was extracted with EtOAc (2×). The combined organic layers were washed with brine, dried over MgSO$_4$, and concentrated in vacuo. The resulting residue was purified via MPLC (ISCO 24 g; product eluted at 20% EtOAc/hexane) with gradient elution 0-40% EtOAc/hexane to give the title compound. $^1$H NMR (500 MHz, CHCl$_3$-d): 0.01 (2s, 18H), 0.92-0.90 (m, 13H), 3.76-3.67 (m, 4H), 4.04 (d, 1H, J=9.34), 4.67 (s, 2H), 4.82-4.74 (m, 3H), 5.24-5.19 (m, 2H), 7.25 (d, 1H), 7.48 (d, 1H); LC/MS (m/z): 472.8 (M+H)$^+$.

Step 3: 2-(1-methoxy-2,2-dimethylpropyl)-3-((2-(trimethylsilyl)ethoxy)methoxy)-6-((2-(trimethylsilyl)ethoxy)methoxy)methyl)pyridine

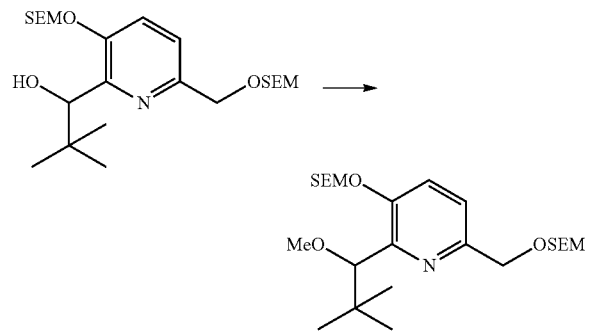

To a solution of 2,2-dimethyl-1-(3-((2-(trimethylsilyl)ethoxy)methoxy)-6-(((2-(trimethylsilyl)ethoxy)methoxy)methyl)pyridin-2-yl)propan-1-ol (0.89 g, 1.90 mmol) in DMF (9 mL) was added NaH (0.114 g, 2.85 mmol), followed by iodomethane (0.166 mL, 2.66 mmol) at ambient temperature under N$_2$. The reaction was stirred at ambient temperature for 14 h, then quenched by the slow addition of water. The reaction mixture was extracted with EtOAc. The organic layer was washed with brine, dried over MgSO$_4$, and concentrated in vacuo to give the title compound. LC/MS (m/z): 486.8 (M+H)$^+$.

Steps 4 and 5: 5-hydroxy-6-(1-methoxy-2,2-dimethylpropyl)picolinaldehyde

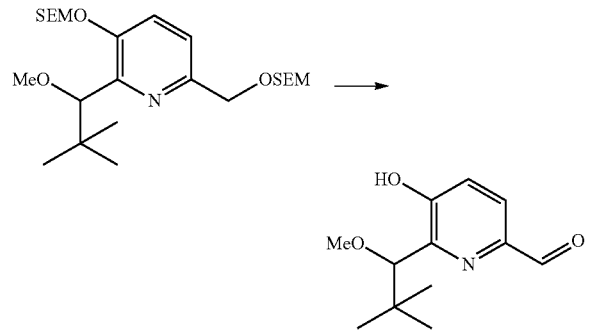

A solution of 2-(1-Methoxy-2,2-dimethylpropyl)-3-((2-(trimethylsilyl)ethoxy)methoxy)-6-(((2-(trimethylsilyl)ethoxy)methoxy)methyl)pyridine (0.923 g, 1.9 mmol) in 4 M HCl in dioxane (15 mL, 22 mmol) was heated to 65° C. for 20 min. Then the reaction was concentrated in vacuo to give an oil. The crude oil was dissolved in isopropyl alcohol (7.6 mL), and MnO$_2$ (1.5 g, 17.25 mmol) was added. The resulting mixture was heated to 90° C. for 1 h, then cooled to ambient temperature. The mixture was then transferred with MeOH to a centrifuge tube and centrifuged for 3 min. The supernatent was decanted and the solids were re-suspended in MeOH. The centrifugation was repeated twice. The supernatents were combined and concentrated in vacuo to give a crude oil, which was purified via MPLC (ISCO 40 g; product eluted at 15% EtOAc/hexane) with gradient elution 0-40% EtOAc/hexane to give the title compound. $^1$H NMR (500 MHz, CHCl$_3$-d): 0.99 (s, 9H), 3.52 (s, 3H), 4.27 (s, 1H), 7.25 (d, 1H), 7.87 (d, 1H), 9.15 (s, 1H), 9.92 (d, 1H).

Step 6: 2-(1-methoxy-2,2-dimethylpropyl)-6-vinylpyridin-3-ol

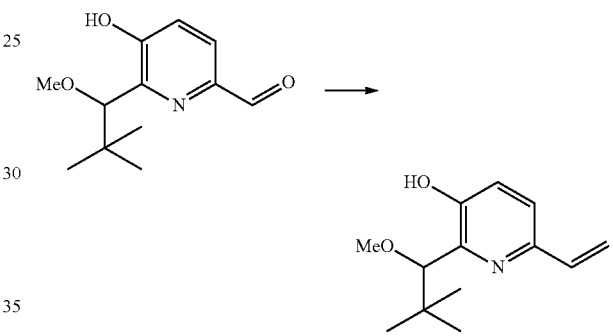

Utilizing the procedure described in Scheme 6 Step 2, with the exception of using 2.5 equivalents of methyltriphenylphosphonium bromide and potassium tert-butoxide, 2-(1-methoxy-2,2-dimethylpropyl)-6-vinylpyridin-3-ol was prepared starting from 5-hydroxy-6-(1-methoxy-2,2-dimethylpropyl)picolinaldehyde. $^1$H NMR (500 MHz, CHCl$_3$-d): 0.98 (s, 9H), 3.48 (s, 3H), 4.17 (s, 1H), 5.31 (d, 1H), 5.97 (d, 1H), 6.73 (dd, 1H), 7.10 (d, 1H), 7.20 (d, 1H), 8.53 (s, 1H).

Scheme 10

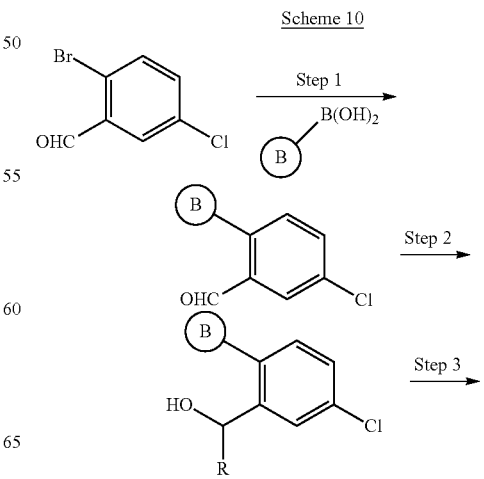

-continued

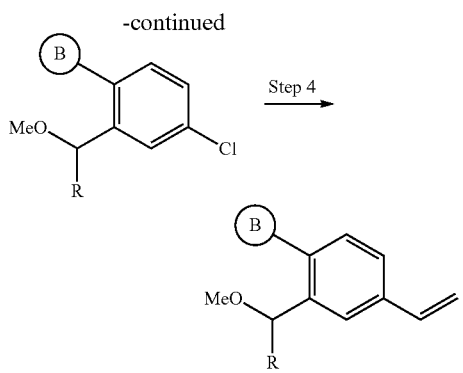

Step 1: Pd(PPh₃)₄, K₂CO₃ (aq), dioxane, 100° C.; Step 2: RMgBr or RMgCl, THF, 0° C.; Step 3: NaH, MeI, DMF; Step 4: vinyltributyltin, Pd(P t-Bu₃)₂, CsF, dioxane, 100° C.

Scheme 10 provides a synthetic procedure for making styrene intermediates, such as Intermediate 15. Site-selective cross-coupling of 2-bromo-5-chlorobenzaldehyde gives the biaryl intermediate. Grignard addition into the aldehyde gives the a secondary alcohol, which is then methylated. Stille vinylation at the chloro position gives the styrene intermediates.

Intermediate 15

2'-fluoro-5'-methoxy-2-(1-methoxy-2,2-dimethylpropyl)-4-vinyl-1,1'-biphenyl

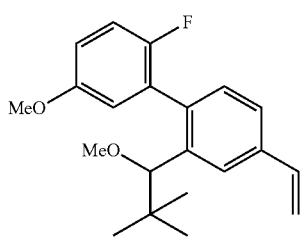 [SMILES: C=Cc1ccc(-c2cc(OC)ccc2F)c(C(OC)C(C)(C)C)c1]

Step 1: 4-chloro-2'-fluoro-5'-methoxy-[1,1'-biphenyl]-2-carbaldehyde

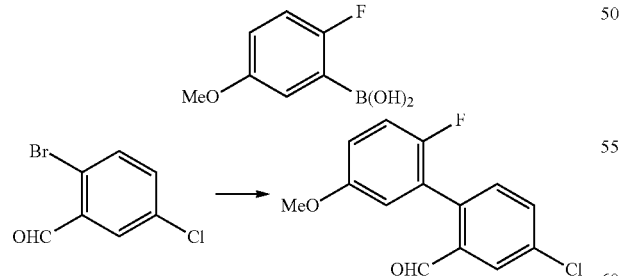

To a nitrogen-purged toluene solution of 2-bromo-5-chlorobenzaldehyde (785 mg, 3.58 mmol), Pd(PPh₃)₄ (207 mg, 0.179 mmol), and (2-fluoro-5-methoxyphenyl)boronic acid (669 mg, 3.93 mmol) was added K₂CO₃ (2.385 ml, 7.15 mmol, 2M solution in water). The reaction mixture was heated 100° C. on a heating block for 16 h, then the reaction was cooled to room temperature and poured into NH₄Cl (saturated, aqueous, 25 mL). The mixture was extracted with EtOAc (2×25 mL). The combined organic layers were dried (MgSO₄) and concentrated. The resulting residue was purified by HPLC (ISCO 120 g, 0 to 40% EtOAc/Hex) to give the title compound. ¹H NMR (500 MHz, CDCl₃) δ9.90 (s, 1H), 8.01 (s, 1H), 7.62 (d, 1H), 7.40 (d, 1H), 7.15 (t, 1H), 7.00 (t, 1H), 6.82 (d, 1H), 3.81 (s, 3H).

Step 2: 1-(4-chloro-2'-fluoro-5'-methoxy-[1,1'-biphenyl]-2-yl)-2,2-dimethylpropan-1-ol

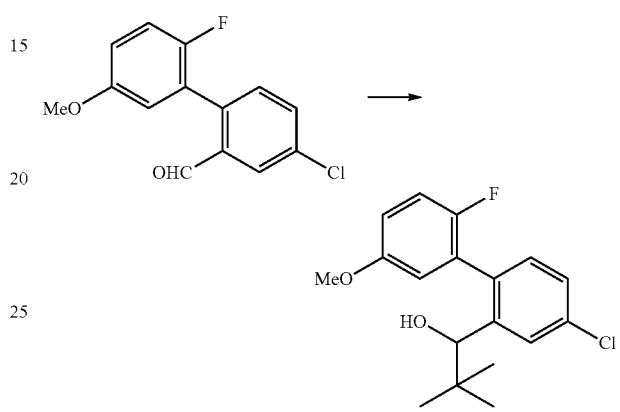

To a cooled (0° C.) THF (10 mL) solution of 4-chloro-2'-fluoro-5'-methoxy-[1,1'-biphenyl]-2-carbaldehyde (320 mg, 1.209 mmol) was added tert-butylmagnesium bromide (1.209 ml, 1.209 mmol) solution (1N, THF). After 2 h, the reaction was quenched by the slow addition of NH₄Cl (10 mL). The reaction mixture was then poured into water (25 mL) and extracted with EtOAc (2×25 mL). The combined organic layers were dried (MgSO₄) and concentrated. The resulting residue was purified by HPLC (ISCO 40 g, 0 to 40% EtOAc/Hex) to give the title compound. ¹H NMR (500 MHz, CDCl₃) δ7.68 (s, 1H), 7.30 (m, 1H), 7.07 (m, 2H), 6.89 (m, 1H), 6.78 (s, 1H), 4.50 (s, 1H), 3.80 (s, 3H), 0.80 (s, 9H)

Step 3: 4-chloro-2'-fluoro-5'-methoxy-2-(1-methoxy-2,2-dimethylpropyl)-1,1'-biphenyl

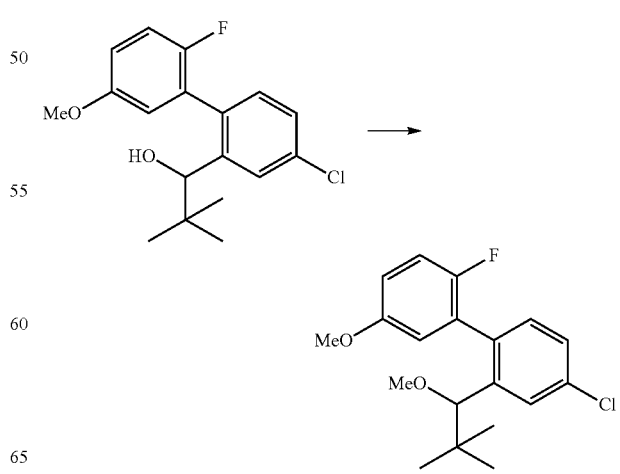

To a DMF solution of alcohol 1-(4-chloro-2'-fluoro-5'-methoxy-[1,1'-biphenyl]-2-yl)-2,2-dimethylpropan-1-ol (130 mg, 0.403 mmol) and MeI (0.030 ml, 0.483 mmol) was added NaH (19.33 mg, 0.483 mmol) in a single portion. The reaction was stirred at room temperature for 16 h, then poured into water (25 mL) and then extracted with EtOAc (2×25 mL). The combined organic layers were dried (MgSO$_4$) and concentrated. The resulting residue was purified by HPLC (ISCO 40 g, 0 to 40% EtOAc/Hex) to give the title compound. $^1$H NMR (500 MHz, CDCl$_3$) δ7.58 (s, 1H), 7.30 (m, 1H), 7.10 (m, 1H), 6.90 (m, 1H), 6.75 (m, 1H), 3.90 (s, 1H), 3.80 (s, 3H), 3.26 (s, 3H), 0.72 (s, 9H).

Step 4: 2'-fluoro-5'-methoxy-2-(1-methoxy-2,2-dimethylpropyl)-4-vinyl-1,1'-biphenyl

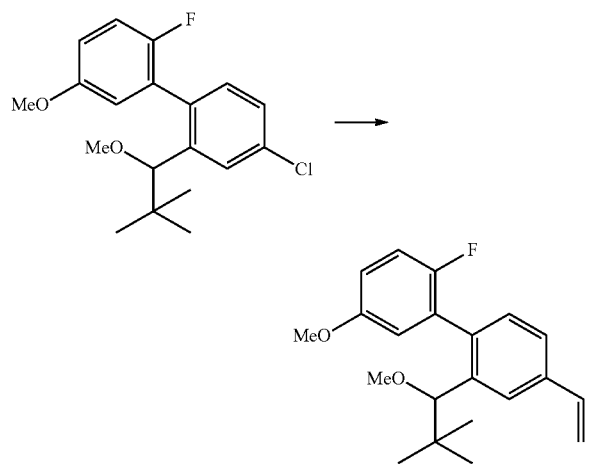 [SMILES: COc1ccc(F)c(-c2ccc(Cl)cc2C(OC)C(C)(C)C)c1 ; C=Cc1ccc(-c2cc(OC)ccc2F)c(C(OC)C(C)(C)C)c1]

To a degassed dioxane solution of 4-chloro-2'-fluoro-5'-methoxy-2-(1-methoxy-2,2-dimethylpropyl)-1,1'-biphenyl (125 mg, 0.371 mmol), CsF (124 mg, 0.816 mmol) and bis(tri-tert-butylphosphine)palladium (0) (5.69 mg, 0.011 mmol) in a vial with a teflon screw cap was added vinyltri-n-butyltin (0.120 ml, 0.408 mmol) via syringe. The reaction was heated to 100° C. on a heating block for 3 h, then filtered through MgSO$_4$ and concentrated. The resulting residue was purified by HPLC (ISCO 40 g, 0 to 40% EtOAc/Hex) to give the title compound. $^1$H NMR (500 MHz, CDCl$_3$) δ7.60 (m, 1H), 7.41 (t, 1H), 7.20 (m, 2H), 6.80 (m, 3H), 5.82 (d, 1H), 5.31 (d, 1H), 3.99 (s, 1H), 3.80 (s, 3H), 3.30 (s, 3H), 0.75 (s, 9H).

Intermediate 16

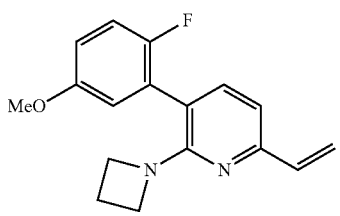 [SMILES: C=Cc1ccc(-c2cc(OC)ccc2F)c(N2CCC2)n1]

Step 1: (5-bromo-6-chloropyridin-2-yl)methanol

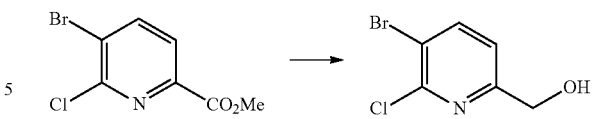

To a −78° C. solution of methyl 5-bromo-6-chloropicolinate (1.6 g, 6.39 mmol) in THF (18.25 ml) was added diisobutylaluminum hydride (15.97 ml, 15.97 mmol) over 5 min. The reaction was slowly warmed to room temperature, and stirred for 5 h. Then the reaction volume was reduced by 80% and the reaction was quenched with saturated aqueous potassium sodium tartrate. After stirring for 1 h, the reaction mixture was partitioned with EtOAc. The layers were separated and the aqueous layer was extracted three times with EtOAc. The organic layers were combined and concentrated to afford a crude residue, which was purified by column chromatography on silica gel (40 g ISCO RediSep Rf column, gradient elution 0% EtOAc in hexanes to 70% EtOAc in hexanes) to afford the desired product.

Step 2: (6-(azetidin-1-yl)-5-bromopyridin-2-yl)methanol

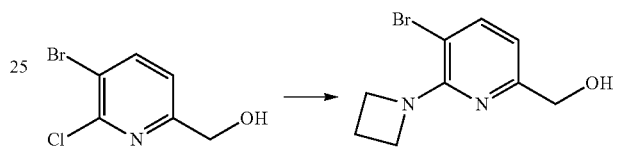

To a stirred solution of (5-bromo-6-chloropyridin-2-yl)methanol (1.29 g, 5.80 mmol) and triethylamine (1.616 ml, 11.60 mmol) in 1,4-dioxane (19.33 ml) was added azetidine (1.563 ml, 23.19 mmol). The reaction mixture was sealed in a reaction vessel and heated at 95° C. for 16 h. The reaction was then cooled to room temperature, unsealed and concentrated. The resulting residue was partitioned between saturated aqueous NaHCO$_3$ and EtOAc. The layers were separated and the aqueous layer was extracted twice with EtOAc. The combined organic layers were concentrated and the resulting residue was purified by column chromatography on silica gel (40 g ISCO RediSep Rf column, gradient elution 0% EtOAc in hexanes to 55% EtOAc in hexanes) to give the title compound. afford the desired product.

Step 3: 2-(azetidin-1-yl)-3-(2-fluoro-5-methoxyphenyl)-6-vinylpyridine

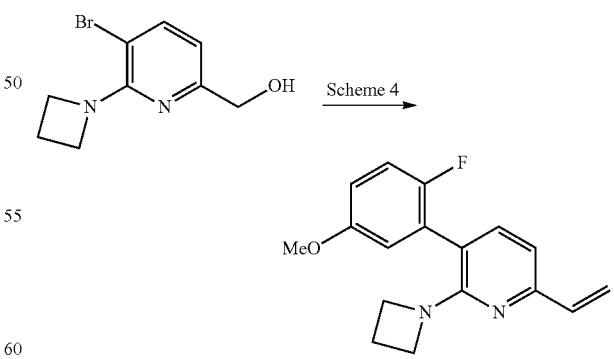

2-(Azetidin-1-yl)-3-(2-fluoro-5-methoxyphenyl)-6-vinylpyridine was prepared starting from (6-(azetidin-1-yl)-5-bromopyridin-2-yl)methanol utilizing the procedure disclosed in Scheme 8. LC/MS (m/z): 285.3 (M+H)$^+$ Intermediates 17-43 were prepared in a similar manner to Schemes 6-10 using the appropriate starting materials.

| INTERMEDIATE No. | Structure | Scheme/ Method | LC/MS (m/z) or H NMR |
|---|---|---|---|
| 17 | 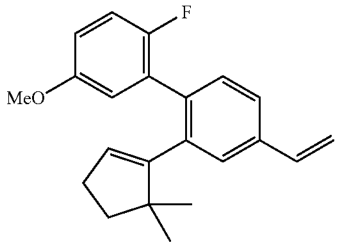 [SMILES: C=Cc1ccc(-c2cc(OC)ccc2F)c(C2=CCCC2(C)C)c1] | Scheme 8* | $(M + H)^+= 323.3$ |
| 18 | 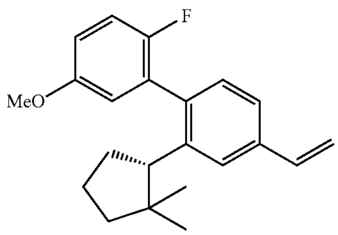 [SMILES: C=Cc1ccc(-c2cc(OC)ccc2F)c([C@H]2CCCC2(C)C)c1] | Scheme 8* | ¹H NMR (500 MHz, Acetone-d₆): 0.58 (2s, 3 H), 0.74 (2s, 3 H), 1.38-1.32 (m, 1 H), 1.55-1.52 (m, 1 H), 1.67-1.63 (m, 1 H), 1.84-1.81 (m, 1 H), 2.11 (m, 2 H), 2.80-3.0 (m, 1 H), 3.81 (d, 3 H), 5.26 (d, 1 H), 5.86 (d, 1 H), 6.87-6.81 (m, 1.5 H), 6.96-6.93 (m, 1 H), 7.17-7.08 (m, 2.5 H), 7.39 (dd, 1 H), 7.52 (2s, 1 H). |
| 19 | 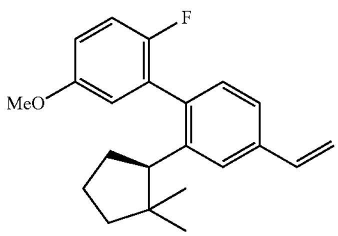 [SMILES: C=Cc1ccc(-c2cc(OC)ccc2F)c([C@@H]2CCCC2(C)C)c1] | Scheme 8* | ¹H NMR (500 MHz, Acetond-d₆): 0.58 (2s, 3 H), 0.74 (2s, 3 H), 1.38-1.32 (m, 1 H), 1.55-1.52 (m, 1 H), 1.67-1.63 (m, 1 H), 1.84-1.81 (m, 1 H), 2.11 (m, 2 H), 2.80-3.0 (m, 1 H), 3.81 (d, 3 H), 5.26 (d, 1 H), 5.86 (d, 1 H), 6.87-6.81 (m, 1.5 H), 6.96-6.93 (m, 1 H), 7.17-7.08 (m, 2.5 H), 7.39 (dd, 1 H), 7.52 (2s, 1 H). |
| 20 | 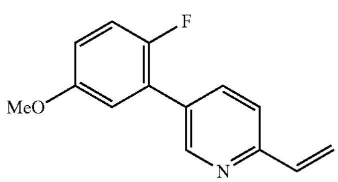 [SMILES: C=Cc1ccc(-c2cc(OC)ccc2F)cn1] | Scheme 6 Method A | ¹H NMR (500 MHz, CHCl₃-d): 3.84 (s, 3 H), 5.54 (d, 1 H), 6.27 (d, 1 H), 6.89-6.84 (m, 2 H), 6.95 (s, 1 H), 7.11 (t, 1 H), 7.43 (d, 1 H), 7.85 (d, 1 H), 8.76 (s, 1 H). |
| 21 | 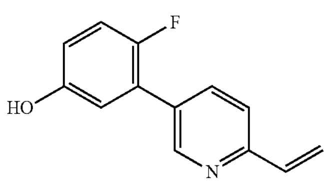 [SMILES: C=Cc1ccc(-c2cc(O)ccc2F)cn1] | Scheme 6 Method A | ¹H NMR (500 MHz, Acetone-d₆): 5.47 (d, 1 H), 6.31 (d, 1 H), 6.90-6.84 (m, 2 H), 6.98 (d, 1 H), 7.09 (t, 1 H), 7.53 (d, 1 H), 7.90 (d, 1 H), 8.70 (s, 1 H). |
| 22 | 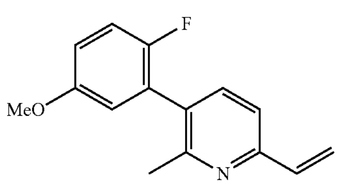 [SMILES: C=Cc1ccc(-c2cc(OC)ccc2F)c(C)n1] | Scheme 7 Route 1 | ¹H NMR (500 MHz, CHCl₃-d): 2.47 (s, 3 H), 3.81 (s, 3 H), 5.50 (d, 1 H), 6.22 (d, 1 H), 6.75 (dd, 1 H), 6.90-6.83 (m, 2 H), 7.08 (t, 1 H), 7.26 (d, 1 H), 7.49 (d, 1 H). |
| 23 | 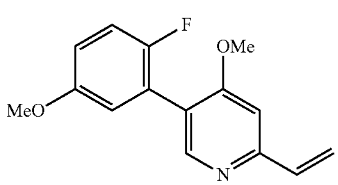 [SMILES: C=Cc1cc(OC)c(-c2cc(OC)ccc2F)cn1] | Scheme 8 Route 1 | ¹H NMR (500 MHz, CHCl₃-d): 3.80 (s, 3 H), 3.89 (s, 3 H), 5.53 (d, 1 H), 6.26 (d, 1 H), 6.87-6.81 (m, 3 H), 6.94 (s, 1 H), 7.07 (t, 1 H), 8.37 (s, 1 H). |

-continued

| INTERMEDIATE No. | Structure | Scheme/ Method | LC/MS (m/z) or H NMR |
|---|---|---|---|
| 24 | (structure) | Scheme 6 Method B | $^1$H NMR (500 MHz, CHCl$_3$-d): 3.94 (s, 3 H), 5.46 (dd, 1 H), 5.91 (dd, 1 H), 6.80 (d, 1 H), 6.90 (dd, 1 H, ), 7.30 (m, 2 H), 7.58 (t, 1 H), 8.07 (d, 1 H, J). |
| 25 | (structure) | Scheme 6 Method B | $^1$H NMR (500 MHz, CHCl$_3$-d): 3.97-3.95 (s, 3 H), 5.66 (d, 1 H), 6.53-6.45 (d, 1 H), 6.83 (d, 1 H), 7.08-7.01 (m, 1 H), 7.68-7.62 (d, 1 H), 8.12 (d, 1 H, J = 2.22), 8.62 (d, 1 H). |
| 26 | (structure) | Scheme 7 Route 2 | (M + H)$^+$ = 298.4 |
| 27 | (structure) | Scheme 6 Method C | $^1$H NMR (500 MHz, CHCl$_3$-d): 3.96 (s, 3 H), 5.58 (dd, 1 H, J = 10.79, 1.12 Hz), 6.31 (dd, 1 H, J = 17.46, 1.13 Hz), 6.90-6.82 (m, 2 H), 7.45 (d, 1 H, J = 8.19), 7.89 (dt, 1 H, J = 8.17, 1.97 Hz), 8.10 (d, 1 H, J = 2.25), 8.80 (s, 1 H). |
| 28 | (structure) | Scheme 7 Route 1 | (M + H)$^+$ = 244.4 |
| 29 | (structure) | Scheme 7 Route 3 | (M + H)$^+$ = 298.4 |
| 30 | (structure) | Scheme 6 Method C | (M + H)$^+$ = 230.3 |
| 31 | (structure) | Scheme 6 Method A | $^1$H NMR (500 MHz, CHCl$_3$-d): 3.99 (s, 3 H), 5.32 (d, 1 H), 5.82 (d, 1 H), 6.76 (dd, 1 H), 6.96 (d, 1 H), 7.11 (dd, 1 H), 7.50 (d, 2 H), 7.59 (d, 2 H), 8.21 (d, 1 H). |

| INTERMEDIATE No. | Structure | Scheme/ Method | LC/MS (m/z) or H NMR |
|---|---|---|---|
| 32 | 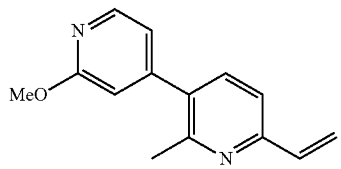 [SMILES: C=Cc1ccc(-c2ccnc(OC)c2)c(C)n1] | Scheme 6 Method C | ¹H NMR (500 MHz, CHCl₃-d): 2.52 (s, 3 H), 3.99 (s, 3 H), 5.52 (d, 1 H), 6.23 (d, 1 H), 6.71 (s, 1 H), 6.85 (m, 2 H), 7.26 (d, 1 H), 7.47 (d, 1 H), 8.22 (d, 1 H). |
| 33 | 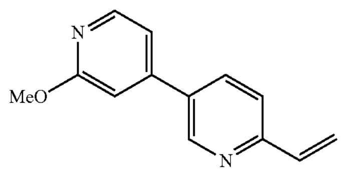 [SMILES: C=Cc1ccc(-c2ccnc(OC)c2)cn1] | Scheme 6 Method C | ¹H NMR (500 MHz, CHCl₃-d): 3.98 (s, 3 H), 5.54 (d, 1 H), 6.27 (d, 1 H), 6.86 (dd, 1 H), 6.94 (s, 1 H), 7.09 (dd, 1 H), 7.42 (d, 1 H), 7.85 (dd, 1 H), 8.24 (d, 1 H), 8.82 (d, 1 H). |
| 34 | 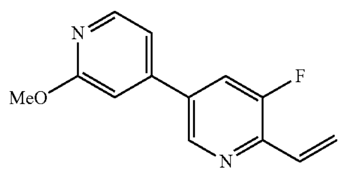 [SMILES: C=Cc1ncc(-c2ccnc(OC)c2)cc1F] | Scheme 6 Method C | ¹H NMR (500 MHz, CHCl₃-d): 4.00 (s, 3 H), 5.66 (dd, 1 H), 6.50 (dd, 1 H), 6.94-6.94 (s, 1 H), 7.09-7.02 (m, 2 H), 7.59 (dd, 1 H), 8.27 (d, 1 H), 8.66 (s, 1 H). |
| 35 | 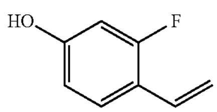 | Scheme 9 Step 6 | ¹H NMR (500 MHz, CHCl₃-d): 5.20 (bs, 1 H), 5.25 (d, 1 H), 5.67 (d, 1 H), 6.60-6.53 (m, 2 H), 6.78 (dd, 1 H), 7.35 (t, 1 H). |
| 36 | 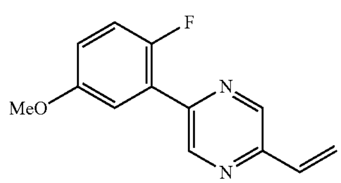 [SMILES: C=Cc1cnc(-c2cc(OC)ccc2F)cn1] | Scheme 8 | $(M + H)^+ = 230.2$ |
| 37 | 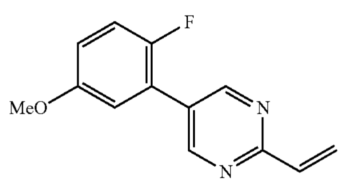 [SMILES: C=Cc1ncc(-c2cc(OC)ccc2F)cn1] | Scheme 7 Route 1 | ¹H NMR (400 MHz, CDCl₃) δ 8.90 (s, 1H), 8.81 (s, 1H), 7.16 (dd, $J_{12}$ = 9.6 Hz, $J_{13}$ = 16.0 Hz, 1H), 6.98~6.91 (m, 2H), 6.68 (d, J = 17.2 Hz, 1H), 5.79 (d, J = 10.4 Hz, 1H), 3.85 (s, 3H). |
| 38 | 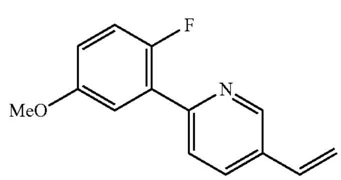 [SMILES: C=Cc1ccc(-c2cc(OC)ccc2F)nc1] | Scheme 7 Method A | ¹H NMR (400 MHz, CDCl₃) δ 8.72 (s, 1 H), 7.80-7.58 (m, 2 H), 7.55 (dd, J = 6.0, 3.2 Hz, 1 H), 7.08-7.05 (m, 1 H), 6.91-6.89 (m, 1 H), 6.76 (dd, J = 17.8, 11.2 Hz, 1 H), 5.89 (d, J = 17.6 Hz, 1 H), 5.42 (d, J = 11.0 Hz, 1 H), 3.87 (s, 3 H). |
| 39 | 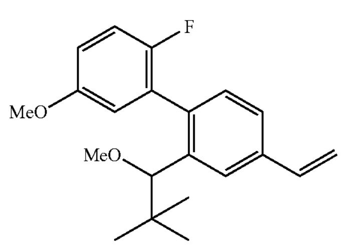 [SMILES: C=Cc1ccc(-c2cc(OC)ccc2F)c(C(OC)C(C)(C)C)c1] | Scheme 10 | ¹H NMR (500 MHz, CHCl₃-d): δ 7.60 (m, 1H), 7.41 (t, 1H), 7.20 (m, 2H), 6.80 (m, 3H), 5.82 (d, 1H), 5.31 (d, 1H), 3.99 (s, 1H), 3.80 (s, 3H), 3.30 (s, 3H), 0.75 (s, 9H) |

| INTERMEDIATE No. | Structure | Scheme/ Method | LC/MS (m/z) or H NMR |
|---|---|---|---|
| 40 | 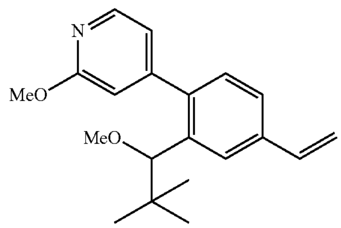 [SMILES: C=Cc1ccc(-c2ccnc(OC)c2)c(C(OC)C(C)(C)C)c1] | Scheme 10 | $^1$H NMR (500 MHz, CHCl$_3$-d): δ 8.20 (d, 1H), 7.60 (s, 1H), 7.40 (d, 1H), 7.10 (d, 1H), 6.81 (d, 1H), 6.79 (dd, 1H), dd, 1H), 6.68 (s, 1H), 5.83 (d, 1H), 5.30 (d, 1H), 4.20 (s, 1H), 4.00 (s, 3H), 3.32 (s, 3H), 0.70 (s, 9H) |
| 41 | 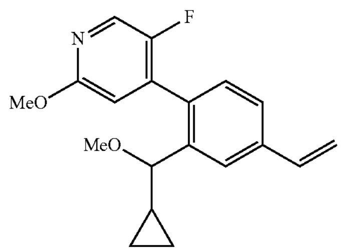 [SMILES: C=Cc1ccc(-c2cc(OC)ncc2F)c(C(OC)C2CC2)c1] | Scheme 10 | (M + H)$^+$ = 314.3 |
| 42 | 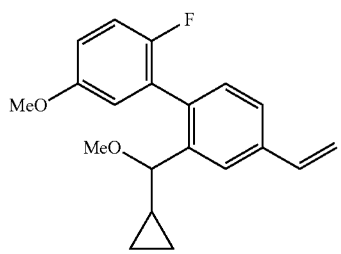 [SMILES: C=Cc1ccc(-c2cc(OC)ccc2F)c(C(OC)C2CC2)c1] | Scheme 10 | (M + H)$^+$ = 313.2 |
| 43 | 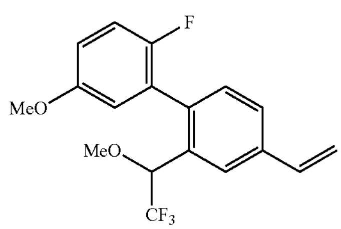 [SMILES: C=Cc1ccc(-c2cc(OC)ccc2F)c(C(OC)C(F)(F)F)c1] | Scheme 10 | (M + H)$^+$ = 341.2 |

*Styrene intermediates 17-19 were prepared by the method outlined in Scheme 8. The benzyl alcohol starting material was prepared as described by Wang, Yincai et al., *ACS Medicinal Chemistry Letters*, 4(6), 551-555 (2013).

Intermediate 44

7-bromo-2-(2'-fluoro-5'-methoxy-[1,1'-biphenyl]-4-yl)chroman

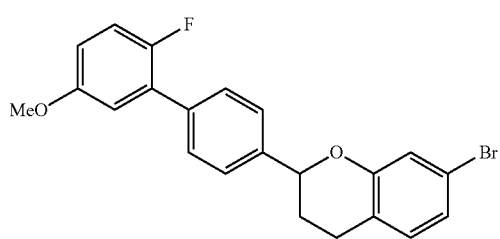 [SMILES: COc1ccc(F)c(-c2ccc(C3CCc4ccc(Br)cc4O3)cc2)c1]

Step A: To a mixture of 4-bromo-2-hydroxybenzoic acid (10.0 g, 46.1 mmol) in THF (100 ml) was added borane (9.22 ml, 92.0 mmol, 10 M dissolved in DMSO) at 0° C. The reaction was stirred at room temperature for 16 hours, then quenched by the slow addition of MeOH (20 mL). The reaction mixture was concentrated to give the crude product. The crude product was purified by silica gel chromatography eluting with PE:EtOAc=5:1 to give 5-bromo-2-(hydroxymethyl-)phenol.

Step B: A mixture of 2-fluoro-5-methoxy-4'-vinyl-1,1'-biphenyl (10.0 g, 43.9 mmol) and 5-bromo-2-(hydroxymethyl)phenol (9.90 g, 43.9 mmol) was stirred at 180° C. for 2 hours under a nitrogen atmosphere. Then the reaction was cooled to room temperature, and diluted with EtOAc (100 mL). The organic layers were separated, washed with brine (30 mL), dried over anhydrous MgSO$_4$ and filtered. The filtrate was concentrated to give a residue, which was purified by flash column chromatography on silica gel (PE:EtOAc=100:1 to 50:1) to give 7-bromo-2-(2'-fluoro-5'-methoxy-[1,1'-biphenyl]-4-yl)chroman. $^1$H NMR (400 MHz, CDCl$_3$) δ: 7.60 (d, J=7.6, 2H), 7.49 (d, J=7.6, 2H), 7.11-6.95 (m, 5H), 6.86-6.83 (m, 1H), 5.13 (d, J=8.4, 1H), 3.84 (s, 3H), 2.96-2.74 (m 2H), 2.29-2.10 (m 2H).

Intermediate 45

2-(2-(2'-fluoro-5'-methoxy-[1,1'-biphenyl]-4-yl)chroman-7-yl)-4,4,5,5-tetramethyl-1,3,2-dioxaborolane

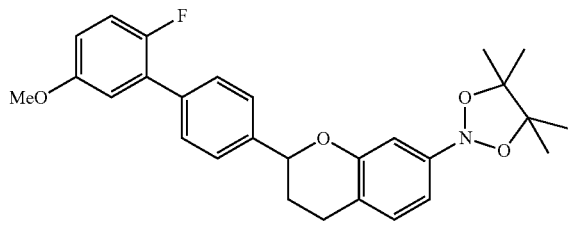 [SMILES: COc1ccc(F)c(-c2ccc(C3CCc4ccc(N5OC(C)(C)C(C)(C)O5)cc4O3)cc2)c1]

To a solution of 7-bromo-2-(2'-fluoro-5'-methoxy-[1,1'-biphenyl]-4-yl)chroman (Intermediate 44, 500 mg, 1.21 mmol) in DMF (10 ml) were added 4,4,4',4',5,5,5',5'-octamethyl-2,2'-bi(1,3,2-dioxaborolane) (369 mg, 1.452 mmol), potassium acetate (356 mg, 3.63 mmol) and Pd(dppf)Cl$_2$ (89.0 mg, 0.121 mmol) under a nitrogen atmosphere. The reaction was stirred at 90° C. for 16 h, then cooled to room temperature, followed by the addition of water (10 mL). The reaction mixture was extracted with EtOAc (10 mL×3). The organic layers were washed with brine (10 mL), dried over anhydrous MgSO$_4$ and filtered. The filtrate was concentrated to give a residue, which was purified by preparative TLC (PE:EtOAc=10:1) to give 2-(2-(2'-fluoro-5'-methoxy-[1,1'-biphenyl]-4-yl)chroman-7-yl)-4,4,5,5-tetramethyl-1,3,2-dioxaborolane. $^1$HNMR (400 MHz, CDCl$_3$) δ: 7.57 (d, J=7.2 Hz, 2H), 7.50 (d, J=8.4 Hz, 2H), 7.42 (s, 1H), 7.32 (d, J=7.6 Hz, 1H), 7.10 (dd, J12=7.6 Hz, J13=17.2 Hz, 2H), 6.97-6.95 (m, 1H), 6.86-6.83 (m, 1H), 5.15 (d, J=8.4 Hz, 1H), 3.84 (s, 3H), 3.07-2.98 (m, 1H), 2.85-2.81 (m, 1H), 2.30-2.27 (m, 1H), 2.15-2.06 (m, 1H), 1.34 (s, 12H).

Intermediate 46 methyl 3-cyclobutyl-3-(3-hydroxy-4-(hydroxymethyl)phenyl)propanoate

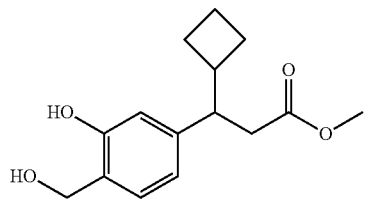 [SMILES: COC(=O)CC(c1ccc(CO)c(O)c1)C1CCC1]

Step A: Cyclobutanecarboxylic acid (50.0 g, 499 mmol) was cooled to 0° C., then thionyl chloride (100 ml) was added dropwise with stirring. Then the reaction mixture was refluxed for 1.5 hours. The product was separated by distillation to give cyclobutanecarbonyl chloride.

Step B: 2,2-dimethyl-1,3-dioxane-4,6-dione (54.2 g, 376 mmol) was dissolved in CHCl$_3$ (400 mL), then pyridine (50.6 mL, 625 mmol, 1.83 eq) was added to the mixture. A solution of cyclobutanecarbonyl chloride (40.5 g, 342 mmol) in CHCl$_3$ (160 mL) was added dropwise to the reaction at a temperature of between 5-10° C. while cooling in an ice-bath. Then the reaction mixture was stirred at 0° C. for 1 hour, and at room temperature for 1 hour. The reaction mixture was then cooled to 0° C., and 1N aqueous HCl (400 mL) was added. Then the reaction mixture was extracted with CHCl$_3$ (300 mL×3). The combined organic layers were washed with water, and dried over anhydrous Na$_2$SO$_4$, followed by concentration under reduced pressure. Then MeOH (400 ml) was added to the residue and the solution was heated under reflux for 3 hours. After cooling to room temperature, the mixture was concentrated under reduced pressure and the resulting residue was distilled to give methyl 3-cyclobutyl-3-oxopropanoate. $^1$H NMR (400 MHz, CDCl$_3$) δ3.68 (s, 3H), 3.36 (s, 2H), 2.27~2.10 (m, 4H), 1.99~1.75 (m, 2H), 1.25~1.19 (m, 1H).

Step C: To a solution of methyl 3-cyclobutyl-3-oxopropanoate (10.0 g, 64.0 mmol) in Et$_2$O (150 ml) was added NaH (3.84 g, 96.0 mmol) in portions at 0° C. The reaction mixture was stirred at 0° C. for 1 hour, then trifluoromethanesulfonic anhydride (19.9 g, 70.4 mmol) was added dropwise via syringe at 0° C. The reaction was allowed to warm to room temperature for 1 hour, then cooled to 0° C. and quenched with water (200 mL). The mixture was extracted with EtOAc (200 mL×2). The combined organic layers were washed with brine, dried over anhydrous Na$_2$SO$_4$ and filtered. The filtrate was concentrated under reduced pressure to give the crude product, which was purified by silica gel chromatography eluted with PE:EtOAc=(1:0~60:1, v/v) to give methyl 3-cyclobutyl-3-(((trifluoromethyl)sulfonyl)oxy)acrylate. $^1$H NMR (400 MHz, CDCl$_3$) δ 5.76 (s, 1H), 3.79 (s, 3H), 3.30~3.24 (m, 1H), 2.31~2.29 (m, 2H), 2.11~1.88 (m, 4H).

Step D: To a solution of (Z)-methyl 3-cyclobutyl-3-(((trifluoromethyl)sulfonyl)oxy)-acrylate (14.5 g, 50.3 mmol) in 1,4-dioxane (200 ml) and water (40.0 ml) were added potassium phosphate (26.3 g, 151 mmol), (3-hydroxyphenyl)boronic acid (8.33 g, 60.4 mmol) and Pd(Ph$_3$P)4 (5.81 g, 5.03 mmol) under nitrogen. The reaction mixture was stirred at 80° C. for 15 h. The mixture was then concentrated under vacuum and then water (50 mL) was added. The aqueous phase was separated and extracted with EtOAc (50 mL×3). The combined organic layers were washed with water (100 mL) and brine (100 mL), dried over anhydrous MgSO$_4$ and filtered. The filtrate was concentrated under reduced pressure. The resulting residue was purified by silica gel chromatography eluted with PE:EtOAc (50:1~10:1, v/v) to give (Z)-methyl 3-cyclobutyl-3-(3-hydroxyphenyl)-acrylate. $^1$H NMR (400 MHz, CDCl$_3$) δ7.17 (t, J=7.8 Hz, 1H), 6.69 (d, J=6.4 Hz, 1H), 6.63 (d, J=7.6 Hz, 1H), 6.54 (s, 1H), 5.81 (s, 1H), 5.69 (s, 1H), 3.59 (s, 3H), 3.28~3.21 (m, 1H), 2.06~1.72 (m, 6H).

Step E: To a mixture of (E)-methyl 3-cyclobutyl-3-(3-hydroxyphenyl)acrylate (9.20 g, 39.6 mmol) in MeOH (100 ml) was added 10% of dry Pd/C (2.11 g, 19.8 mmol) under nitrogen. The reaction mixture was stirred at room temperature under hydrogen balloon pressure for 5 h. The mixture was then filtered, and the filtrate was concentrated under reduced pressure to give methyl 3-cyclobutyl-3-(3-hydroxyphenyl) propanoate, which was used directly for the next step. $^1$H NMR (400 MHz, CDCl$_3$) δ 7.02 (t, J=8.4 Hz, 1H), 6.56~6.54 (m, 3H), 3.46 (s, 3H), 2.86~2.81 (m, 1H), 2.55~2.36 (m, 2H), 2.05~1.95 (m, 1H), 1.75-1.52 (m, 5H).

Step F: To a solution of methyl 3-cyclobutyl-3-(3-hydroxyphenyl)propanoate (8.95 g, 38.2 mmol) in acetonitrile (100 ml) were added paraformaldehyde (5.74 g, 191 mmol), magnesium chloride (5.46 g, 57.3 mmol) and TEA (20.0 ml, 143 mmol) at room temperature. The reaction mixture was heated to reflux for 5 hours, then cooled to room temperature, and filtered through Centel™. Water was added to the filtrater, and the mixture was filtered through a Celite™ pad again. The filtrate was extracted with EtOAc (150 mL×3). The combined organic layers were washed with water (200 mL) and brine (200 mL), dried over anhydrous MgSO₄ and filtered. The filtrate was concentrated under reduced pressure. The resulting residue was purified by chromatography column (PE:EtOAc=25:1~5:1, v/v) to give methyl 3-cyclobutyl-3-(2-formyl-3-hydroxyphenyl-)propanoate. ¹H NMR (400 MHz, CDCl₃) δ 10.66 (s, 1H), 10.14 (s, 1H), 7.57 (d, J=8.0 Hz, 1H), 6.84~6.80 (m, 2H), 3.47 (s, 3H), 2.96~2.92 (m, 1H), 2.67~2.56 (m, 2H), 2.05~1.95 (m, 1H), 1.70~1.54 (m, 5H).

Step G: A solution of methyl 3-cyclobutyl-3-(4-formyl-3-hydroxyphenyl)propanoate (E1-7) (8.50 g, 32.4 mmol) in EtOH (100 ml) was stirred at 0° C. under a nitrogen atmosphere. Then NaBH₄ (1.23 g, 32.4 mmol) was added in portions at 0° C. The reaction mixture was stirred at 0° C. for 30 min, then was quenched with water (50 mL). The mixture was then extracted with EtOAc (50 mL×2). The combined organic layers were washed with brine (100 mL), dried over anhydrous MgSO₄ and filtered. The filtrate was concentrated in vacuo to give the crude product. The crude product was purified by silica gel chromatography eluted with PE:EtOAc (10:1~2:1, v/v) to give methyl 3-cyclobutyl-3-(3-hydroxy-4-(hydroxymethyl)phenyl)propanoate. ¹H NMR (400 MHz, CDCl₃) δ 7.30 (s, 1H), 6.93 (d, J=7.2 Hz, 1H), 6.70~6.63 (m, 2H), 4.81 (s, 2H), 3.56 (s, 3H), 2.99~2.97 (m, 1H), 2.57~2.40 (m, 4H), 1.74~1.56 (m, 5H).

Intermediate 47

(2S,3R)-Methyl 3-cyclopropyl-3-(3-hydroxy-4-iodophenyl)-2-methylpropanoate

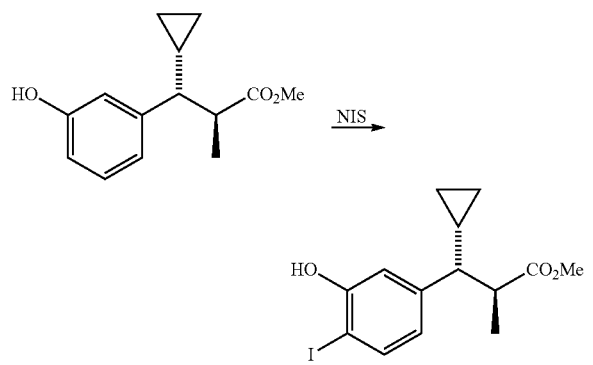

To a solution of (2S,3R)-methyl 3-cyclopropyl-3-(3-hydroxyphenyl)-2-methylpropanoate (1.47 g, 6.27 mmol) in DCM (50 ml) was added NIS (1.69 g, 7.53 mmol). The reaction was stirred at ambient temperature for 2 h, then diluted with DCM and aqueous saturated sodium thiosulfate solution. The layers were separated, and the combined organic layers were washed with brine, dried over MgSO₄, filtered, and concentrated in vacuo. The resulting residue was purified by silica gel column chromatography (ISCO system, RediSep 80 g column) using a gradient of 0-50% EtOAc/Hexanes as eluent to provide the title compound. LC/MS: m/z=361.17 [M+1]. ¹H NMR δ (ppm)(CDCl₃): −0.03 (1H, s), 0.26 (1H, s), 0.35 (1H, s), 0.58 (1H, s), 0.96 (3H, d, J=6.76 Hz), 1.89 (1H, t, J=10.14 Hz), 2.79 (1H, s), 3.74 (3H, s), 5.29 (1H, s), 6.52 (1H, d, J=8.08 Hz), 6.84 (1H, s), 7.59 (1H, d, J=8.16 Hz).

Intermediate 48

(2S,3R)-Methyl 3-cyclopropyl-3-(2-fluoro-3-hydroxy-4-iodophenyl)-2-methylpropanoate

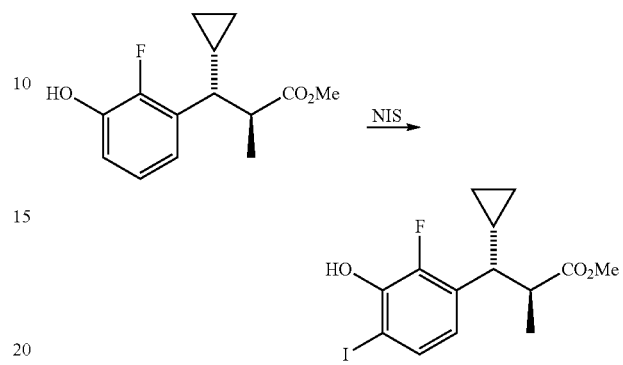

To a solution of (2S,3R)-Methyl 3-cyclopropyl-3-(2-fluoro-3-hydroxyphenyl)-2-methylpropanoate (152 mg, 0.603 mmol) in DCM (4 mL) was added NIS (136 mg, 0.603 mmol) slowly in several small portions. The reaction was stirred at ambient temperature overnight, then diluted with DCM and aqueous saturated sodium thiosulfate solution. The organic layer was separated, washed with brine, dried over MgSO₄, filtered, and concentrated in vacuo. The resulting residue was purified by silica gel column chromatography (ISCO system, RediSep 40 g column) using a gradient of 0-25% EtOAc/Hexanes as eluent to give (2S,3R)-methyl 3-cyclopropyl-3-(2-fluoro-3-hydroxy-4-iodophenyl)-2-methylpropanoate. LC/MS: m/z=379.16 [M+1]. ¹H NMR δ (ppm)(CHCl₃-d): −0.01 (1H, s), 0.35-0.26 (2H, m), 0.60-0.55 (1H, m), 0.97 (3H, d, J=6.92 Hz), 1.10-1.08 (1H, m), 2.28 (1H, t, J=10.24 Hz), 2.91-2.85 (1H, m), 3.73 (3H, s), 5.53 (1H, d, J=3.95 Hz), 6.56 (1H, t, J=7.48 Hz), 7.41 (1H, dd, J=8.33, 1.68 Hz).

Intermediates 49 and 50

(2R,3R)-Methyl 3-cyclopropyl-3-(2-fluoro-3-hydroxyphenyl)-2-methylpropanoate and (2S,3R)-methyl 3-cyclopropyl-3-(2-fluoro-3-hydroxyphenyl)-2-methylpropanoate

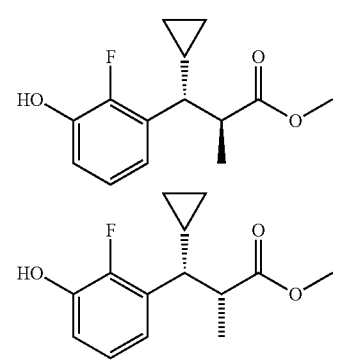

Intermediates 49 and 50 were prepared according to the procedure used to make Intermediates 5 and 6, starting from 2-fluoro-3-hydroxybenzaldehyde (Method 1). Intermediate 49: LC/MS (m/z): 253.1 (M+H)⁺ Intermediate 50: LC/MS (m/z): 253.1 (M+H)⁺

Intermediates 51 and 52

(2R,3R)-Methyl 3-cyclopropyl-3-(4-hydroxyphenyl)-2-methylpropanoate and (2S,3R)-Methyl 3-cyclopropyl-3-(4-hydroxyphenyl)-2-methylpropanoate

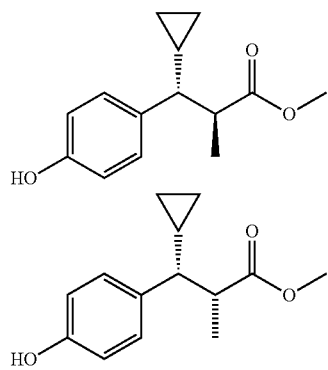

Intermediates 51 and 52 were prepared according to the procedure used to make Intermediates 5 and 6 starting from 4-hydroxybenzaldehyde (Method 1). Intermediate 49: LC/MS (m/z): 235.1 (M+H)$^+$ Intermediate 50: LC/MS (m/z): 235.1 (M+H)$^+$

Intermediate 53

(2S,3R)-Methyl 3-cyclopropyl-3-(4-hydroxy-3-iodophenyl)-2-methylpropanoate

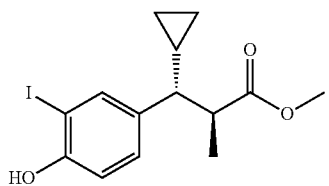 [SMILES: COC(=O)[C@@H](C)[C@H](c1ccc(O)c(I)c1)C1CC1]

Intermediate 53 was prepared according to the procedure of Intermediate 47, starting from (2R,3R)-Methyl 3-cyclopropyl-3-(4-hydroxyphenyl)-2-methylpropanoate. $^1$H NMR δ (ppm) (CDCl$_3$): 0.00 (1H, m), 0.35-0.26 (2H, m), 0.60-0.55 (1H, m), 0.89 (3H, d, J=6.92 Hz), 1.01 (1H, m), 1.9 (1H, m), 2.75 (1H, m), 3.71 (3H, s), 6.9 (1H, d), 7.10 (1H, m), 7.45 (1H, s).

Intermediate 54

(R)-Methyl 3-(4-hydroxy-3-iodophenyl)hex-4-ynoate

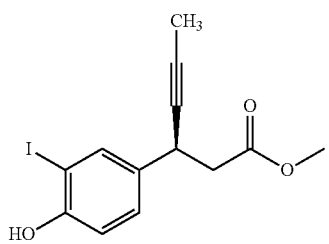 [SMILES: CC#C[C@@H](CC(=O)OC)c1ccc(O)c(I)c1]

Intermediate 54 was prepared according to the procedure of Intermediate 47, starting from (3S)-Methyl 3-(4-hydroxyphenyl)hex-4-ynoate. LC/MS: m/z=345.15 [M+1]

Example 1

3-(2-(2',6'-dimethyl-[1,1'-biphenyl]-3-yl)chroman-6-yl)propanoic acid

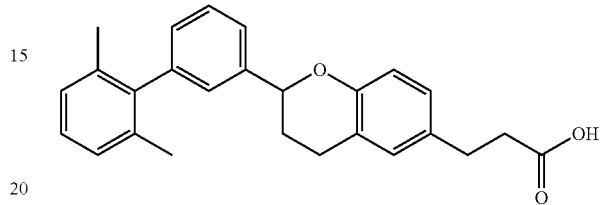

Step A: (E)-methyl 3-(2-(2',6'-dimethyl-[1,1'-biphenyl]-3-yl)chroman-6-yl)acrylate

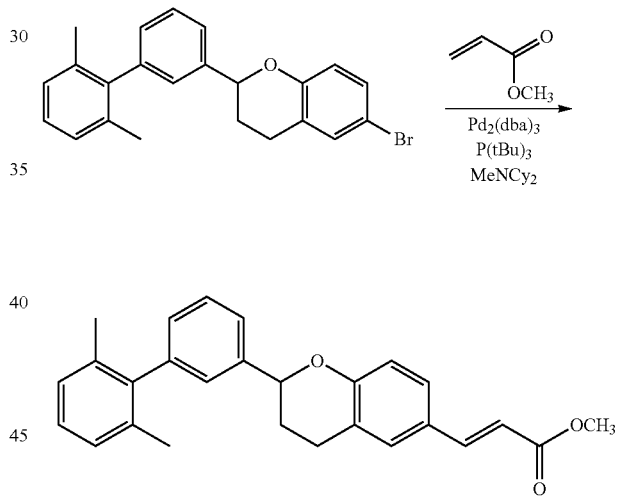

To a nitrogen-purged vial containing 6-bromo-2-(2',6'-dimethyl-[1,1'-biphenyl]-3-yl)chroman (165 mg, 0.420 mmol), Pd$_2$(dba)$_3$ (7.68 mg, 8.39 μmol), and tri-t-butylphosphine (3.39 mg, 0.017 mmol) sealed with a teflon screw cap was added dioxane. N-cyclohexyl-N-methylcyclo-hexanamine (90 mg, 0.461 mmol) and methyl acrylate (0.076 ml, 0.839 mmol) were then added via syringe. The mixture was stirred at room temperature for 12 h. The reaction mixture was then poured into water (10 mL) and then extracted with diethyl ether (2×10 mL). The combined organic layers were dried (MgSO$_4$) and concentrated. The resulting residue was purified by HPLC (ISCO 24 gram cartridge, 0 to 50% EA/Hex) to give the title compound. $^1$H NMR (500 MHz, CDCl3) δ7.65 (d, 1H), 7.51-7.10 (m, 9H), 6.94 (d, 1H), 6.34 (d, 1H), 5.19 (d, 1H), 3.81 (s, 3H), 3.02 (m, 1H), 2.82 (m, 1H), 2.31 (m, 1H), 2.13 (m, 1H), 2.04 (d, 6H).

Step B: Methyl 3-(2-(2',6'-dimethyl-[1,1'-biphenyl]-3-yl)chroman-6-yl)propanoate Step C: 3-(2-(2',6'-dimethyl-[1,1'-biphenyl]-3-yl)chroman-6-yl)propanoic acid

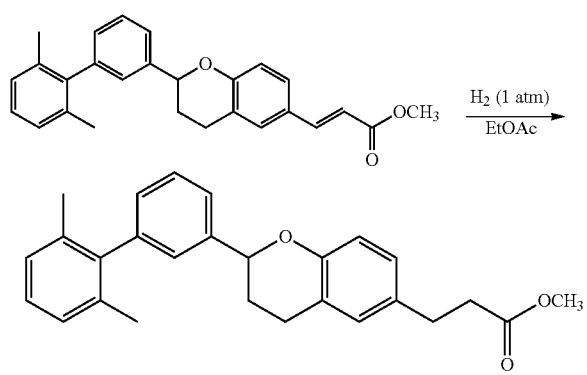

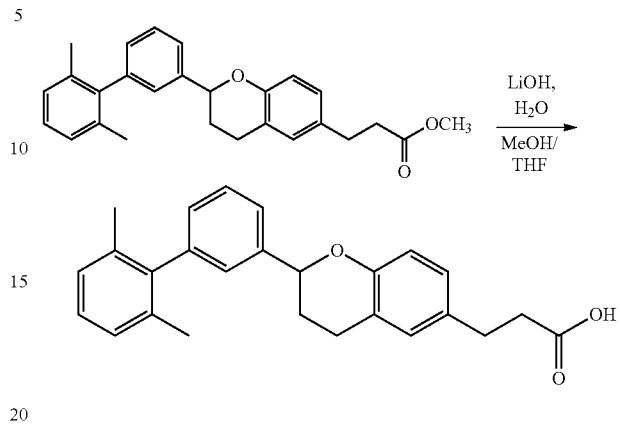

To an EtOAc (2 mL) solution of (E)-methyl 3-(2-(2',6'-dimethyl-[1,1'-biphenyl]-3-yl)chroman-6-yl)acrylate (135 mg, 0.339 mmol) was added Pd(OH)$_2$ (20% wt, 13 mg, 0.019 mmol). The mixture was purged and then backfilled with a balloon of hydrogen gas (1 atm). The mixture was vigorously stirred under a hydrogen atmosphere for 1 h. The reaction mixture was then filtered through Celite™ and concentrated in vacuo. The resulting residue was purified by HPLC (0 to 50% EA/Hex) to give the product. $^1$H NMR (500 MHz, CDCl$_3$) δ7.52-7.41 (m, 2H), 7.24-7.12 (m, 5H), 7.00 (d, 1H), 6.98 (s, 1H), 6.87 (d, 1H), 5.12 (d, 1H), 3.72 (s, 3H), 3.00 (m, 1H), 2.91 (t, 2H), 2.80 (dt, 1H), 2.62 (t, 2H) 2.25 (m, 1H), 2.12 (m, 1H) 2.08 (d, 6H).

To a THF/MeOH/water (1:1:1, 1.5 mL) solution of methyl 3-(2-(2',6'-dimethyl-[1,1'-biphenyl]-3-yl)chroman-6-yl)propanoate (120 mg, 0.30 mmol) was added LiOH (72 mg, 3.0 mmol). The reaction was then heated to 60° C. on a heating block. After 12 h, the reaction was poured into 1N HCl (10 mL) and extracted with EtOAc (2×10 mL). The combined organic layers were dried (MgSO$_4$) and concentrated. The resulting residue was purified by HPLC (ISCO, 24 g, 0 to 50% MeOH/DCM) to give the product. $^1$H NMR (500 MHz, CDCl$_3$) δ7.47 (m, 2H), 7.24-7.12 (m, 5H), 7.00 (m, 2H), 6.90 (d, 1H), 5.14 (d, 1H), 3.01 (m, 1H), 2.95 (t, 2H), 2.80 (dt, 1H), 2.70 (t, 2H), 2.24 (m, 1H), 2.15 (m, 1H), 2.04 (d, 6H).

Examples 2-6 were prepared in a similar manner to Example 1 using the appropriate starting materials and the boronate from Intermediate 1.

| Example No. | Structure | Stereoisomers | Mass spec, M + 1$^+$, m/e |
|---|---|---|---|
| 2 | 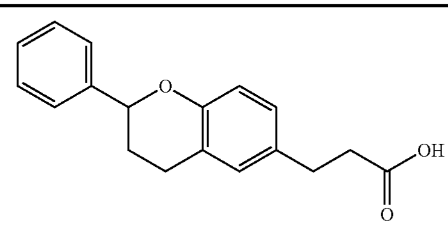 | Racemic mixture | 283.3 |
| 3 | 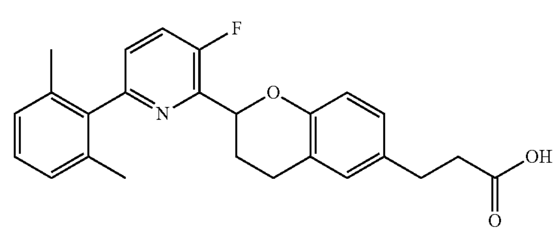 [SMILES: Cc1cccc(C)c1-c1ccc(F)c(C2CCc3cc(CCC(=O)O)ccc3O2)n1] | Racemic mixture | 406.4 |
| 4 | 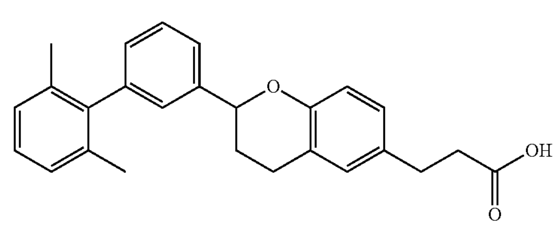 [SMILES: Cc1cccc(C)c1-c1cccc(C2CCc3cc(CCC(=O)O)ccc3O2)c1] | isomer A | 387.4 |

| Example No. | Structure | Stereoisomers | Mass spec, M + 1+, m/e |
|---|---|---|---|
| 5 | 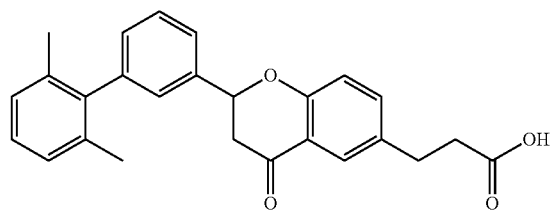 | isomer B | 387.4 |
| 6 | 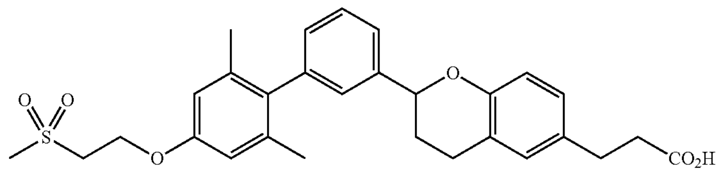 [SMILES: Cc1cc(OCCS(C)(=O)=O)cc(C)c1-c1cccc(C2CCc3cc(CCC(=O)O)ccc3O2)c1] | Racemic mixture | 509.4 |

Example 7

3-(2-(2',6'-dimethyl-[1,1'-biphenyl]-3-yl)-4-oxochroman-6-yl)propanoic acid

Step A: 6-bromo-2-(3-chlorophenyl)chroman-4-one

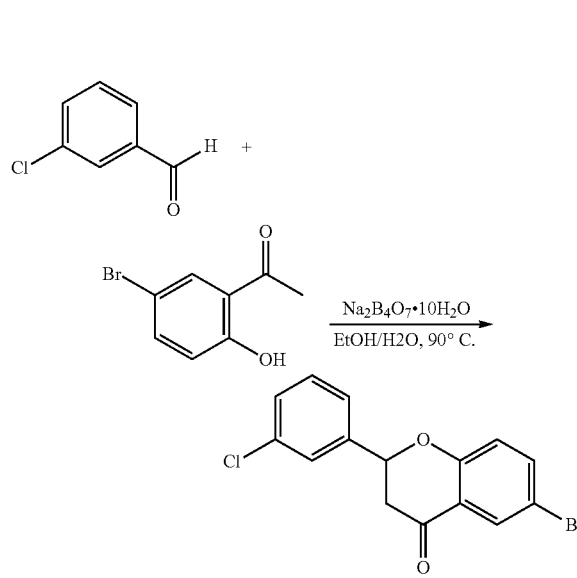

A solution of 5'-bromo-2'-hydroxyacetophenone (5.00 g, 23.3 mmol), and 3-chlorobenzaldehyde (2.65 mL, 23.3 mmol) in EtOH (31 mL)/water (52 mL) was treated with sodium tetraborate decahydrate (8.87 g, 23.3 mmol). The reaction mixture was heated to 90° C. using a heating block and stirred overnight. The reaction mixture was then cooled to room temperature, diluted with EtOAc (500 mL) and partitioned with deionized water (200 mL). The organic layer was separated, dried ($Na_2SO_4$), filtered and concentrated in vacuo. The resulting crude residue was purified via MPLC (ISCO 330 g) with gradient elution 0-10% EtOAc/hexane. The desired fractions were combined, concentrated and dried in vacuo to afford 6-bromo-2-(3-chlorophenyl)chroman-4-one. $^1$H NMR (500 MHz, $CDCl_3$) δ8.40 (d, 1H), 7.60 (dd, 1H), 7.50 (s, 1H), 7.38 (d, 2H), 7.33 (m, 1H), 6.98 (d, 1H), 5.45 (dd, 1H), 3.05 (dd, 1H), 2.80 (dd, 1H).

Step B: 6-bromo-2-(3-chlorophenyl)spiro[chroman-4,2'-[1,3]dioxolane]

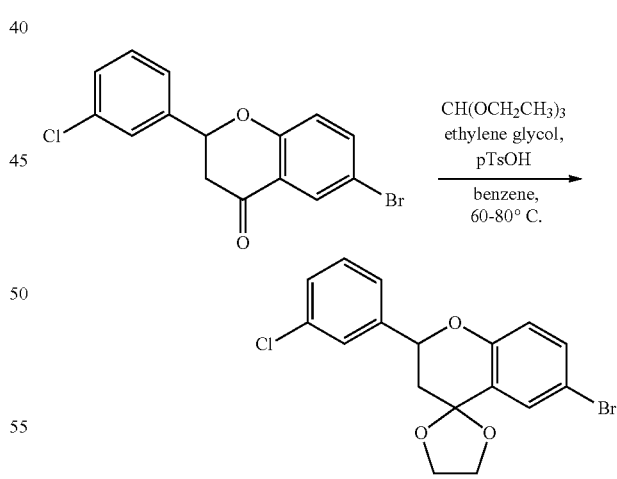

A solution of 6-bromo-2-(3-chlorophenyl)chroman-4-one (1.00 g, 2.96 mmol) in benzene (19.8 mL) was treated with ethylene glycol (1.65 mL, 29.6 mmol), triethyl orthoformate (2.47 mL, 14.8 mmol) and pTsOH (5.71 mg, 0.03 mmol). The reaction mixture was heated at 60° C. overnight using a heating block. Additional pTsOH (5.71 mg, 0.03 mmol), ethylene glycol (1.65 mL, 29.6 mmol) and triethyl orthoformate (2.47 mL, 14.8 mmol) were added and the reaction temperature was increased to 80° C. After an additional 24 h, the reaction mixture was cooled to room temperature, diluted with saturated aq. NaHCO$_3$ (100 mL) and partitioned with EtOAc (350 mL). The organic layer was separated, dried (Na$_2$SO$_4$), filtered and concentrated in vacuo. The crude residue was purified via MPLC (ISCO 40 g) with gradient elution using 0-10% EtOAc/hexane. The desired fractions were combined, concentrated and dried in vacuo to afford 6-bromo-2-(3-chlorophenyl)spiro[chroman-4,2'-[1,3]dioxolane]. $^1$H NMR (500 MHz, CDCl$_3$) δ7.56 (d, 1H), 7.46 (s, 1H), 7.34 (m, 4H), 6.81 (d, 1H), 5.30 (dd, 1H), 4.30 (m, 1H), 4.20 (m, 1H), 4.10 (m, 2H), 2.25 (m, 2H).

Step C: ethyl 3-(2-(3-chlorophenyl)spiro[chroman-4,2'-[1,3]dioxolan]-6-yl)propanoate

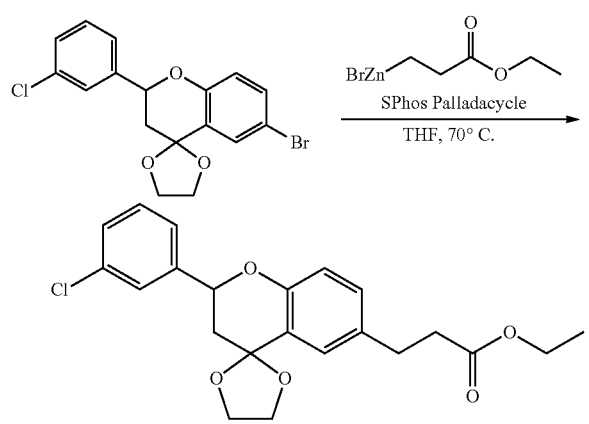

To a solution of 6-bromo-2-(3-chlorophenyl)spiro[chroman-4,2'-[1,3]dioxolane] (887 mg, 2.32 mmol) and S-Phos (Pd) (177 mg, 0.232 mmol, Strem Chemical Co.) in THF (10.0 mL) was added a 0.5 MTHF solution of (3-ethoxy-3-oxopropyl)zinc(II) bromide (13.9 mL, 6.95 mmol) via syringe. The reaction mixture was sparged for 5 min with nitrogen to degas and then heated at 70° C. overnight using a heating block. The reaction mixture was cooled to room temperature and then poured into saturated aq. NH$_4$Cl (30 mL). The aqueous medium was then extracted with EtOAc (350 mL), the organic layer was separated, dried (Na$_2$SO$_4$), filtered and concentrated in vacuo. The resulting crude residue was purified via MPLC (ISCO 40 g) with gradient elution using 0-35% EtOAc/hexane. The desired fractions were combined, concentrated and dried in vacuo to afford ethyl 3-(2-(3-chlorophenyl)spiro-[chroman-4,2'-[1,3]dioxolan]-6-yl)propanoate. $^1$H NMR (500 MHz, CDCl$_3$) δ7.48 (s, 1H), 7.33 (m, 3H), 7.29 (d, 1H), 7.12 (dd, 1H), 6.85 (d, 1H), 5.30 (dd, 1H), 4.30 (dd, 1H), 4.20 (dd, 1H), 4.15 (m, 4H), 2.90 (t, 2H), 2.60 (t, 2H), 2.25 (m, 2H), 1.25 (t, 3H).

Step D: ethyl 3-(2-(2',6'-dimethyl-[1,1'-biphenyl]-3-yl)spiro[chroman-4,2'-[1,3]dioxolan]-6-yl)propanoate

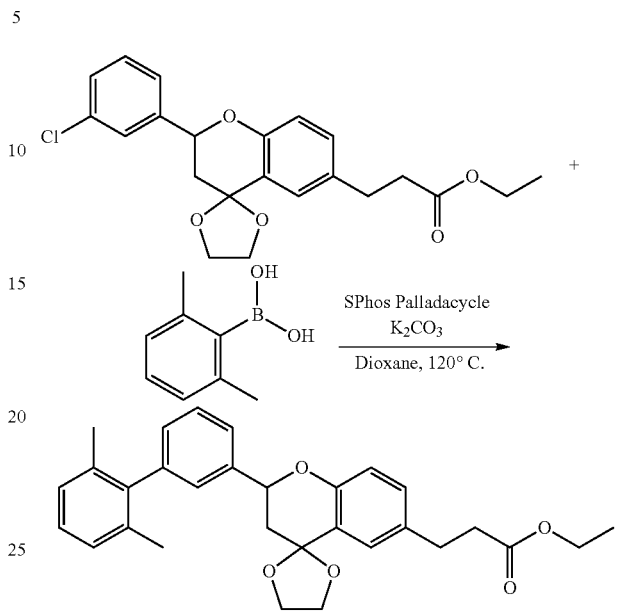

A solution of ethyl 3-(2-(3-chlorophenyl)spiro[chroman-4,2'-[1,3]dioxolan]-6-yl)propanoate (353 mg, 0.877 mmol), (2,6-dimethylphenyl)boronic acid (263 mg, 1.75 mmol) and SPhos Palladacycle (66.7 mg, 0.088 mmol) in dioxane (4.39 mL) was treated with an aq. 3M solution of potassium carbonate (0.585 mL, 1.754 mmol). The reaction mixture was sparged for 5 min with nitrogen and then placed in a microwave reactor and heated at 120° C. (120 W) over 1 h. The reaction mixture was cooled to room temperature, and partitioned between EtOAc (250 mL) and DI H$_2$O/saturated aq. NaCl (50 mL). The organic layer was separated, dried (Na$_2$SO$_4$), filtered and concentrated in vacuo. The resulting crude material was purified via MPLC ISCO 24 g) with gradient elution using 0-30% EtOAc/hexane. The desired fractions were combined, concentrated and dried in vacuo to afford ethyl 3-(2-(2',6'-dimethyl-[1,1'-biphenyl]-3-yl)spiro [chroman-4,2'-[1,3]dioxolan]-6-yl)propanoate. $^1$H NMR (500 MHz, CDCl$_3$) δ7.47 (m, 2H), 7.28 (dd, 2H), 7.14 (m, 5H), 6.86 (d, 1H), 5.35 (dd, 1H), 4.32 (dd, 1H), 4.25 (dd, 1H), 4.15 (m, 4H), 2.90 (t, 2H), 2.60 (t, 2H), 2.30 (m, 2H), 2.08 (d, 6H), 1.25 (t, 3H).

Step E: 3-(2-(2',6'-dimethyl-[1,1'-biphenyl]-3-yl)-4-oxochroman-6-yl)propanoic acid

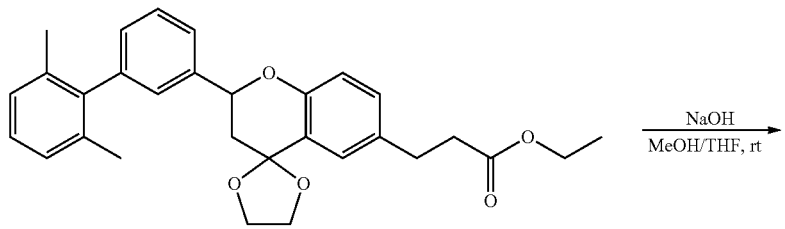

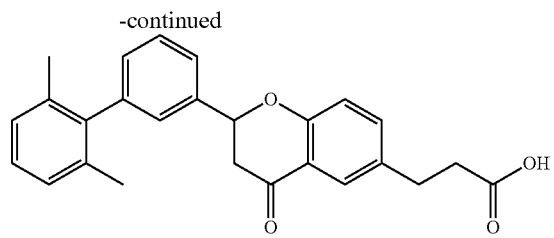

A solution of ethyl 3-(2-(2',6'-dimethyl-[1,1'-biphenyl]-3-yl)spiro[chroman-4,2'-[1,3]dioxolan]-6-yl)propanoate (34.1 mg, 0.072 mmol) in THF (1 mL)/MeOH (0.5 mL) was treated with an aq. 1M solution of sodium hydroxide (0.5 mL, 0.500 mmol). The reaction mixture was stirred at room temperature overnight and then diluted with $CH_3CN/H_2O$ (1 mL), and then concentrated in vacuo. The resulting residue was purified via reverse phase HPLC using a YMC-Pack Pro 5 mm C18 100×20 mm column with gradient elution 30-100% $CH_3CN/H_2O$+v 0.1% TFA. The desired fractions were combined, concentrated and dried in vacuo and lyophilized to afford 3-(2-(2',6'-dimethyl-[1,1'-biphenyl]-3-yl)-4-oxochroman-6-yl)propanoic acid. $^1$H NMR (500 MHz, $CDCl_3$) δ7.76 (s, 1H), 7.48 (m, 2H), 7.38 (d, 1H), 7.27 (d, 1H), 7.18 (m, 2H), 7.12 (m, 2H), 7.01 (d, 1H), 5.50 (d, 1H), 3.10 (m, 1H), 2.95 (m, 3H), 2.70 (t, 2H), 2.05 (d, 6H).

Example 8

3-(2-(2',6'-dimethyl-[1,1'-biphenyl]-3-yl)-4,4-difluorochroman-6-yl)propanoic acid

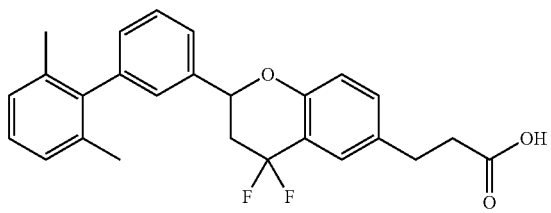 [SMILES: Cc1cccc(C)c1-c1cccc(C2CC(F)(F)c3cc(CCC(=O)O)ccc3O2)c1]

Step A: ethyl 3-(2-(2',6'-dimethyl-[1,1'-biphenyl]-3-yl)-4-oxochroman-6-yl)propanoate

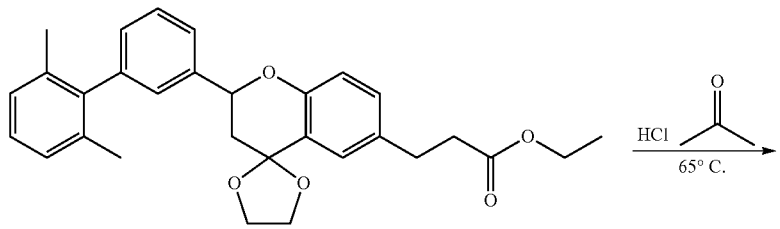

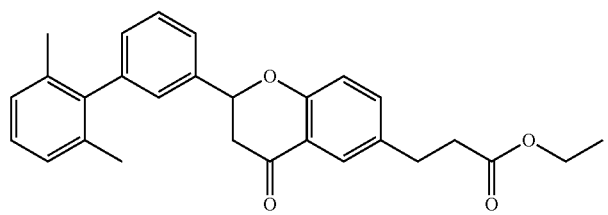

A solution of ethyl 3-(2-(2',6'-dimethyl-[1,1'-biphenyl]-3-yl)spiro[chroman-4,2'-[1,3]dioxolan]-6-yl)propanoate (241 mg, 0.509 mmol) in acetone (5 mL) was treated with 10% aq. HCl (0.1 mL, 10.00 µmol). The reaction mixture was heated to 65° C. using a heating block and stirred over 1 h. The reaction mixture was then cooled to room temperature, neutralized with NEt₃ (1 mL) and concentrated in vacuo. The resulting crude residue was purified via MPLC (ISCO 24 g) with gradient elution using 0-30% EtOAc/hexane. The desired fractions were combined, concentrated and dried in vacuo to afford ethyl 3-(2-(2',6'-dimethyl-[1,1'-biphenyl]-3-yl)-4-oxochroman-6-yl)propanoate. ¹H NMR (500 MHz, CDCl₃) δ7.76 (d, 1H), 7.47 (m, 2H), 7.37 (dd, 1H), 7.27 (s, 1H), 7.18 (m, 2H), 7.12 (m, 2H), 7.00 (d, 1H), 5.50 (dd, 1H), 4.13 (q, 2H), 3.08 (dd, 1H), 2.94 (m, 3H), 2.60 (t, 2H), 2.04 (d, 6H), 1.25 (t, 3H).

Step B: ethyl 3-(2-(2',6'-dimethyl-[1,1'-biphenyl]-3-yl)-4,4-difluorochroman-6-yl)propanoate

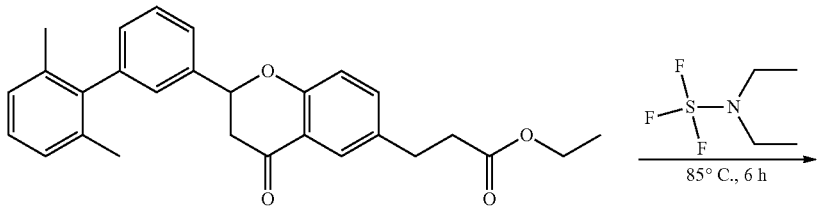

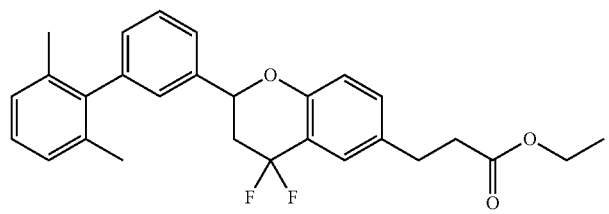

Ethyl 3-(2-(2',6'-dimethyl-[1,1'-biphenyl]-3-yl)-4-oxochroman-6-yl)propanoate (45 mg, 0.105 mmol) was treated with DAST (0.099 mL, 0.749 mmol) at room temperature, placed into a pre-heated 85° C. heating block and then stirred for 6 h. The reaction mixture was cooled to room temperature, diluted with EtOAc (40 mL) and poured into ice-water (5 mL). The organic layer was separated, washed with DI H₂O (10 mL), saturated aq. NaHCO₃ (10 mL), dried (Na₂SO₄), filtered and concentrated in vacuo. The resulting crude residue was purified via (ISCO 12 g) with gradient elution using 0-10% EtOAc/hexane. The desired fractions were combined, concentrated and dried in vacuo to afford ethyl 3-(2-(2',6'-dimethyl-[1,1'-biphenyl]-3-yl)-4,4-difluorochroman-6-yl)propanoate. ¹H NMR (500 MHz, CDCl₃) δ7.48 (m, 3H), 7.28 (s, 1H), 7.23 (d, 1H), 7.18 (t, 2H), 7.12 (d, 2H), 6.92 (d, 1H), 5.30 (d, 1H), 4.15 (q, 2H), 2.95 (t, 2H), 2.65 (m, 4H), 2.05 (d, 6H), 1.25 (t, 3H).

Step C: 3-(2-(2',6'-dimethyl-[1,1'-biphenyl]-3-yl)-4,4-difluorochroman-6-yl)propanoic acid

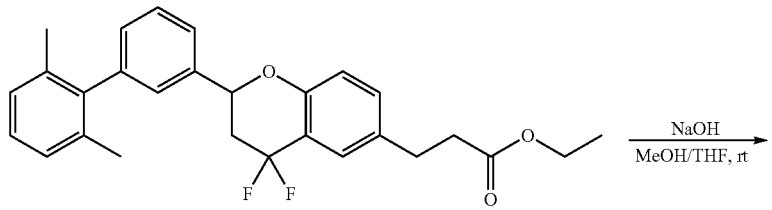

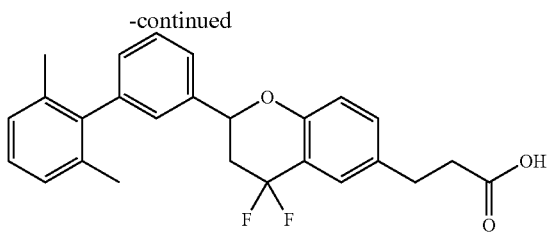

A solution of ethyl 3-(2-(2',6'-dimethyl-[1,1'-biphenyl]-3-yl)-4,4-difluorochroman-6-yl)propanoate (9 mg, 0.020 mmol) in THF (1 mL)/MeOH (0.5 mL) and treated with an aq. 1M solution of sodium hydroxide (0.5 mL, 0.500 mmol). The reaction mixture was stirred at room temperature overnight. The reaction mixture was concentrated in vacuo, diluted with aq. 1M HCl (1 mL) and extracted with EtOAc (20 mL). The organic layer was separated, dried ($Na_2SO_4$), filtered, concentrated and dried in vacuo to afford 3-(2-(2',6'-dimethyl-[1,1'-biphenyl]-3-yl)-4,4-difluorochroman-6-yl)propanoic acid. $^1$H NMR (500 MHz, $CDCl_3$) δ7.50 (m, 3H), 7.28 (dd, 2H), 7.22 (t, 2H), 7.15 (d, 2H), 6.96 (d, 1H), 5.35 (d, 1H), 3.00 (t, 2H), 2.70 (m, 4H), 2.06 (d, 6H).

Examples 7 and 8 were prepared as shown in Examples 7 and 8 above.

Step A: 2-(2-(2',6'-dimethyl-[1,1'-biphenyl]-3-yl)chroman-6-yl)-4,4,5,5-tetramethyl-1,3,2-dioxaborolane

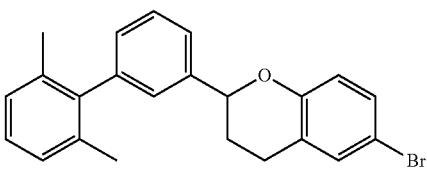

| Example No. | Structure | Stereoisomers | Mass spec, M + 1⁺, m/e |
|---|---|---|---|
| 7 | 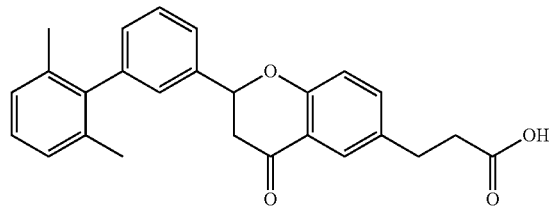 [SMILES: Cc1cccc(C)c1-c1cccc(C2CC(=O)c3cc(CCC(=O)O)ccc3O2)c1] | racemate | 401 |
| 8 | 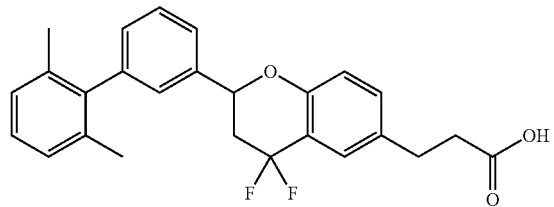 | racemate | 403 (M + H − F) |

Example 9

(1R)-5-(2-(2',6'-dimethyl-[1,1'-biphenyl]-3-yl)chroman-6-yl)isothiazol-3(2H)-one 1-oxide dioxaborolane

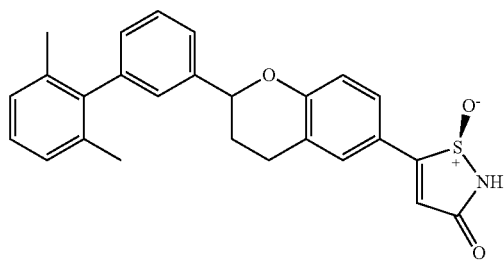

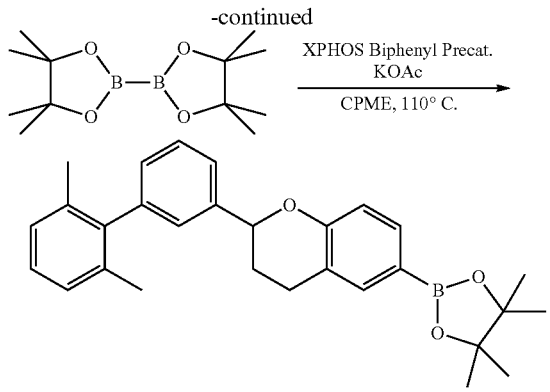

A sealed tube was charged with 6-bromo-2-(2',6'-dimethyl-[1,1'-biphenyl]-3-yl)chroman (105 mg, 0.269 mmol), bispinacolatodiboron (136 mg, 0.537 mmol), potassium acetate (52.7 mg, 0.537 mmol) and X-Phos Biphenyl precatalyst (2-Dicyclohexylphosphino-2',4',6'-triisopropylbiphenyl, 10.6 mg, 0.013 mmol, Strem Chemical Co.). The vessel was sealed, evacuated and backfilled with $N_2$ (3 cycles) and then treated with dry, degassed cyclopentylmethyl ether (1.34 mL). The reaction mixture was then heated thermally at 110° C. for 12 h. The reaction was cooled to room temperature and concentrated in vacuo. The resulting residue was purified via MPLC with a gradient elution using 0-30% EtOAc/hexane. The desired fractions were combined, concentrated and dried in vacuo to give the product. $^1$H NMR (500 MHz, CDCl$_3$): δ 7.58-7.57 (m, 2H), 7.42-7.41 (m, 2H), 7.20 (s, 1H), 7.12-7.09 (m, 4H), 6.91 (d, 1H), 5.14 (d, 1H), 2.97 (m, 1H), 2.82 (m, 1H), 2.24 (m, 1H), 2.10 (m, 1H), 2.04 (d, 6H), 1.34 (s, 12H).

Step B: (1R)-5-(2-(2',6'-dimethyl-[1,1'-biphenyl]-3-yl)chroman-6-yl)isothiazol-3(2H)-one 1-oxide

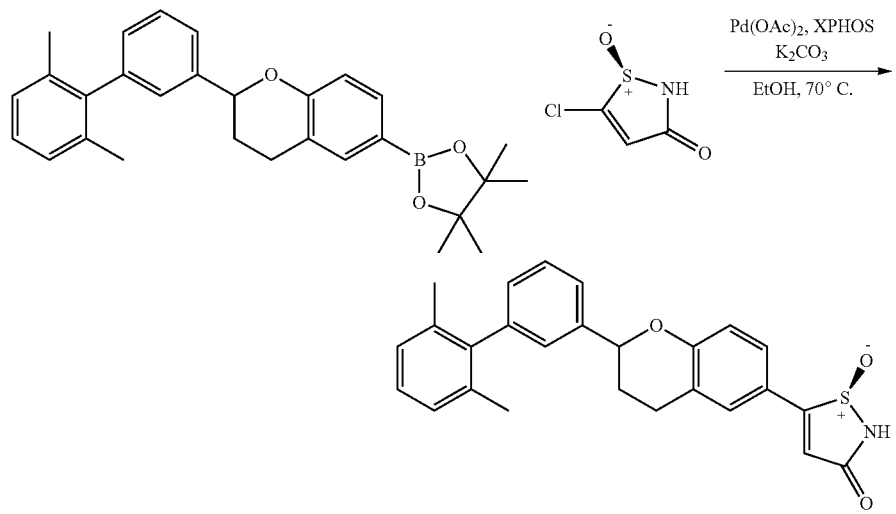

A solution of 2-(2-(2',6'-dimethyl-[1,1'-biphenyl]-3-yl)chroman-6-yl)-4,4,5,5-tetramethyl-1,3,2-dioxaborolane (41.3 mg, 0.094 mmol) in ethanol (1 mL) was added to a sealed tube containing (R)-5-chloroisothiazol-3(2H)-one 1-oxide (15.6 mg, 0.103 mmol), palladium(II) acetate (2.11 mg, 9.38 μmol) and 2-(dicyclohexylphosphino)-2',4',6'-triisopropylbiphenyl (8.94 mg, 0.019 mmol). An aqueous 3M solution of potassium carbonate (0.094 mL, 0.281 mmol) was added, and the vessel was sealed, sparged with $N_2$ over 5 min and heated thermally at 70° C. over 3 h. Then the reaction mixture was cooled to room temperature and partitioned between EtOAc and saturated aq. NaCl. The organic layer was separated, dried (Na$_2$SO$_4$), filtered and concentrated in vacuo. The resulting residue was purified by PrepTLC eluting with 100% EtOAc (1×20 cm$^2$; 1000 micron). The desired band was isolated, suspended in acetone, agitated over 10 min and filtered. The filtrate was concentrated and dried in vacuo to give the product. $^1$H NMR (500 MHz, CDCl$_3$): δ 8.28 (s, 1H), 7.52 (s, 2H), 7.46 (t, 1H), 7.38 (d, 1H), 7.17-7.13 (m, 5H), 7.03 (d, 1H), 6.60 (s, 1H), 5.21 (d, 1H), 3.04-2.97 (m, 1H), 2.89-2.82 (m, 1H), 2.31 (m, 1H), 2.18 (m, 1H), 2.04 (d, 6H).

Example 10

3-(2-(2',6'-dimethyl-[1,1'-biphenyl]-3-yl)-3,4-dihydro-2H-pyrano[3,2-b]pyridin-6-yl)propanoic acid

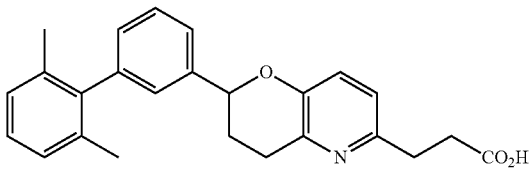 [SMILES: Cc1cccc(C)c1-c1cccc(C2CCc3nc(CCC(=O)O)ccc3O2)c1]

Step A: methyl 6-bromo-3-hydroxypicolinate

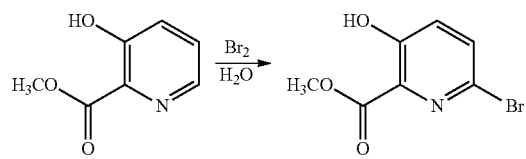

To a water (20 mL) solution of methyl 3-hydroxypicolinate (500 mg, 3.27 mmol) was added dropwise bromine (225 μl, 4.37 mmol). A precipitate formed. After 30 min, the reaction was extracted with DCM (2×20 mL). The combined organic layers were dried (Na$_2$SO$_4$), filtered and concentrated to give the title compound. $^1$H NMR (500 MHz, CDCl$_3$): δ 10.71 (s, 1H), 7.59 (d, 1H), 7.25 (d, 1H), 4.04 (s, 3H).

Step B: 6-bromo-2-(hydroxymethyl)pyridin-3-ol

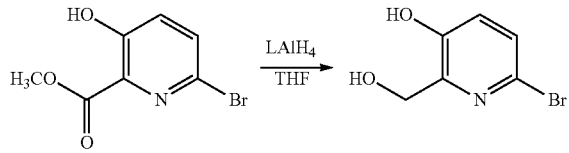 [SMILES: COC(=O)c1nc(Br)ccc1O ; OCc1nc(Br)ccc1O ; "THF"]

To a THF (8 mL) solution of methyl 6-bromo-3-hydroxypicolinate (500 mg, 2.15 mmol) was added a LAH solution (1M in THF, 4 ml, 8.0 mmol. After 30 minutes at room temp, the reaction was quenched by the sequential addition of water (0.30 mL), 15% NaOH (0.30 mL), and water (0.90 mL). The mixture was then stirred vigorously as a white precipitate formed. The resulting mixture was filtered and concentrated to give the title compound. $^1$H NMR (500 MHz, CDCl$_3$): δ 7.31 (d, 1H), 7.10 (d, 1H), 4.65 (s, 2H), 3.30 (br, 1H).

Step C: 6-bromo-2-(2',6'-dimethyl-[1,1'-biphenyl]-3-yl)-3,4-dihydro-2H-pyrano[3,2-b]pyridine

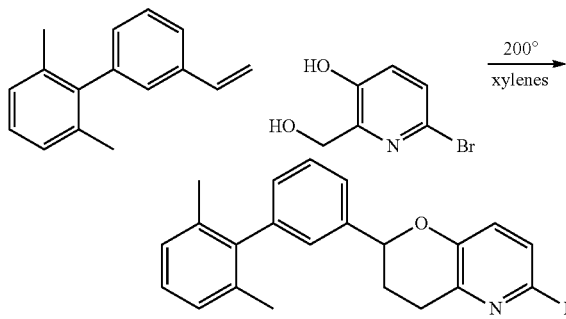

To a xylenes (1 mL) solution of 6-bromo-2-(hydroxymethyl)pyridin-3-ol (30 mg, 0.147 mmol) was added 2,6-dimethyl-3'-vinyl-1,1'-biphenyl (92 mg, 0.441 mmol). The mixture was heated to 200° C. After 2 h, the reaction was cooled to room temperature. The resulting viscous mixture was then loaded directly onto an ISCO cartridge (40 g) and purified by HPLC (0 to 40% EtOAc/hex) to give the title compound. $^1$H NMR (500 MHz, CDCl$_3$): δ 7.50 (t, 1H), 7.40 (d, 1H), 7.26-7.08 (m, 6H), 5.18 (d, 1H), 3.16 (m, 1H), 3.00 (m, 1H), 2.20 (m, 1H), 2.12 (m, 1H), 2.04 (d, 6H).

Step D: ethyl 3-(2-(2',6'-dimethyl-[1,1'-biphenyl]-3-yl)-3,4-dihydro-2H-pyrano[3,2-b]pyridin-6-yl)propanoate

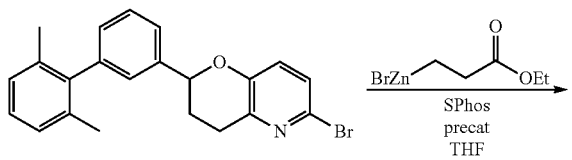

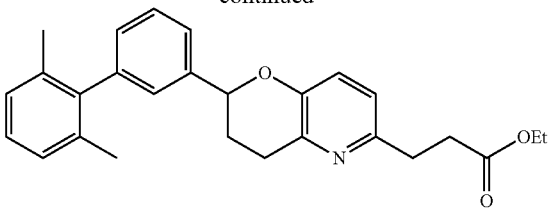

To a degassed THF (1 mL) solution of 6-bromo-2-(2',6'-dimethyl-[1,1'-biphenyl]-3-yl)-3,4-dihydro-2H-pyrano[3,2-b]pyridine (40 mg, 0.101 mmol) and S-Phos Indoline Palladacycle (chloro(2-dicyclohexylphosphino-2',6'-dimethoxy-1,1'-biphenyl)[2-(2-aminoethylphenyl)]-palladium(II)-methyl-t-butyl ether adduct, 7.72 mg, 10.1 μmol, Sigma-Aldrich Co., CAS-No. 1028206-60-1) was added 3-ethoxy-3-oxopropyl)zinc(II) bromide (609 μl, 0.304 mmol, 0.5M, Rieke Metals, Inc.) via syringe. The mixture was then heated to 70° C. on a heating block. After 16 h, the reaction was cooled to room temperature and then poured into NH$_4$Cl (saturated, aq, 10 mL). The mixture was then extracted with EtOAc (2×10 mL), dried (MgSO$_4$), and concentrated. The resulting residue was purified by HPLC (0 to 50% EtOAc in Hex) to give the title compound. $^1$H NMR (500 MHz, CDCl$_3$): δ 7.50-7.40 (m, 2H), 7.24-7.10 (m, 6H), 7.00 (d, 1H), 5.18 (d, 1H), 4.19 (q, 1H), 3.12 (m, 1H), 3.06 (t, 2H), 2.99 (m, 1H), 2.79 (t, 2H), 2.40 (m, 1H), 2.22 (m, 1H), 2.04 (d, 6H), 1.16 (t, 3H).

Step E: 3-(2-(2',6'-dimethyl-[1,1'-biphenyl]-3-yl)-3,4-dihydro-2H-pyrano[3,2-b]pyridin-6-yl)propanoic acid

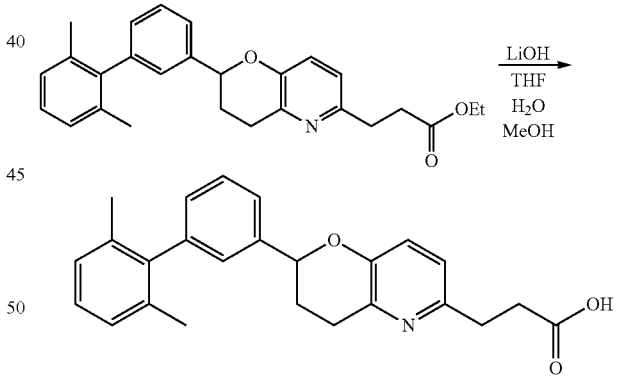

To a THF/MeOH/water (1:1:1, 1.5 mL) solution of ethyl 3-(2-(2',6'-dimethyl-[1,1'-biphenyl]-3-yl)-3,4-dihydro-2H-pyrano[3,2-b]pyridin-6-yl)propanoate (27 mg, 0.065 mmol) was added LiOH (15.56 mg, 0.650 mmol). The reaction was stirred at room temp. After 12 h, the reaction was poured into 1N HCl (10 mL) and extracted with EtOAc (2×10 mL). The combined organic layers were dried (MgSO$_4$) and concentrated. The resulting residue was purified by HPLC (ISCO, 24 g, 0 to 100% EA/Hex) to give the title compound. $^1$H NMR (500 MHz, CDCl$_3$): δ 7.50 (t, 1H), 7.40 (d, 1H), 7.32-7.12 (m, 6H), 7.06 (d, 1H), 5.06 (d, 1H), 3.19 (m, 1H), 3.10 (m, 2H), 3.04 (m, 1H), 2.84 (m, 2H), 2.42 (m, 1H), 2.25 (m, 1H), 2.06 (d, 6H); M+1 m/e=388.4.

Example 11

3-(2-(2',6'-dimethyl-[1,1'-biphenyl]-3-yl)chroman-6-yl)hex-4-ynoic acid

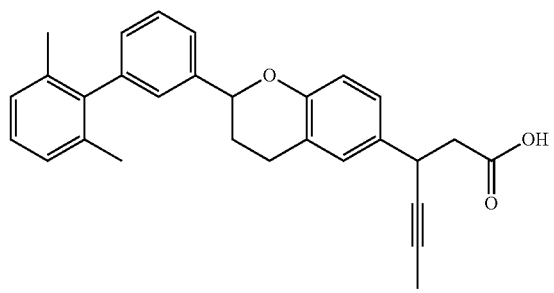 [SMILES: CC#CC(CC(=O)O)c1ccc2c(c1)CCC(c1cccc(-c3c(C)cccc3C)c1)O2]

(3S)-Methyl 3-(4-hydroxyphenyl)hex-4-ynoate

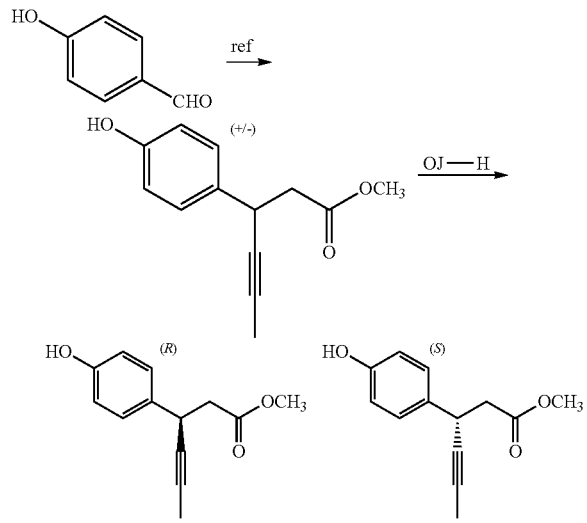

Preparation of racemic methyl 3-(4-hydroxyphenyl)hex-4-ynoate was performed as described by the procedure in *Bioorganic & Medicinal Chemistry Letters* 21(11) 3390, 2011. Separation of the enantiomers was performed by SFC (OJ-H column, 6% IPA/CO$_2$) to give the (R) (faster peak) and (S) (slower peak) enantiomers. $^1$H NMR (500 MHz, acetone-d$_6$) δ 8.2 (br, 1H), 7.20 (d, 2H), 6.77 (d, 2H), 3.98 (m, 1H), 3.60 (s, 3H), 2.65 (m, 2H), 1.78 (s, 3H).

(S)-3-(4-hydroxyphenyl)hex-4-ynoic acid (proof of configuration)

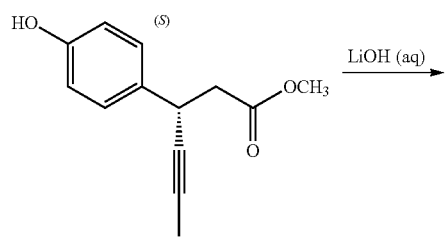

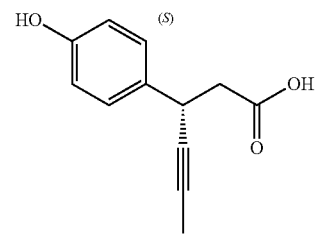

To a solution of (S)-methyl 3-(4-hydroxyphenyl)hex-4-ynoate (slower peak OJ column, 250 mg, 1.145 mmol) in THF/H$_2$O/MeOH in a vial was added LiOH (274 mg, 11.45 mmol). The mixture was heated to 50 0° C. on a heating block. After 12 h, the reaction was poured into 1 N HCl (25 mL) and extracted with EtOAc (2×25 mL). The combined organics were dried (MgSO$_4$) and concentrated. The resulting residue was purified by HPLC (ISCO 40 g, 0 to 50% MeOH/DCM) to give the title compound. $^1$H NMR (500 MHz, DMSO-d$_6$) δ12.2 (s, 1H), 9.27 (s, 1H), 7.12 (d, 2H), 6.67 (d, 2H), 3.87 (m, 1H), 2.54 (m, 2H), 1.82 (s, 3H). $[\alpha]^{23}_D$=+16.36° (c 2.2, CDCl$_3$) (literature $[\alpha]^{23}_D$=+10.09, *Organic Process Research & Development* 2011, v15(3), 570-580).

Step A: 3-(3-formyl-4-hydroxyphenyl)hex-4-ynoic acid

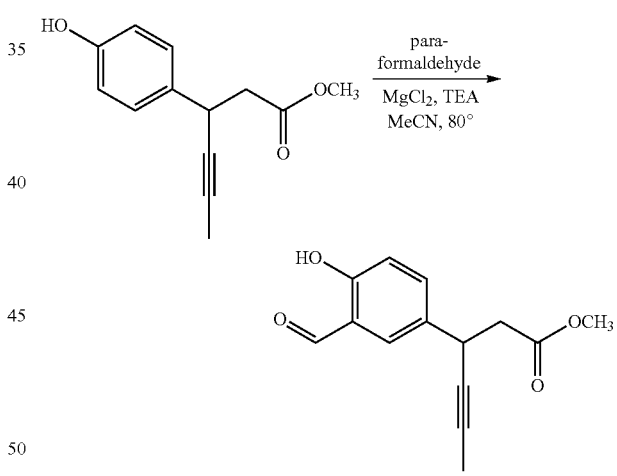

To an acetonitrile (305 ml) solution of methyl 3-(4-hydroxyphenyl)hex-4-ynoate (2.00 g, 9.16 mmol), magnesium chloride (1.31 g, 13.8 mmol), and paraformaldehyde (1.38 g, 45.8 mmol) was added TEA (4.79 mL, 34.4 mmol). The resulting slurry was heated to reflux with an attached condensor. After 3 h, the homogenous yellow solution was cooled to room temperature and then poured into 5% HCl (200 mL). The mixture was then extracted with ethyl acetate (2×250 mL). The combined organic layers were dried (MgSO$_4$) and concentrated. The resulting residue was purified by HPLC (ISCO 120 g, 0 to 50% EA/Hex) to give the title compound. $^1$H NMR (500 MHz, CDCl$_3$) δ10.98 (s, 1H), 9.90 (s, 1H), 7.60 (s, 1H), 7.59 (d, 1H), 6.99 (d, 1H), 4.15 (m, 1H), 3.68 (s, 3H), 2.68 (ddd, 2H), 1.85 (s, 3H).

Step B: methyl 3-(4-hydroxy-3-(hydroxymethyl)phenyl)hex-4-ynoate

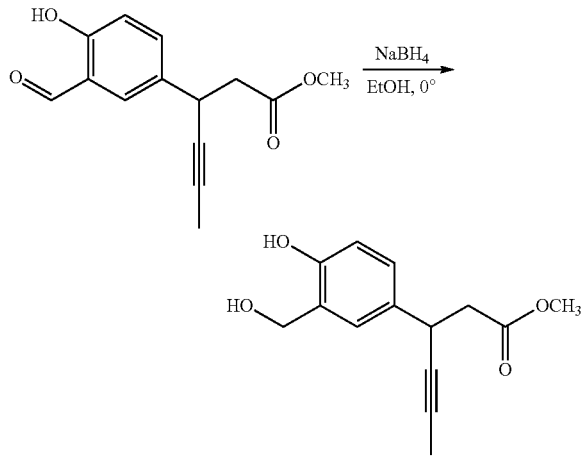

To a cooled (0° C.) ethanol (24 mL) solution of methyl 3-(3-formyl-4-hydroxyphenyl)hex-4-ynoate (1.175 g, 4.77 mmol) was added sodium borohydride (0.181 g, 4.77 mmol) in a single portion. After 30 minutes, the reaction was quenched by the dropwise addition of 1N HCl (20 mL) at 0° C. The mixture was then poured into saturated ammonium chloride (50 mL) and extracted with EtOAc (2×50 mL). The combined organics were dried (MgSO$_4$) and concentrated. The resulting residue was purified by HPLC (ISCO 80 gram, 0 to 80% EA/Hex) to give the title compound. $^1$H NMR (500 MHz, CDCl$_3$) δ7.38 (s, 1H), 7.20 (d, 1H), 7.05 (s, 1H), 6.82 (d, 1H), 4.83 (br, 2H), 4.02 (m, 1H), 3.66 (s, 3H), 2.71 (ddd, 2H), 2.42 (br, 1H), 1.81 (s, 3H).

Step C: methyl 3-(2-(3-bromophenyl)chroman-6-yl)hex-4-ynoate

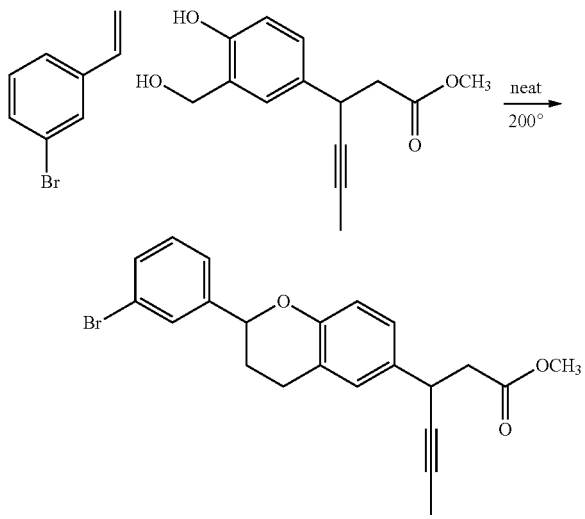

3-Bromostyrene (6.24 mL, 47.9 mmol) and methyl 3-(4-hydroxy-3-(hydroxymethyl)phenyl)-hex-4-ynoate (1.19 g, 4.79 mmol) were combined and then heated neat to 200° C. on a heating block in a sealed tube. After 2 h, the mixture was cooled to room temperature to give a plastic-like semi-solid (styrene had mostly polymerized). The product-containing polymer was then taken up in DCM (5 mL) and diluted with hexanes (200 mL). The insoluble polystyrenes were filtered and the volatiles removed in vacuo. The resulting residue was purified by HPLC (ISCO, 0 to 20% EA/Hex) to give the title compound. $^1$H NMR (500 MHz, CDCl3) δ 7.60 (s, 1H), 7.47 (d, 1H), 7.36 (d, 1H), 7.28 (d, 1H), 7.15 (d, 1H), 7.11 (s, 1H), 6.89 (d, 1H), 5.01 (d, 1H), 4.06 (m, 1H), 3.70, (s, 3H), 3.00 (m, 1H), 2.80 (m, 2H), 2.69 (dd, 1H), 2.21 (m, 1H) 2.02 (m, 1H), 1.82 (s, 3H).

Step D: methyl 3-(2-(2',6'-dimethyl-[1,1'-biphenyl]-3-yl)chroman-6-yl)hex-4-ynoate

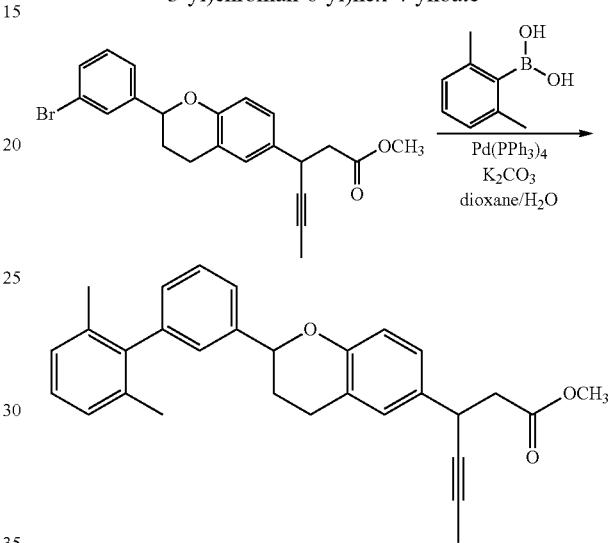

To a nitrogen-purged dioxane (1 mL) solution of methyl 3-(2-(3-bromophenyl)chroman-6-yl)hex-4-ynoate (40 mg, 0.097 mmol), (2,6-dimethylphenyl)boronic acid (22 mg, 0.15 mmol), and tetrakis(triphenylphosphine)palladium(0) (5.6 mg, 4.8 µmol, Strem Chemical Co.) was added K$_2$CO$_3$ solution (2 N in water, 100 µL, 0.2 mmol). The resulting mixture was heated to 100° C. on a heating block. After 12 h, the reaction was cooled to room temp and then poured into NH4Cl (sat, aq, 10 mL) and extracted with EA (2×10 mL). The combined organic layers were dried (MgSO$_4$) and concentrated. The resulting residue was purified HPLC (ISCO, 0 to 50% EA/Hex) to give the title compound. $^1$H NMR (500 MHz, CDCl$_3$) δ7.50-7.41 (m, 2H), 7.22-7.09 (m, 7H), 6.86 (d, 1H), 5.12 (d, 1H), 4.05 (m, 1H), 3.70 (s, 3H), 2.99 (m, 1H), 2.80 (m, 2H), 2.68 (dd, 1H), 2.25 (m, 1H), 2.08 (m, 1H), 2.04 (d, 6H), 1.82 (s, 3H).

Step E: 3-(2-(2',6'-dimethyl-[1,1'-biphenyl]-3-yl)chroman-6-yl)hex-4-vnoic acid

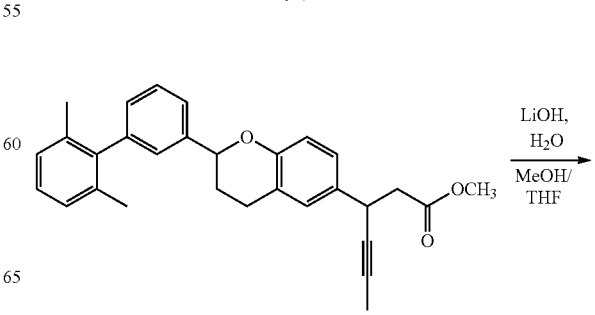

-continued

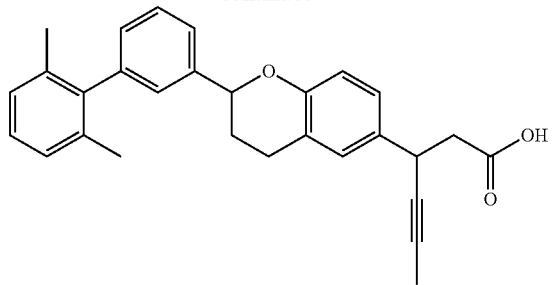 [SMILES: CC#CC(CC(=O)O)c1ccc2c(c1)CCC(c1cccc(-c3c(C)cccc3C)c1)O2]

To a THF/MeOH/water (1:1:1, 1.5 mL) solution of methyl 3-(2-(2',6'-dimethyl-[1,1'-biphenyl]-3-yl)chroman-6-yl)hex-4-ynoate (36 mg, 0.082 mmol) was added LiOH (20 mg, 0.82 mmol). The reaction was then heated to 60° C. on a heating block. After 12 h, the reaction was poured into 1N HCl (10 mL) and extracted EtOAc (2×10 mL). The combined organic layers were dried (MgSO$_4$) and concentrated. The resulting residue was purified by HPLC (ISCO, 24 g, 0 to 100% EA/hex) to give the title compound. $^1$H NMR (500 MHz, CDCl$_3$) δ7.47-7.40 (m, 2H), 7.22-7.10 (m, 7H), 6.88 (d, 1H), 5.15 (d, 1H), 4.05 (m, 1H), 3.00 (m, 1H), 2.80 (m, 3H), 2.28 (m, 1H), 2.12 (m, 1H), 2.06 (d, 6H), 1.85 (s, 3H).

Example 11 was prepared as shown in Example 11 above. Examples 12-55 were prepared in a similar manner to Example 11 using the appropriate starting materials and substituted boronate as described in Intermediate 1.

| Example No. | Structure | Stereoisomers | Mass spec, M + 1$^+$, m/e |
|---|---|---|---|
| 11 | 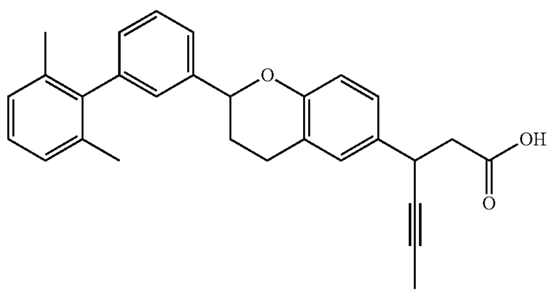 [SMILES: CC#CC(CC(=O)O)c1ccc2c(c1)CCC(c1cccc(-c3c(C)cccc3C)c1)O2] | Mixture of four stereoisomers | 425.4 |
| 12 | 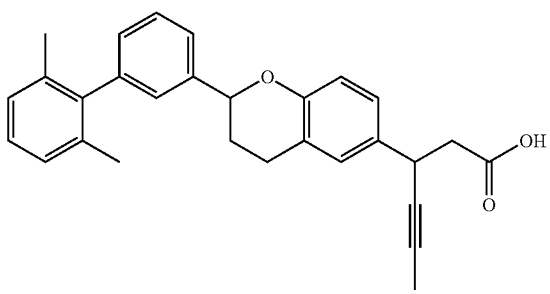 [SMILES: CC#CC(CC(=O)O)c1ccc2c(c1)CCC(c1cccc(-c3c(C)cccc3C)c1)O2] | single isomer A | 425.4 |
| 13 | 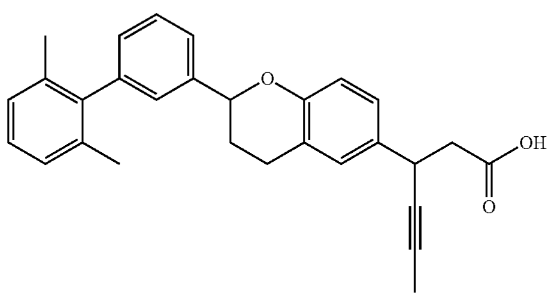 [SMILES: CC#CC(CC(=O)O)c1ccc2c(c1)CCC(c1cccc(-c3c(C)cccc3C)c1)O2] | single isomer B | 425.4 |
| 14 | 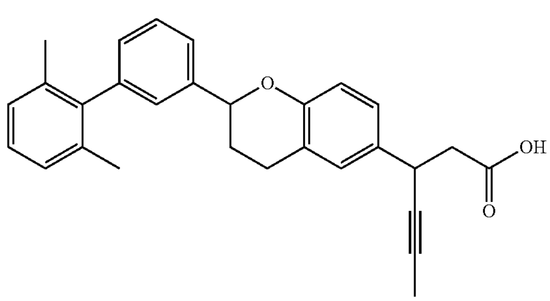 | single isomer C | 425.4 |

-continued

| Example No. | Structure | Stereoisomers | Mass spec, M + 1⁺, m/e |
|---|---|---|---|
| 15 | 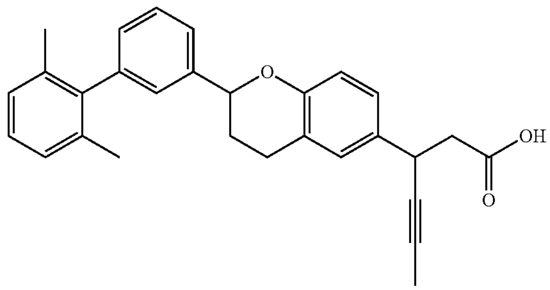 [SMILES: CC#CC(CC(=O)O)c1ccc2c(c1)CCC(c1cccc(-c3c(C)cccc3C)c1)O2] | single isomer D | 425.4 |
| 16 | 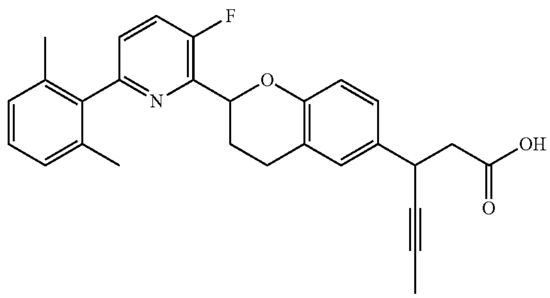 | Mixture of four stereoisomers | 444.4 |
| 17 | 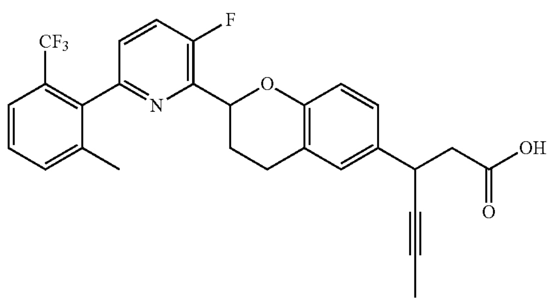 | Mixture of four stereoisomers | 484.2 |
| 18 | 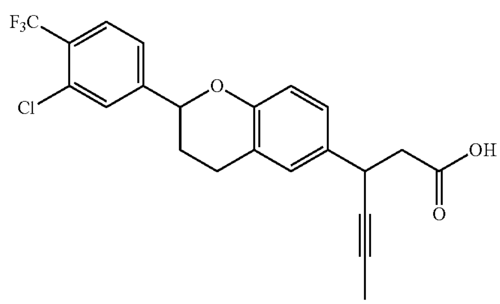 [SMILES: CC#CC(CC(=O)O)c1ccc2c(c1)CCC(c1ccc(C(F)(F)F)c(Cl)c1)O2] | Mixture of four stereoisomers | 423.1 |
| 19 | 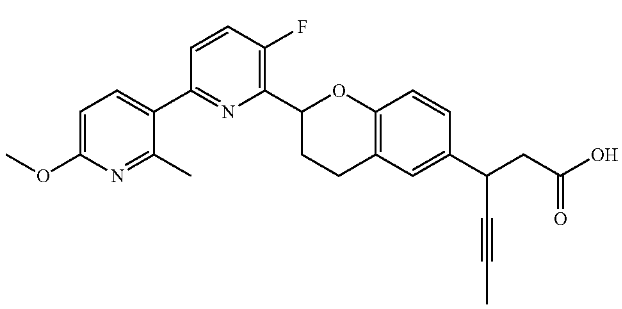 [SMILES: CC#CC(CC(=O)O)c1ccc2c(c1)CCC(c1nc(-c3ccc(OC)nc3C)ccc1F)O2] | Mixture of four stereoisomers | 461.2 |

-continued

| Example No. | Structure | Stereoisomers | Mass spec, M + 1⁺, m/e |
|---|---|---|---|
| 20 | 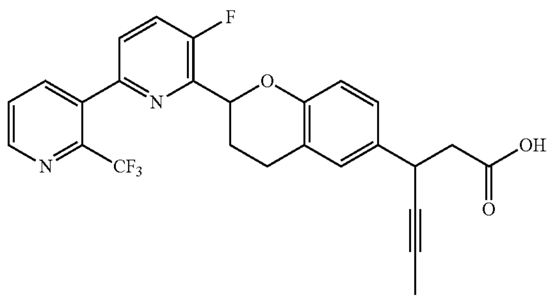 [SMILES: CC#CC(CC(=O)O)c1ccc2c(c1)CCC(c1nc(-c3cccnc3C(F)(F)F)ccc1F)O2] | Mixture of four stereoisomers | 485.3 |
| 21 | 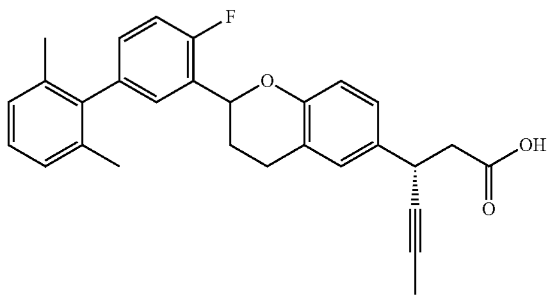 [SMILES: CC#C[C@@H](CC(=O)O)c1ccc2c(c1)CCC(c1cc(-c3c(C)cccc3C)ccc1F)O2] | single isomer | 443 |
| 22 | 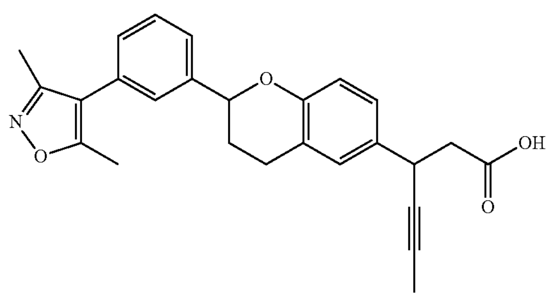 [SMILES: CC#CC(CC(=O)O)c1ccc2c(c1)CCC(c1cccc(-c3c(C)noc3C)c1)O2] | Mixture of four stereoisomers | 416.2 |
| 23 | 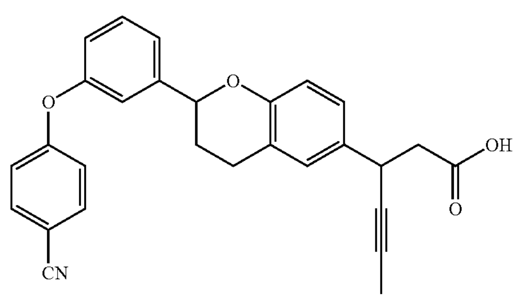 [SMILES: CC#CC(CC(=O)O)c1ccc2c(c1)CCC(c1cccc(Oc3ccc(C#N)cc3)c1)O2] | Mixture of two diastereomers | 438.4 |
| 24 | 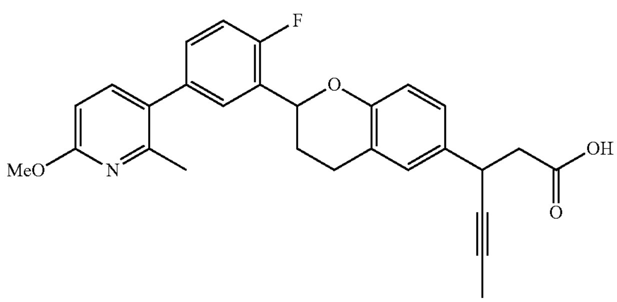 [SMILES: CC#CC(CC(=O)O)c1ccc2c(c1)CCC(c1cc(-c3ccc(OC)nc3C)ccc1F)O2] | Mixture of two diastereomers | 460 |

-continued
| Example No. | Structure | Stereoisomers | Mass spec, M + 1⁺, m/e |
|---|---|---|---|
| 25 | 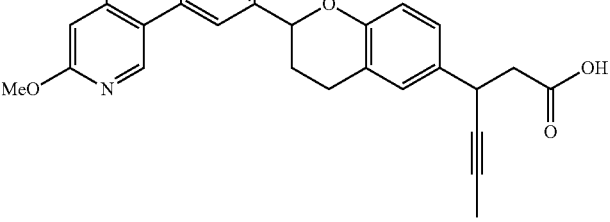 | Mixture of two diastereomers | 442 |
| 26 | 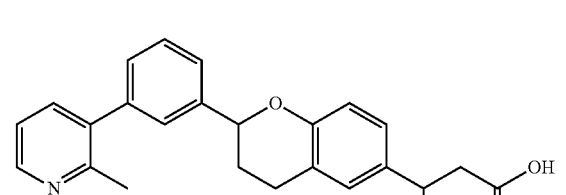 | Mixture of four stereoisomers | 412 |
| 27 | 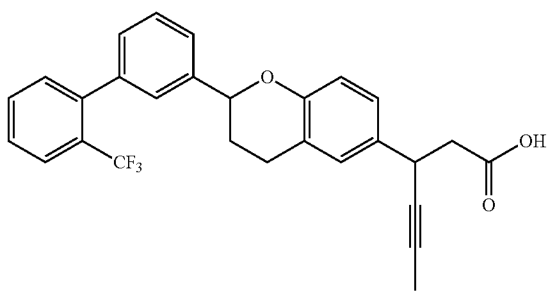 [SMILES: CC#CC(CC(=O)O)c1ccc2c(c1)CCC(c1cccc(-c3ccccc3C(F)(F)F)c1)O2] | Mixture of four stereoisomers | 465 |
| 28 | 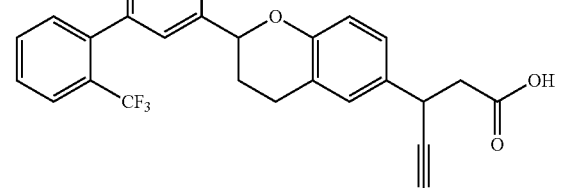 | Mixture of two diastereomers | 417/419 |
| 29 | 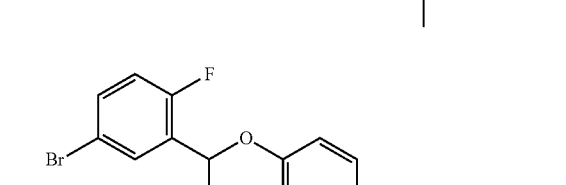 | Mixture of two diastereomers | 483 |

-continued

| Example No. | Structure | Stereoisomers | Mass spec, M + 1+, m/e |
|---|---|---|---|
| 30 | 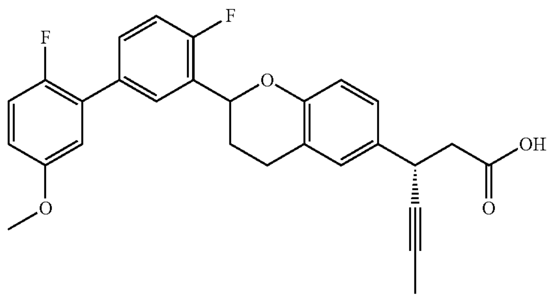 [SMILES: CC#C[C@@H](CC(=O)O)c1ccc2c(c1)CCC(c1cc(-c3cc(OC)ccc3F)ccc1F)O2] | Mixture of two diastereomers | 463 |
| 31 | 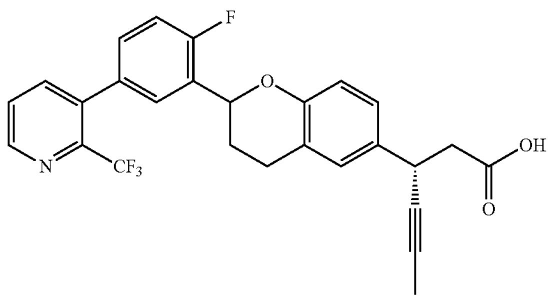 [SMILES: CC#C[C@@H](CC(=O)O)c1ccc2c(c1)CCC(c1cc(-c3cccnc3C(F)(F)F)ccc1F)O2] | Mixture of two diastereomers | 484 |
| 32 | 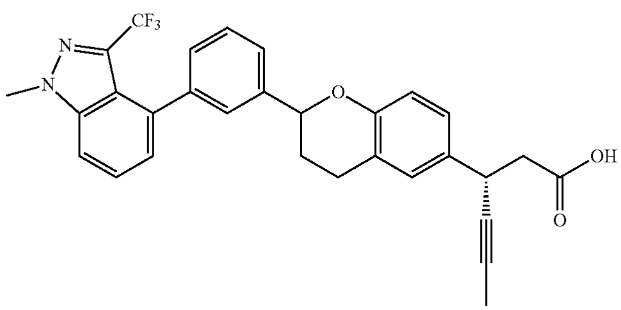 [SMILES: CC#C[C@@H](CC(=O)O)c1ccc2c(c1)CCC(c1cccc(-c3cccc4c3c(C(F)(F)F)nn4C)c1)O2] | Mixture of two diastereomers | 519 |
| 33 | 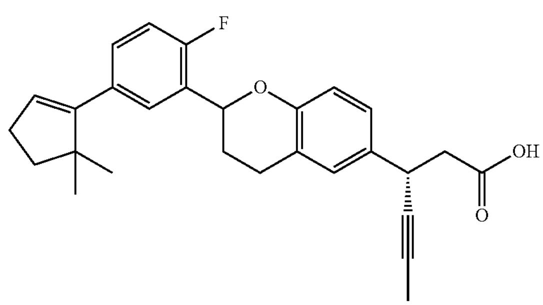 [SMILES: CC#C[C@@H](CC(=O)O)c1ccc2c(c1)CCC(c1cc(C3=CCCC3(C)C)ccc1F)O2] | Mixture of two diastereomers | 433 |
| 34 | 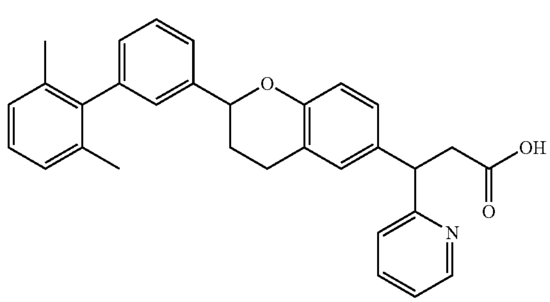 [SMILES: Cc1cccc(C)c1-c1cccc(C2CCc3cc(C(CC(=O)O)c4ccccn4)ccc3O2)c1] | Mixture of four diastereomers | 464 |

-continued

| Example No. | Structure | Stereoisomers | Mass spec, M + 1⁺, m/e |
|---|---|---|---|
| 35 | 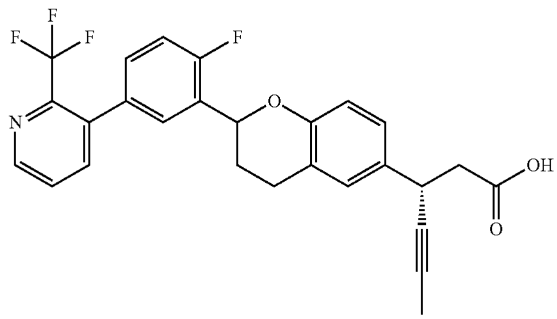 [SMILES: CC#C[C@@H](CC(=O)O)c1ccc2c(c1)CCC(c1cc(-c3cccnc3C(F)(F)F)ccc1F)O2] | single isomer A | 484 |
| 36 | 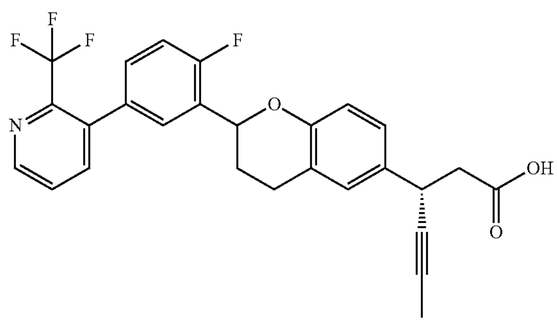 [SMILES: CC#C[C@@H](CC(=O)O)c1ccc2c(c1)CCC(c1cc(-c3cccnc3C(F)(F)F)ccc1F)O2] | single isomer B | 484 |
| 37 | 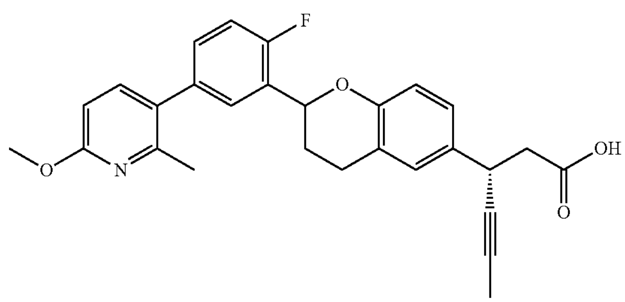 [SMILES: CC#C[C@@H](CC(=O)O)c1ccc2c(c1)CCC(c1cc(-c3ccc(OC)nc3C)ccc1F)O2] | single isomer A | 460 |
| 38 | 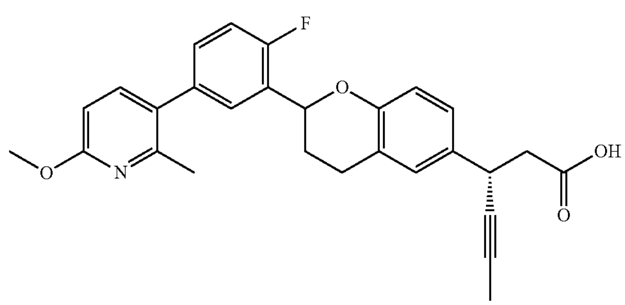 [SMILES: CC#C[C@@H](CC(=O)O)c1ccc2c(c1)CCC(c1cc(-c3ccc(OC)nc3C)ccc1F)O2] | single isomer B | 460 |
| 39 | 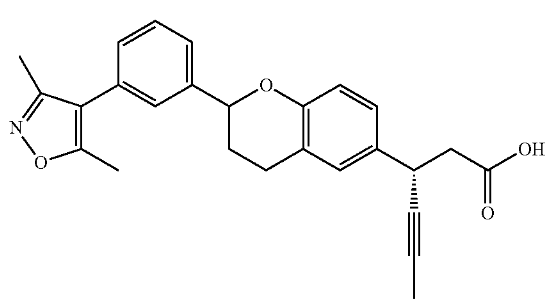 | single isomer A | 416 |

-continued

| Example No. | Structure | Stereoisomers | Mass spec, M + 1⁺, m/e |
|---|---|---|---|
| 40 | 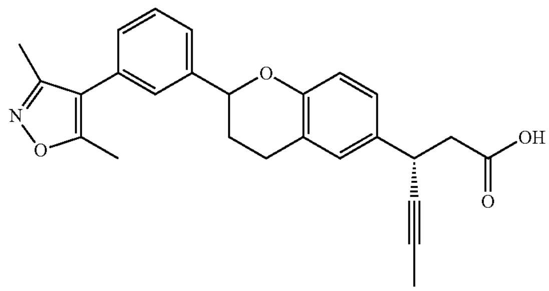 | single isomer B | 416 |
| 41 | 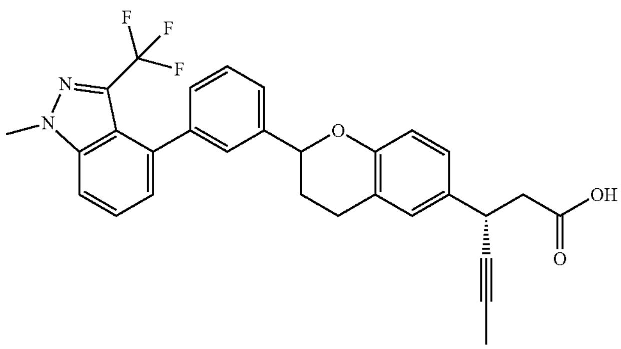 [SMILES: CC#C[C@@H](CC(=O)O)c1ccc2c(c1)CCC(c1cccc(-c3cccc4c3c(C(F)(F)F)nn4C)c1)O2] | single isomer A | 519 |
| 42 | 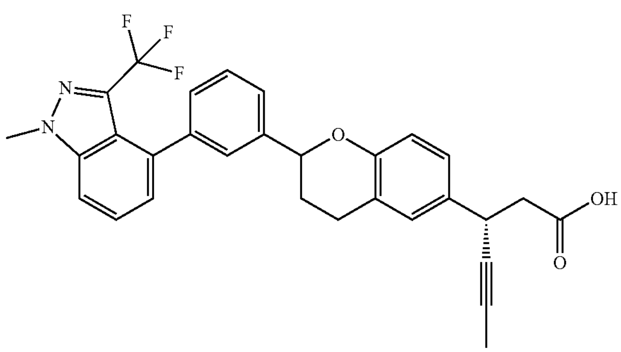 [SMILES: CC#C[C@@H](CC(=O)O)c1ccc2c(c1)CCC(c1cccc(-c3cccc4c3c(C(F)(F)F)nn4C)c1)O2] | single isomer B | 519 |
| 43 | 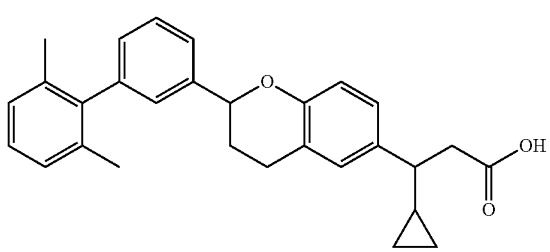 [SMILES: Cc1cccc(C)c1-c1cccc(C2CCc3cc(C(CC(=O)O)C4CC4)ccc3O2)c1] | Mixture of four diastereomers | 427 |
| 44 | 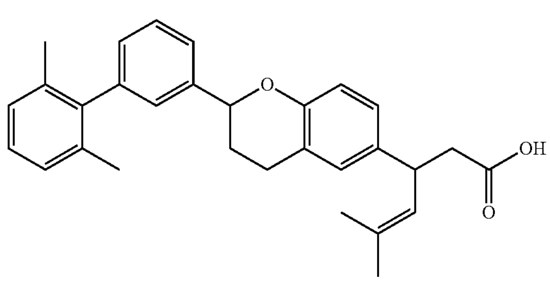 [SMILES: CC(C)=CC(CC(=O)O)c1ccc2c(c1)CCC(c1cccc(-c3c(C)cccc3C)c1)O2] | Mixture of four diastereomers | 441 458 (M + H + NH3) |

| Example No. | Structure | Stereoisomers | Mass spec, M + 1⁺, m/e |
|---|---|---|---|
| 45 | 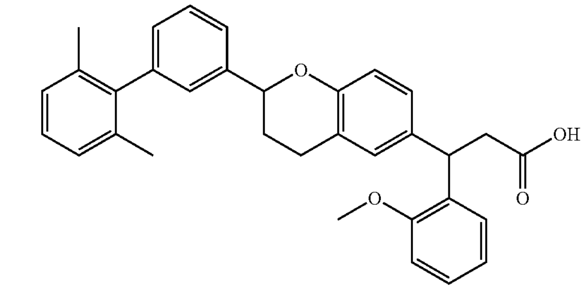 [SMILES: COc1ccccc1C(CC(=O)O)c1ccc2c(c1)CCC(c1cccc(-c3c(C)cccc3C)c1)O2] | Mixture of four diastereomers | 510 (M + H + NH3) |
| 46 | 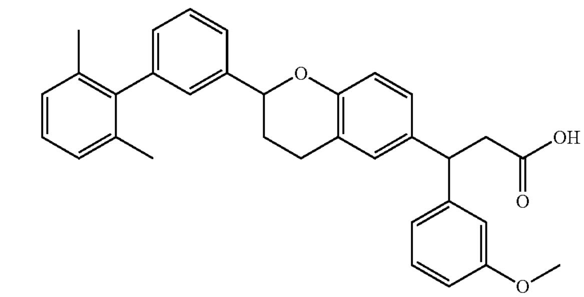 [SMILES: COc1cccc(C(CC(=O)O)c2ccc3c(c2)CCC(c2cccc(-c4c(C)cccc4C)c2)O3)c1] | Mixture of four diastereomers | 510 (M + H + NH3) |
| 47 | 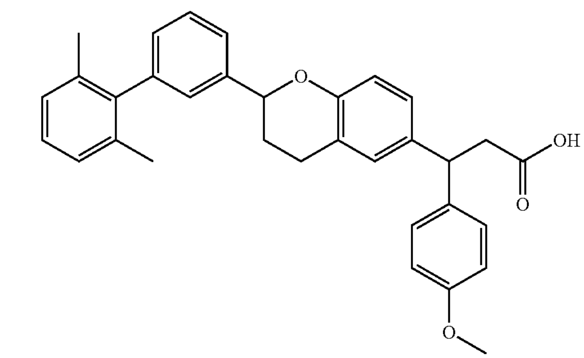 [SMILES: COc1ccc(C(CC(=O)O)c2ccc3c(c2)CCC(c2cccc(-c4c(C)cccc4C)c2)O3)cc1] | Mixture of four diastereomers | 510 (M + H + NH3) |
| 48 | 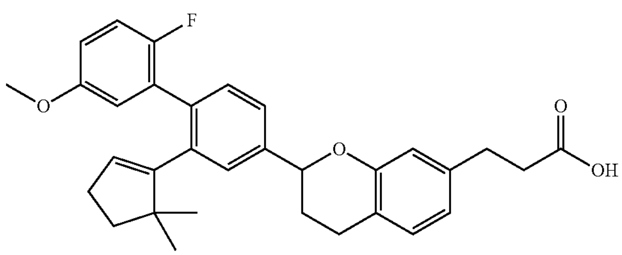 [SMILES: COc1ccc(F)c(-c2ccc(C3CCc4ccc(CCC(=O)O)cc4O3)cc2C2=CCCC2(C)C)c1] | Racemic mixture | 501 |
| 49 | 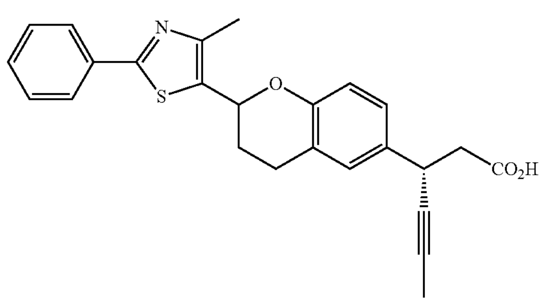 [SMILES: CC#C[C@@H](CC(=O)O)c1ccc2c(c1)CCC(c1sc(-c3ccccc3)nc1C)O2] | Mixture of two diastereomers | 417.2 |

-continued

| Example No. | Structure | Stereoisomers | Mass spec, M + 1⁺, m/e |
|---|---|---|---|
| 50 | 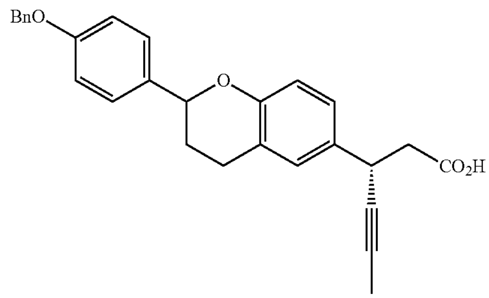 [SMILES: CC#C[C@@H](CC(=O)O)c1ccc2c(c1)CCC(c1ccc(OCc3ccccc3)cc1)O2] | Mixture of two diastereomers | 427.2 |
| 51 | 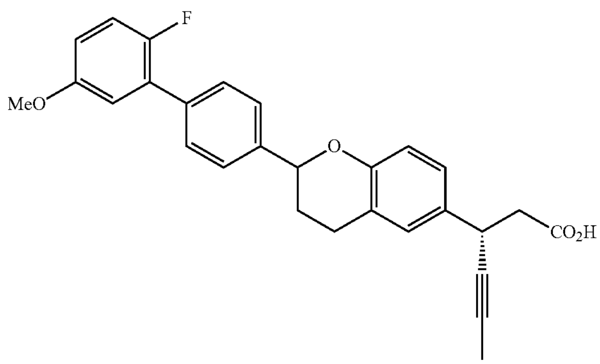 [SMILES: CC#C[C@@H](CC(=O)O)c1ccc2c(c1)CCC(c1ccc(-c3cc(OC)ccc3F)cc1)O2] | Mixture of two diastereomers | 445.2 |
| 52 | 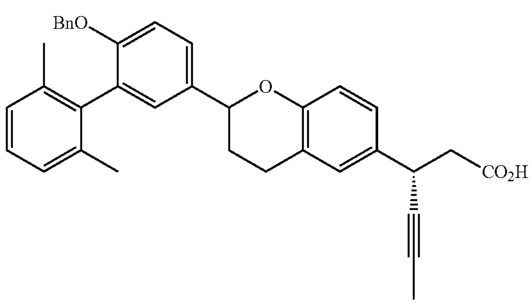 [SMILES: CC#C[C@@H](CC(=O)O)c1ccc2c(c1)CCC(c1ccc(OCc3ccccc3)c(-c3c(C)cccc3C)c1)O2] | Mixture of two diastereomers | 531.2 |
| 53 | 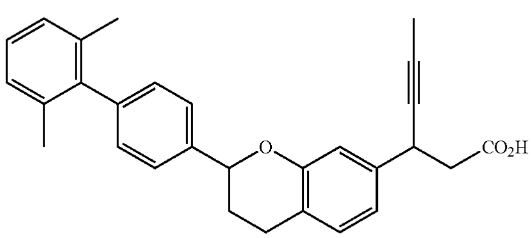 [SMILES: CC#CC(CC(=O)O)c1ccc2c(c1)OC(c1ccc(-c3c(C)cccc3C)cc1)CC2] | single isomer A | 425.2 |
| 54 | 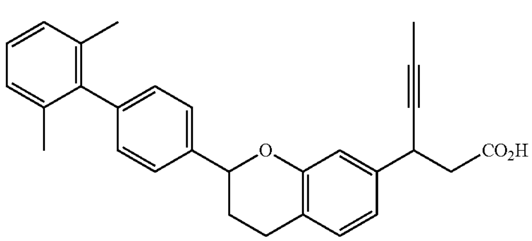 [SMILES: CC#CC(CC(=O)O)c1ccc2c(c1)OC(c1ccc(-c3c(C)cccc3C)cc1)CC2] | single isomer B | 425.2 |

Example 55

2-((3S)-7-(2',6'-dimethyl-[1,1'-biphenyl]-3-yl)-3,5,6,7-tetrahydro-2H-furo[3,2-g]chromen-3-yl)acetic acid

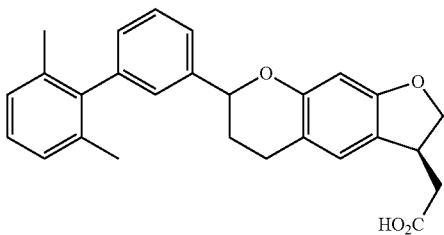 [SMILES: Cc1cccc(C)c1-c1cccc(C2CCc3cc4c(cc3O2)OC[C@H]4CC(=O)O)c1]

Step A: (S)-methyl 2-(2-phenyl-6,7-dihydro-4H-[1,3,2]dioxaborinino[5,4-f]benzofuran-6-yl)acetate

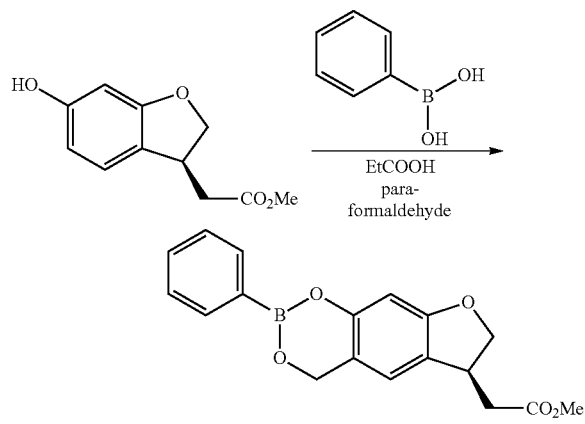

To a benzene (25 mL) slurry of (S)-methyl 2-(6-hydroxy-2,3-dihydrobenzofuran-3-yl)acetate (3.00 g, 14.4 mmol), phenylboronic acid (2.11 g, 17.3 mmol), and paraformaldehyde (3.46 g, 115 mmol) was added propionic acid (0.539 ml, 7.20 mmol). A Dean Stark trap was attached to the flask and then the resulting mixture was heated to reflux. After 4 h, the reaction was cooled to room temperature. The homogenous solution was stripped to give the crude product, which was purified by HPLC (ISCO 0 to 100% EtOAc/Hex) to give the title compound. $^1$H NMR (500 MHz, CDCl$_3$) δ7.50-7.40 (m, 5H), 6.81 (s, 1H), 6.60 (s, 1H), 5.10 (s, 2H), 4.80 (t, 1H), 4.31 (dd, 1H), 3.84 (m, 1H), 3.79 (s, 3H), 2.79 (dd, 1H), 2.62 (dd, 1H).

Step B: methyl 2-((3S)-7-(3-bromophenyl)-3,5,6,7-tetrahydro-2H-furo[3,2-g]chromen-3-yl)acetate

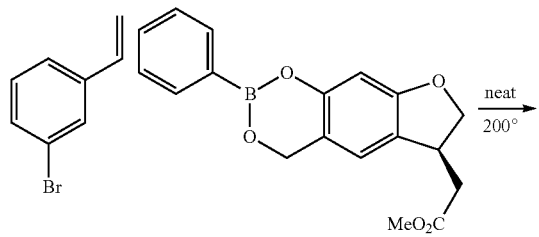

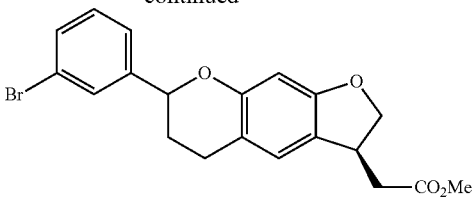

1-bromo-3-vinylbenzene (1000 mg, 5.46 mmol) and (S)-methyl 2-(2-phenyl-6,7-dihydro-4H-[1,3,2]dioxaborinino[5,4-f]benzofuran-6-yl)acetate (200 mg, 0.617 mmol) were combined neat in a sealed tube. The mixture was then heated to 200° C. After 2 h, the reaction was cooled to room temperature and the residue purified by HPLC (ISCO 0 to 50% EtOAc/Hex) to give the title compound. $^1$H NMR (500 MHz, CDCl$_3$) δ7.60 (s, 1H), 7.46 (d, 1H), 7.38 (d, 1H), 7.28 (d, 1H), 6.88 (s, 1H), 6.40 (s, 1H), 5.00 (d, 1H), 4.77 (t, 1H), 4.23 (m, 1H), 3.80 (m, 1H), 3.75 (s, 3H), 2.90 (m, 1H), 2.78 (m, 2H), 2.60 (dd, 1H), 2.20 (m, 1H).

Step C: methyl 2-((3S)-7-(2',6'-dimethyl-[1,1'-biphenyl]-3-yl)-3,5,6,7-tetrahydro-2H-furo[3,2-g]chromen-3-yl)acetate

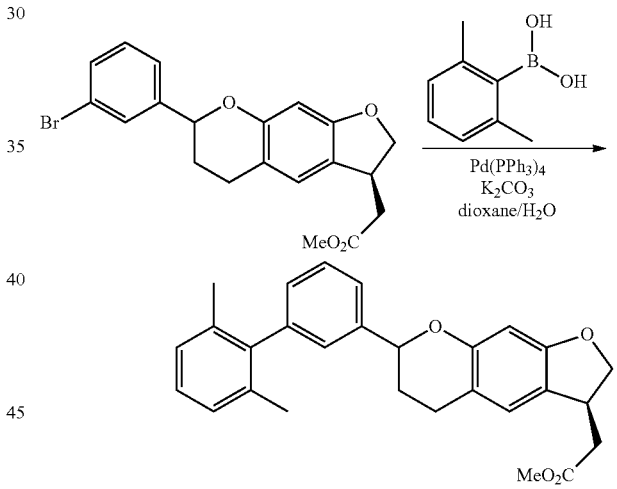

To a nitrogen-purged toluene (0.50 mL) solution of (2,6-dimethylphenyl)boronic acid (22 mg, 0.15 mmol), methyl 2-((3S)-7-(3-bromophenyl)-3,5,6,7-tetrahydro-2H-furo[3,2-g]chromen-3-yl)acetate (40 mg, 0.10 mmol), and tetrakis(triphenylphosphine)palladium(0) (5.7 mg, 5.0 μmol) was added a K$_2$CO$_3$ solution (2 N in water, 0.1 mL, 0.20 mmol). The resulting mixture was heated to 100° C. on a heating block. After 12 h, the reaction was cooled to room temperature and then poured into NH$_4$Cl (sat, aq, 10 mL) and extracted with EA (2×10 mL). The combined organic layers were dried (MgSO$_4$) and concentrated. The resulting residue was purified by HPLC (ISCO 0 to 50% EtOAc/Hex) to give the title compound. $^1$H NMR (500 MHz, CDCl$_3$) δ7.50-7.40 (m, 2H), 7.22-7.10 (m, 5H), 6.85 (s, 1H), 6.40 (s, 1H), 5.10 (d, 1H), 4.75 (t, 1H), 4.22 (t, 1H), 3.81 (m, 1H), 3.75 (s, 3H), 2.92 (m, 1H), 2.75 (m, 2H), 2.60 (m, 1H), 2.22 (m, 1H), 2.10 (m, 1H), 2.05 (d, 6H).

Step D. 2-((3S)-7-(2',6'-dimethyl-[1,1'-biphenyl]-3-yl)-3,5,6,7-tetrahydro-2H-furo[3,2-g]chromen-3-yl)acetic acid

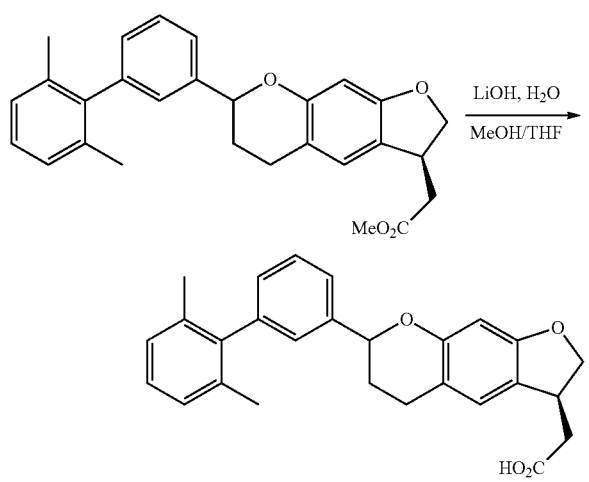

To a THF/water/MeOH solution of methyl 2-((3S)-7-(2',6'-dimethyl-[1,1'-biphenyl]-3-yl)-3,5,6,7-tetrahydro-2H-furo[3,2-g]chromen-3-yl)acetate (40 mg, 0.093 mmol) was added LiOH (22.35 mg, 0.933 mmol). The mixture was then heated to 60° C. on a heating block. After 12 h, the reaction mixture was poured into 1 N HCl (10 mL) and extracted with EtOAc (2×10 mL). The combined organic layers were dried (MgSO$_4$) and concentrated. The resulting residue was purified by HPLC (ISCO, 24 gram, 0 to 100% EA/hex) to give the title compound. $^1$H NMR (500 MHz, CDCl$_3$) δ7.49-7.40 (m, 2H), 7.21-7.10 (m, 5H), 6.90 (s, 1H), 6.40 (s, 1H), 5.10 (d, 1H), 4.78 (t, 1H), 4.29 (t, 1H), 3.80 (m, 1H), 2.95 (m, 1H), 2.82 (dd, 1H), 2.75 (dt, 1H), 2.64 (m, 1H), 2.22 (m, 1H), 2.08 (m, 1H), 2.02 (d, 6H).

Example 55 was prepared as shown in Example 55 above. Examples 56-59 were prepared in a similar manner to Example 55 using the appropriate starting materials and a substituted boronate as in Intermediate 1.

| Example No. | Structure | Mass spec, M + 1$^+$, m/e |
|---|---|---|
| 55 | 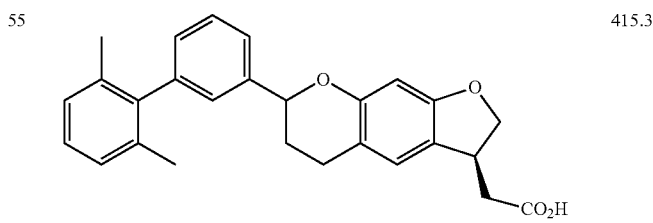 | 415.3 |
| 56 | 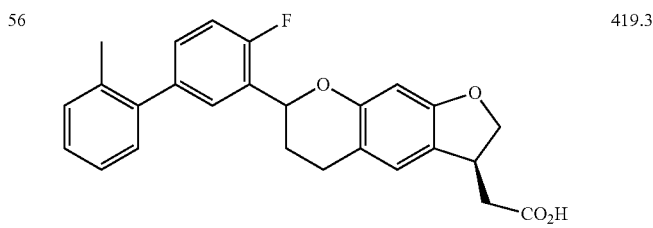 | 419.3 |
| 57 | 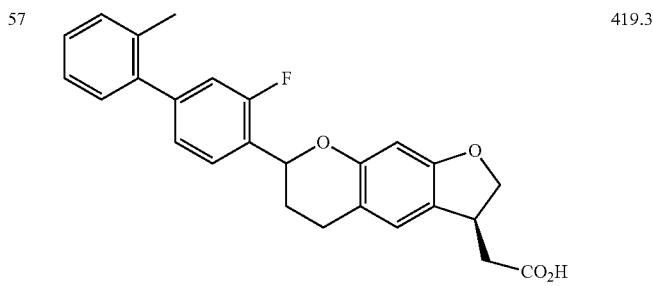 | 419.3 |

-continued

| Example No. | Structure | Mass spec, M + 1⁺, m/e |
|---|---|---|
| 58 | 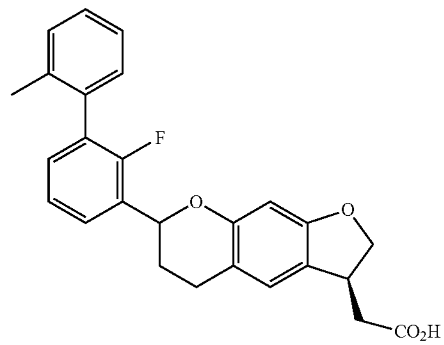 [SMILES: Cc1ccccc1-c1cccc(C2CCc3cc4c(cc3O2)OC[C@H]4CC(=O)O)c1F] | 419.3 |
| 59 | 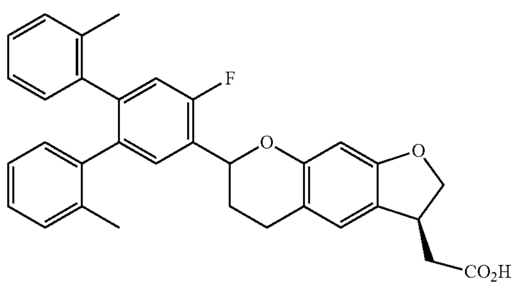 [SMILES: Cc1ccccc1-c1cc(F)c(C2CCc3cc4c(cc3O2)OC[C@H]4CC(=O)O)cc1-c1ccccc1C] | 509.3 |

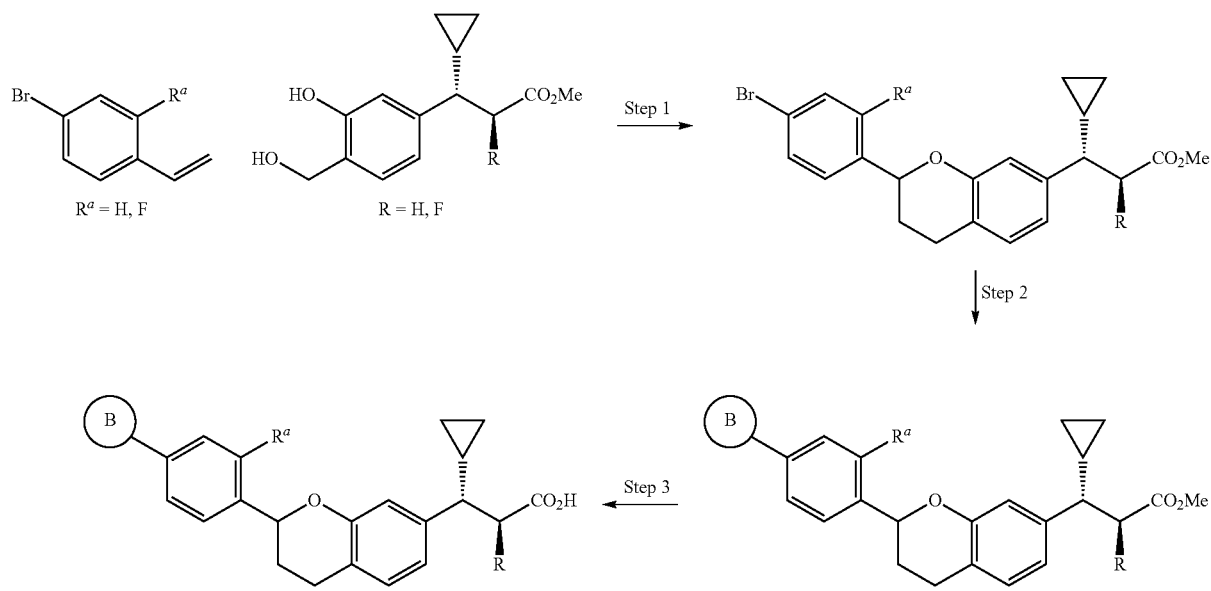

Scheme 11

Step 1: Montmorillonite K10, LiClO₄, MeNO₂, water; Step 2: Pd(PPh₃)₄, K₂CO₃, Dioxane, 100° C.; Step 3: THF/MeOH/1M LiOH, 60° C., Substituted chromans may be prepared according to the procedure in Scheme 11, as shown in Example 60. Lewis acid-promoted Diels Alder cycloaddition is used to establish the chroman core. Suzuki cross-coupling of the aryl bromide with arylboronic acids delivers the biaryl chroman compounds. Hydrolysis of the ester results in the acid.

Example 60

(3S)-3-cyclopropyl-3-(2-(2'-fluoro-5'-methoxy-[1,1'-biphenyl]-4-yl) chroman-7-yl)propanoic acid

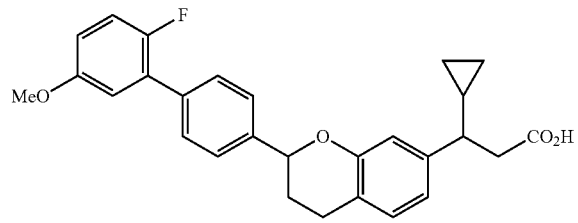 [SMILES: COc1ccc(F)c(-c2ccc(C3CCc4ccc(C(CC(=O)O)C5CC5)cc4O3)cc2)c1]

Step 1: (3S)-methyl 3-(2-(4-bromophenyl)chroman-7-yl)-3-cyclopropylpropanoate

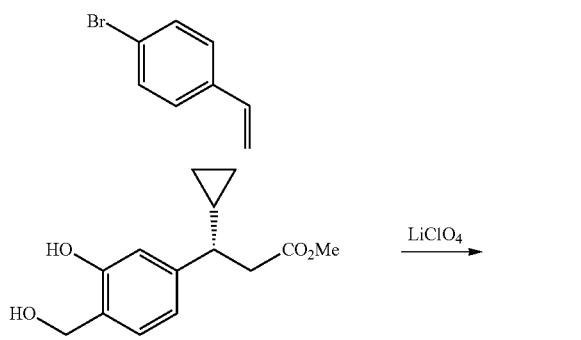

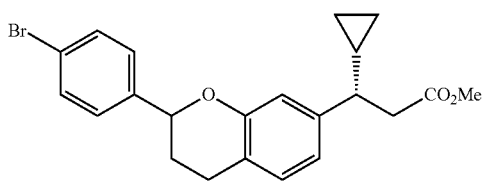

To a nitromethane (50 mL) solution of (S)-methyl 3-cyclopropyl-3-(3-hydroxy-4-(hydroxymethyl)phenyl)propanoate (1.00 g, 4.00 mmol), 1-bromo-4-vinylbenzene (1.05 mL, 7.99 mmol), and lithium perchlorate (527 mg, 4.95 mmol) was added montmorillonite K10 (1.00 gram) and water (0.893 mL, 49.4 mmol). The reaction was sealed and heated to 75° C. on a heating block. After 3 h, the mixture was cooled to room temperature, filtered and concentrated. The resulting residue was purified by HPLC (ISCO 80 gram, 0 to 50% EtOAc/Hex) to give the title compound. $^1$H NMR (500 MHz, CDCl$_3$) δ7.50 (d, 2H), 7.30 (d, 2 h), 7.00 (d, 1 h), 6.80 (m, 2H), 5.00 (d, 1H), 3.60 (s, 3H), 2.95 (m, 1H), 2.70 (m, 3H), 2.30 (q, 1H), 2.19 (m, 1H), 2.00 (m, 1H), 1.00 (m, 1 h), 0.59 (m, 1H), 0.41 (m, 1H), 0.22 (m, 1H), 0.18 (m, 1H).

Step 2: (3S)-methyl 3-cyclopropyl-3-(2-(2'-fluoro-5'-methoxy-[1,1'-biphenyl]-4-yl)chroman-7-yl)propanoate

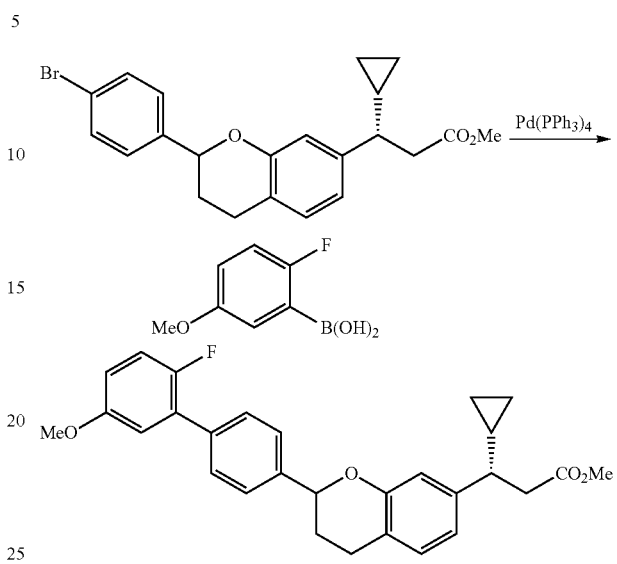

To a nitrogen-sparged dioxane (2 mL) solution of (3S)-methyl 3-(2-(4-bromophenyl)-chroman-7-yl)-3-cyclopropylpropanoate (100 mg, 0.241 mmol), (2-fluoro-5-methoxyphenyl)boronic acid (61.4 mg, 0.361 mmol), and Tetrakis (13.91 mg, 0.012 mmol) was added K$_2$CO$_3$ (361 μl, 0.722 mmol) (2 M solution). The reaction mixture was heated to 100° C. and stirred on a heating block for 16 h. Then the reaction was cooled to room temp and poured into saturated NH$_4$Cl (25 mL). The mixture was extracted with EtOAc (2×25 mL). The combined organic layers were dried (MgSO$_4$) and concentrated. The resulting residue was purified by HPLC (ISCO 40 gram, 0 to 50% EtOAc/Hex) to give the title compound. $^1$H NMR (500 MHz, CDCl$_3$) δ7.59 (d, 2H), 7.50 (d, 2H), 7.05 (t, 1H), 7.02 (d, 1H), 6.95 (m, 1H), 6.90 (m, 2H), 6.88 (d, 1H), 5.05 (d, 1H), 3.80 (s, 3H), 3.60 (s, 3H), 3.00 (m, 1H), 2.80 (m, 1H), 2.70 (m, 2H), 2.30 (m, 1 h), 2.22 (m, 1H), 2.12 (m, 1H), 1.00 (m, 1H), 0.55 (m, 1H), 0.41 (m, 1H), 0.22 (m, 1H), 0.18 (m, 1H).

Step 3: (3S)-3-cyclopropyl-3-(2-(2'-fluoro-5'-methoxy-[1,1'-biphenyl]-4-yl)chroman-7-yl)propanoic acid

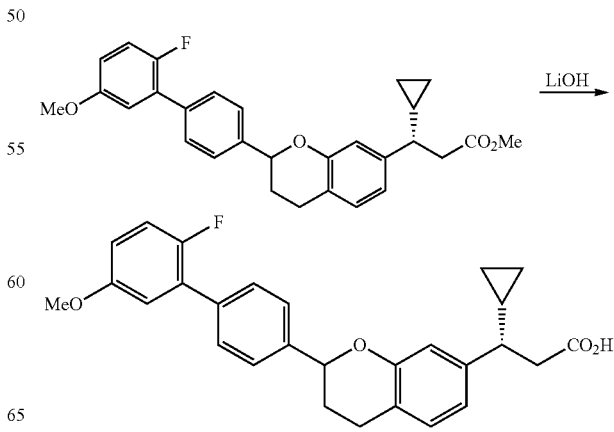

To a MeOH/THF/water (3 mL, 1:1:1) solution of (3S)-methyl 3-cyclopropyl-3-(2-(2'-fluoro-5'-methoxy-[1,1'-biphenyl]-4-yl)chroman-7-yl)propanoate (55 mg, 0.119 mmol) was added LiOH (28.6 mg, 1.194 mmol). The reaction mixture was heated to 60° C. and stirred on a heating block for 16 h. Then the reaction was poured into 1N HCl (10 mL) and extracted with EtOAc (2×10 mL). The combined organic layers were dried (MgSO$_4$) and concentrated. The resulting residue was purified by HPLC (ISCO 40 g, 0 to 100% EtOAc/Hex) to give the title compound. Separation of diastereomers into isomer A and isomer B was performed by SFC: OJ-H column, 25% MeOH/CO$_2$. $^1$H NMR (both isomers) (500 MHz, CDCl$_3$) δ7.60 (d, 2H), 7.50 (d, 2H), 7.02 (m, 2H), 6.96 (m, 1H), 6.80 (m, 2H), 6.78 (m, 1H), 5.02 (d, 1H), 3.80 (s, 1H), 3.00 (m, 1H), 2.80 (m, 3H), 2.32 (q, 1H), 2.22 (m, 1H), 2.12 (m, 1H), 1.00 (m, 1H), 0.60 (m, 1H), 0.45 (m, 1H), 0.29 (m, 1H), 0.19 (m, 1H).

Examples 61 and 62 were prepared as shown in Example 60 above.

methoxy-[1,1'-biphenyl]-4-yl)chroman-7-yl)propanoate was converted into (3 S)-methyl 3-cyclopropyl-3-(2-(2'-fluoro-5'-methoxy-[1,1'-biphenyl]-4-yl)chroman-7-yl)propanoate as a mixture of 4 diastereomers.

Step 2

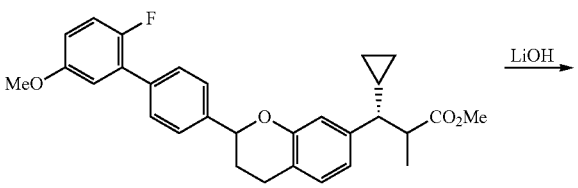

| Example No. | Structure | Stereoisomer/ Chiral Conditions | Mass Spec M + 1, m/e |
|---|---|---|---|
| 61 | 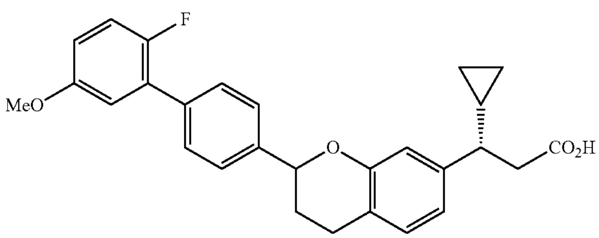 [SMILES: COc1ccc(F)c(-c2ccc(C3CCc4ccc([C@@H](CC(=O)O)C5CC5)cc4O3)cc2)c1] | Isomer A OJ-H (0.46 × 25 mm) 25% MeOH(DEA)/ CO$_2$ | 447.2 |
| 62 | 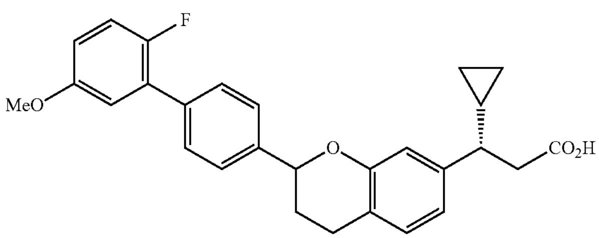 [SMILES: COc1ccc(F)c(-c2ccc(C3CCc4ccc([C@@H](CC(=O)O)C5CC5)cc4O3)cc2)c1] | Isomer B OJ-H (0.46 × 25 mm) 25% MeOH(DEA)/ CO$_2$ | 447.3 |

Examples 63-66

Step 1

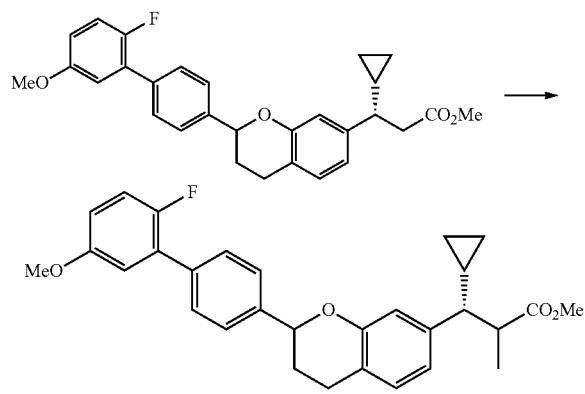

Utilizing a method similar to Step B of Intermediates 5 and 6, (3S)-Methyl 3-cyclopropyl-3-(2-(2'-fluoro-5'-

-continued

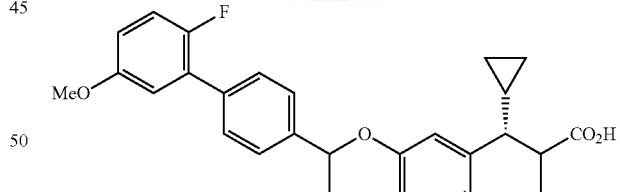

Utilizing a method similar to that employed in Step 3 of Example 60, (3S)-methyl 3-cyclopropyl-3-(2-(2'-fluoro-5'-methoxy-[1,1'-biphenyl]-4-yl)chroman-7-yl)propanoate was converted to (3R)-3-cyclopropyl-3-(2-(2'-fluoro-5'-methoxy-[1,1'-biphenyl]-4-yl)chroman-7-yl)-2-methylpropanoic acid as a mixture of 4 diastereomers, which were separated via chiral SFC chromatography (ChiralPak AD-H, (21.2×250 mm) 45% EtOH(DEA)/CO$_2$) to give the compounds in Examples 63-66 (listed in order of elution, earliest to latest).

| Example No. | Structure | Chiral Chromatography conditions | Mass Spec M + 1, m/e |
|---|---|---|---|
| 63 | MeO-[biphenyl-F]-[chromane]-CH(cyclopropyl)-CH(Me)-CO₂H | Isomer A AD-H (21.2 × 250 mm) 45% EtOH(DEA)/CO₂ | 461.2 |
| 64 | MeO-[biphenyl-F]-[chromane]-CH(cyclopropyl)-CH(Me)-CO₂H | Isomer B AD-H (21.2 × 250 mm) 45% EtOH(DEA)/CO₂ | 461.2 |
| 65 | MeO-[biphenyl-F]-[chromane]-CH(cyclopropyl)-CH(Me)-CO₂H | Isomer C AD-H (21.2 × 250 mm) 45% EtOH(DEA)/CO₂ | 461.2 |
| 66 | MeO-[biphenyl-F]-[chromane]-CH(cyclopropyl)-CH(Me)-CO₂H | Isomer D AD-H (21.2 × 250 mm) 45% EtOH(DEA)/CO₂ | 461.2 |

Examples 67 and 68 were prepared in a similar manner to Scheme 12 using the appropriate method and the appropriate starting materials.

| Example No. | Structure | Scheme 12 Step 1 | Stereoisomers Chiral Conditions | LC/MS (M + H)⁺ |
|---|---|---|---|---|
| 67 | HO-[biphenyl-F]-[chromane]-CH(cyclopropyl)-CH(Me)-CO₂H | C | Isomer A AD-H (4.6 × 250 mm) 40% (1:1 MeOH/MeCN)/CO₂ | 469.5 (M + Na) |

-continued

| Example No. | Structure | Scheme 12 Step 1 | Stereoisomers Chiral Conditions | LC/MS (M + H)+ |
|---|---|---|---|---|
| 68 | (structure: 2-fluoro-5-hydroxyphenyl biphenyl chroman cyclopropyl methyl CO2H) | C | Isomer B AD-H (4.6 × 250 mm) 40% (1:1 MeOH/ MeCN)/CO2 | 469.6 (M + Na) |

Examples 69-96 were prepared in a similar manner to Example 60 using the appropriate starting materials and substituted boronate.

| Example No. | Structure | Stereoisomer/ Chiral Conditions | Mass Spec M + 1, m/e |
|---|---|---|---|
| 69 | (structure) | 2 Diastereomers | 415.13 |
| 70 | (structure) | 2 Diastereomers | 483.19 |
| 71 | (structure) | 2 Diastereomers | 448.14 |
| 72 | (structure) | 2 Diastereomers | 447.00 |

| Example No. | Structure | Stereoisomer/ Chiral Conditions | Mass Spec M + 1, m/e |
|---|---|---|---|
| 73 | 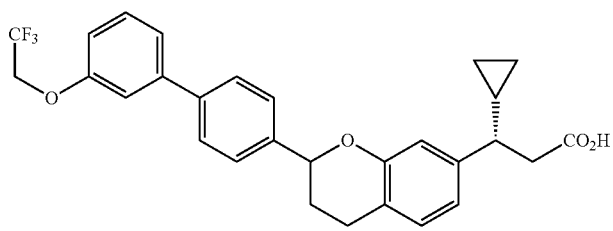 [SMILES: O=C(O)C[C@H](c1ccc2c(c1)OC(c1ccc(-c3cccc(OCC(F)(F)F)c3)cc1)CC2)C1CC1] | 2 Diastereomers | 497.05 |
| 74 | 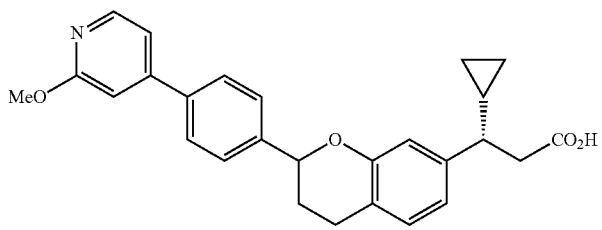 [SMILES: COc1cc(-c2ccc(C3CCc4ccc([C@@H](CC(=O)O)C5CC5)cc4O3)cc2)ccn1] | 2 Diastereomers | 430.22 |
| 75 | 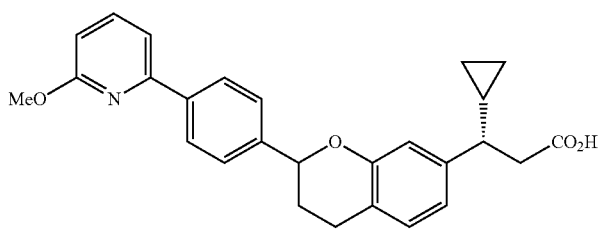 [SMILES: COc1cccc(-c2ccc(C3CCc4ccc([C@@H](CC(=O)O)C5CC5)cc4O3)cc2)n1] | 2 Diastereomers | 430.21 |
| 76 | 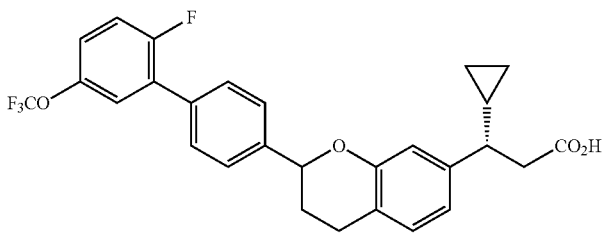 [SMILES: O=C(O)C[C@H](c1ccc2c(c1)OC(c1ccc(-c3cc(OC(F)(F)F)ccc3F)cc1)CC2)C1CC1] | 2 Diastereomers | 501.03 |
| 77 | 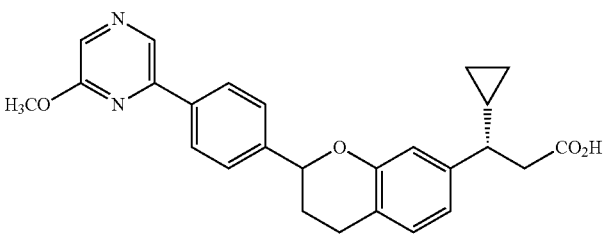 [SMILES: COc1cncc(-c2ccc(C3CCc4ccc([C@@H](CC(=O)O)C5CC5)cc4O3)cc2)n1] | 2 Diastereomers | 431.16 |
| 78 | 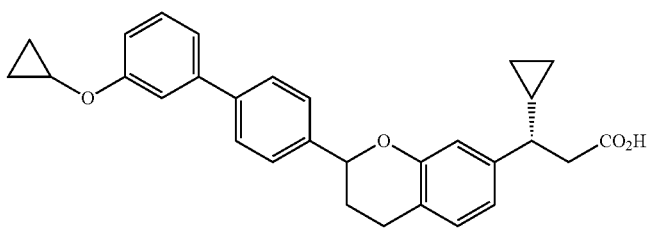 [SMILES: O=C(O)C[C@H](c1ccc2c(c1)OC(c1ccc(-c3cccc(OC4CC4)c3)cc1)CC2)C1CC1] | 2 Diastereomers | 455.18 |

-continued

| Example No. | Structure | Stereoisomer/ Chiral Conditions | Mass Spec M + 1, m/e |
|---|---|---|---|
| 79 | 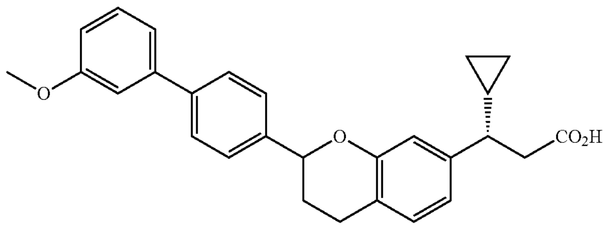 [SMILES: COc1cccc(-c2ccc(C3CCc4ccc([C@@H](CC(=O)O)C5CC5)cc4O3)cc2)c1] | 2 Diastereomers | 429.22 |
| 80 | 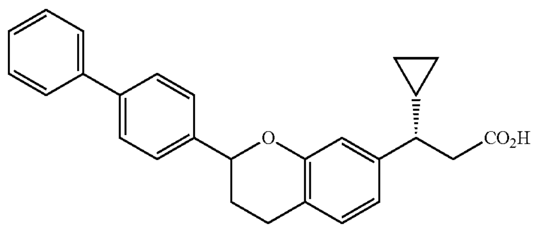 [SMILES: O=C(O)C[C@H](c1ccc2c(c1)OC(c1ccc(-c3ccccc3)cc1)CC2)C1CC1] | 2 Diastereomers | 399.22 |
| 81 | 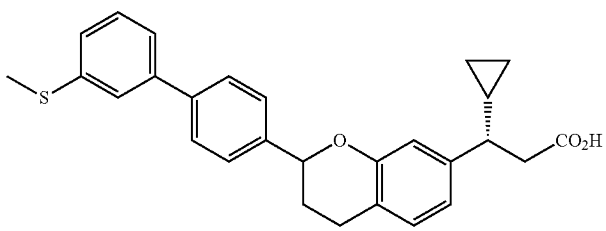 [SMILES: CSc1cccc(-c2ccc(C3CCc4ccc([C@@H](CC(=O)O)C5CC5)cc4O3)cc2)c1] | 2 Diastereomers | 445.23 |
| 82 | 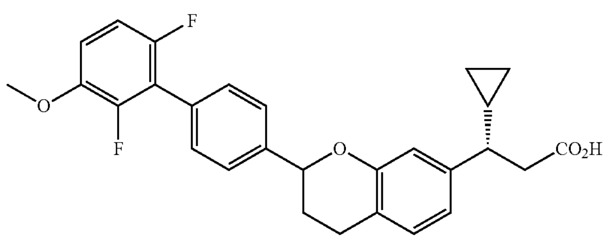 [SMILES: COc1ccc(F)c(-c2ccc(C3CCc4ccc([C@@H](CC(=O)O)C5CC5)cc4O3)cc2)c1F] | 2 Diastereomers | 465.13 |
| 83 | 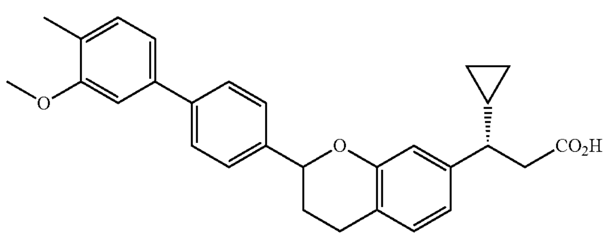 [SMILES: COc1cc(-c2ccc(C3CCc4ccc([C@@H](CC(=O)O)C5CC5)cc4O3)cc2)ccc1C] | 2 Diastereomers | 443.14 |
| 84 | 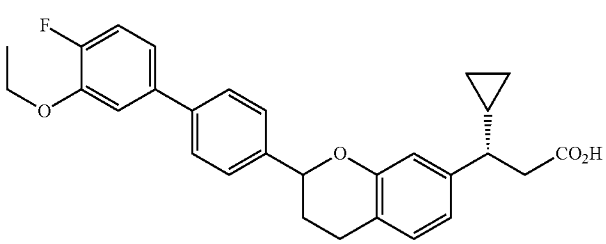 [SMILES: CCOc1cc(-c2ccc(C3CCc4ccc([C@@H](CC(=O)O)C5CC5)cc4O3)cc2)ccc1F] | 2 Diastereomers | 461.25 |

-continued
| Example No. | Structure | Stereoisomer/ Chiral Conditions | Mass Spec M + 1, m/e |
|---|---|---|---|
| 85 | 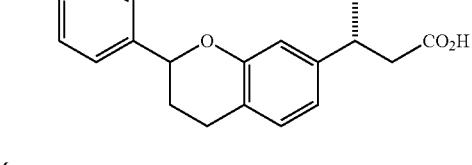 | 2 Diastereomers | 432.3 |
| 86 | 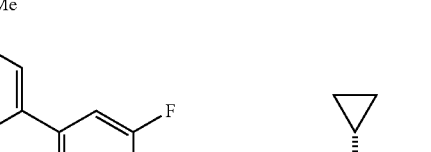 | 2 Diastereomers | 448.3 |
| 87 | 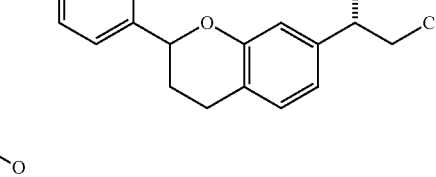 | 2 Diastereomers | 488.2 |
| 88 | 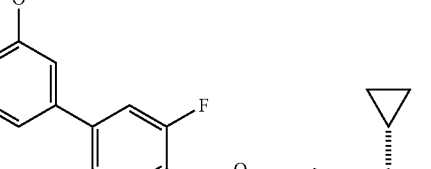 | 2 Diastereomers | 465.2 |
| 89 | 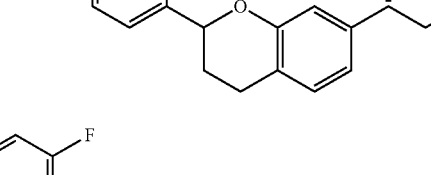 | 2 Diastereomers | 436.3 |
| 90 | 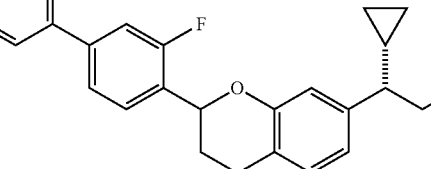 | 2 Diastereomers | 447.3 |

-continued

| Example No. | Structure | Stereoisomer/ Chiral Conditions | Mass Spec M + 1, m/e |
|---|---|---|---|
| 91 | 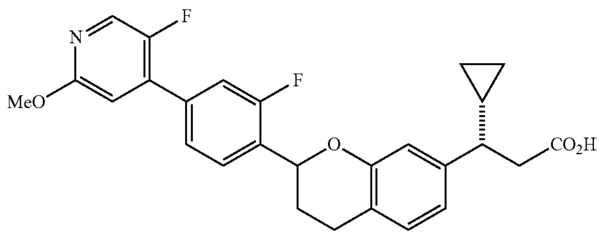 | 2 Diastereomers | 466.2 |
| 92 | 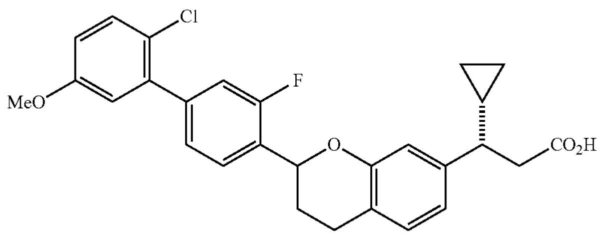 | 2 Diastereomers | 481.2 |
| 93 | 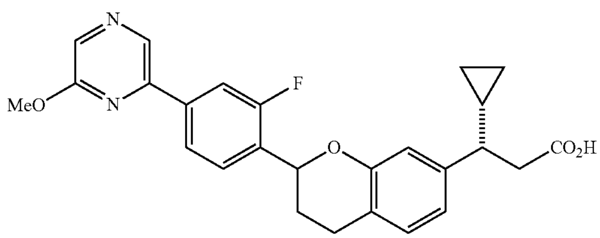 | 2 Diastereomers | 449.2 |
| 94 | 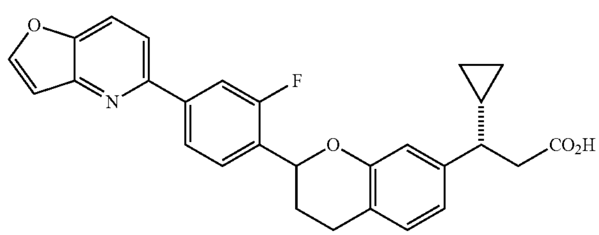 | 2 Diastereomers | 458.3 |
| 95 | 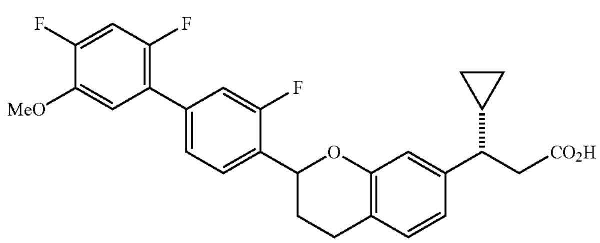 | 2 Diastereomers | 483.2 |
| 96 | 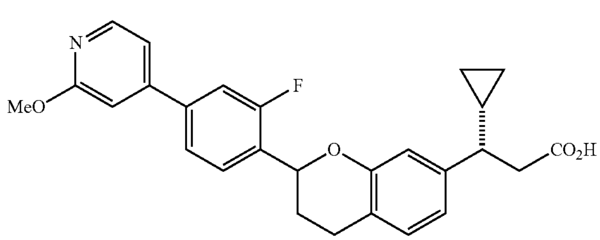 | 2 Diastereomers | 448.3 |

185

Alternate Route to Example 63

Step 1: (2S,1R)-methyl 3-cyclopropyl-3-(3-hydroxy-4-iodophenyl-2-methylpropanoate

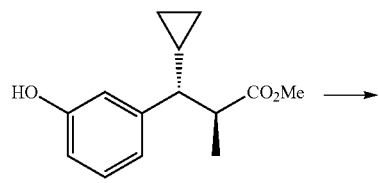

To a cooled DCM solution of (2S,3R)-methyl 3-cyclopropyl-3-(3-hydroxyphenyl)-2-methylpropanoate (5 g, 21.34 mmol) at 0° C. was added NIS (4.66 g, 20.70 mmol) in 4 portions over 1.5 h. After stirring 3 h, aqueous saturated sodium thiosulfate (100 mL) and MTBE (100 mL) were added. The layers were separated and the aqueous layer was back extracted with 3×MTBE/DCM. The organic layers were combined and washed with 20% brine, dried over $Na_2SO_4$, and concentrated. The resulting residue was purified by ISCO 330 gram SiO2 column, 0 to 50% EtOAc/Hex to give the title compound.

1-(2'-fluoro-5'-methoxy-[1,1'-biphenyl]-4-yl)prop-2-en-1-ol

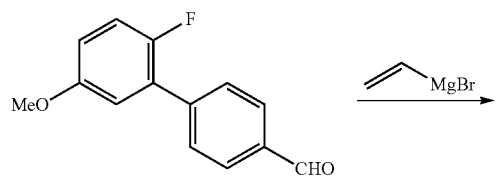

186

-continued

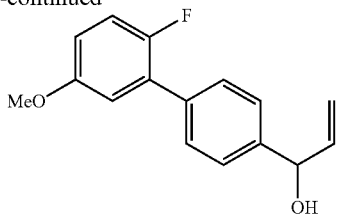

A solution of 2'-fluoro-5'-methoxy-[1,1'-biphenyl]-4-carbaldehyde (19.5 g, 85 mmol) in THF (423 ml) was cooled in a dry ice/acetone bath, then vinylmagnesium bromide (102 ml, 102 mmol) was added dropwise. The reaction was allowed to warm to room temperature over 2 h and stirred at room temperature for 1 hour. Then the reaction was quenched with 20% $NH_4Cl$ and diluted with MTBE. The organic layer were separated, washed with 20% $NH_4Cl$ and brine, and concentrated. The crude product was purified via silica gel on a 220 g column using a 10-70% EtOAc/Hexane gradient to give the title compound.

Step 2: (2S,3R)-methyl 3-cyclopropyl-3-(4-(3-(2'-fluoro-5'-methoxy-[1,1'-biphenyl]-4-yl)-3-oxopropyl)-3-hydroxyphenyl)-2-methylpropanoate

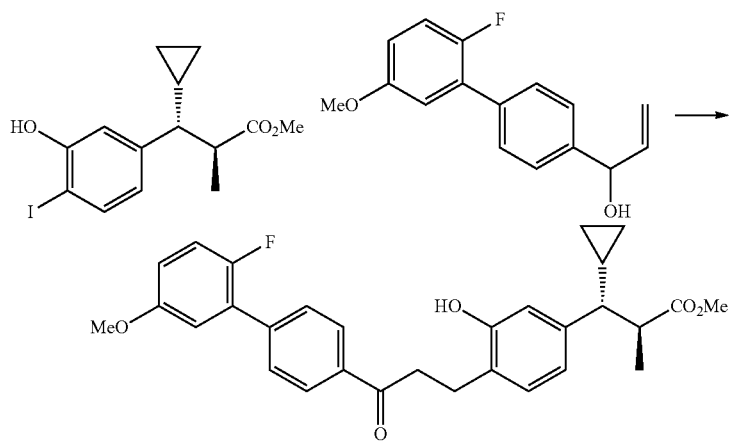

A solution of 1-(2'-fluoro-5'-methoxy-[1,1'-biphenyl]-4-yl)prop-2-en-1-ol (4.09 g, 15.83 mmol), (2S,3R)-methyl 3-cyclopropyl-3-(3-hydroxy-4-iodophenyl)-2-methylpropanoate (4.75 g, 13.19 mmol), and t-buxphos-palladacycle (0.453 g, 0.659 mmol) in toluene (105 ml) was degassed for 5 minutes. Then N,N-dicyclohexylmethylamine (4.24 ml, 19.78 mmol) was added, and the mixture was heated at 90° C. overnight. Then the reaction was cooled in an ice bath and a precipitate formed. The resulting reaction mixture was filtered, and then washed with toluene. The filtrate was adsorbed onto silica and purified using a 220 g column using 0-100% Hexane/EtOAc to afford the title compound.

Step 3: (2S,3R)-methyl 3-cyclopropyl-3-(4-((R)-3-(2'-fluoro-5'-methoxy-[1,1'-biphenyl]-4-yl)-3-hydroxypropyl)-3-hydroxyphenyl)-2-methylpropanoate

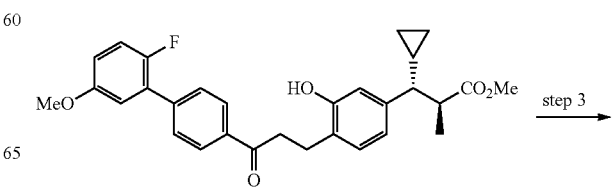

-continued

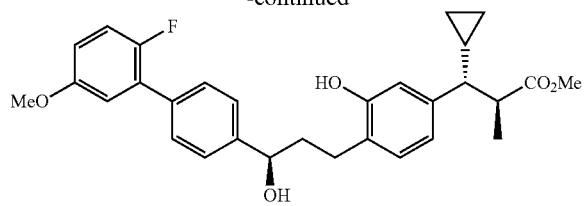

A solution of (2S,3R)-methyl 3-cyclopropyl-3-(4-(3-(2'-fluoro-5'-methoxy-[1,1'-biphenyl]-4-yl)-3-oxopropyl)-3-hydroxyphenyl)-2-methylpropanoate (3.6 g, 7.34 mmol) in acetonitrile (36.7 ml) was degassed for 5 min, then triethylamine (3.07 ml, 22.02 mmol), formic acid (1.119 ml, 25.7 mmol) and RuCl[(R,R)-TSDPEN](mesitylene) (229 mg, 0.367 mmol; 5 mol %) were added and the reaction was stirred at RT overnight. Additional triethylamine (3.07 ml, 22.02 mmol), formic acid (1.119 ml, 25.7 mmol) and RuCl[(R,R)-TSDPEN](mesitylene) (229 mg, 0.367 mmol; 5 mol %) were added and the reaction was stirred for 24 h. Then the reaction was partitioned between ethyl acetate and water. The organic layer was separated, washed with 10% brine, dried over sodium sulfate, filtered and concentrated in vacuo. The resulting crude product was chromatographed, eluting with 100% hexanes to 100% EtOAc over 12 CV, to afford the title compound.

Step 4: (2S,3R)-methyl 3-cyclopropyl-3-((S)-2-(2'-fluoro-5'-methoxy-[1,1'-biphenyl]-4-yl)chroman-7-yl)-2-methylpropanoate

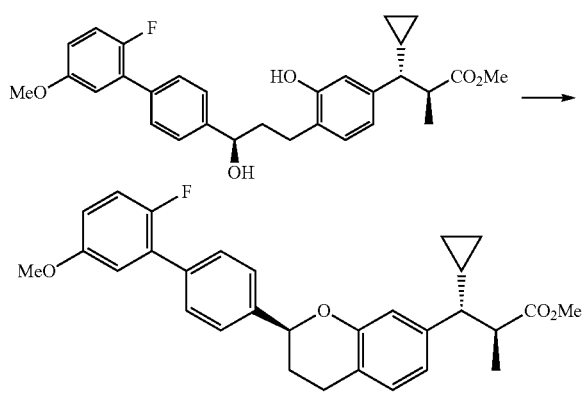

To a solution of (2S,3R)-methyl 3-cyclopropyl-3-(4-((R)-3-(2'-fluoro-5'-methoxy-[1,1'-biphenyl]-4-yl)-3-hydroxypropyl)-3-hydroxyphenyl)-2-methylpropanoate (3.5 g, 7.11 mmol) in DCM (35.5 ml) was added triphenylphosphine (2.61 g, 9.95 mmol). Then the reaction was cooled to 0° C., and a solution of DIAD (1.934 ml, 9.95 mmol) in DCM (0.5 mL) was added slowly over 1 h at 0° C. The reaction was stirred at 0° C. for 4 h, then loaded onto a ISCO cartridge and chromatographed eluting with 100% hexanes to 100% EtOAc over 12 CV, to give the title compound.

Step 5: (2S,3R)-3-cyclopropyl-3-((S)-2-(2'-fluoro-5'-methoxy-[1,1'-biphenyl]-4-yl)chroman-7-yl)-2-methylpropanoate diisopropyl ammonium salt

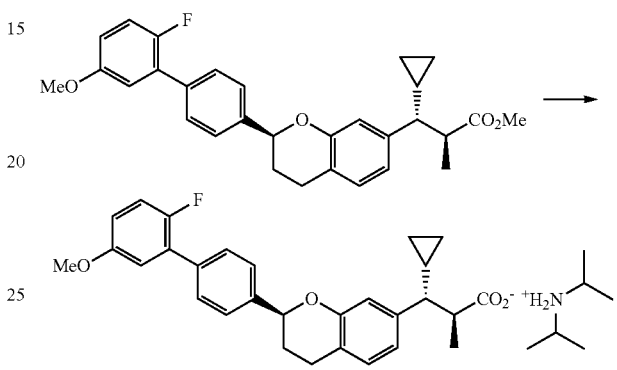

To a MeOH/THF/water (ratio?, amounts?) solution of (2S,3R)-methyl 3-cyclopropyl-3-((S)-2-(2'-fluoro-5'-methoxy-[1,1'-biphenyl]-4-yl)chroman-7-yl)-2-methylpropanoate (2.8 g, 5.90 mmol) was added lithium hydroxide monohydrate (2.476 g, 59.0 mmol). The mixture was heated to and stirred on a heating block at 60° C. After 16 h, the reaction volatiles were removed in vacuo. Then 6 N HCl was slowly added to the resulting aqueous mixture until the pH was <2. After acidification, a precipitate formed. The precipitate was removed by filtration and washed with water. After drying, the precipitate was purified by SFC on a AD-H column (4.6×250 mm, 45% EtOH (0.1% diisopropyl amine modifier)/CO$_2$). LC/MS: m/z=461.3 [M+1]. $^1$H NMR δ (ppm)(CHCl$_3$-d): 7.55 (d, 2H), 7.50 (d, 2H), 7.05 (t, 1H), 7.00 (d, 1H), 6.92 (m, 1H), 6.80 (m, 1H), 6.73 (s, 1H), 6.70 (d, 1H), 5.05 (d, 1H), 3.80 (s, 3H), 3.17 (m, 1H), 2.99 (m, 1H), 2.75 (m, 2H), 2.21 (m, 1H), 2.10 (m, 1H), 1.95 (t, 1H), 1.22 (d, 6H), 1.09 (m, 1H), 0.95 (d, 3H), 0.58 (m, 1H), 0.40 (m, 1H), 0.32 (m, 1H), 0.00 (m, 1H).

Step 6: sodium (2S,3R)-3-cyclopropyl-3-((S)-2-(2'-fluoro-5'-methoxy-[1,1'-biphenyl]-4-yl)chroman-7-yl)-2-methylpropanoate

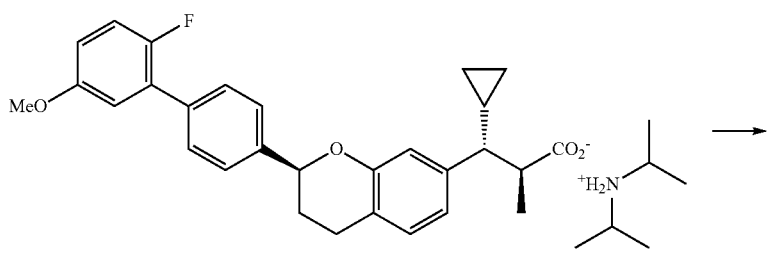

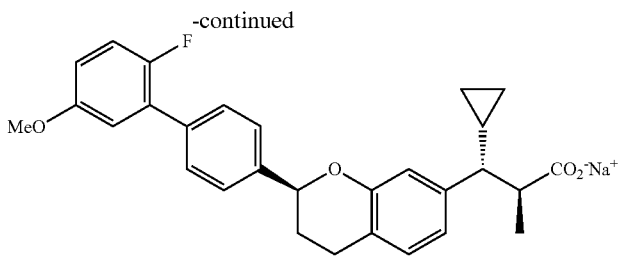

The diisopropylamine salt of (2S,3R)-3-cyclopropyl-3-((S)-2-(2'-fluoro-5'-methoxy-[1,1'-biphenyl]-4-yl)chroman-7-yl)-2-methylpropanoic acid was dissolved in EtOAc (100 mL) and poured into 1 N HCl (100 mL). The resulting layers were separated, and the aqueous phase was back-extracted with EtOAc (100 mL). The combined organic layers were dried (MgSO$_4$) and concentrated to give the free acid. To an acetonitrile/water solution (2:1, 10 mL) of (2S,3R)-3-cyclopropyl-3-((S)-2-(2'-fluoro-5'-methoxy-[1,1'-biphenyl]-4-yl)chroman-7-yl)-2-methylpropanoic acid (1.97 g, 4.29 mmol) was added NaOH (4.29 ml, 4.29 mmol). The solution was frozen in a dry ice bath and then lyophylized overnight to give sodium (2S,3R)-3-cyclopropyl-3-((S)-2-(2'-fluoro-5'-methoxy-[1,1'-biphenyl]-4-yl)chroman-7-yl)-2-methylpropanoate. $^1$H NMR δ (ppm)(CD$_3$OD): 7.60 (q, 4H), 7.18 (t, 1H), 7.05 (m, 2H), 6.95 (m, 1H), 6.78 (m, 2H), 5.18 (d, 1H), 3.89 (s, 3H), 3.05 (m, 1H), 2.85 (m, 1H), 2.70 (m, 1H), 2.31 (m, 1H), 2.12 (m, 1H), 2.00 (t, 1H), 1.15 (m, 1H), 0.94 (d, 3H), 0.61 (m, 1H), 0.50 (m, 1H), 0.30 (m, 1H), 0.00 (m, 1H).

Scheme 12

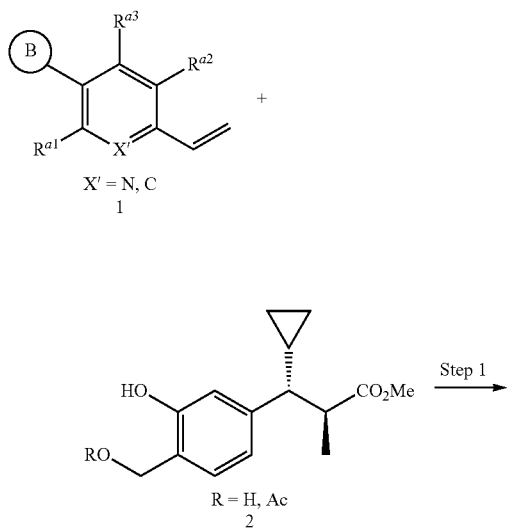

-continued

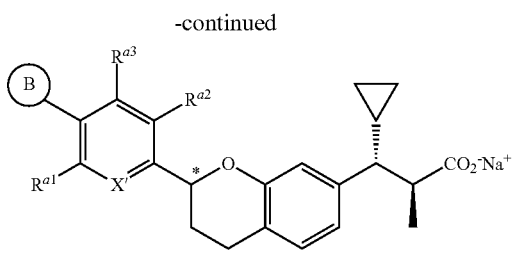

Step 1: Method A: R = Ac, xylenes, 165-170° C.; Method B: R = H, xylenes, 200° C.; Method C: R = H, Montmorillonite K10, LiClO$_4$, MeNO$_2$, water (Scheme 10 Step 1); Step 2: THF/MeOH/1M LiOH 65° C.; Step 3: Chiral resolution; Step 4: 1M NaOH (1 equiv)

The sequence shown in Scheme 12 may be used to make substituted chromans, such as Example 97, using either Methods A, B or C in Step 1. Thermally-promoted Diels-Alder cycloaddition of the hydroxybenzyl acetate (Method A) or diol (Method B) is used to establish the chroman core. Alternatively, Lewis acid-promoted Diels-Alder reaction is used to deliver the cycloadduct in Method C. The methyl ester is then hydrolyzed (Step 2) and the diastereomers separated by SFC (Step 3). The final enantiopure products are converted to the sodium salts (Step 4).

Example 97

Step 2: (2S,3R)-3-cyclopropyl-3-(2-(5'-fluoro-2'-methoxy-[3,4'-bipyridin]-6-yl)chroman-7-yl)-2-methylpropanoic acid

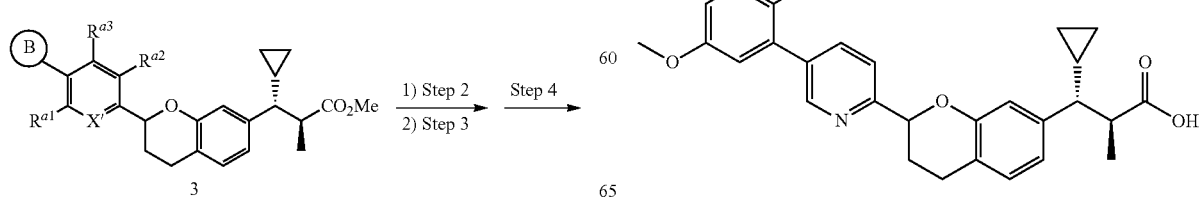

Step 1: Method A: (2S,3R)-methyl 3-cyclopropyl-3-(2-(5-(2-fluoro-5-methoxyphenyl)-6-methylpyridin-2-yl)chroman-7-yl)-2-methylpropanoate

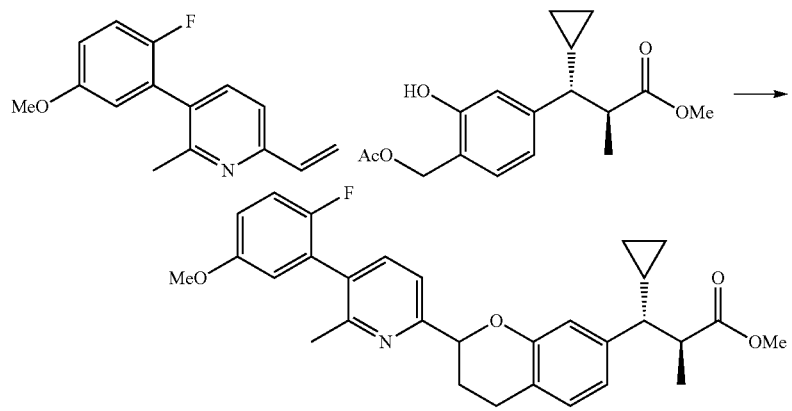

A microwave vial equipped with a stir bar was charged with 3-(2-fluoro-5-methoxy-phenyl)-2-methyl-6-vinylpyridine (1.2650 g, 5.20 mmol), (2S,3R)-methyl 3-(4-(acetoxymethyl)-3-hydroxyphenyl)-3-cyclopropyl-2-methylpropanoate (0.6558 g, 2.14 mmol), and xylenes (2.5 mL). The mixture was evacuated and filled with $N_2$ (3×). Then the reaction vessel was sealed and heated to 170° C. in a heating block for 45 min. The reaction was concentrated in vacuo and the resulting crude residue was purified via MPLC (ISCO 40 g; product eluted at 40% EtOAc/hexane) with gradient elution 0-40% EtOAc/hexane to give the title compound. $^1$H NMR (500 MHz, $CHCl_3$-d): 0.04 (m, 1H), 0.24 (dt, 1H), 0.35 (m, 1H), 0.53-0.57 (m, 1H), 0.97 (d, 3H), 1.05 (m, 1H), 1.84-1.91 (t, 1H), 2.10 (m, 1H), 2.46 (s, 3H), 2.47 (m, 1H), 2.75-2.81 (m, 2H), 3.01 (ddd, 1H), 3.72 (s, 3H), 3.81 (s, 3H), 5.19 (d, 1H), 6.68 (d, 1H), 6.76-6.73 (m, 2H), 6.90-6.87 (m, 1H), 7.02-7.10 (m, 2H), 7.47 (d, 1H), 7.57 (d, 1H).

Step 1: Method B: (2S,3R)-methyl 3-cyclopropyl-3-(2-(5-(2-fluoro-5-methoxyphenyl)-pyridin-2-yl)chroman-7-yl)-2-methylpropanoate To a microwave vial equipped with a stirrer was added (2S,3R)-methyl 3-cyclopropyl-3-(3-hydroxy-4-(hydroxymethyl)phenyl)-2-methylpropanoate (1.88 g, 7.11 mmol), 5-(2-fluoro-5-methoxyphenyl)-2-vinylpyridine (3.26 g, 14.23 mmol), and Xylene (15 ml). The resulting solution was degassed and filled with $N_2$ (3×). The vial was sealed and heated conventionally at 200° C. for 1 h. The reaction was then cooled to ambient temperature and concentrated in vacuo. The resulting residue was purified via MPLC (ISCO 40 g; product eluted at 28% EtOAc/hexane) with gradient elution 0-40% EtOAc/hexane to give the title compound. $^1$H NMR (500 MHz, $CHCl_3$-d): 0.04 (m, 1H), 0.25 (m, 1H), 0.36 (m, 1H), 0.56 (m, 1H), 0.98 (d, 3H), 1.06 (m, 1H), 1.88 (t, 1H), 2.15 (m, 1H), 2.48 (m, 1H), 2.77-2.81 (m, 2H), 3.00 (m, 1H), 3.74 (s, 3H), 3.84 (s, 3H), 5.24 (d, 1H), 6.70 (d, 1H), 6.79 (s, 1H), 6.89 (d, 1H), 6.96 (s, 1H), 7.04 (d, 1H), 7.12 (t, 1H), 7.66 (d, 1H), 7.93 (d, 1H), 8.77 (s, 1H).

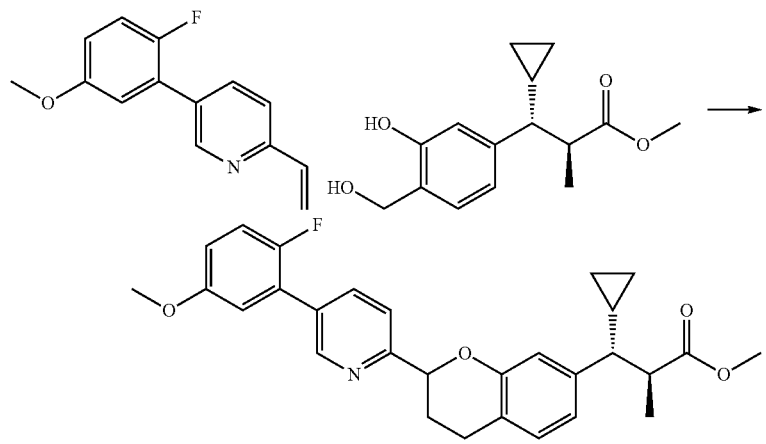

Step 1: Method C: (3S)-methyl 3-(2-(4-bromophenyl)chroman-7-yl)-3-cyclopropylpropanoate

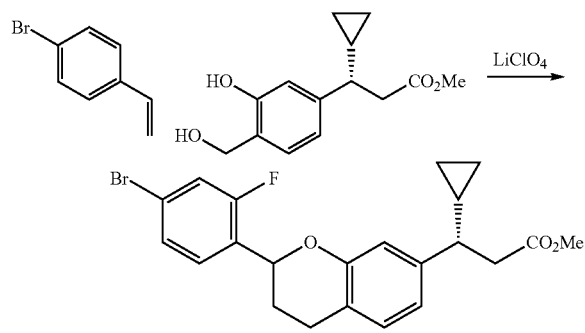

To a nitromethane (50 mL) solution of (S)-methyl 3-cyclopropyl-3-(3-hydroxy-4-(hydroxymethyl)phenyl)propanoate (1.00 g, 4.00 mmol), 1-bromo-4-vinylbenzene (1.05 mL, 7.99 mmol), and lithium perchlorate (527 mg, 4.95 mmol) was added Montmorillonite K10 (1.00 gram) and water (0.893 mL, 49.4 mmol). The reaction was sealed and then heated to 75° C. on a heating block. After 3 h, the mixture was cooled to room temperature, filtered and then concentrated. The resulting residue was purified by HPLC (ISCO 80 gram, 0 to 50% EtOAc/Hex) to give the title compound. $^1$H NMR (500 MHz, CDCl$_3$) δ 7.50 (d, 2H), 7.30 (d, 2 h), 7.00 (d, 1 h), 6.80 (m, 2H), 5.00 (d, 1H), 3.60 (s, 3H), 2.95 (m, 1H), 2.70 (m, 3H), 2.30 (q, 1H), 2.19 (m, 1H), 2.00 (m, 1H), 1.00 (m, 1 h), 0.59 (m, 1H), 0.41 (m, 1H), 0.22 (m, 1H), 0.18 (m, 1H).

Subsequently, the bromide-substituted phenyl may be converted to the B substituted phenyl using the procedure described in Scheme 10, Step 1.

Step 2: (2S,3R)-3-cyclopropyl-3-(2-(5'-fluoro-2'-methoxy-[3,4'-bipyridin]-6-yl)chroman-7-yl)-2-methylpropanoic acid

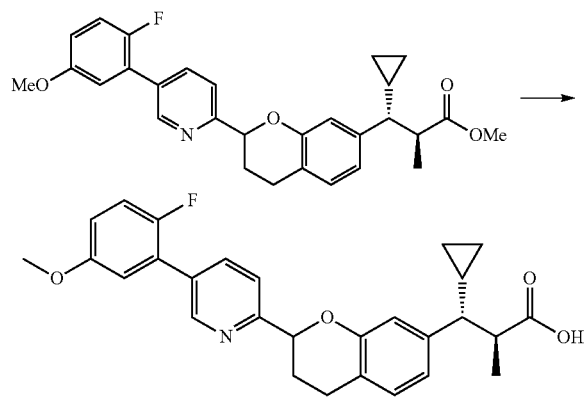

To a solution of (2S,3R)-methyl 3-cyclopropyl-3-(2-(5-(2-fluoro-5-methoxyphenyl)-pyridin-2-yl)chroman-7-yl)-2-methylpropanoate (0.3862 g, 0.789 mmol) in THF (8 ml)/MeOH (8 ml) was added 1 M LiOH (8 mL, 8.00 mmol) at ambient temperature. The reaction mixture was heated to 65° C. for 19 h, then concentrated in vacuo. The resulting residue was suspended in EtOAc and 1 N HCl (8.5 mL) was added. The resulting mixture was partitioned between EtOAc and brine. The aqueous layer was separated and back-extracted with EtOAc (2×). The combined organic layers were dried over MgSO$_4$, and concentrated in vacuo. The resulting residue was purified via MPLC (ISCO 24 g; product eluted at 48% EtOAc/hexane) with gradient elution 0-100% EtOAc/hexane to give the title compound. $^1$H NMR (500 MHz, CHCl$_3$-d): 0.07 (s, 1H), 0.37 (m, 2H), 0.63-0.61 (m, 1H), 1.00 (d, 3H), 1.13 (m, 1H), 1.95 (t, 1H), 2.11 (m, 1H), 2.47 (s, 3H), 2.48 (m, 1H), 2.77 (m, 1H), 2.85 (m, 1H), 3.00 (m, 1H), 3.81 (s, 3H), 5.20 (d, 1H), 6.71 (d, 1H), 6.78-6.74 (m, 2H), 6.90-6.88 (m, 1H), 7.09-7.02 (m, 2H), 7.48 (d, 1H), 7.58 (d, 1H); LC/MS (m/z): 476.6 (M+H)$^+$.

Step 3: Chiral Resolution

The mixture of diastereomers were resolved on a Chiralpak AS (20×250 mm; 18% (IPA+0.2% DEA)/CO$_2$ to give 2 fractions (Peak/Isomer A and Peak/Isomer B). Both fractions were separately dissolved in EtOAc and washed with saturated NH$_4$Cl. The organic layer was separated, washed with brine, dried over MgSO$_4$, and concentrated in vacuo to give the separated diastereomer of the title product:

Peak/Isomer—Example 97a: (0.1458 g); Retention time=7.47 min.; $^1$H NMR (500 MHz, CHCl$_3$-d): 0.05 (m, 1H), 0.40-0.35 (m, 2H), 0.64-0.58 (m, 1H), 1.01 (d, 3H), 1.11 (m, 1H), 1.95 (t, 1H), 2.10 (m, 1H), 2.47 (s, 3H), 2.47 (m, 1H), 2.83-2.72 (m, 2H), 3.00 (ddd, 1H), 5.21 (d, 1H), 6.77-6.68 (m, 3H), 6.89-6.86 (m, 1H), 7.08-7.01 (m, 2H), 7.48 (d, 1H), 7.58 (d, 1H); LC/MS (m/z): 476.6 (M+H)$^+$.

Peak/Isomer Example 97c: (0.1542 g); Retention time=9.52 min.; $^1$H NMR (500 MHz, CHCl$_3$-d): 0.05 (m, 1H), 0.40-0.36 (m, 2H), 0.63-0.58 (m, 1H), 1.02 (d, 3H), 1.13-1.10 (m, 1H), 1.95 (t, 1H), 2.10 (m, 1H), 2.47 (s, 3H), 2.84-2.72 (m, 2H), 2.99 (ddd, 1H), 5.21 (bd, 1H), 6.78-6.69 (m, 3H), 6.89 (dt, 1H), 7.09-7.01 (m, 2H), 7.48 (d, 1H), 7.58 (d, 1H).

Step 4: Sodium (2S,3R)-3-cyclopropyl-3-(2-(5-(2-fluoro-5-methoxyphenyl)-6-methylpyridin-2-yl)chroman-7-yl)-2-methylpropanoate

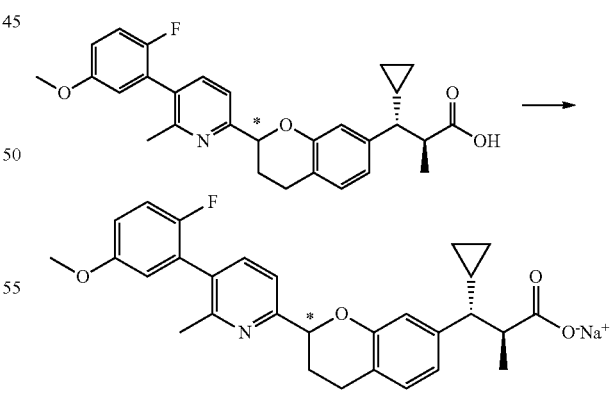

To a solution of (2S,3R)-3-cyclopropyl-3-(2-(5'-fluoro-2'-methoxy-[3,4'-bipyridin]-6-yl)chroman-7-yl)-2-methylpropanoic acid (Fraction A, 0.1458 g, 0.307 mmol) in acetonitrile (2 ml)/Water (1 ml) was added sodium hydroxide (0.307 ml, 0.307 mmol) at ambient temperature. The reaction was sonicated to ensure all of the sodium hydroxide went into solution. The resulting pale yellow solution was lyophilized overnight to give the title compound. $^1$H NMR (500 MHz, CHCl$_3$-d): 0.05 (m, 1H), 0.38-0.25 (m, 2H), 0.50 (m, 1H), 0.89 (d, 3H), 1.92 (t, 1H), 2.13-2.01 (m, 1H), 2.41 (m, 1H), 2.42 (s, 3H), 2.52 (s, 3H), 2.63 (m, 1H), 2.70 (m, 1H), 3.78 (s, 3H), 5.14 (dd, 1H), 6.74-6.68 (m, 3H), 6.86 (dt, 1H), 6.98 (d, 1H), 7.05 (t, 1H), 7.45-7.43 (m, 1H), 7.55 (d, 1H); LC/MS (m/z): 476.6 (M+H)$^+$.

Examples 97a-97d were prepared in a similar fashion to Examples 63-66 using the appropriate starting materials.

| Example No. | Structure | Chiral Chromatography conditions | Mass Spec M + 1, m/e |
|---|---|---|---|
| 97a | 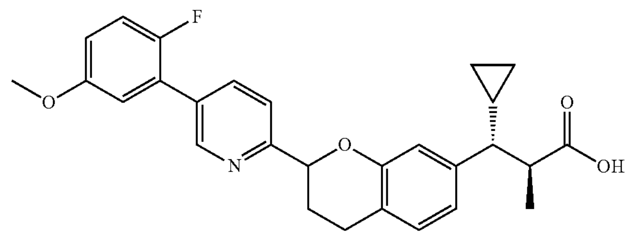 [SMILES: COc1ccc(F)c(-c2ccc(C3CCc4ccc([C@H](C5CC5)[C@H](C)C(=O)O)cc4O3)nc2)c1] | First eluting isomer Chiral-pak AS (20 × 250 mm; 18% (IPA + 0.2% DEA)/CO$_2$ | 462.7 |
| 97b | 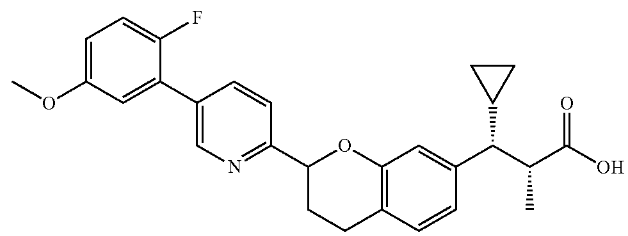 [SMILES: COc1ccc(F)c(-c2ccc(C3CCc4ccc([C@H](C5CC5)[C@@H](C)C(=O)O)cc4O3)nc2)c1] | Second eluting isomer Chiral-pak AS (20 × 250 mm; 18% (IPA + 0.2% DEA)/CO$_2$ | 462.7 |
| 97c | 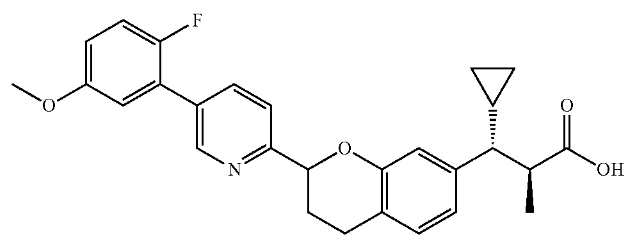 [SMILES: COc1ccc(F)c(-c2ccc(C3CCc4ccc([C@H](C5CC5)[C@H](C)C(=O)O)cc4O3)nc2)c1] | Third eluting isomer Chiral-pak AS (20 × 250 mm; 18% (IPA + 0.2% DEA)/CO2 | 462.7 |
| 97d | 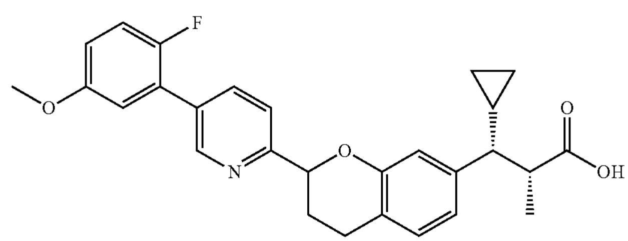 [SMILES: COc1ccc(F)c(-c2ccc(C3CCc4ccc([C@H](C5CC5)[C@@H](C)C(=O)O)cc4O3)nc2)c1] | Fourth eluting isomer Chiral-pak AS (20 × 250 mm; 18% (IPA + 0.2% DEA)/CO$_2$ | 462.7 |

Examples 98-132 were prepared in a similar manner to Scheme 12 using the appropriate method and the appropriate starting materials.

| Example No. | Structure | Scheme 12 Step 1 Method | Stereoisomers/ Chiral Conditions | LC/MS (M + H)$^+$ |
|---|---|---|---|---|
| 98 | 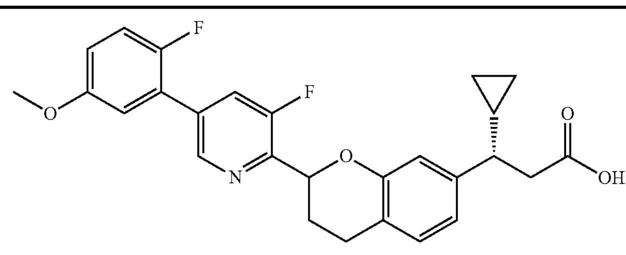 | A | mixture of 2 diastereomers | 467.5 |

-continued

| Example No. | Structure | Scheme 12 Step 1 Method | Stereoisomers/ Chiral Conditions | LC/MS (M + H)+ |
|---|---|---|---|---|
| 99 | 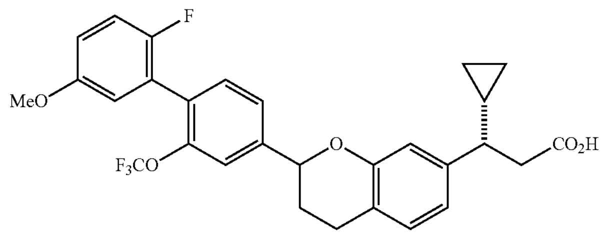 [SMILES: COc1ccc(F)c(-c2ccc(C3CCc4ccc([C@@H](CC(=O)O)C5CC5)cc4O3)cc2OC(F)(F)F)c1] | B | mixture of 2 diastereomers | 531.5 |
| 100 | 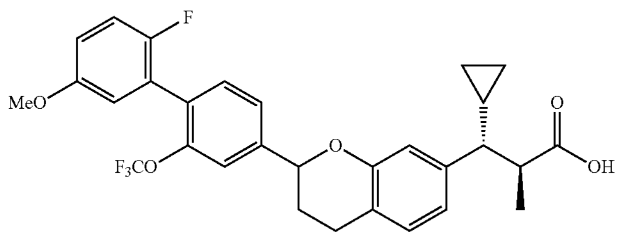 [SMILES: COc1ccc(F)c(-c2ccc(C3CCc4ccc([C@H](C5CC5)[C@H](C)C(=O)O)cc4O3)cc2OC(F)(F)F)c1] | B | mixture of 2 diastereomers | 545.5 |
| 101 | 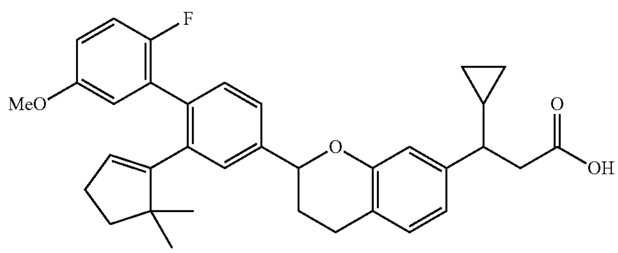 [SMILES: COc1ccc(F)c(-c2ccc(C3CCc4ccc(C(CC(=O)O)C5CC5)cc4O3)cc2C2=CCCC2(C)C)c1] | C | 4 single diastereomers: AC-H, 12% EtOH (+0.2% DIPA)/ CO$_2$ | 541.3 |
| 102 | 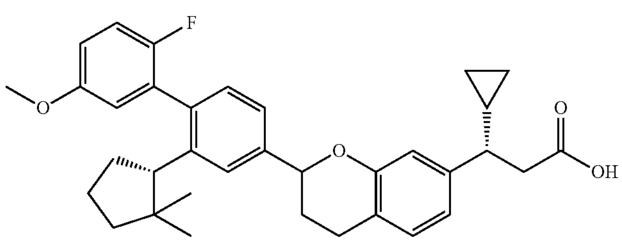 [SMILES: COc1ccc(F)c(-c2ccc(C3CCc4ccc([C@@H](CC(=O)O)C5CC5)cc4O3)cc2[C@H]2CCCC2(C)C)c1] | C | mixture of 2 diastereomers | 543.0 |
| 103 | 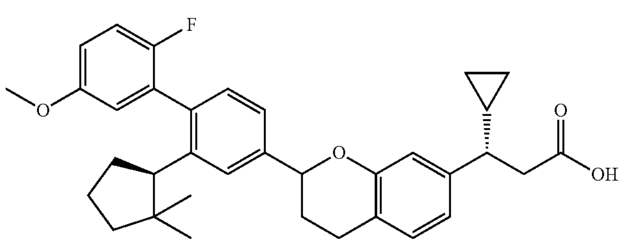 [SMILES: COc1ccc(F)c(-c2ccc(C3CCc4ccc([C@@H](CC(=O)O)C5CC5)cc4O3)cc2[C@@H]2CCCC2(C)C)c1] | C | mixture of 2 diastereomers | 543.0 |
| 104 | 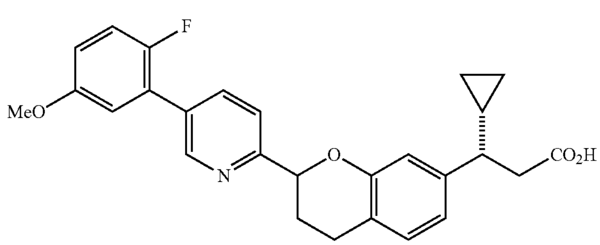 | A | mixture of 2 diastereomers | 448.3 |

| Example No. | Structure | Scheme 12 Step 1 Method | Stereoisomers/ Chiral Conditions | LC/MS (M + H)+ |
|---|---|---|---|---|
| 105 | 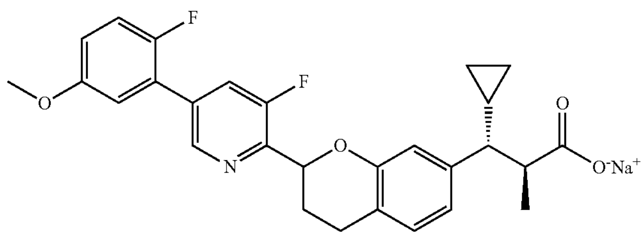 | B | 2 single diastereomers: IC(20 × 250 mm), 15% MeOH/$CO_2$ | 480.4 |
| 106 | 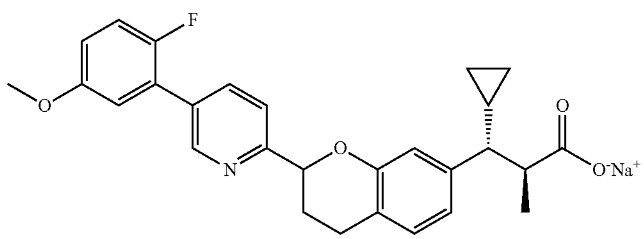 | B | 2 single diastereomers: AD-H (50 × 250 mm), 60% EtOH (+0.2% DIPA)/ $CO_2$ | 462.7 |
| 107 | 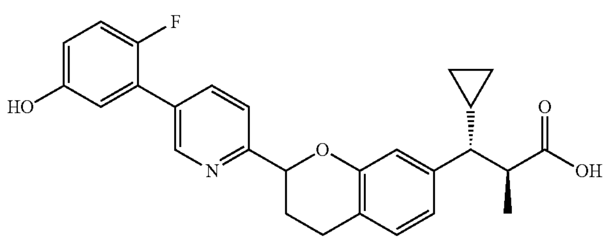 [SMILES: C[C@H](C(=O)O)[C@H](c1ccc2c(c1)OC(c1ccc(-c3cc(O)ccc3F)cn1)CC2)C1CC1] | B | mixture of 2 diastereomers | 448.6 |
| 108 | 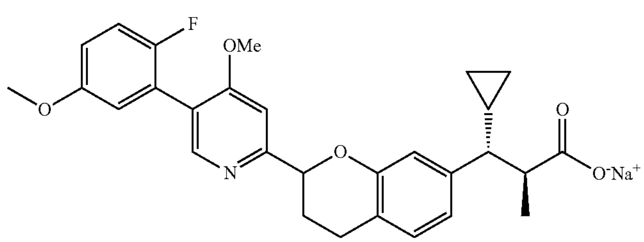 | B | 2 single diastereomers: AS-H (2 × 15 cm), 25% (1:1 heptane/iPrOH (+0.15% DEA)/ $CO_2$ | 492.6 |
| 109 | 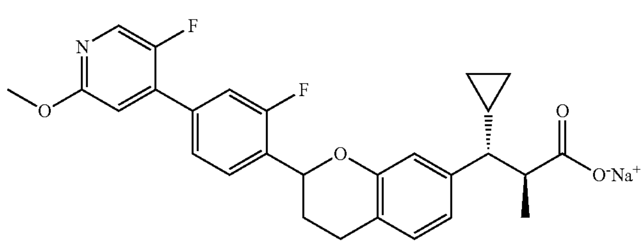 | B | 2 single diastereomers: AS-H (2 × 25 cm), 25% MeOH/$CO_2$ | 480.6 |
| 110 | 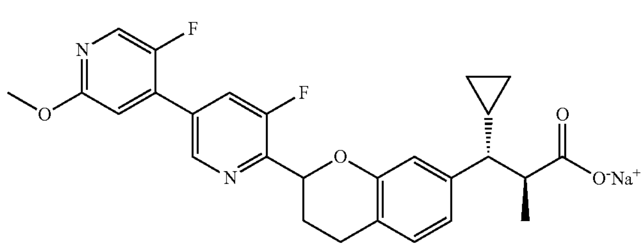 | A | 2 single diastereomers: IA (30 × 250 mm), 65% EtOH/$CO_2$ | 481.4 |

-continued

| Example No. | Structure | Scheme 12 Step 1 Method | Stereoisomers/ Chiral Conditions | LC/MS (M + H)+ |
|---|---|---|---|---|
| 111 | 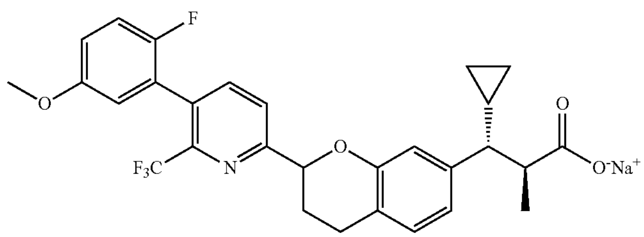 | A | 2 single diastereomers: AS-H (21 × 250 mm), 30% EtOH/CO$_2$ | 530.3 |
| 112 | 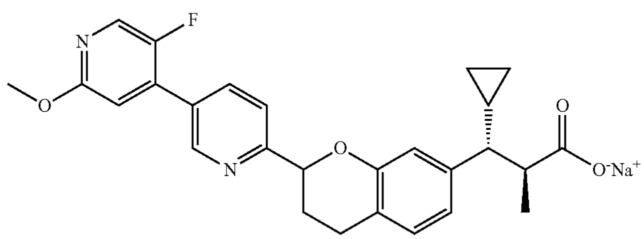 | A | 2 single diastereomers: AD-H (50 × 250 mm), 65% MeOH/CO$_2$ | 463.6 |
| 113 | 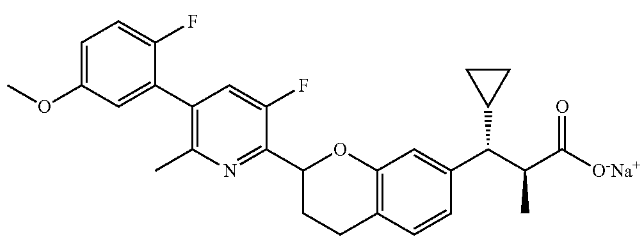 | A | 2 single diastereomers: AD-H (21 × 250 mm), 45% MeOH/CO$_2$ | 494.7 |
| 114 | 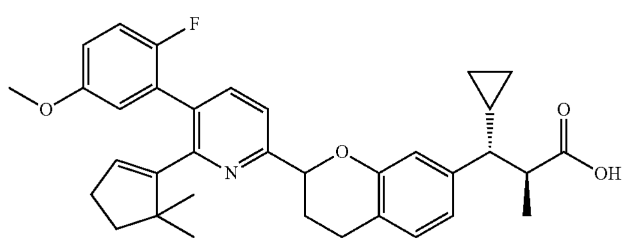 [SMILES: COc1ccc(F)c(-c2ccc(C3CCc4ccc([C@H](C5CC5)[C@H](C)C(=O)O)cc4O3)nc2C2=CCCC2(C)C)c1] | A | mixture of 2 diastereomers | 556.7 |
| 115 | 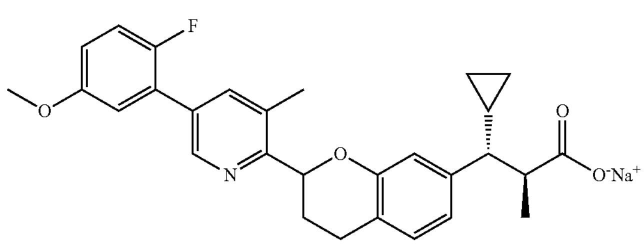 | A | 2 single diastereomers: IC (2 × 250 mm), 30% (1:1 MeOH/ AcCN)/CO$_2$ | 476.6 |
| 116 | 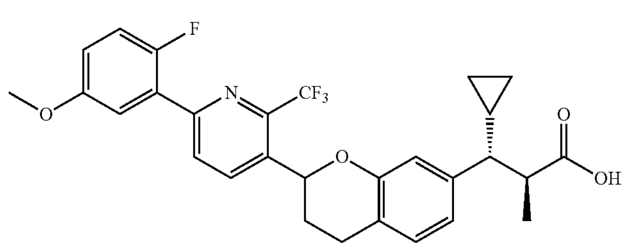 [SMILES: COc1ccc(F)c(-c2ccc(C3CCc4ccc([C@H](C5CC5)[C@H](C)C(=O)O)cc4O3)c(C(F)(F)F)n2)c1] | A | mixture of 2 diastereomers | 530.6 |

-continued

| Example No. | Structure | Scheme 12 Step 1 Method | Stereoisomers/ Chiral Conditions | LC/MS (M + H)+ |
|---|---|---|---|---|
| 117 | 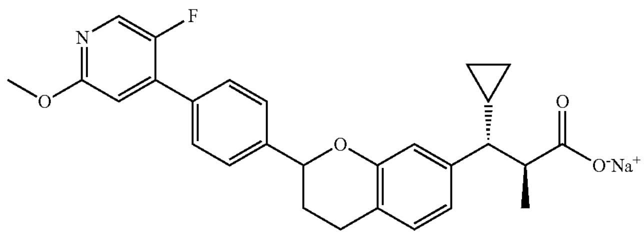 | B | 2 single diastereomers: AD-H (21 × 250 mm), 45% (1:1 MeOH/ AcCN)/CO$_2$ | 462.5 |
| 118 | 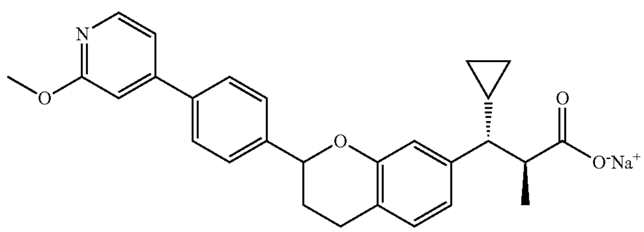 | A | 2 single diastereomers: OJ-H (21 × 250 mm), 60% MeOH/CO$_2$ | 444.3 |
| 119 | 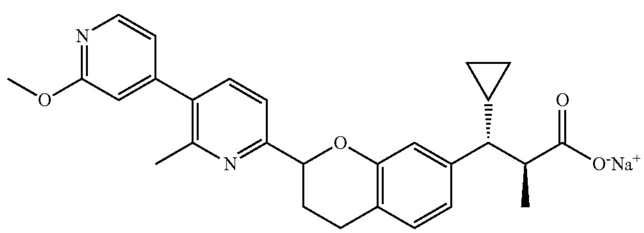 | A | 2 single diastereomers: AS-H (2 × 15 cm), 13% MeOH (0.1% DEA)/CO$_2$ | 459.5 |
| 120 | 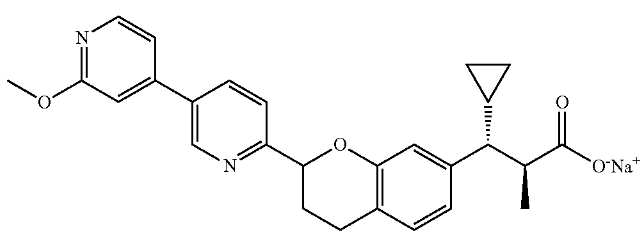 | A | 2 single diastereomers: AD-H (21 × 250 mm), 55% EtOH/CO$_2$ | 445.5 |
| 121 | 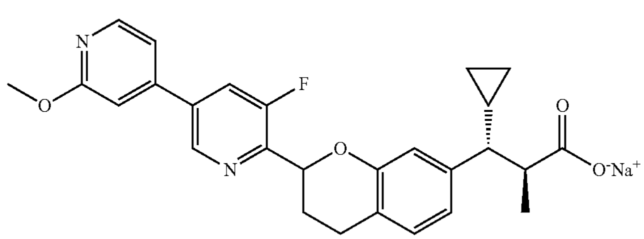 | A | mixture of 2 diastereomers | 463.6 |
| 122 | 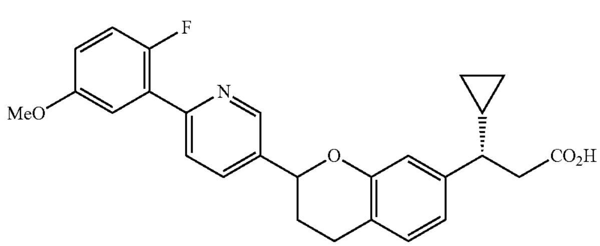 [SMILES: COc1ccc(F)c(-c2ccc(C3CCc4ccc([C@@H](CC(=O)O)C5CC5)cc4O3)cn2)c1] | B | 2 single diastereomers AS-H (4.6 × 150 mm) 5-40% EtOH (0.05% DEA)/ CO2 | 448.1 |

-continued

| Example No. | Structure | Scheme 12 Step 1 Method | Stereoisomers/ Chiral Conditions | LC/MS (M + H)+ |
|---|---|---|---|---|
| 123 | 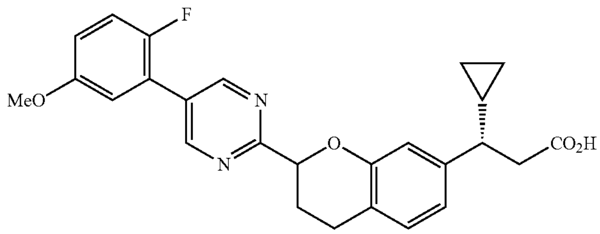 [SMILES: COc1ccc(F)c(-c2cnc(C3CCc4ccc([C@@H](CC(=O)O)C5CC5)cc4O3)nc2)c1] | B | 2 single diastereomers AD-3 60% EtOH (0.1% DEA)/CO2 | 449.1 |
| 124 | 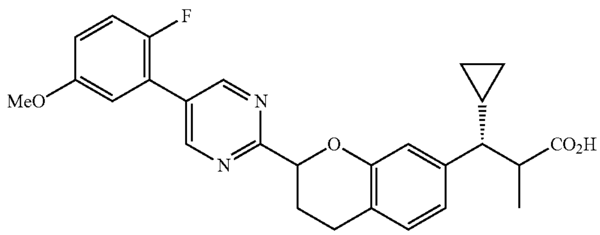 [SMILES: COc1ccc(F)c(-c2cnc(C3CCc4ccc([C@H](C5CC5)C(C)C(=O)O)cc4O3)nc2)c1] | B | Mixture of 4 diastereomers | 463.1 |
| 125 | 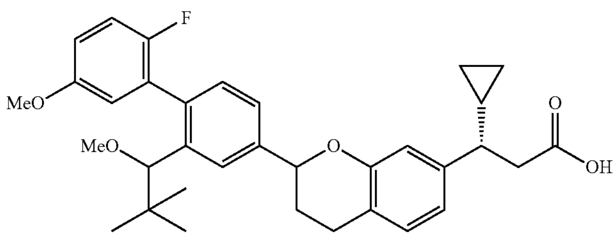 | B | 4 single diastereomers AD-H 30% IPA/CO2 | 515.2 (M + 1 − MeOH) |
| 126 | 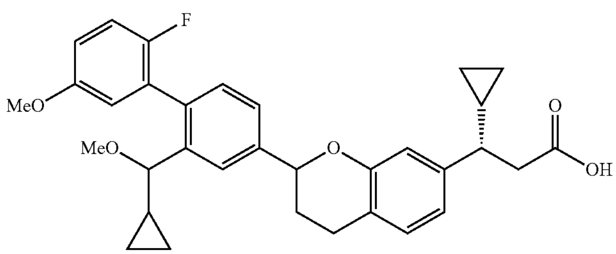 [SMILES: COc1ccc(F)c(-c2ccc(C3CCc4ccc([C@@H](CC(=O)O)C5CC5)cc4O3)cc2C(OC)C2CC2)c1] | B | 4 single diastereomers AD (4.6 × 250 mm) 20% MeOH/CO2 | 499 (M + 1 − MeOH) |
| 127 | 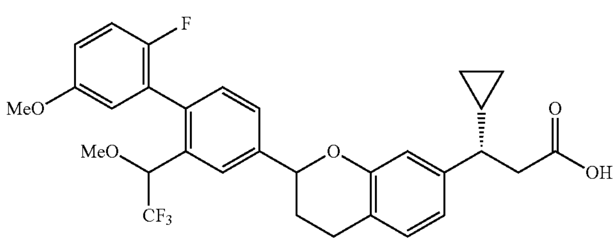 [SMILES: COc1ccc(F)c(-c2ccc(C3CCc4ccc([C@@H](CC(=O)O)C5CC5)cc4O3)cc2C(OC)C(F)(F)F)c1] | B | mixture of 4 diastereomers | 559.3 |
| 128 | 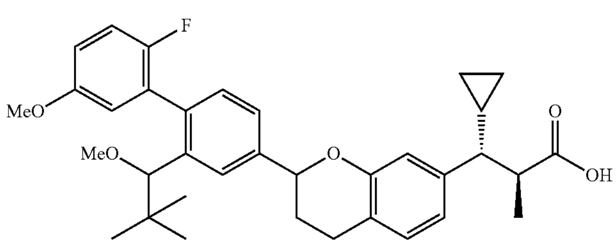 | C | 4 single diastereomers AD-H (21 × 250 mm) 30% IPA/CO2 | 529 (M + 1 − MeOH) |

-continued
| Example No. | Structure | Scheme 12 Step 1 Method | Stereoisomers/ Chiral Conditions | LC/MS (M + H)+ |
|---|---|---|---|---|
| 129 | 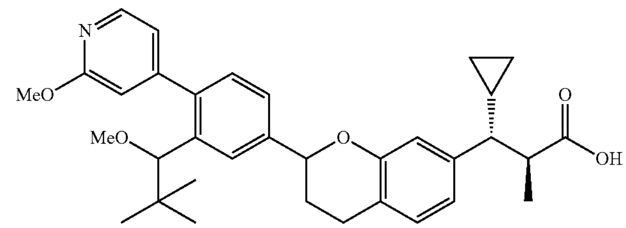 [SMILES: COc1cc(-c2ccc(C3CCc4ccc([C@H](C5CC5)[C@H](C)C(=O)O)cc4O3)cc2C(OC)C(C)(C)C)ccn1] | A | 4 single diastereomers AD-H (21 × 250 mm) 25% IPA/CO2 | 544.3 |
| 130 | 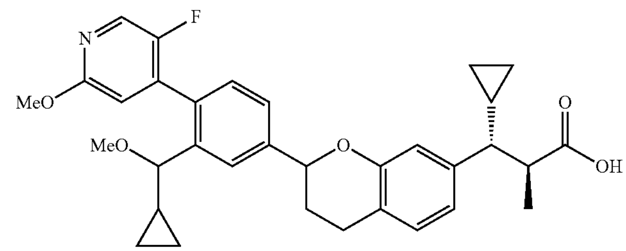 | A | mixture of 4 diastereomers | 514.5 (M + 1 − MeOH) |
| 131 | 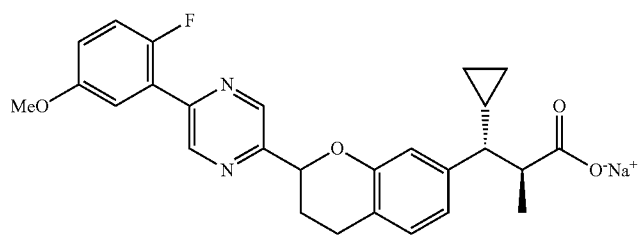 | A | 2 single diastereomers AD-H (21 × 250 mm) 45% IPA/CO2 | 463 |
| 132 | 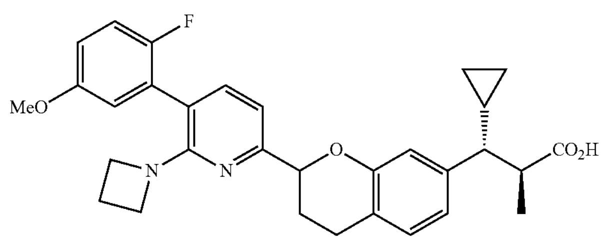 [SMILES: COc1ccc(F)c(-c2ccc(C3CCc4ccc([C@H](C5CC5)[C@H](C)C(=O)O)cc4O3)nc2N2CCC2)c1] | A | mixture of 2 diastereomers | 517.2 |
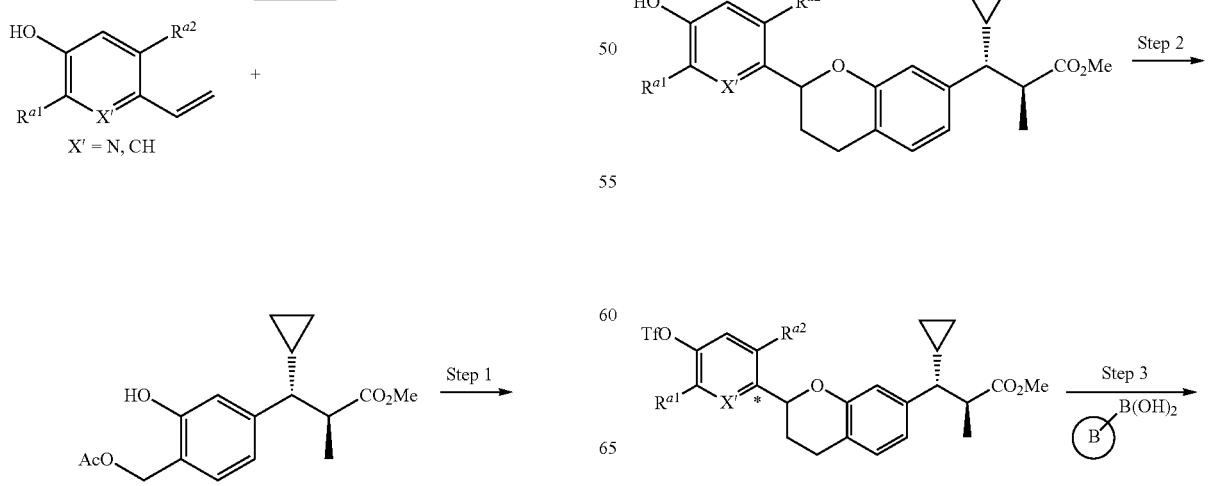

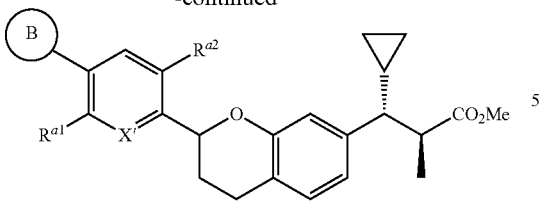

Step 1: Xylenes, 165-170° C.; Step 2: Tf$_2$O, pyridine, DCM, 0° c.; Step 3: SPhos precat., 3M K$_3$PO$_4$, THF, 80° C.

The synthetic procedure of Scheme 13 may be used to prepare chromans, such as Example 133. The vinylphenol (or vinyl pyridinol) is heated with a hydroxybenzyl acetate to give the chroman cycloaddition products. The phenol is then converted to an aryl triflate. Cross-coupling of the aryl triflate with an arylboronic acid provides the biaryl chorman compounds. Hydrolysis, SFC separation, and conversion into the sodium salt is perfored as previously described in Scheme 12.

Example 133

(2S,3R)-3-cyclopropyl-3-(2-(2-fluoro-4-(2-methoxypyridin-4-yl)phenyl)chroman-7-yl)-2-methylpropanoic acid

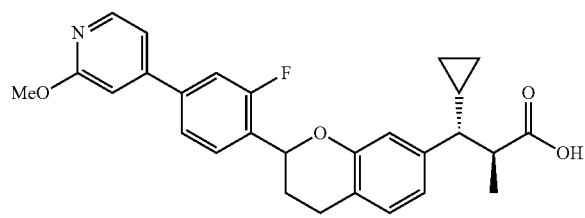 [SMILES: COc1cc(-c2ccc(C3CCc4ccc([C@H](C5CC5)[C@H](C)C(=O)O)cc4O3)c(F)c2)ccn1]

Step 1: (2S,3R)-methyl 3-cyclopropyl-3-(2-(2-fluoro-4-hydroxyphenyl)chroman-7-yl)-2-methylpropanoate

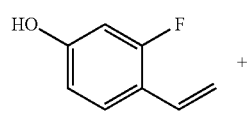

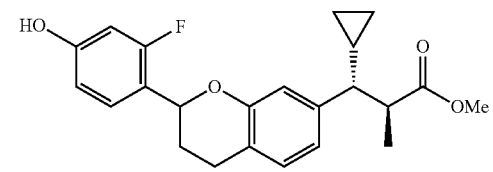

Utilizing the procedure described in Scheme 12, Step 1, Method A, (2S,3R)-methyl 3-cyclopropyl-3-(2-(2-fluoro-4-hydroxyphenyl)chroman-7-yl)-2-methylpropanoate was prepared starting from 3-fluoro-4-vinylphenol. $^1$H NMR (500 MHz, CHCl$_3$-d): 0.07 (m, 1H), 0.24-0.19 (m, 1H), 0.35-0.31 (m, 1H), 0.55-0.51 (m, 1H), 0.96 (d, 3H), 1.03 (m, 1H), 1.84 (t, 1H), 2.08-2.05 (m, 1H), 2.17 (m, 1H), 2.79-2.76 (m, 2H), 3.02-2.95 (m, 1H), 3.72 (s, 3H), 5.24 (bs, 1H), 5.25 (d, 2H), 6.60 (d, 1H), 6.69-6.65 (m, 3H), 7.03 (d, 1H), 7.40-7.36 (t, 1H).

Step 2: (2S,3R)-methyl 3-cyclopropyl-3-(2-(2-fluoro-4-(((trifluoromethyl)sulfonyl-)oxy)phenyl)chroman-7-yl)-2-methylpropanoate

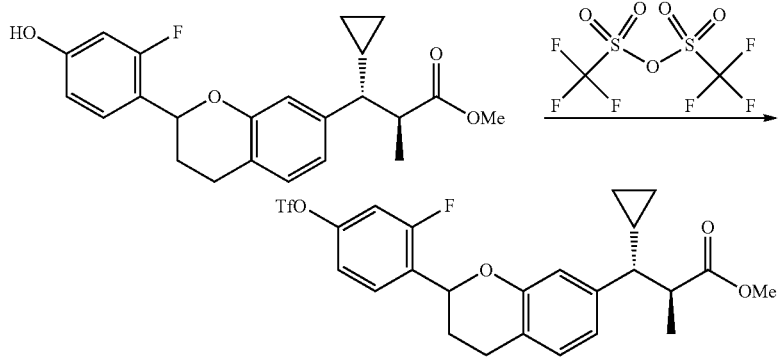

To a solution of (2S,3R)-methyl 3-cyclopropyl-3-(2-(2-fluoro-4-hydroxyphenyl)-chroman-7-yl)-2-methylpropanoate (0.6792 g, 1.767 mmol) in DCM (10 ml) at 0° C. was added pyridine (0.286 ml, 3.53 mmol), followed by trifluoromethanesulfonic anhydride (0.448 ml, 2.65 mmol). After 30 min., the reaction mixture was diluted with DCM and washed with water/brine. The aqueous layer was separated and back-extracted with EtOAc. The organic layers were combined, dried over MgSO$_4$, and concentrated in vacuo. The resulting residue was purified via MPLC (ISCO 40 g, product eluted at 15% EtOAc/hexane) with gradient elution 0-40% EtOAc/hexane to give the title compound. $^1$H NMR (500 MHz, CHCl$_3$-d): 0.03 (m, 1H), 0.23 (m, 1H), 0.35 (m, 1H), 0.55 (m, 1H), 0.97 (d, 3H), 1.04 (m, 1H), 1.87 (t, 1H), 2.01 (m, 1H), 2.26 (m, 1H), 2.80 (m, 2H), 3.01-2.98 (m, 1H), 3.73 (s, 3H), 5.36 (d, 1H), 6.71 (bs, 2H), 7.06 (m, 2H), 7.14 (d, 1H), 7.68 (t, 1H).

Step 3: (2S,3R)-methyl 3-cyclopropyl-3-(2-(2-fluoro-4-(2-methoxypyridin-4-yl)phenyl)chroman-7-yl)-2-methylpropanoate

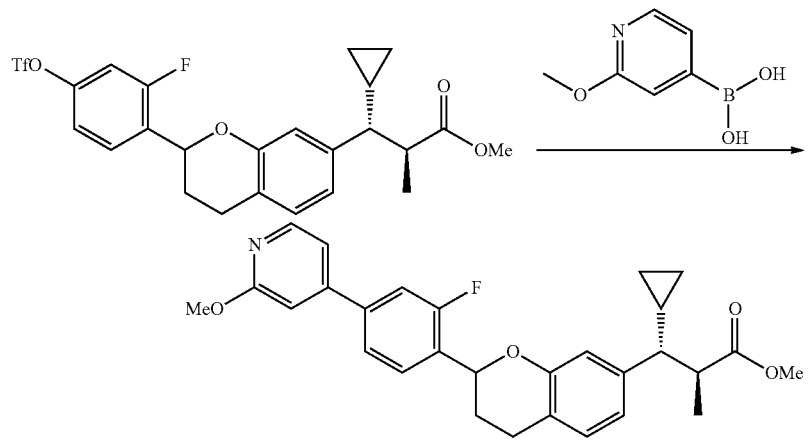

Utilizing the procedure to prepare Intermediate 10 described in Scheme 6, Step 1, Method C, (2S,3R)-methyl 3-cyclopropyl-3-(2-(2-fluoro-4-(((trifluoromethyl)sulfonyl)-oxy)phenyl)chroman-7-yl)-2-methylpropanoate (0.7013 g, 1.358 mmol) and (2-methoxypyridin-4-yl)boronic acid (0.3143 g, 2.055 mmol) were coupled to give (2S,3R)-methyl 3-cyclopropyl-3-(2-(2-fluoro-4-(2-methoxypyridin-4-yl)phenyl)chroman-7-yl)-2-methylpropanoate. $^1$H NMR (500 MHz, CHCl$_3$-d): 0.02 (m, 1H), 0.26-0.21 (m, 1H), 0.35 (m, 1H), 0.57-0.53 (m, 1H), 0.97 (d, 3H), 1.08-1.02 (m, 1H), 1.26 (t, 7H), 1.86 (t, 1H), 2.05 (m, 1H), 2.28 (m, 1H), 2.82-2.78 (m, 2H), 3.06-2.99 (m, 2H), 3.72 (s, 3H), 3.99 (s, 3H), 5.40 (d, 1H), 6.73-6.69 (m, 2H), 6.94-6.93 (m, 1H), 7.09-7.03 (m, 2H), 7.33 (d, 1H), 7.45 (d, 1H), 7.66 (t, 1H), 8.24 (d, 1H). LC/MS (m/z): 476.7 (M+H)$^+$.

Step 4: (2S,3R)-3-cyclopropyl-3-(2-(2-fluoro-4-(2-methoxypyridin-4-yl)phenyl)-chroman-7-yl)-2-methylpropanoic acid

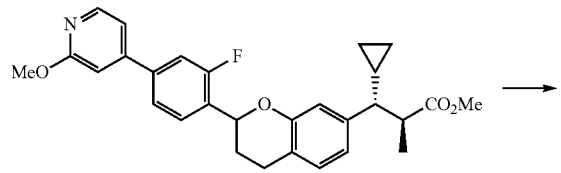

-continued

To a MeOH/THF (15 mL, 1:1) solution of (2S,3R)-methyl 3-cyclopropyl-3-(2-(2-fluoro-4-(2-methoxypyridin-4-yl)phenyl)chroman-7-yl)-2-methylpropanoate (370 mg, 0.80 mmol) was added 1 M LiOH (8 mL, 8.00 mmol) at ambient temperature. The reaction mixture was heated to 65° C. for 19 h, then concentrated in vacuo. The resulting residue was suspended in EtOAc, and 1 N HCl (8.5 mL) was added. The resulting mixture was partitioned between EtOAc and brine. The aqueous layer was separated and back-extracted with EtOAc (2×). The combined organic layers were dried over MgSO$_4$, and concentrated in vacuo. The resulting residue was purified via MPLC (ISCO 24 g; product eluted at 48% EtOAc/hexane) with gradient elution 0-100% EtOAc/hexane to give the title compound. (m/z): 462.7 (M+H)$^+$.

Examples 134 and 135 were prepared in a similar manner to Scheme 13 using the styrenes prepared according to Scheme 9.

| Example No. | Structure | Stereoisomers/Chiral Conditions | LC/MS M + 1 |
|---|---|---|---|
| 134 | ![structure] | 2 single diastereomers: AD (30 × 250 mm), 37% IPA/CO$_2$ | 462.3 |

| Example No. | Structure | Stereoisomers/ Chiral Conditions | LC/MS M + 1 |
|---|---|---|---|
| 135 | 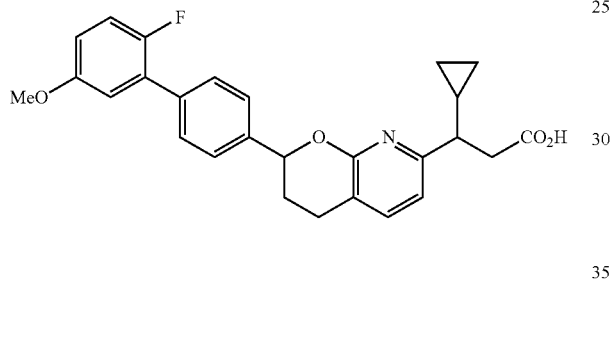 | 4 single diastereomers 1st separation: AS (21 × 250 mm), 15% IPA + 0.2% DEA/CO2; 2nd separation: IC (21 × 200 cm), 15% IPA + 0.2% DEA/CO2 | 562.6 |

Example 136

3-cyclopropyl-3-(2-(2'-fluoro-5'-methoxy-[1,1'-biphenyl]-4-yl)-3,4-dihydro-2H-pyrano[2,3-b]pyridin-7-yl)propanoic acid

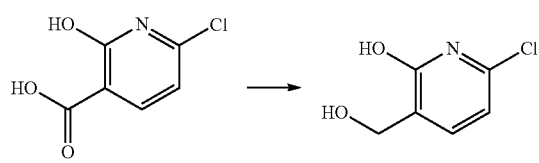 [SMILES: O=C(O)c1ccc(Cl)nc1O ; OCc1ccc(Cl)nc1O]

Step 1:
6-chloro-3-(hydroxymethyl)pyridin-2(1H)-one

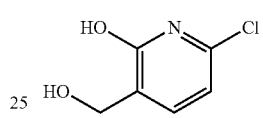

To a cooled (−78° C.) THF (10 mL) solution of 6-chloro-2-hydroxynicotinic acid (1 g, 5.76 mmol) was added LAH (0.547 g, 14.40 mmol). After 1 h, the reaction was heated to 60° C. After 1 h, the reaction was cooled to room temp and Feezer quenched by addition of 0.5 mL water, followed by 0.5 mL 15% NaOH, and followed by 1 mL water. The resulting mixture was stirred vigorously for 1 h, then partitioned between water/DCM. The organic layers were combined, dried (Na2SO4) and concentrated. The resulting residue was purified by HPLC (ISCO 80 g, 0 to 100% EtOAc) to give the title compound. $^1$H NMR (500 MHz, DMSO-d6): 7.59 (d, 1H), 6.68 (d, 1H), 4.90 (br, 2H).

Step 2: 7-chloro-2-(2'-fluoro-5'-methoxy-[1,1'-biphenyl]-4-yl)-3,4-dihydro-2H-pyrano[2,3-b]pyridine

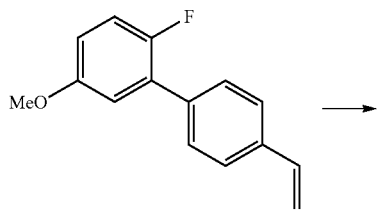

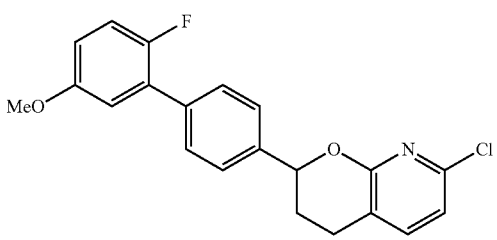

To a nitromenthane (3 mL) solution of 6-chloro-3-(hydroxymethyl)pyridin-2(1H)-one (858 mg, 3.76 mmol), 2-fluoro-5-methoxy-4'-vinyl-1,1'-biphenyl (300 mg, 1.880 mmol), lithium perchlorate (250 mg, 2.350 mmol), and montmorilite K10 (300 mg) was added water (423 µl, 23.50 mmol). The resulting slurry was heated in a sealed vial on a heating block to 80° C. After 16 h, the reaction mixture was cooled to room temperature. Then the reaction was filtered (MgSO4) and concentrated. The resulting residue was purified by HPLC (ISCO 120 g, 0 to 50% EtOAc/Hex) to give the title compound. $^1$H NMR (500 MHz, CHCl3-d): 7.59 (d, 2H), 7.50 (d, 2H), 7.40 (d, 1H), 7.09 (t, 1H), 6.95 (m, 2H), 6.82 (d, 1H), 5.35 (d, 1H), 3.81 (s, 3H), 2.98 (m, 1H), 2.80 (d, 1H), 2.32 (d, 1H), 2.12 (q, 1H).

Step 3: (2-(2'-fluoro-5'-methoxy-[1,1'-biphenyl]-4-yl)-3,4-dihydro-2H-pyrano[2,3-b]pyridin-7-yl)boronic acid

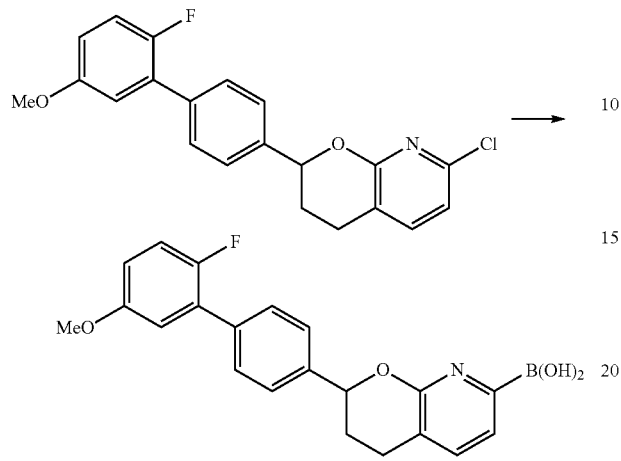

To a nitrogen-sparged dioxane (4 mL) solution of 7-chloro-2-(2'-fluoro-5'-methoxy-[1,1'-biphenyl]-4-yl)-3,4-dihydro-2H-pyrano[2,3-b]pyridine (240 mg, 0.649 mmol), 1,1'-bis(diphenylphosphino)ferrocene-palladium (II) dichloride dichloromethane complex (26.5 mg, 0.032 mmol), and 4,4,4',4',5,5,5',5'-octamethyl-2,2'-bi(1,3,2-dioxaborolane) (181 mg, 0.714 mmol) was added potassium acetate (191 mg, 1.947 mmol). The reaction mixture was heated on a heating block to 100° C. After 16 h, the mixture was poured into NaHCO$_3$ (saturated aqueous, 10 mL) and extracted with EtOAc (2×25 mL). The combined organic layers were dried (MgSO$_4$) and concentrated. The resulting crude residue was used without further purification. (m/z): 380.47 (M+H)$^+$.

Step 4: (Z)-methyl 3-cyclopropyl-3-(2-(2'-fluoro-5'-methoxy-[1,1'-biphenyl]-4-yl)-3,4-dihydro-2H-pyrano[2,3-b]pyridin-7-yl)acrylate

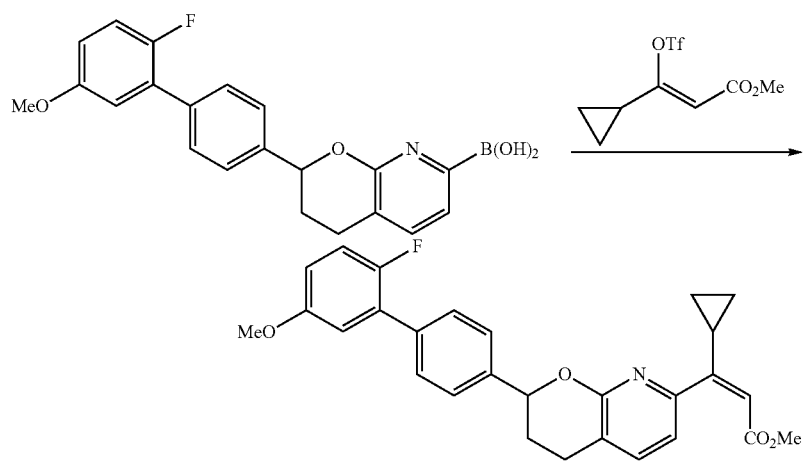

To a nitrogen-purged dioxane (1.5 ml) solution of (2-(2'-fluoro-5'-methoxy-[1,1'-biphenyl]-4-yl)-3,4-dihydro-2H-pyrano[2,3-b]pyridin-7-yl)boronic acid (76 mg, 0.2 mmol),
Tetrakis (11.56 mg, 10.00 μmol), and (Z)-methyl 3-cyclopropyl-3-(((trifluoromethyl)sulfonyl)oxy)acrylate (54.8 mg, 0.200 mmol) was added K$_2$CO$_3$ (0.20 ml, 0.40 mmol, 2 N solution in water). The reaction mixture was then heated 100° C. on a heating block. After 16 h, the reaction was cooled to room temperature and poured into NH$_4$Cl (sat, aq, 10 mL). The mixture was then extracted with EtOAc (2×10 mL). The combined organic layers were dried (MgSO$_4$) and concentrated. The resulting residue was purified by HPLC (ISCO 120 g, 0 to 40% EtOAc/Hex) to give the title compound. $^1$H NMR (500 MHz, CHCl$_3$-d): 7.55 (m, 4H), 7.45 (d, 1H), 7.08 (t, 1H), 6.95 (q, 1H), 6.80 (m, 2H), 5.88 (s, 1H), 5.35 (d, 1H), 3.81 (s, 3H), 3.58 (s, 3H), 3.00 (m, 1H), 2.82 (d, 1H), 2.30 (d, 1H), 2.15 (m, 1H), 1.81 (m, 1H), 0.90 (s, 2H), 0.70 (s, 2H).

Step 5: methyl 3-cyclopropyl-3-(2-(2'-fluoro-5'-methoxy-[1,1'-biphenyl]-4-yl)-3,4-dihydro-2H-pyrano[2,3-b]pyridin-7-yl)propanoate

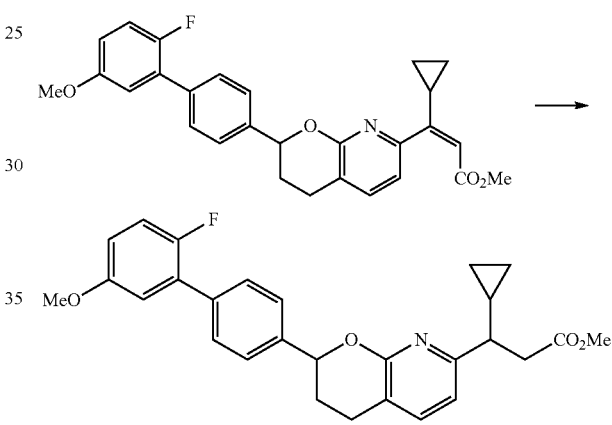

To an ethyl acetate (1 mL) solution of (Z)-methyl 3-cyclopropyl-3-(2-(2'-fluoro-5'-methoxy-[1,1'-biphenyl]-4-yl)-3,4-dihydro-2H-pyrano[2,3-b]pyridin-7-yl)acrylate (6 mg, 0.013 mmol) was added Rhodium on Alumina (powder, 5% by wt). The reaction was purged and then backfilled with hydrogen gas. The mixture was stirred vigorously under a balloon of hydrogen. After 16 h, the reaction was vented into the hood. Then the reaction was filtered over Celite™ and the filtrate was concentrated. The resulting residue was purified by HPLC (ISCO 24 g, 0 to 50% EtOAc/Hex) to give the title compound. (m/z): 462.51 (M+H)$^+$.

Step 6: 3-cyclopropyl-3-(2-(2'-fluoro-5'-methoxy-[1,1'-biphenyl]-4-yl)-3,4-dihydro-2H-pyrano[2,3-b]pyridin-7-yl)propanoic acid

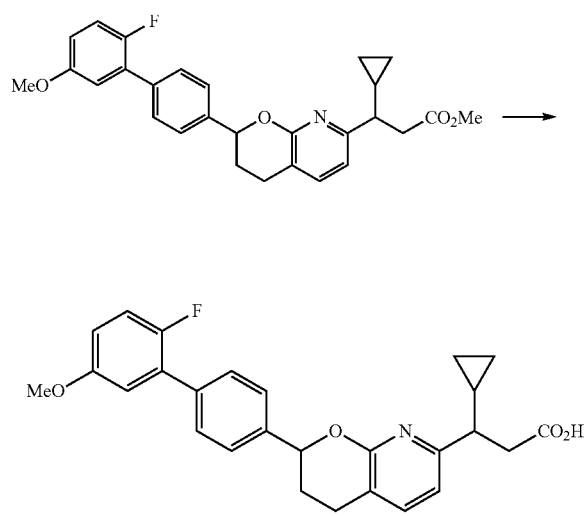

To a MeOH/THF/water (3 mL, 1:1:1) solution of methyl 3-cyclopropyl-3-(2-(2'-fluoro-5'-methoxy-[1,1'-biphenyl]-4-yl)-3,4-dihydro-2H-pyrano[2,3-b]pyridin-7-yl)propanoate (4 mg, 8.67 μmol) was added LiOH (2.076 mg, 0.087 mmol). After 16 h, the reaction was poured into saturated NH$_4$Cl (10 mL) and extracted with EtOAc (2×10 mL). The combined organic layers were dried (MgSO$_4$) and concentrated. The resulting residue was purified by HPLC (ISCO 40 g, 0 to 100% EtOAc/Hex) to give the title compound. (m/z): 448.60 (M+H)$^+$.

Example 137 was prepared in a similar manner to Scheme 13 using the appropriate starting materials.

Example 138

(S or R)-3-((R or S)-2-(2'-fluoro-5'-methoxy-[1,1'-biphenyl]-4-yl) chroman-7-yl)butanoic acid

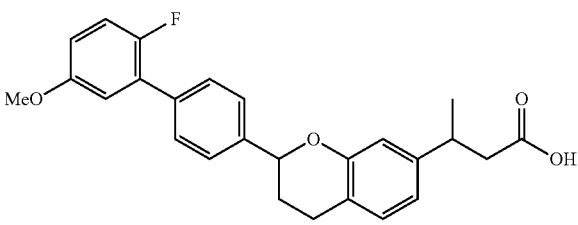

Step A: (E)-methyl 3-(2-(2'-fluoro-5'-methoxy-[1,1'-biphenyl]-4-yl)chroman-7-yl) but-2-enoate

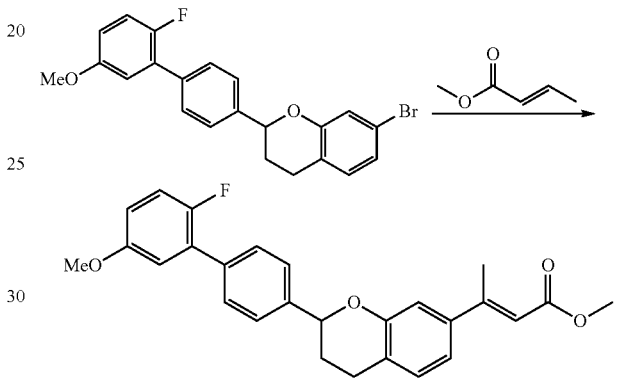

A mixture of 7-bromo-2-(2'-fluoro-5'-methoxy-[1,1'-biphenyl]-4-yl)chroman (1.00 g, 2.42 mmol, 1.0 eq), PdOAc$_2$ (54.3 mg, 0.242 mmol), TEA (1.01 ml, 7.26 mmol, 0.726 g/mL, 3.0 eq), (Z)-methyl but-2-enoate (727 mg, 7.26 mmol) and tri-o-tolylphosphine (73.6 mg, 0.242 mmol) in DMF (15 ml) was stirred at 120° C. for 16 hours under a N$_2$ atmosphere. The reaction mixture was cooled to room temperature, then the solvent was removed under vacuum. The reaction was quenched with water (15 mL), and the mixture was extracted with DCM (15 mL) twice. The combined organic layers were dried over anhydrous Na$_2$SO$_4$, and concentrated in vacuum to give the crude product. The crude product was purified by silica gel chromatography eluted with PE:EtOAc=50:1 to give the title compound. $^1$H NMR (400 MHz, CDCl$_3$) δ: 7.59 (d, J=7.6, 2H), 7.51 (d, J=7.6, 2H), 7.11-6.95 (m, 5H), 6.84-6.82 (m, 1H), 5.14 (d, J=8.4, 1H), 3.82 (s, 3H), 3.74 (s, 3H), 3.02-2.82 (m 2H), 2.55 (s, 3H), 2.29-2.04 (m 2H).

| Example No. | Structure | Stereoisomers/ Chiral Conditions | LC/MS M + 1 |
|---|---|---|---|
| 137 | 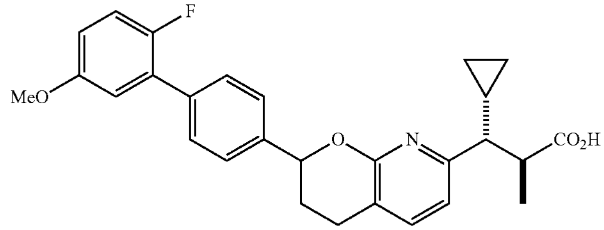 [SMILES: COc1ccc(F)c(-c2ccc(C3CCc4ccc([C@H](C5CC5)[C@H](C)C(=O)O)nc4O3)cc2)c1] | 4 Diastereomers | 462.19 |

Step B: methyl 3-(2-(2'-fluoro-5'-methoxy-[1,1'-biphenyl]-4-yl)chroman-7-yl)butanoate

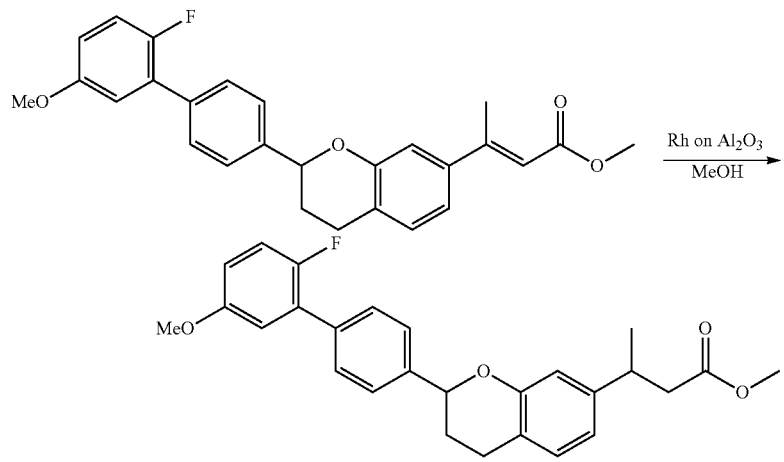

A mixture of (E)-methyl 3-(2-(2'-fluoro-5'-methoxy-[1,1'-biphenyl]-4-yl)chroman-7-yl) but-2-enoate (2.40 g, 5.55 mmol) and Rh/Al$_2$O$_3$ (57.0 mg, 0.277 mmol) in MeOH (20 ml) was stirred at room temperature for 16 hours under a H$_2$ atmosphere. Then the mixture was filtered and the filtrate was concentrated to give the crude product. The crude product was dissolved in DCM (25 mL), and washed with water (20 mL). The organic layer was separated, dried over anhydrous Na$_2$SO$_4$, and concentrated in vacuo to give the title compound as a mixture of 4 diastereomers.

Step C: (S or R)-methyl 3-((R or S)-2-(2'-fluoro-5'-methoxy-[1,1'-biphenyl]-4-yl)chroman-7-yl)butanoate

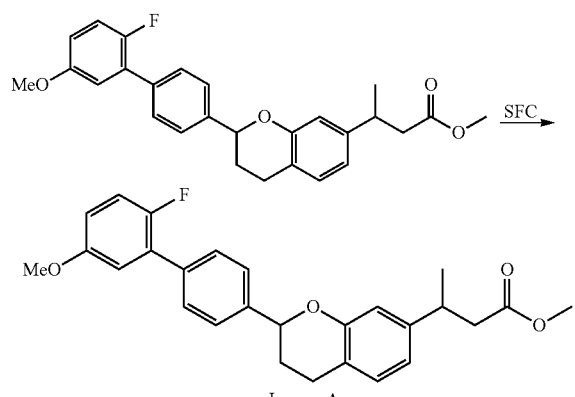

Isomer A

Isomer B

-continued

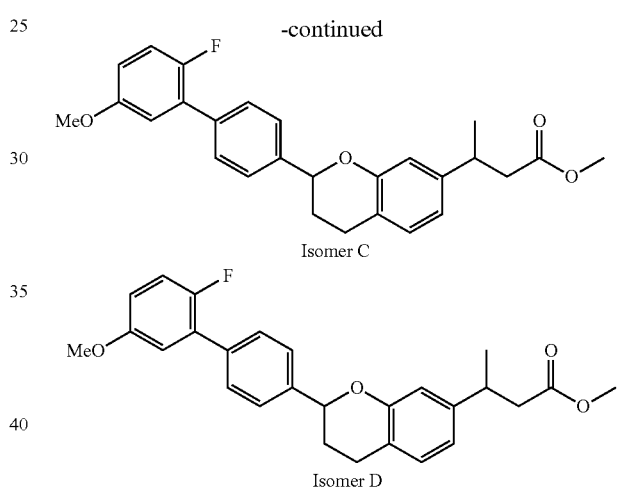

Isomer C

Isomer D

The diastereomeric mixture of Step B was separated via SFC using a Chiralcel Column OJ H 250×4.6 mm I.D., 5 um Mobile phase: iso propanol (0.05% DEA) in CO$_2$ from 5% to 40% Flow rate: 2.5 mL/min Wavelength: 220 nm) to give in order of elution: methyl 3-(2-(2'fluoro-5'-methoxy-[1,1'-biphenyl]-4-yl)chroman-7-yl)butanoate (Isomer A); methyl 3-(2-(2'fluoro-5'-methoxy-[1,1'-biphenyl]-4-yl)chroman-7-yl)butanoate (Isomer B); methyl 3-(2-(2'fluoro-5'-methoxy-[1,1'-biphenyl]-4-yl)chroman-7-yl)butanoate (Isomer C); and methyl 3 (2-(2'-fluoro-5'-methoxy-[1,1'-biphenyl]-4-yl)chroman-7-yl)butanoate (Isomer D).

Step D

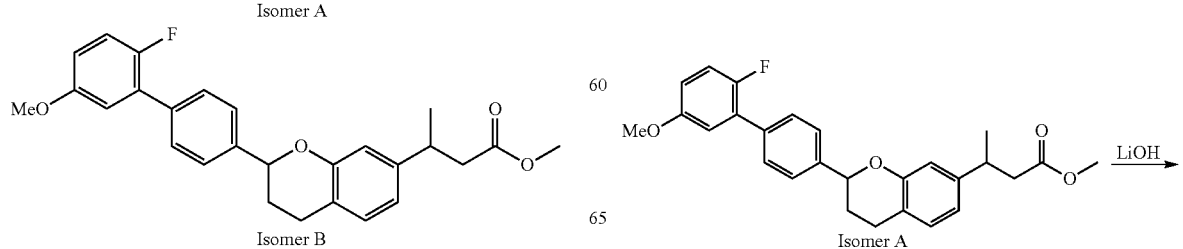

Isomer A

-continued

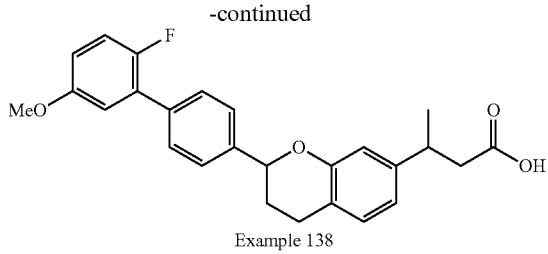

Example 138

A mixture of lithium hydroxide (21.3 mg, 0.892 mmo) and methyl 3-(2-(2'-fluoro-5'-methoxy-[1,1'-biphenyl]-4-yl)chroman-7-yl)butanoate (Isomer A) (40.0 mg, 0.0890 mmol) in water (1.0 ml), THF (1.0 ml) and MeOH (1.0 ml) was stirred at room temperature for 2 hours. Then the reaction mixture was diluted with DCM (10 mL), and washed with water (20 ml). The combined organic layers were dried over anhydrous $Na_2SO_4$, and concentrated in vacuo to give the crude product. The crude product was purified by prep-HPLC (on a GILSON 281 instrument fitted with a Phenomenex Synergi C18 100*21.2 mm*4 um using water and acetonitrile as the eluents. Mobile phase A: water (containing 0.1% TFA, v/v), mobile phase B: acetonitrile. Gradient: 60-80% B, 0-10 min; 100% B, 10.5-12.5 min; 5% B, 13-15 min) to give the product. $^1$H NMR (400 MHz, $CDCl_3$) δ: 7.56 (d, J=7.6, 2H), 7.49 (d, J=7.6, 2H), 7.06-6.92 (m, 3H), 6.78-6.74 (m, 3H), 5.08 (d, J=9.2, 1H), 3.81 (s, 3H), 3.23-3.20 (m, 1H), 2.97-2.96 (m, 1H), 2.80-2.79 (m, 1H), 2.69-2.56 (m, 2H), 2.21-2.11 (m, 2H), 1.30 (d, J=7.2, 3H).

Examples 139-141 were prepared in a similar manner to Example 138 using the appropriate intermediates and commercially available starting materials.

| Example No. | Structure | M.W. | Starting Material | LC/MS (ESI) observed [M + 1]+ |
|---|---|---|---|---|
| 139 | 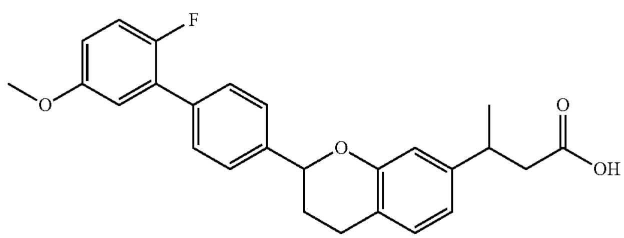 [SMILES: COc1ccc(F)c(-c2ccc(C3CCc4ccc(C(C)CC(=O)O)cc4O3)cc2)c1] | 420 | methyl 3-(2-(2'-fluoro-5'-methoxy-[1,1'-biphenyl]-4-yl)chroman-7-yl)butanoate (Isomer B) | 421 |
| 140 | 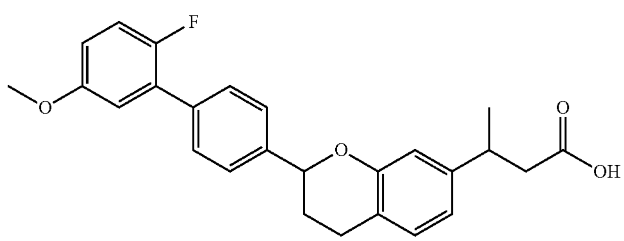 [SMILES: COc1ccc(F)c(-c2ccc(C3CCc4ccc(C(C)CC(=O)O)cc4O3)cc2)c1] | 420 | methyl 3-(2-(2'-fluoro-5'-methoxy-[1,1'-biphenyl]-4-yl)chroman-7-yl)butanoate (Isomer C) | 421 |
| 141 | 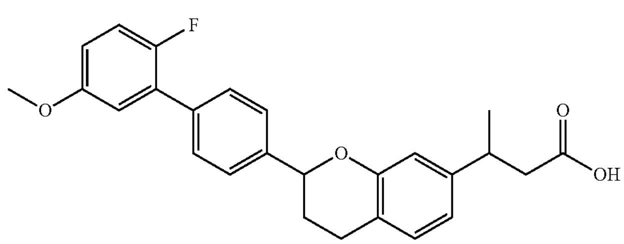 [SMILES: COc1ccc(F)c(-c2ccc(C3CCc4ccc(C(C)CC(=O)O)cc4O3)cc2)c1] | 420 | methyl 3-(2-(2'-fluoro-5'-methoxy-[1,1'-biphenyl]-4-yl)chroman-7-yl)butanoate (Isomer D) | 421 |

Example 142

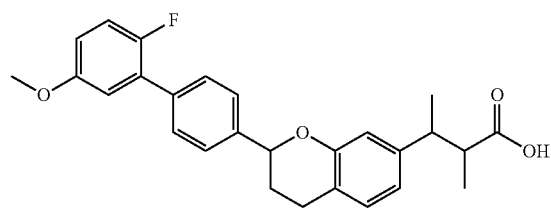 [SMILES: COc1ccc(F)c(-c2ccc(C3CCc4ccc(C(C)C(C)C(=O)O)cc4O3)cc2)c1]

Step A

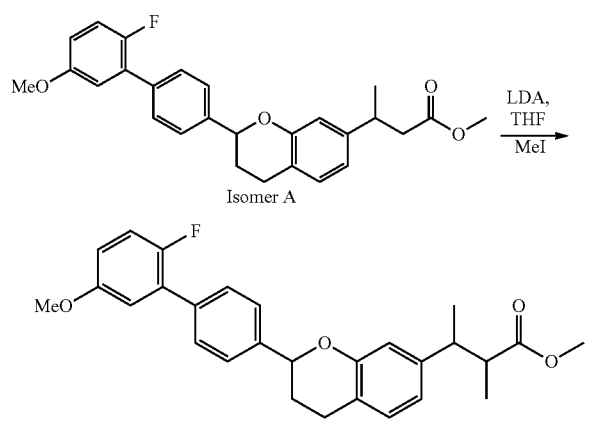

A mixture of methyl 3-(2-(2'-fluoro-5'-methoxy-[1,1'-biphenyl]-4-yl)chroman-7-yl)butanoate (Isomer A) (200 mg, 0.460 mmol,) in THF (10 ml) was stirred at −78° C. under a $N_2$ atmosphere. Then LDA (2.30 mL, 4.60 mmol, 2M in THF) was added dropwise at −78° C., and the reaction mixture was stirred at −78° C. for 30 min. Then iodomethane (653 mg, 4.60 mmol) was added dropwise at −78° C., and the reaction mixture was stirred at room temperature for 1 hour. The reaction was quenched by the addition of HCl (2 M, 20 mL), then the reaction solvent was removed under vacuum, and the resulting mixture was extracted with DCM (20 mL) twice. The combined organic layers were dried over anhydrous $Na_2SO_4$, and concentrated in vacuo to give the crude product, which was purified by prep-TLC (PE:EtOAc=5:1) to give the desired product as a mixture of two diastereomers.

Step B

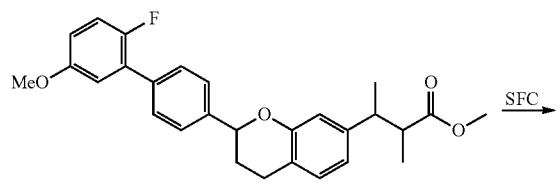

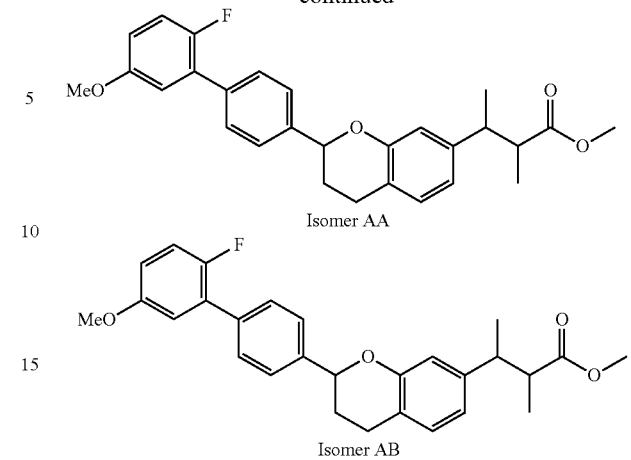

The product from Step A was separated into two diastereomers via SFC (Chiralpak Column AD-H 250×4.6 mm I.D., 5um Mobile phase: 40% ethanol (0.05% DEA) in $CO_2$ Flow rate: 2.35 mL/min Wavelength: 220 nm) to give methyl 3-(2-(2'-fluoro-5'-methoxy-[1,1'-biphenyl]-4-yl)chroman-7-yl)-2-methylbutanoate (Isomer AA, faster eluting isomer); and methyl 3-(2-(2'-fluoro-5'-methoxy-[1,1'-biphenyl]-4-yl)chroman-7-yl)-2-methylbutanoate (Isomer AB, slower eluting isomer).

Step C

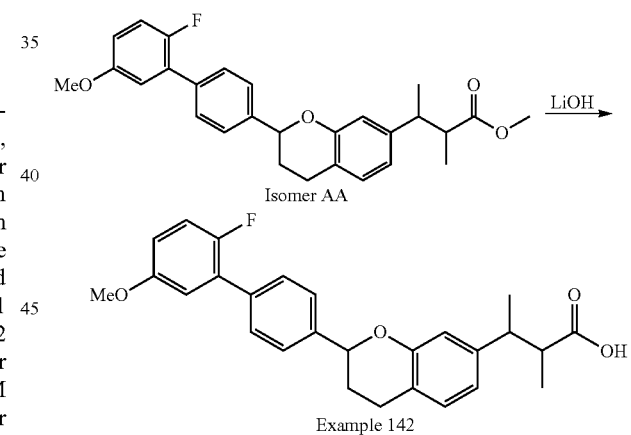

A mixture of lithium hydroxide (21.3 mg, 0.892 mmol) and methyl 3-(2-(2'-fluoro-5'-methoxy-[1,1'-biphenyl]-4-yl)chroman-7-yl)-2-methylbutanoate (Isomer AA) (40.0 mg, 0.0890 mmol) in water (1.0 ml), THF (1.0 ml) and MeOH (1.0 ml) was stirred at room temperature for 2 hours. Then the reaction mixture was diluted with DCM (10 mL). The organic layer was separated, washed with water (20 ml), dried over anhydrous $Na_2SO_4$, and concentrated in vacuo to the crude product. The crude product was purified by prep-HPLC (on a GILSON 281 instrument fitted with a Phenomenex Synergi C18 100*21.2 mm*4 um using water and acetonitrile as the eluents. Mobile phase A: water (containing 0.1% TFA, v/v), mobile phase B: acetonitrile. Gradient: 60-80% B, 0-10 min; 100% B, 10.5-12.5 min; 5% B, 13-15 min) to give Example 142. $^1$H NMR (400 MHz, $CDCl_3$) δ: 7.56 (d, J=7.6, 2H), 7.49 (d, J=7.6, 2H), 7.05-6.92

(m, 3H), 6.78-6.73 (m, 3H), 5.07 (d, J=9.2, 1H), 3.80 (s, 3H), 3.11-2.96 (m, 2H), 2.75-2.68 (m, 2H), 2.21-2.09 (m, 2H), 1.24 (d, J=7.2, 3H), 1.15 (d, J=7.2, 3H).

Examples 143-147c were prepared in a similar manner to Example 142 using the appropriate intermediates and commercially available starting materials.

| Ex. No. | Material from Example 138 Step C | Material from Example 142, Step B | Structure | LC/MS (ESI) observed [M + 1]+ |
|---|---|---|---|---|
| 143 | methyl 3-(2-(2'-fluoro-5'-methoxy-[1,1'-biphenyl]-4-yl)chroman-7-yl)butanoate (Isomer A) | methyl 3-(2-(2'-fluoro-5'-methoxy-[1,1'-biphenyl]-4-yl)chroman-7-yl)-2-methylbutanoate (Isomer AB) | 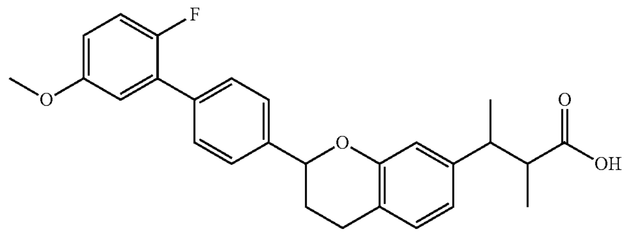 [SMILES: COc1ccc(F)c(-c2ccc(C3CCc4ccc(C(C)C(C)C(=O)O)cc4O3)cc2)c1] | 435 |
| 144 | methyl 3-(2-(2'-fluoro-5'-methoxy-[1,1'-biphenyl]-4-yl)chroman-7-yl)butanoate (Isomer B) | methyl 3-(2-(2'-fluoro-5'-methoxy-[1,1'-biphenyl]-4-yl)chroman-7-yl)-2-methylbutanoate (Isomer BA, faster eluting isomer) | 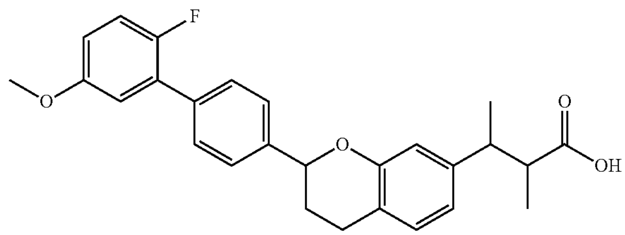 [SMILES: COc1ccc(F)c(-c2ccc(C3CCc4ccc(C(C)C(C)C(=O)O)cc4O3)cc2)c1] | 435 |
| 145 | methyl 3-(2-(2'-fluoro-5'-methoxy-[1,1'-biphenyl]-4-yl)chroman-7-yl)butanoate (Isomer B) | methyl 3-(2-(2'-fluoro-5'-methoxy-[1,1'-biphenyl]-4-yl)chroman-7-yl)-2-methylbutanoate (Isomer BB, slower eluting isomer) | 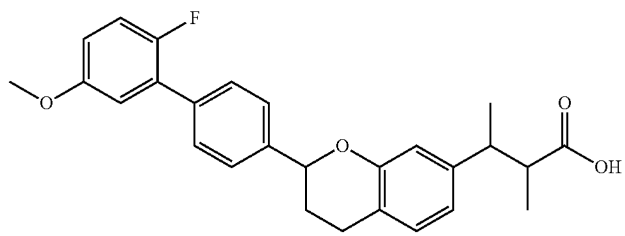 [SMILES: COc1ccc(F)c(-c2ccc(C3CCc4ccc(C(C)C(C)C(=O)O)cc4O3)cc2)c1] | 435 |
| 146 | methyl 3-(2-(2'-fluoro-5'-methoxy-[1,1'-biphenyl]-4-yl)chroman-7-yl)butanoate (Isomer C) | methyl 3-(2-(2'-fluoro-5'-methoxy-[1,1'-biphenyl]-4-yl)chroman-7-yl)-2-methylbutanoate (Isomer CA, faster eluting isomer) | 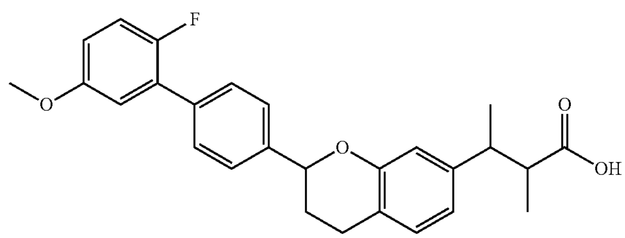 [SMILES: COc1ccc(F)c(-c2ccc(C3CCc4ccc(C(C)C(C)C(=O)O)cc4O3)cc2)c1] | 435 |
| 147a | methyl 3-(2-(2'-fluoro-5'-methoxy-[1,1'-biphenyl]-4-yl)chroman-7-yl)butanoate (Isomer C) | methyl 3-(2-(2'-fluoro-5'-methoxy-[1,1'-biphenyl]-4-yl)chroman-7-yl)-2-methylbutanoate (Isomer CB, Slower eluting isomer) | 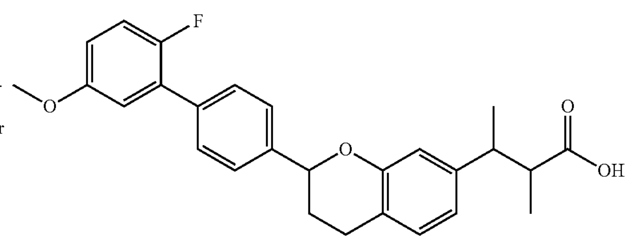 | 435 |
| 147b | methyl 3-(2-(2'-fluoro-5'-methoxy-[1,1'-biphenyl]-4-yl)chroman-7-yl)butanoate (Isomer D) | methyl 3-(2-(2'-fluoro-5'-methoxy-[1,1'-biphenyl]-4-yl)chroman-7-yl)-2-methylbutanoate (Isomer DA, faster eluting isomer) | 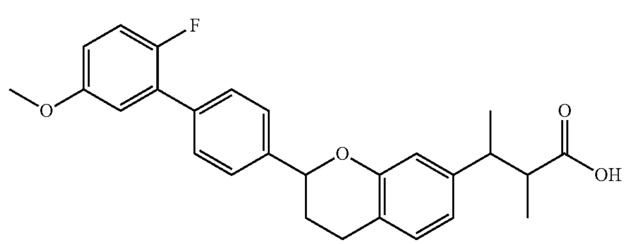 [SMILES: COc1ccc(F)c(-c2ccc(C3CCc4ccc(C(C)C(C)C(=O)O)cc4O3)cc2)c1] | 435 |

| Ex. No. | Material from Example 138 Step C | Material from Example 142, Step B | Structure | LC/MS (ESI) observed [M + 1]+ |
|---|---|---|---|---|
| 147c | methyl 3-(2-(2'-fluoro-5'-methoxy-[1,1'-biphenyl]-4-yl)chroman-7-yl)butanoate (Isomer D) | methyl 3-(2-(2'-fluoro-5'-methoxy-[1,1'-biphenyl]-4-yl)chroman-7-yl)-2-methylbutanoate (Isomer DB, Slower eluting isomer) | 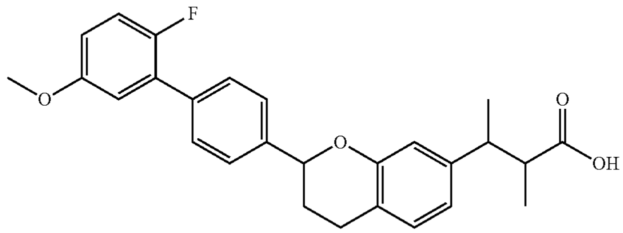 [SMILES: COc1ccc(F)c(-c2ccc(C3CCc4ccc(C(C)C(C)C(=O)O)cc4O3)cc2)c1] | 435 |

Example 148

(3R)-3-cyclobutyl-3-((R or S)-(2-(2'-fluoro-5'-methoxy-[1,1'-biphenyl]-4-yl)chroman-7-yl)propanoic acid Step A: methyl 3-cyclobutyl-3-(2-(2'-fluoro-5'-methoxy-[1,1'-biphenyl]-4-yl)chroman-7-yl)propanoate 2-fluoro-5-methoxy-4'-vinyl-1,1'-biphenyl (6.37 g, 27.9 mmol) and methyl 3-cyclobutyl-3-(3-hydroxy-4-(hydroxymethyl)phenyl)propanoate (4.10 g, 15.5 mmol) were mixed together under nitrogen. The reaction mixture was stirred at 160° C. for 0.5 hour, and then cooled to room temperature. Then water (25 mL) was added to the mixture. The aqueous phase was separated and extracted with EtOAc (25 mL×3). The combined organic layers were washed with water (25 mL) and brine (25 mL), dried over anhydrous MgSO$_4$ and filtered. The filtrate was concentrated under reduced pressure. The resulting residue was purified by silica gel chromatography eluted with PE/EtOAc (1:0~20:1, v/v) to give methyl 3-cyclobutyl-3-(2-(2'-fluoro-5'-methoxy-[1,1'-biphenyl]-4-yl)chroman-7-yl)propanoate (E1-9) as a mixture of four diastereomers.

Step B: (3R)-methyl 3-cyclobutyl-3-((R or S)-(2-(2'-fluoro-5'-methoxy-[1,1'-biphenyl]-4-yl)chroman-7-yl)propanoate, (3S)-methyl 3-cyclobutyl-3-((R or S)-(2-(2'-fluoro-5'-methoxy-[1,1'-biphenyl]-4-yl)chroman-7-yl)propanoate, (3S)-methyl 3-cyclobutyl-3-((R or S)-(2-(2'-fluoro-5'-methoxy-[1,1'-biphenyl]-4-yl)chroman-7-yl)propanoate and (3R)-methyl 3-cyclobutyl-3-((R or S)-(2-(2'-fluoro-5'-methoxy-[1,1'-biphenyl]-4-yl)chroman-7-yl)propanoate

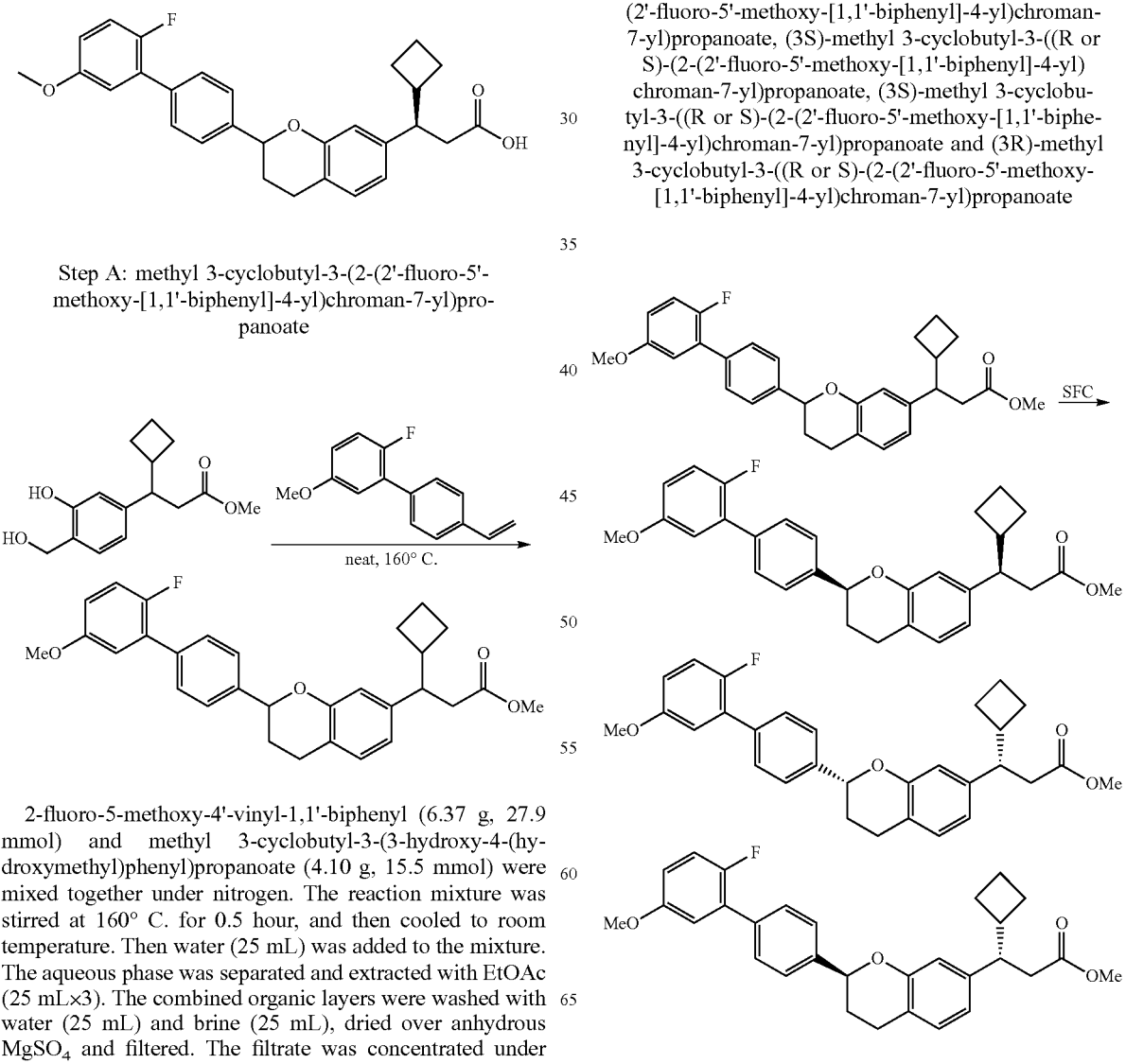

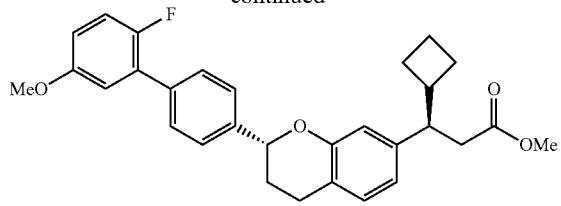

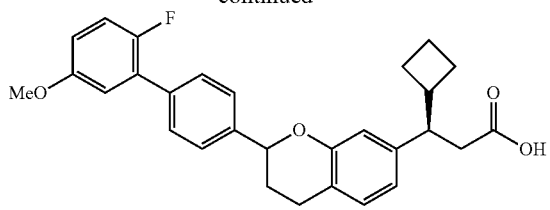

The diastereomeric mixture of methyl 3-cyclobutyl-3-(2-(2'-fluoro-5'-methoxy-[1,1'-biphenyl]-4-yl)chroman-7-yl)propanoate (2.30 g, 4.85 mmol) was separated via SFC using Column: Chiralpak AD-3 50*4.6 mm I.D., 3 um Mobile phase: iso-propanol (0.05% DEA) in $CO_2$ from 5% to 40% Flow rate: 4 mL/min Wavelength: 220 nm) to give two peaks, each a mixture of two diastereomers.

The first peak (950 mg, 2.00 mmol) was separated into its individual diastereomers via a second SFC separation using Column: Chiralpak AD-H 250×4.6 mm I.D., 5um Mobile phase: 40% ethanol (0.05% DEA) in $CO_2$ Flow rate: 2.35 mL/min Wavelength: 220 nm to give (3R)-methyl 3-cyclobutyl-3-((R or S)-(2-(2'-fluoro-5'-methoxy-[1,1'-biphenyl]-4-yl)chroman-7-yl)propanoate; and (3S)-methyl 3-cyclobutyl-3-((R or S)-(2-(2'-fluoro-5'-methoxy-[1,1'-biphenyl]-4-yl)chroman-7-yl)propanoate.

The second peak (1.05 g, 2.21 mmol) was separated into its individual diastereomers via a second SFC separation using Column: Chiralpak AD-H 250×4.6 mm I.D., 5um Mobile phase: 40% ethanol (0.05% DEA) in $CO_2$ Flow rate: 2.35 mL/min Wavelength: 220 nm to give (3S)-methyl 3-cyclobutyl-3-((R or S)-(2-(2'-fluoro-5'-methoxy-[1,1'-biphenyl]-4-yl)chroman-7-yl)propanoate; and (3R)-methyl 3-cyclobutyl-3-((R or S)-(2-(2'-fluoro-5'-methoxy-[1,1'-biphenyl]-4-yl)chroman-7-yl)propanoate.

Step C: (3R)-3-cyclobutyl-3-((R or S)-(2-(2'-fluoro-5'-methoxy-[1,1'-biphenyl]-4-yl)chroman-7-yl)propanoic acid

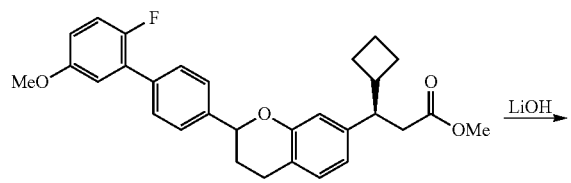

To a solution of (3R)-methyl 3-cyclobutyl-3-((R or S)-(2-(2'-fluoro-5'-methoxy-[1,1'-biphenyl]-4-yl)chroman-7-yl)-propanoate (25.0 mg, 0.0531 mmol) in THF (1.0 mL), MeOH (1.0 mL) and $H_2O$ (1.0 mL) was added LiOH (25.2 mg, 1.05 mmol). The reaction mixture was stirred at room temperature for 12 h. Then aqueous HCl (1.0 M) was added to the solution to adjust the pH to 5. The resulting solution was extracted with EtOAc (5.0 mL×3). The combined organic layers were concentrated under reduced pressure. The resulting residue was purified by preparative HPLC (on a GILSON 281 instrument fitted with Waters XSELECT C18 150*30 mm*5um using water and acetonitrile as the eluents. Mobile phase A: water (containing 0.1% TFA, v/v), mobile phase B: acetonitrile. Gradient: 65-85% B, 0-10 min; 100% B, 10.5-12.5 min; 5% B, 13-15 min) to give (3R)-3-cyclobutyl-3-((R or S)-(2-(2'-fluoro-5'-methoxy-[1,1'-biphenyl]-4-yl)chroman-7-yl)propanoic acid. $^1$H NMR (400 MHz, CDCl$_3$) δ7.57 (d, J=7.6 Hz, 2H), 7.51 (d, J=7.2 Hz, 2H), 7.08 (t, J=9.6 Hz, 1H), 7.05~6.95 (m, 2H), 6.86~6.83 (m, 1H), 6.73~6.70 (m, 2H), 5.08 (d, J=8.8 Hz, 1H), 3.83 (s, 3H), 3.03~2.94 (m, 2H), 2.81~2.77 (m, 1H), 2.63~2.57 (m, 1H), 2.50~2.44 (m, 2H), 2.25~2.10 (m, 3H), 1.80~1.70 (m, 4H), 1.68~1.60 (m, 1H).

Examples 149-151 were prepared in a similar manner to Example 148 using the appropriate intermediates and commercially available materials.

| Example No. | Structure | M.W. | Compound Name | LC/MS (ESI) observed [M + 1]+ |
|---|---|---|---|---|
| 149 | 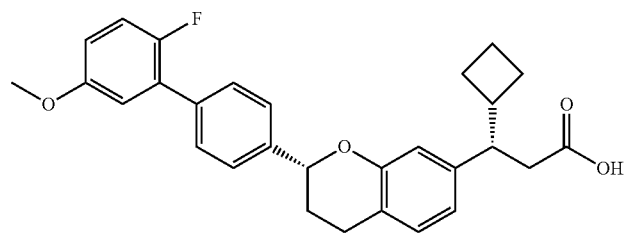 [SMILES: COc1ccc(F)c(-c2ccc([C@H]3CCc4ccc([C@@H](CC(=O)O)C5CCC5)cc4O3)cc2)c1] | 461 | (3S)-3-cyclobutyl-3-((R or S)-(2-(2'-fluoro-5'-methoxy-[1,1'-biphenyl]-4-yl)chroman-7-yl)propanoic acid | 461.1 |

| Example No. | Structure | M.W. | Compound Name | LC/MS (ESI) observed [M + 1]+ |
|---|---|---|---|---|
| 150 | 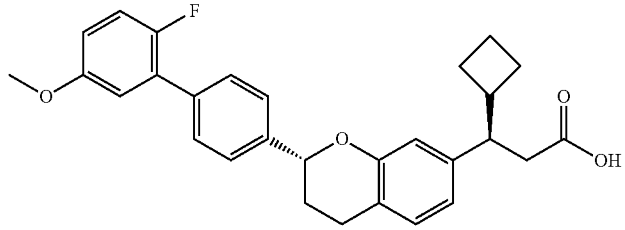 [SMILES: COc1ccc(F)c(-c2ccc([C@H]3CCc4ccc([C@H](CC(=O)O)C5CCC5)cc4O3)cc2)c1] | 461 | (3R)-3-cyclobutyl-3-((R or S)-(2-(2'-fluoro-5'-methoxy-[1,1'-biphenyl]-4-yl)chroman-7-yl)propanoic acid | 461.1 |
| 151 | 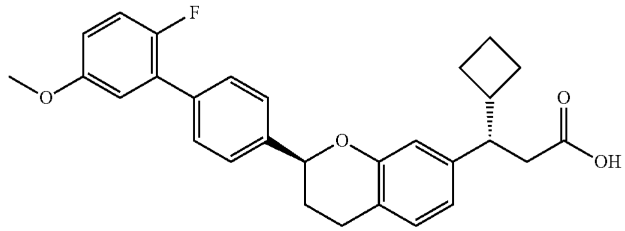 [SMILES: COc1ccc(F)c(-c2ccc([C@@H]3CCc4ccc([C@@H](CC(=O)O)C5CCC5)cc4O3)cc2)c1] | 461 | (3S)-3-cyclobutyl-3-((R or S)-(2-(2'-fluoro-5'-methoxy-[1,1'-biphenyl]-4-yl)chroman-7-yl)propanoic acid | 461.1 |

Example 152

(2S,3S)-3-cyclobutyl-3-((R or S)-2-(2'-fluoro-5'-methoxy-[1,1'-biphenyl]-4-yl)chroman-7-yl)-2-methylpropanoic acid

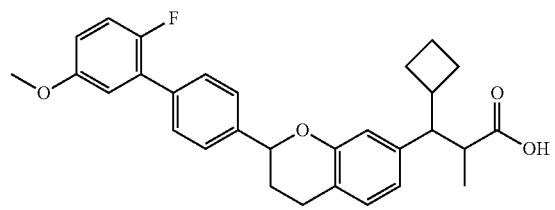 [SMILES: COc1ccc(F)c(-c2ccc(C3CCc4ccc(C(C5CCC5)C(C)C(=O)O)cc4O3)cc2)c1]

Step A: (2R or 2S, 3S)-methyl 3-cyclobutyl-3-((R or S)—((S)-2-(2'-fluoro-5'-methoxy-[1,1'-biphenyl]-4-yl)chroman-7-yl)-2-methylpropanoate To a solution of methyl 3-cyclobutyl-3-(2-(2'-fluoro-5'-methoxy-[1,1'-biphenyl]-4-yl)chroman-7-yl)propanoate (Isomer A) (200 mg, 0.421 mmol) in anhydrous THF (4.0 mL) was added LDA (0.632 mL, 1.26 mmol) dropwise at −78° C. under nitrogen. The mixture was stirred at −78° C. for 30 min, then iodomethane (179 mg, 1.26 mmol) was added dropwise to the mixture. The reaction mixture was stirred at −78 C for 1 h, then quenched with water (5.0 mL). The aqueous phase was separated and extracted with EtOAc (5 mL×3). The combined organic layers were washed with water (5.0 mL) and brine (5.0 mL), dried over anhydrous MgSO$_4$ and filtered. The filtrate was concentrated under reduced pressure. The resulting residue was purified by preparative TLC (PE:EtOAc=5:1, v/v) to give methyl 3-cyclobutyl-3-(2-(2'-fluoro-5'-methoxy-[1,1'-biphenyl]-4-yl)chroman-7-yl)-2-methylpropanoate as a mixture of two diastereomers.

Step B: (2S,3S)-methyl 3-cyclobutyl-3-((R or S)-(2-(2'-fluoro-5'-methoxy-[1,1'-biphenyl]-4-yl)chroman-7-yl)-2-methylpropanoate and (2R,3S)-methyl 3-cyclobutyl-3-((R or S)-(2-(2'-fluoro-5'-methoxy-[1,1'-biphenyl]-4-yl)chroman-7-yl)-2-methylpropanoate

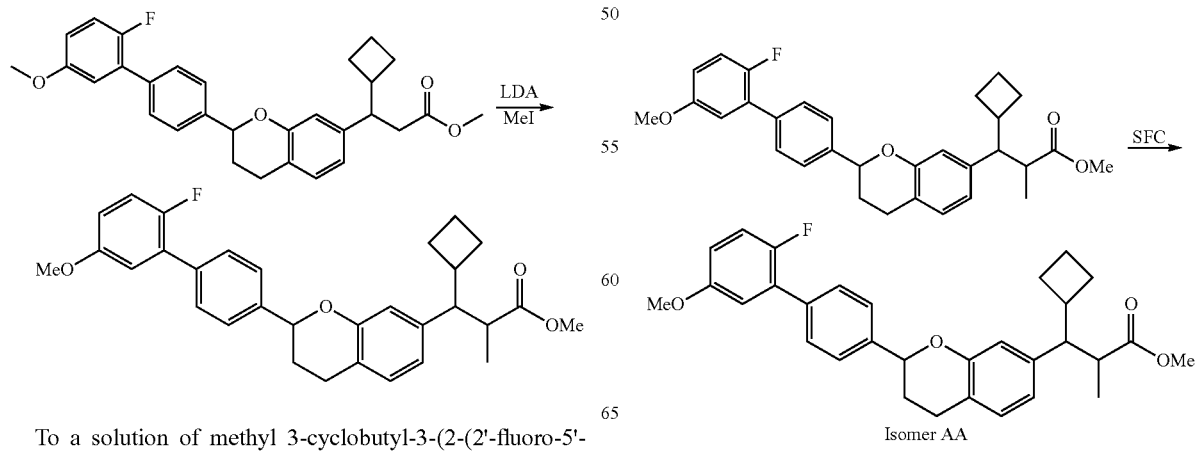

Isomer AA

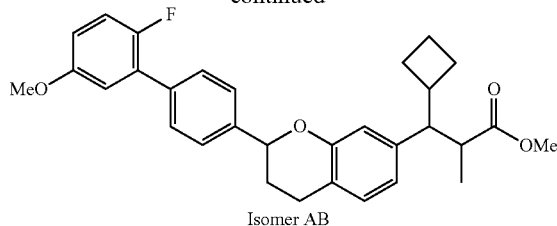

Isomer AB

The product from Step A (165 mg, 0.338 mmol) was separated via SFC using Column: Chiralpak AD-3 150×4.6 mm I.D., 3 um Mobile phase: 40% of methanol (0.05% DEA) in $CO_2$ Flow rate: 2.5 mL/min Wavelength: 254 nm to give methyl 3-cyclobutyl-3-(2-(2'-fluoro-5'-methoxy-[1,1'-biphenyl]-4-yl)chroman-7-yl)-2-methylpropanoate (Isomer AA); and methyl 3-cyclobutyl-3-(2-(2'-fluoro-5'-methoxy-[1,1'-biphenyl]-4-yl)chroman-7-yl)-2-methylpropanoate (Isomer AB).

Step C: (2S,3S)-3-cyclobutyl-3-((R or S)-2-(2'-fluoro-5'-methoxy-[1,1'-biphenyl]-4-yl)chroman-7-yl)-2-methylpropanoic acid

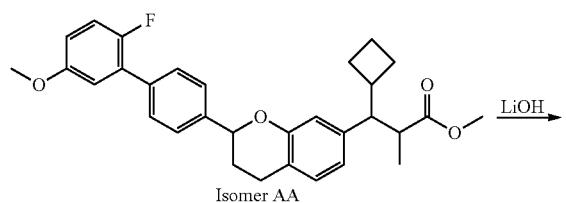

Isomer AA → LiOH

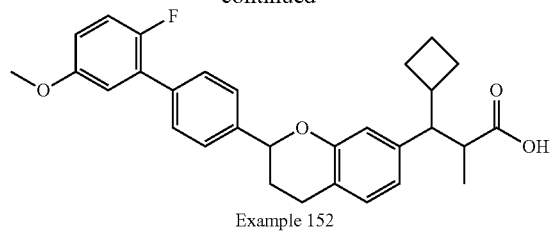

Example 152

To a solution of methyl 3-cyclobutyl-3-(2-(2'-fluoro-5'-methoxy-[1,1'-biphenyl]-4-yl)chroman-7-yl)-2-methylpropanoate (Isomer AA) (83.0 mg, 0.170 mmol) in THF (1.0 mL), MeOH (1.0 mL) and $H_2O$ (1.0 mL) was added LiOH (143 mg, 3.40 mmol). The reaction mixture was stirred at 50° C. for 12 h. Then aqueous HCl (1.0 M) was added to the solution to adjust the pH to 5. The solution was extracted with EtOAc (5 mL×3). The combined organic layers were concentrated under reduced pressure. The resulting residue was purified by preparative HPLC (on a GILSON 281 instrument fitted with Phenomenex Synergi C18 100*21.2 mm*4 um using water and acetonitrile as the eluents. Mobile phase A: water (containing 0.1% TFA, v/v), mobile phase B: acetonitrile. Gradient: 72-92% B, 0-10 min; 100% B, 10.5-12.5 min; 5% B, 13-15 min) to give Example 152. $^1$H NMR (400 MHz, $CDCl_3$) δ7.58 (d, J=7.6 Hz, 2H), 7.50 (d, J=8.4 Hz, 2H), 7.08 (t, J=9.6 Hz, 1H), 6.99~6.95 (m, 2H), 6.86~6.83 (m, 1H), 6.71~6.66 (m, 2H), 5.08 (d, J=8.4 Hz, 1H), 3.84 (s, 3H), 3.02~2.70 (m, 5H), 2.25~2.09 (m, 3H), 1.85~1.68 (m, 4H), 1.53~1.52 (m, 1H), 1.13 (d, J=7.2 Hz, 3H).

Examples 153-159 were prepared in a similar manner to Example 152 using the appropriate intermediates and commercially available starting materials.

| Ex. No. | Starting material from Example 148, Step B | Methylated Isomer | Structure | LC/MS (ESI) observed [M + 1]+ |
|---|---|---|---|---|
| 153 | methyl 3-cyclobutyl-3-(2-(2'-fluoro-5'-methoxy-[1,1'-biphenyl]-4-yl)chroman-7-yl)propanoate (Isomer A) | methyl 3-cyclobutyl-3-(2-(2'-fluoro-5'-methoxy-[1,1'-biphenyl]-4-yl)chroman-7-yl)-2-methylpropanoate (Isomer AB) | 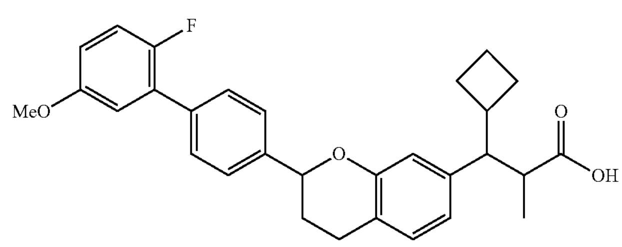 [SMILES: COc1ccc(F)c(-c2ccc(C3CCc4ccc(C(C5CCC5)C(C)C(=O)O)cc4O3)cc2)c1] | 475.1 |
| 154 | methyl 3-cyclobutyl-3-(2-(2'-fluoro-5'-methoxy-[1,1'-biphenyl]-4-yl)chroman-7-yl)propanoate (Isomer B) | methyl 3-cyclobutyl-3-(2-(2'-fluoro-5'-methoxy-[1,1'-biphenyl]-4-yl)chroman-7-yl)-2-methylpropanoate (Isomer BA, Faster eluting isomer) | 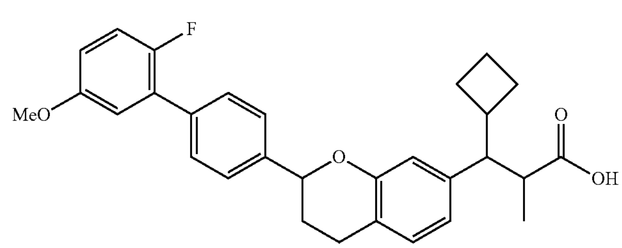 [SMILES: COc1ccc(F)c(-c2ccc(C3CCc4ccc(C(C5CCC5)C(C)C(=O)O)cc4O3)cc2)c1] | 475.1 |

-continued

| Ex. No. | Starting material from Example 148, Step B | Methylated Isomer | Structure | LC/MS (ESI) observed [M + 1]+ |
|---|---|---|---|---|
| 155 | methyl 3-cyclobutyl-3-(2-(2'-fluoro-5'-methoxy-[1,1'-biphenyl]-4-yl)chroman-7-yl)propanoate (Isomer B) | methyl 3-cyclobutyl-3-(2-(2'-fluoro-5'-methoxy-[1,1'-biphenyl]-4-yl)chroman-7-yl)-2-methyl-propanoate (Isomer BB, slower eluting isomer) | 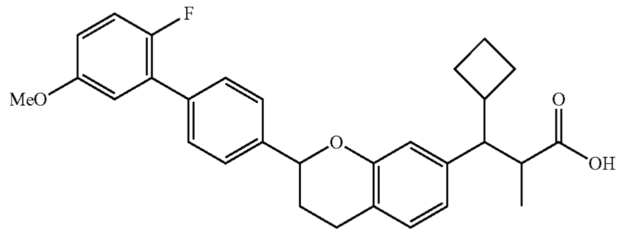 [SMILES: COc1ccc(F)c(-c2ccc(C3CCc4ccc(C(C5CCC5)C(C)C(=O)O)cc4O3)cc2)c1] | 475.1 |
| 156 | methyl 3-cyclobutyl-3-(2-(2'-fluoro-5'-methoxy-[1,1'-biphenyl]-4-yl)chroman-7-yl)propanoate (Isomer C) | methyl 3-cyclobutyl-3-(2-(2'-fluoro-5'-methoxy-[1,1'-biphenyl]-4-yl)chroman-7-yl)-2-methyl-propanoate (Isomer CA, faster eluting isomer) | 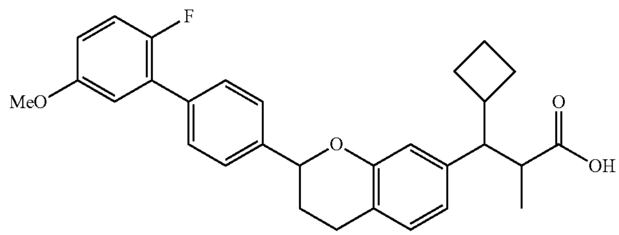 [SMILES: COc1ccc(F)c(-c2ccc(C3CCc4ccc(C(C5CCC5)C(C)C(=O)O)cc4O3)cc2)c1] | 475.1 |
| 157 | methyl 3-cyclobutyl-3-(2-(2'-fluoro-5'-methoxy-[1,1'-biphenyl]-4-yl)chroman-7-yl)propanoate (Isomer C) | methyl 3-cyclobutyl-3-(2-(2'-fluoro-5'-methoxy-[1,1'-biphenyl]-4-yl)chroman-7-yl)-2-methyl-propanoate (Isomer CB, slower eltuing isomer) | 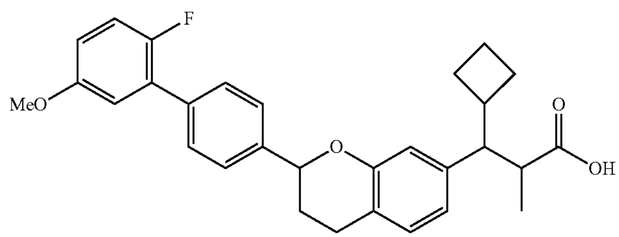 [SMILES: COc1ccc(F)c(-c2ccc(C3CCc4ccc(C(C5CCC5)C(C)C(=O)O)cc4O3)cc2)c1] | 475.1 |
| 158 | methyl 3-cyclobutyl-3-(2-(2'-fluoro-5'-methoxy-[1,1'-biphenyl]-4-yl)chroman-7-yl)propanoate (Isomer D) | methyl 3-cyclobutyl-3-(2-(2'-fluoro-5'-methoxy-[1,1'-biphenyl]-4-yl)chroman-7-yl)-2-methyl-propanoate (Isomer DA, faster eluting isomer) | 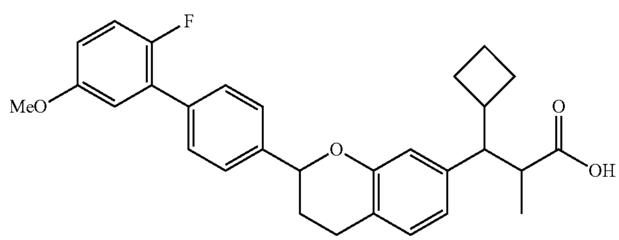 [SMILES: COc1ccc(F)c(-c2ccc(C3CCc4ccc(C(C5CCC5)C(C)C(=O)O)cc4O3)cc2)c1] | 475.1 |
| 159 | methyl 3-cyclobutyl-3-(2-(2'-fluoro-5'-methoxy-[1,1'-biphenyl]-4-yl)chroman-7-yl)propanoate (Isomer D) | methyl 3-cyclobutyl-3-(2-(2'-fluoro-5'-methoxy-[1,1'-biphenyl]-4-yl)chroman-7-yl)-2-methylpropanoate (Isomer DB, slower eluting isomer) | 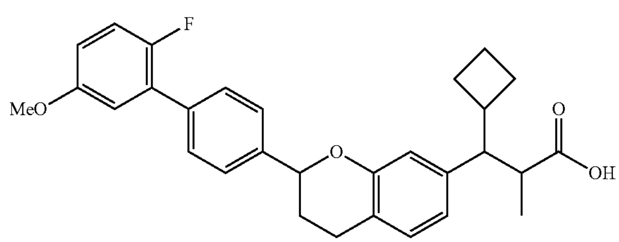 [SMILES: COc1ccc(F)c(-c2ccc(C3CCc4ccc(C(C5CCC5)C(C)C(=O)O)cc4O3)cc2)c1] | 475.1 |

Scheme 14 Method A

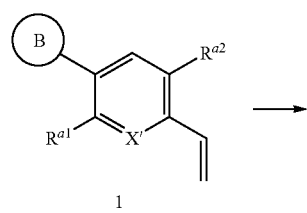

1

-continued

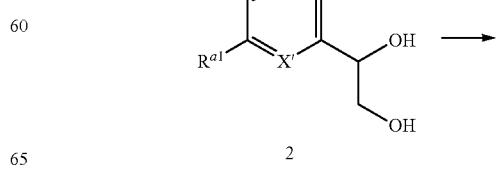

2

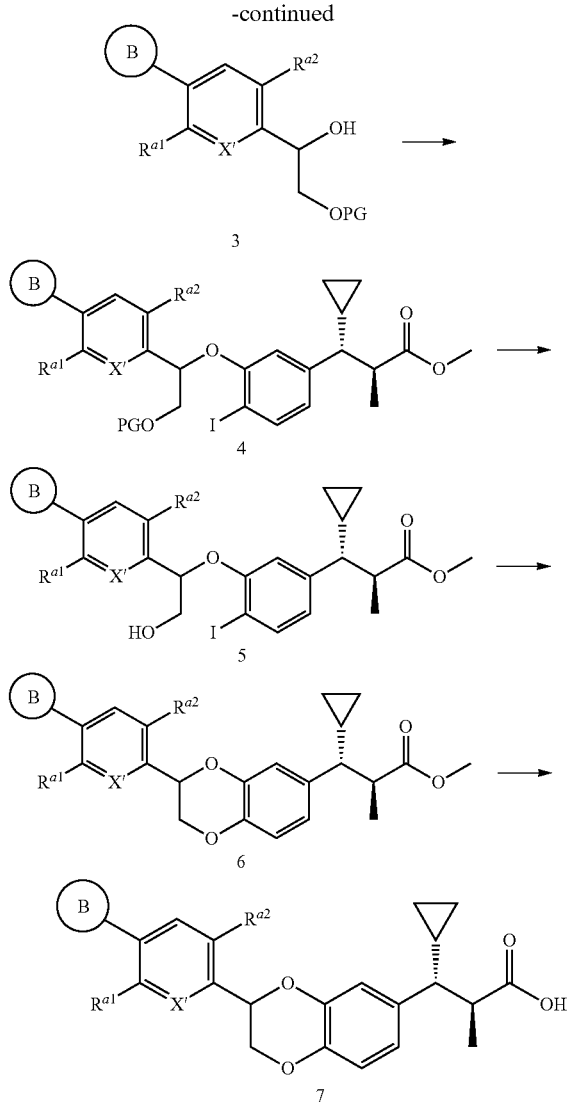

Dioxanes may be prepared as shown in Scheme 14 using Method A. A styrene such as compound 1 can be dihydroxylated using standard dihydroxylation procedures to give compound 2. Subsequent monoprotection of one alcohol provides compound 3, and followed by a Mitsonobu coupling to a phenol gives compound 4. The protecting group PG is removed through standard methods to give compound 5, and a Pd mediated C—O coupling is performed to provide compound 6. Hydrolysis of compound 6 is achieved using LiOH to obtain compound 7.

Examples 160 and 161

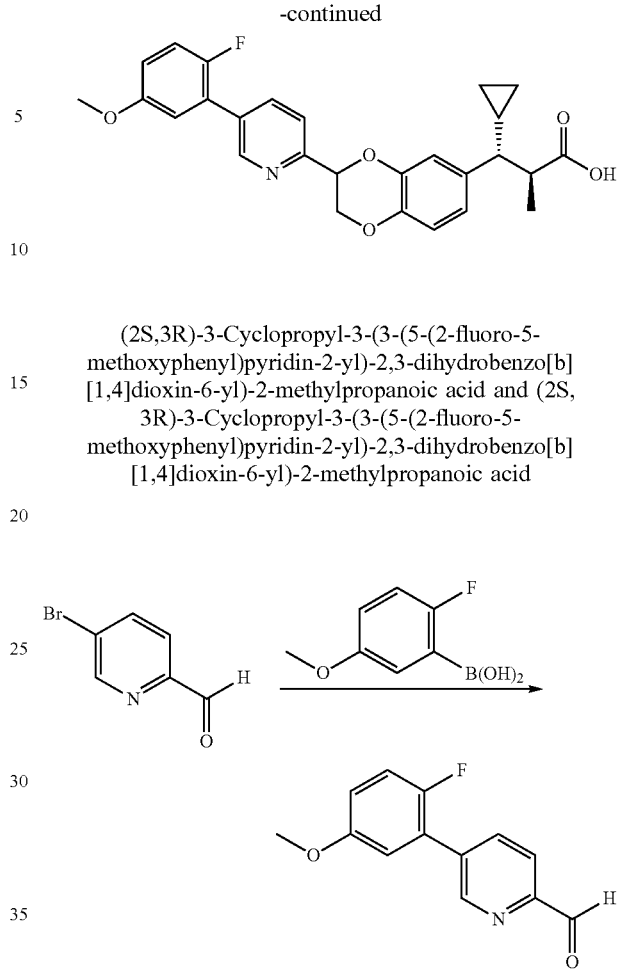

(2S,3R)-3-Cyclopropyl-3-(3-(5-(2-fluoro-5-methoxyphenyl)pyridin-2-yl)-2,3-dihydrobenzo[b][1,4]dioxin-6-yl)-2-methylpropanoic acid and (2S, 3R)-3-Cyclopropyl-3-(3-(5-(2-fluoro-5-methoxyphenyl)pyridin-2-yl)-2,3-dihydrobenzo[b][1,4]dioxin-6-yl)-2-methylpropanoic acid Step A: To a solution of 5-bromopicolinaldehyde (9.9 g, 53.2 mmol), 2-fluoro-5-methoxyphenylboronic acid (11 g, 64.7 mmol), and Pd(PPh$_3$)$_4$ (3.08 g, 2.66 mmol) in 1,4-Dioxane (100 mL) was added 3M aqueous K$_2$CO$_3$ (35.5 ml, 106 mmol). The solution was sparged with a stream of N$_2$ for 15 minutes, then sealed and heated to 100° C. under N$_2$ for 2 h. The mixture was then cooled and allowed to stir at ambient temperature overnight. Then the reaction was diluted with EtOAc, washed with aqueous saturated NH$_4$Cl solution (2×), and brine (1×). The organic layer was separated, dried over MgSO$_4$, filtered, and concentrated in vacuo. The resulting residue was purified by silica gel column chromatography (ISCO system, RediSep 220 g column) using a gradient of 0-100% EtOAc/Hexanes as eluent to provide 5-(2-fluoro-5-methoxyphenyl)picolinaldehyde. LC/MS: m/z=232.17 [M+1].

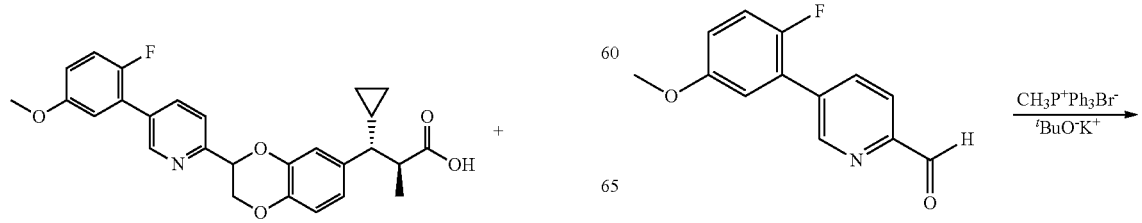

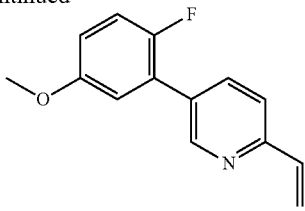

Step B: To a solution of methyltriphenylphosphonium bromide (18.73 g, 52.4 mmol) in THF (150 mL) at 0° C. was added 1M potassium tert-butoxide in THF (52.4 mL, 52.4 mmol). After stirring at 0° C. for 35 minutes, 5-(2-fluoro-5-methoxyphenyl)-picolinaldehyde (9.7 g, 42.0 mmol) in THF (160 mL) was added from an addition funnel over a period of 30 minutes. The reaction mixture stirred at ambient temperature for 45 minutes, then poured into aqueous saturated NH$_4$Cl solution and extracted with EtOAc. The combined organic extracts were washed with brine, dried over MgSO$_4$, filtered, and concentrated in vacuo. The resulting residue was purified by silica gel column chromatography (ISCO system, RediSep 220 g column) using a gradient of 0-70% EtOAc/Hexanes as eluent to provide 5-(2-fluoro-5-methoxyphenyl)-2-vinylpyridine. LC/MS: m/z=230.20 [M+1].

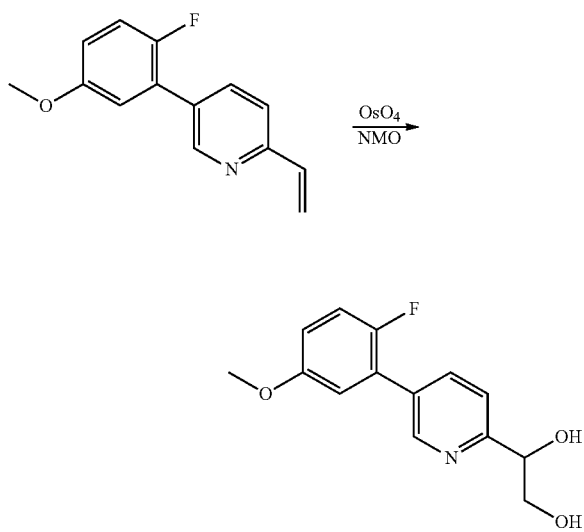

Step C: To a solution of the 5-(2-fluoro-5-methoxyphenyl)-2-vinylpyridine (4.65 g, 20.28 mmol) in acetonitrile (80 mL) and Water (8.00 mL) was added NMO (2.85 g, 24.34 mmol) in several portions. Then OsO$_4$ (82 mg, 0.323 mmol) was added and the reaction mixture was stirred at ambient temperature overnight. An additional amount of NMO (713 mg, 6.09 mmol) and OsO$_4$ (110 mg, 0.43 mmol) were added and the reaction was stirred for 24 h. Then the reaction mixture was concentrated in vacuo, diluted with H$_2$O, and extracted with EtOAc. The combined organic extracts were washed with brine, dried over MgSO$_4$, filtered, and concentrated in vacuo onto silica gel. The crude product was purified via silica gel column chromatography (ISCO system, RediSep 120 g column) using a gradient of 0-100% EtOAc to give 1-(5-(2-fluoro-5-methoxy-phenyl)pyridin-2-yl)ethane-1,2-diol. LC/MS: m/z=264.16 [M+1].

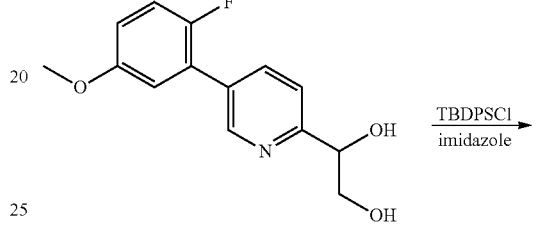

Step D: To a solution of 1-(5-(2-fluoro-5-methoxyphenyl)pyridin-2-yl)ethane-1,2-diol (1.31 g, 4.98 mmol) in CH$_2$Cl$_2$ (24.88 mL) was added imidazole (0.610 g, 8.96 mmol) and tert-butylchlorodiphenylsilane (1.4 mL, 5.5 mmol). The reaction was stirred at ambient temperature for 3.5 h. The resulting precipitate was removed by filtration and the filtrate concentrated in vacuo to give a residue. The resulting residue was purified by silica gel column chromatography (ISCO system, RediSep 80 g column) using a gradient of 0-70% EtOAc/Hexanes as eluent to give 2-((tert-butyldiphenylsilyl)oxy)-1-(5-(2-fluoro-5-methoxyphenyl)pyridin-2-yl)ethanol. LC/MS: m/z=502.40 [M+1].

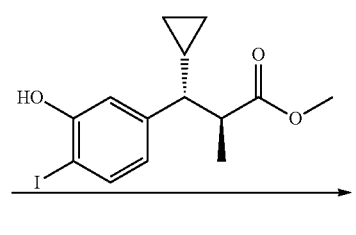

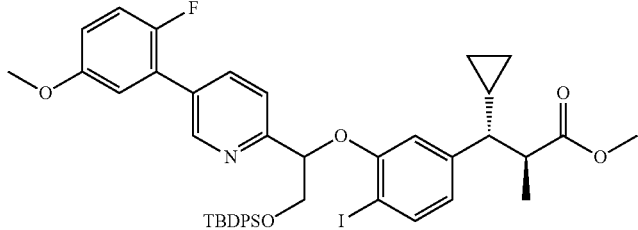

Step E: To a solution of the 2-((tert-butyldiphenylsilyl)oxy)-1-(5-(2-fluoro-5-methoxyphenyl)pyridin-2-yl)ethanol (2.4 g, 4.75 mmol) in THF (24 mL) was added (2S,3R)-methyl 3-cyclopropyl-3-(3-hydroxy-4-iodophenyl)-2-methylpropanoate (1.967 g, 5.46 mmol) and tri-n-butylphosphine (2.3 mL, 9.50 mmol). After stirring for 5 min, 1,1'-(azodicarbonyl)dipiperidine (2.4 g, 9.50 mmol) was added in small portions. Additional THF (12 mL) was added, and the reaction mixture was stirred at ambient temperature for 42 h. Then hexanes (40 mL) was added and the resulting precipitate was removed by filtration. The filtrate was concentrated in vacuo and the resulting residue was purified by silical gel column chromatography (ISCO system, RediSep 80 g column, 0-40% EtOAc: hexanes) to give (2S,3R)-methyl 3-(3-(2-((tert-butyldiphenylsilyl)oxy)-1-(5-(2-fluoro-5-methoxyphenyl)pyridin-2-yl)ethoxy)-4-iodophenyl)-3-cyclopropyl-2-methylpropanoate. LC/MS: m/z=844.49 [M+1].

Step F: To (2S,3R)-methyl 3-(3-(2-((tert-butyldiphenylsilyl)oxy)-1-(5-(2-fluoro-5-methoxyphenyl)pyridin-2-yl)ethoxy)-4-iodophenyl)-3-cyclopropyl-2-methylpropanoate (2.89 g, 3.42 mmol) in THF (49 mL) was added TBAF (5.1 mL, 5.1 mmol, 1 M in THF) and the reaction was stirred at ambient temperature for 45 minutes. Then the reaction was quenched with saturated aqueous NH$_4$Cl, diluted with water, and extracted with EtOAc. The combined organic extracts were washed with brine, dried over MgSO$_4$, filtered, and concentrated in vacuo. The resulting residue was purified by silica gel column chromatography (ISCO system, RediSep 80 g column, 0-50% EtOAc: hexanes) to give (2S,3R)-methyl 3-cyclopropyl-3-(3-(1-(5-(2-fluoro-5-methoxyphenyl)pyridin-2-yl)-2-hydroxyethoxy)-4-iodophenyl)-2-methylpropanoate. LC/MS: m/z=606.36 [M+1].

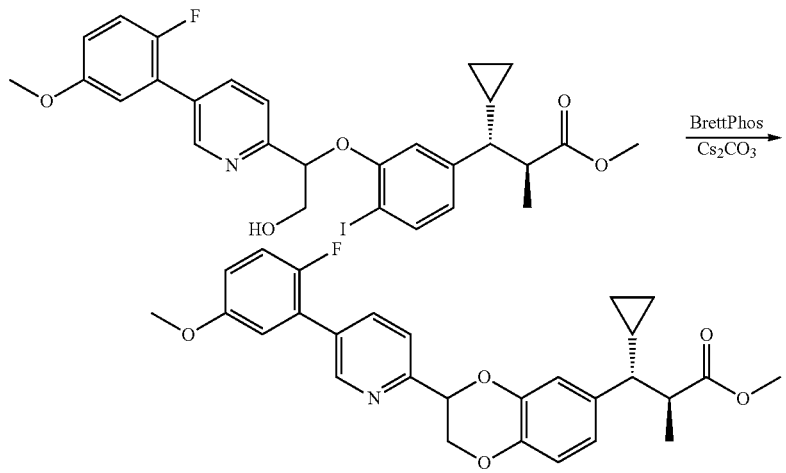

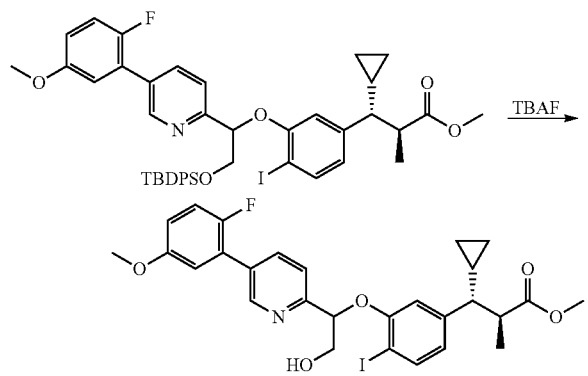

Step G: (2S,3R)-methyl 3-cyclopropyl-3-(3-(1-(5-(2-fluoro-5-methoxyphenyl)pyridin-2-yl)-2-hydroxyethoxy)-4-iodophenyl)-2-methylpropanoate (600 mg, 0.991 mmol), BrettPhos palladacycle (79 mg, 0.099 mmol), and Cs$_2$CO$_3$ (646 mg, 1.982 mmol) were suspended in 1,4-dioxane (41 mL). A stream of N$_2$ gas was bubbled through a septum into the solution for 15 minutes and the resultant mixture heated at 100° C. for 14 h. Then the reaction was cooled, diluted with EtOAc, and washed with H$_2$O, and brine (2×). The combined organic extracts were dried over MgSO$_4$, filtered, concentrated in vacuo. The resulting residue was purified by silica gel column chromatography (ISCO system, RediSep 40 g column, 0-50% EtOAc:hexanes) to give (2S,3R)-methyl 3-cyclopropyl-3-(3-(5-(2-fluoro-5-methoxyphenyl)pyridin-2-yl)-2,3-dihydrobenzo[b][1,4]dioxin-6-yl)-2-methylpropanoate. LC/MS: m/z=478.39 [M+1].

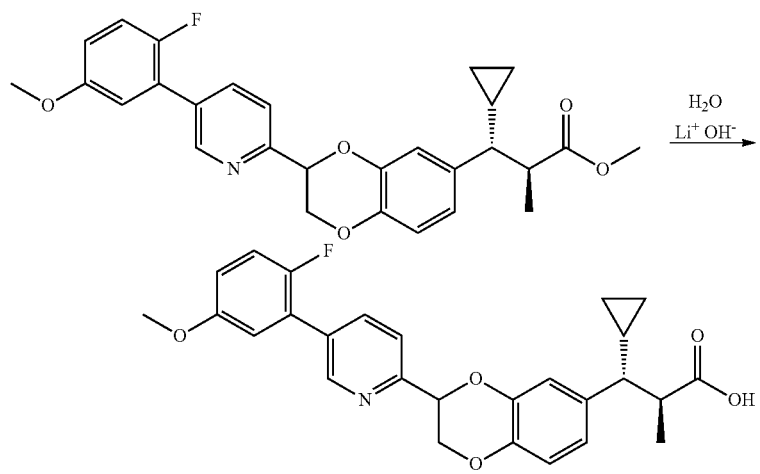

Step H: (2S,3R)-methyl 3-cyclopropyl-3-(3-(5-(2-fluoro-5-methoxyphenyl)pyridin-2-yl)-2,3-dihydrobenzo[b][1,4]dioxin-6-yl)-2-methylpropanoate (511 mg, 1.070 mmol) was suspended in THF (5 mL), MeOH (5 mL), and H$_2$O (5 mL). Then THF was added until complete dissolution of solids was achieved. LiOH (449 mg, 10.70 mmol) was added and the reaction mixture was heated at 65° C. for 10 h. After cooling to ambient temperature, the reaction mixture was acidified to pH 2 with 2 N HCl, then diluted with H$_2$O, and extracted with EtOAc. The organic extracts were washed with brine (3×), dried over MgSO$_4$, filtered, and concentrated in vacuo to give (2S,3R)-3-cyclopropyl-3-(3-(5-(2-fluoro-5-methoxyphenyl)pyridin-2-yl)-2,3-dihydrobenzo[b][1,4]dioxin-6-yl)-2-methylpropanoic acid as a mixture of stereoisomers. LC/MS: m/z=464.39 [M+1].

Step I: (2S,3R)-3-cyclopropyl-3-(3-(5-(2-fluoro-5-methoxyphenyl)pyridin-2-yl)-2,3-dihydrobenzo[b][1,4]dioxin-6-yl)-2-methylpropanoic acid and (2S,3R)-3-cyclopropyl-3-(3-(5-(2-fluoro-5-methoxyphenyl)pyridin-2-yl)-2,3-dihydro-benzo[b][1,4]dioxin-6-yl)-2-methylpropanoic acid The stereoisomeric mixture of (2S,3R)-3-cyclopropyl-3-(3-(5-(2-fluoro-5-methoxyphenyl)pyridin-2-yl)-2,3-dihydrobenzo[b][1,4]dioxin-6-yl)-2-methylpropanoic acid was separated by Chiral SFC (OJ column, 21×250 mm, 15% EtOH/CO$_2$, 60 mL/min, 35° C., 100 bar, 254 nM, 39 mg/mL in DCM/EtOH) to afford the following two stereoisomers:

Stereoisomer 1: (Peak 1, Faster-eluting isomer) $^1$H NMR δ (ppm)(CDCl$_3$): 0.08-0.05 (1H, m), 0.42-0.37 (2H, m), 0.67-0.63 (1H, m), 1.03 (3H, d, J=6.86 Hz), 1.13-1.11 (1H, m), 1.96 (1H, t, J=9.85 Hz), 2.86-2.80 (1H, m), 3.84 (3H, s), 4.24 (1H, dd, J=11.33, 7.91 Hz), 4.66 (1H, dd, J=11.34, 2.54 Hz), 5.37 (1H, d, J=7.75 Hz), 6.71 (1H, dd, J=8.28, 2.05 Hz), 6.96-6.88 (4H, m), 7.12 (1H, t, J=9.38 Hz), 7.66 (1H, d, J=8.15 Hz), 7.96 (1H, d, J=8.19 Hz), 8.79 (1H, s).

Stereoisomer 2: (Peak 2, Slower-eluting isomer)$^1$H NMR δ (ppm)(CDCl$_3$): 0.08-0.05 (1H, m), 0.41-0.36 (2H, m), 0.66-0.62 (1H, m), 1.03 (3H, d, J=6.87 Hz), 1.13-1.09 (1H, m), 1.96 (1H, t, J=9.85 Hz), 2.85-2.79 (1H, m), 3.83 (3H, s), 4.23 (1H, dd, J=11.33, 7.91 Hz), 4.65 (1H, dd, J=11.34, 2.55 Hz), 5.36 (1H, d, J=7.77 Hz), 6.70 (1H, dd, J=8.30, 2.05 Hz), 6.95-6.87 (4H, m), 7.12 (1H, t, J=9.38 Hz), 7.65 (1H, d, J=8.15 Hz), 7.95 (1H, d, J=8.20 Hz), 8.79 (1H, s).

Scheme 15 Method B

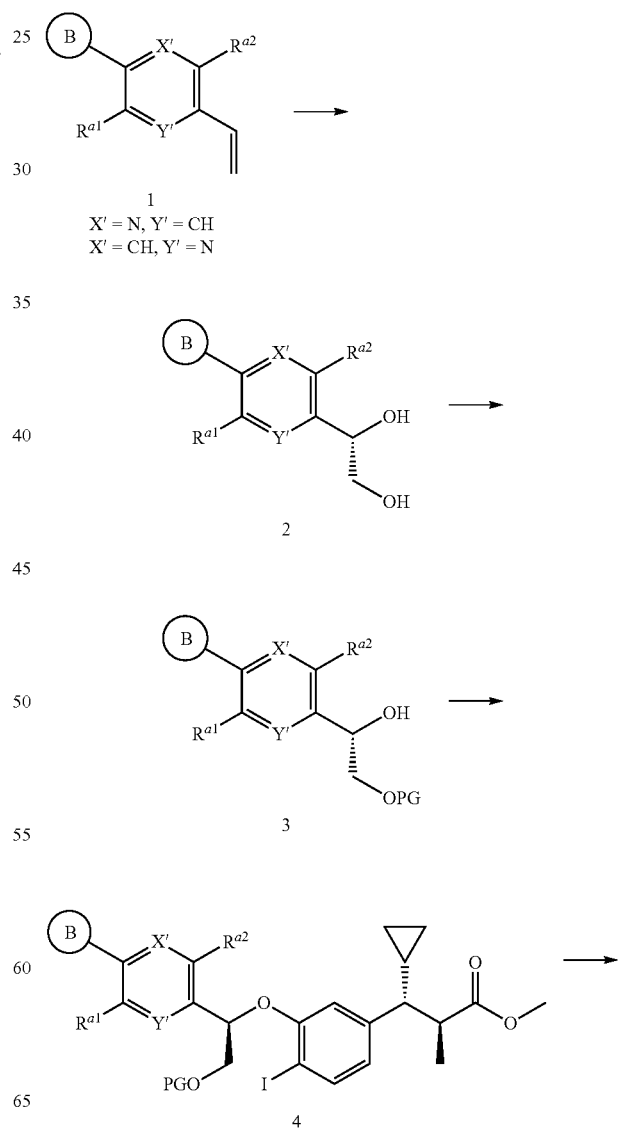

1
X' = N, Y' = CH
X' = CH, Y' = N

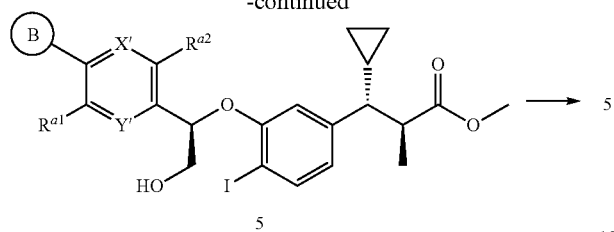

5

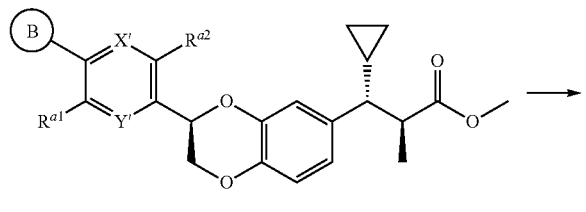

6

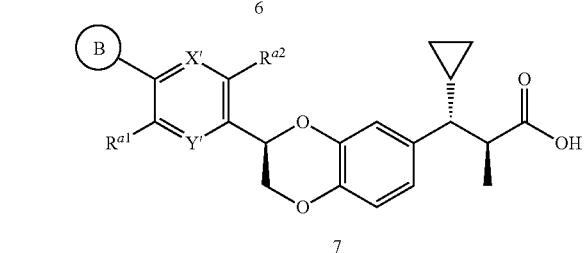

7

Dioxanes, such as Example 162, may be synthesized according to the procedure in Scheme 15, Method B. A styrene such as compound 1 may be dihydroxylated using standard asymmetric dihydroxylation procedures, such as treatment with AD-Mix. Subsequent monoprotection and Mitsonobu coupling to a phenol provides compound 4. The protecting group is removed through standard methods and a Pd mediated C-O coupling using a Pd precatalyst provides dioxane 6. Hydrolysis of the methyl ester of 6 with LiOH provides acid 7.

Example 162

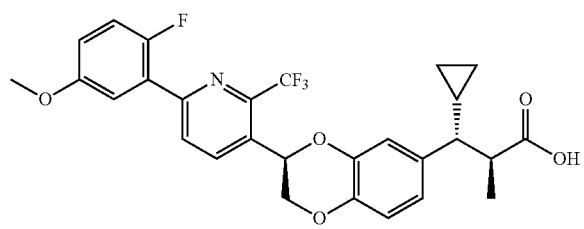 [SMILES: COc1ccc(F)c(-c2ccc([C@@H]3COc4ccc([C@H](C5CC5)[C@H](C)C(=O)O)cc4O3)c(C(F)(F)F)n2)c1]

(2S,3R)-3-cyclopropyl-3-((R)-3-(6-(2-fluoro-5-methoxyphenyl)-2-(trifluoromethyl)-pyridin-3-yl)-2,3-dihydrobenzo[b][1,4]dioxin-6-yl)-2-methylpropanoic acid

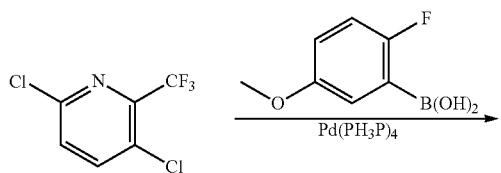

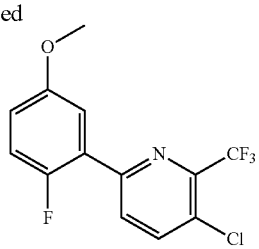

Step A: A mixture of 3,6-dichloro-2-(trifluoromethyl) pyridine (1.01 g, 4.68 mmol), (2-fluoro-5-methoxyphenyl) boronic acid (1.192 g, 7.01 mmol), and Pd(PPh$_3$)$_4$ (0.270 g, 0.234 mmol) was suspended in dioxane (9 mL) and 3M aqueous K$_2$CO$_3$ (3.12 mL, 9.35 mmol). A stream of N$_2$ was bubbled into the solution through a septum for 10 minutes, then the reaction mixture was sealed and heated at 100° C. for 1.5 h. The reaction was then cooled, poured into saturated aqueous NH$_4$Cl solution and extracted with EtOAc. The combined organic extracts were washed with H$_2$O (1×), and brine (1×), dried over MgSO$_4$, filtered, and concentrated in vacuo. The resulting residue was purified by silica gel column chromatography (ISCO system, RediSep 40 g column) using a gradient of 0-15% EtOAc/Hexanes as eluent to give 3-chloro-6-(2-fluoro-5-methoxyphenyl)-2-(trifluoromethyl)pyridine. LC/MS: m/z=306.15 [M+1].

Step B: To a solution of 3-chloro-6-(2-fluoro-5-methoxyphenyl)-2-(trifluoromethyl)-pyridine (1.21 g, 3.96 mmol) potassium vinyltrifluoroborate (0.795 g, 5.94 mmol), and S-Phos Second Generation Precatalyst (0.143 g, 0.198 mmol) in acetonitrile (30 mL) and water (7.5 mL) was added potassium phosphate tribasic (2.52 g, 11.88 mmol). The mixture was sparged with a stream of N$_2$ for 10 minutes, then heated at 75° C. for 5 h. Additional potassium vinyltrifluoroborate (400 mg, 2.99 mmol) and S-Phos Second Generation Precatalyst (80 mg, 0.11 mmol) were added, and the reaction mixture was sparged with N$_2$ for an additional 15 minutes, then heated at 75° C. for 5 h. The reaction mixture was then cooled, poured into saturated aqueous NH$_4$Cl solution and extracted with EtOAc. The combined organic extracts were washed with brine (1×), dried over MgSO$_4$, filtered, and concentrated in vacuo. The resulting residue was purified by silica gel column chromatography (ISCO system, RediSep 80 g column) using a gradient of 0-15% EtOAc/Hexanes as eluent to give 6-(2-fluoro-5-methoxyphenyl)-2-(trifluoromethyl)-3-vinylpyridine. LC/MS: m/z=298.17 [M+1].

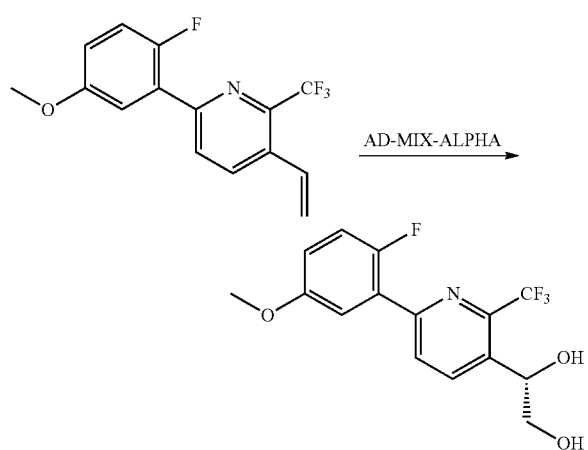

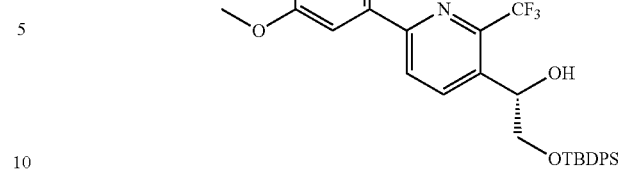

Step C: To 6-(2-fluoro-5-methoxyphenyl)-2-(trifluoromethyl)-3-vinylpyridine (1 g, 3.36 mmol) was suspended in t-BuOH (17.00 mL) and H₂O (17.00 mL). Then THF (4 mL) was added until complete dissolution of solids was achieved. AD-MIX-ALPHA (4.7 g, 3.36 mmol, Sigma Aldrich) was Step D: To (S)-1-(6-(2-fluoro-5-methoxyphenyl)-2-(trifluoromethyl)pyridin-3-yl)ethane-1,2-diol (1.21 g, 3.65 mmol) in CH₂Cl₂ (18 mL) were added imidazole (0.448 g, 6.57 mmol) and tert-butylchlorodiphenylsilane (1.0 mL, 4.0 mmol). After stirring at ambient temperature for 20 minutes, the resulting precipitate was removed by filtration and the filtrate concentrated in vacuo to give a residue. The residue was purified by silica gel column chromatography (ISCO system, RediSep 80 g column) using a gradient of 0-40% EtOAC/Hexanes as eluent to provide (S)-2-((tert-butyldiphenylsilyl)oxy)-1-(6-(2-fluoro-5-methoxyphenyl)-2-(trifluoromethyl)pyridin-3-yl)ethanol. LC/MS: m/z=570.45 [M+1].

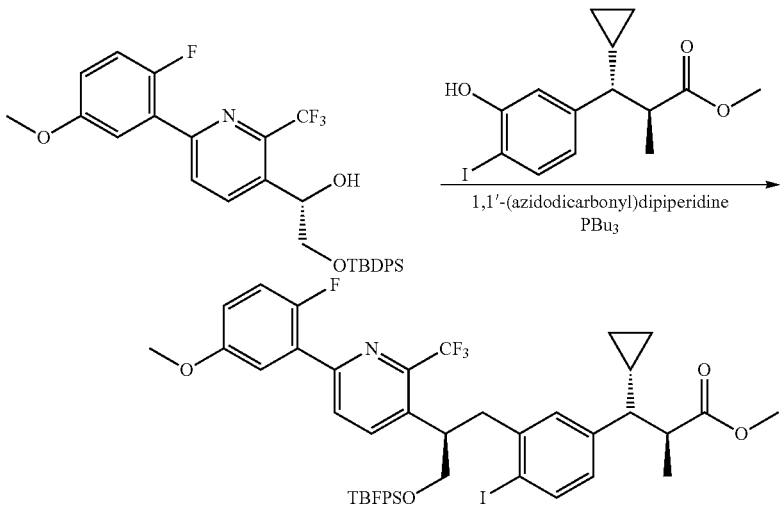

added to the reaction in several portions, and the reaction mixture was stirred at ambient temperature for 20 h. Then the reaction was diluted with H₂O, and extracted with EtOAc. The combined organic extracts washed with brine (1×), dried over MgSO₄, filtered, and concentrated in vacuo. The resulting residue was purified by silica gel column chromatography (ISCO system, RediSep 40 g column) using a gradient of 0-100% EtOAc/Hexanes to give (S)-1-(6-(2-fluoro-5-methoxyphenyl)-2-(trifluoro-methyl)pyridin-3-yl)ethane-1,2-diol. LC/MS: m/z=332.19 [M+1].

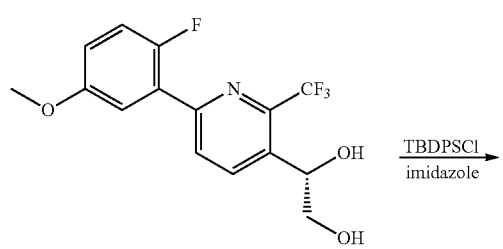

Step E: A solution of (S)-2-((tert-butyldiphenylsilyl)oxy)-1-(6-(2-fluoro-5-methoxyphenyl)-2-(trifluoromethyl)pyridin-3-yl)ethanol (464 mg, 0.815 mmol) and (2S,3R)-methyl 3-cyclopropyl-3-(3-hydroxy-4-iodophenyl)-2-methylpropanoate (323 mg, 0.896 mmol) in THF (5 mL) was treated with Bu₃P (0.402 mL, 1.629 mmol). After stirring for 5 minutes 1,1'-(azodicarbonyl)dipiperidine (411 mg, 1.629 mmol) was added, and the reaction was stirred at ambient temperature for 48 h. Additional (2S,3R)-methyl 3-cyclopropyl-3-(3-hydroxy-4-iodophenyl)-2-methylpropanoate (88 mg, 0.24 mmol) was added and the reaction was stirred for 24 h. Then the reaction mixture was concentrated in vacuo to give a residue. The residue was suspended in hexanes, and the resulting precipitate was removed by filtration. The filtrate was concentrated in vacuo and the resulting residue was purified by silica gel column chromatography (ISCO system RediSep 40 g column) using a gradient of 0-45% EtOAc/Hexanes as eluent to give (2S, 3R)-methyl 3-(3-((R)-2-((tert-butyldiphenylsilyl)oxy)-1-(6-(2-fluoro-5-methoxyphenyl)-2-(trifluoromethyl)pyridin-3- yl)ethoxy)-4-iodophenyl)-3-cyclopropyl-2-methylpropanoate. $^1$H NMR δ (ppm)(CHCl$_3$-d): 8.85 (1H, d, J=8.36 Hz), 8.26 (1H, d, J=8.37 Hz), 8.08 (1H, d, J=8.34 Hz), 7.74-7.55 (7H, m), 7.46-7.24 (5H, m), 7.07-7.12 (1H, m), 6.94 (1H, dt, J=8.74, 3.17 Hz), 6.49-6.52 (1H, m), 5.62 (1H, s), 4.04-4.16 (2H, m), 3.88 (3H, s), 3.69 (3H, s, 3:1 mixture of rotamers), 2.74-2.58 (1H, m), 1.84-1.74 (1H, m), 1.12-1.02 (9H, s, 3:1 mixture of rotamers), 0.96 (1H, m), 0.86 (3H, m) 0.60-0.45 (1H, m), 0.34-0.04 (2H, m), −0.05-0.28 (1H, m).

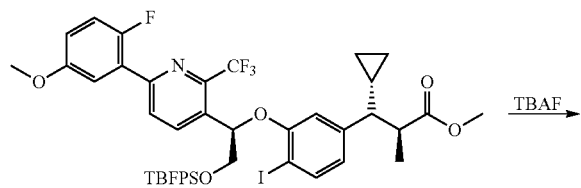

Step F: (2S,3R)-Methyl 3-(3-((R)-2-((tert-butyldiphenyl-silyl)oxy)-1-(6-(2-fluoro-5-methoxyphenyl)-2-(trifluoromethyl)pyridin-3-yl)ethoxy)-4-iodophenyl)-3-cyclopropyl-2-methylpropanoate (417 mg, 0.457 mmol) was taken up in THF (6 mL), and TBAF (0.7 mL, 0.7 mmol, 1M in THF) was added dropwise. The reaction was stirred for 30 minutes, then quenched by the addition of aqueous saturated NH$_4$Cl solution, and poured into EtOAc and H$_2$O. The layers were separated, and the organic layers were washed with brine, dried over MgSO$_4$, filtered, and concentrated in vacuo onto silica gel. The crude product was purified by column chromatography (ISCO system, RediSep 24 g column) using a gradient of 0-30-80% EtOAc/Hexanes as eluent to give (2S,3R)-methyl 3-cyclopropyl-3-(3-((R)-1-(6-(2-fluoro-5-methoxyphenyl)-2-(trifluoromethyl)pyridin-3-yl)-2-hydroxyethoxy)-4-iodophenyl)-2-methylpropanoate. LC/MS: m/z=674.27 [M+1].

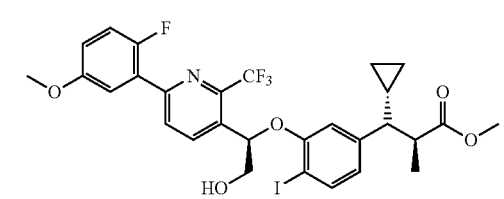

Step G: (2S,3R)-methyl 3-cyclopropyl-3-(3-((R)-1-(6-(2-fluoro-5-methoxyphenyl)-2-(trifluoromethyl)pyridin-3-yl)-2-hydroxyethoxy)-4-iodophenyl)-2-methylpropanoate (403 mg, 0.598 mmol), BrettPhos palladacycle precatalyst (47.8 mg, 0.060 mmol), and Cs$_2$CO$_3$ (390 mg, 1.197 mmol) were suspended in 1,4-dioxane (24 mL). The reaction mixture was sparged with N$_2$ for 10 minutes, then heated to 100° C. under N$_2$ for 14 h. The reaction was then cooled, and diluted with EtOAc. The organic layer was separated, washed with H$_2$O and brine (2×), dried over MgSO$_4$, filtered, and concentrated in vacuo. Purification of the resulting residue by silica gel column chromatography (ISCO system, RediSep 24 g column) using a gradient of 0-30% EtOAc/Hexanes as eluent to give (2S,3R)-methyl 3-cyclopropyl-3-((R)-3-(6-(2-fluoro-5-methoxyphenyl)-2-(trifluoro-methyl)-pyridin-3-yl)-2,3-dihydrobenzo[b][1,4]dioxin-6-yl)-2-methylpropanoate. LC/MS: m/z=546.42 [M+1].

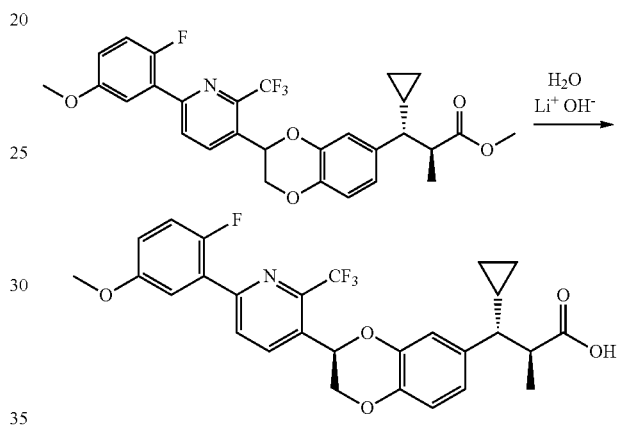

Step H: (2S,3R)-Methyl 3-cyclopropyl-3-((R)-3-(6-(2-fluoro-5-methoxyphenyl)-2-(trifluoromethyl)pyridin-3-yl)-2,3-dihydrobenzo[b][1,4]dioxin-6-yl)-2-methylpropanoate (330 mg, 0.605 mmol) was suspended in THF (3 mL), MeOH (3 mL), and water (3 mL). Additional THF was added to dissolve the solids. Then lithium hydroxide monohydrate (254 mg, 6.05 mmol) was added and the reaction mixture was heated at 65° C. under N$_2$ for 5.5 h. The reaction was then allowed to stir at ambient temperature overnight,

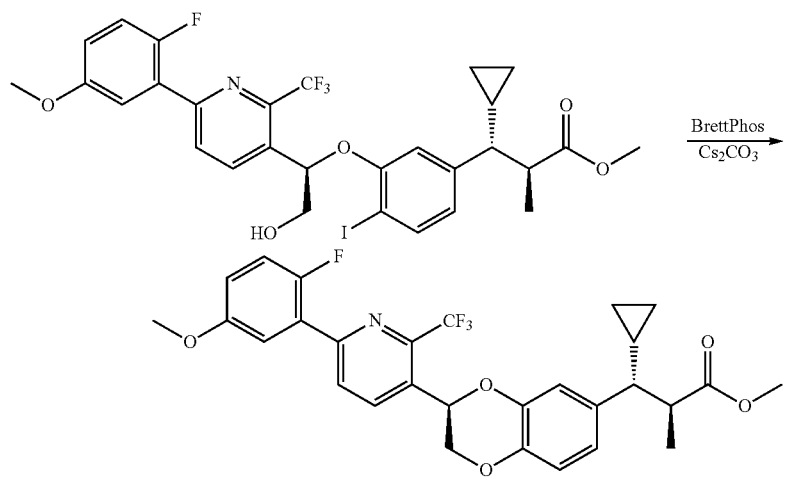

followed by acidification to pH 2 with 2N HCl. The reaction mixture was diluted with H₂O and extracted with EtOAc. The combined organic layers were washed with brine (3×), dried over MgSO₄, filtered, and concentrated in vacuo. The resulting residue was purified by silica gel column chromatography (ISCO system, RediSep 40 g column) using a gradient of 0-60% EtOAc/Hexanes as eluent to give (2S, 3R)-3-cyclopropyl-3-((R)-3-(6-(2-fluoro-5-methoxyphenyl)-2-(trifluoromethyl)pyridin-3-yl)-2,3-dihydrobenzo[b]-[1,4]dioxin-6-yl)-2-methylpropanoic acid. LC/MS: m/z=532.35 [M+1]. ¹H NMR δ (ppm)(CDCl₃): 0.09-0.05 (1H, m), 0.42-0.37 (2H, m), 0.67-0.63 (1H, m), 1.03 (3H, d, J=6.87 Hz), 1.13-1.08 (1H, m), 1.96 (1H, t, J=9.88 Hz), 2.86-2.80 (1H, m), 3.88 (3H, s), 3.97-3.92 (1H, m), 4.48-4.45 (1H, m), 5.57 (1H, d, J=8.23 Hz), 6.74 (1H, ddd, J=8.30, 5.68, 2.06 Hz), 6.82 (1H, dd, J=3.69, 2.04 Hz), 6.98-6.92 (2H, m), 7.11 (1H, dd, J=10.70, 8.98 Hz), 7.68 (1H, dt, J=6.21, 3.30 Hz), 8.16-8.14 (2H, m).

Examples 163-186 were prepared according to the procedure of Method A (Scheme 14) or Method B (Scheme 15) and the appropriate starting materials.

| Example | Structure | Method | Stereochemistry | LC/MS: found m/z [M + 1] |
|---|---|---|---|---|
| 163 | 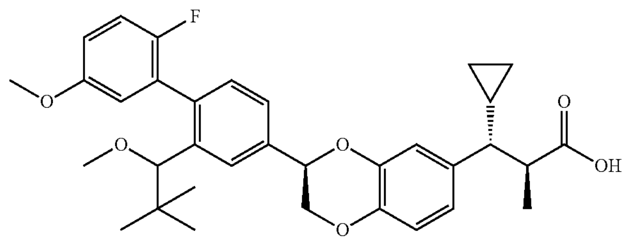 [SMILES: COc1ccc(F)c(-c2ccc([C@@H]3COc4ccc([C@H](C5CC5)[C@H](C)C(=O)O)cc4O3)cc2C(OC)C(C)(C)C)c1] | B | R or S, R, 2S, 3R | 580.57 [M + 18] |
| 164 | 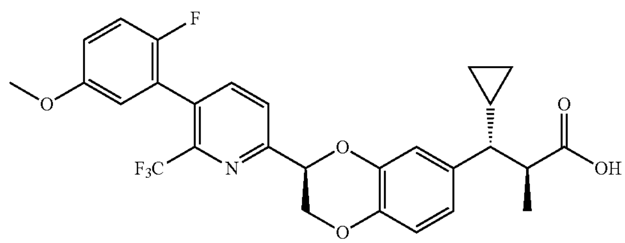 [SMILES: COc1ccc(F)c(-c2ccc([C@@H]3COc4ccc([C@H](C5CC5)[C@H](C)C(=O)O)cc4O3)nc2C(F)(F)F)c1] | B | R, 2S, 3R | 532.32 |
| 165 | 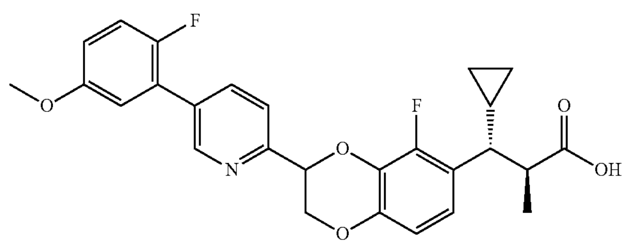 [SMILES: COc1ccc(F)c(-c2ccc(C3COc4ccc([C@H](C5CC5)[C@H](C)C(=O)O)c(F)c4O3)nc2)c1] | A | RS, 2S, 3R | 482.34 |
| 166 | 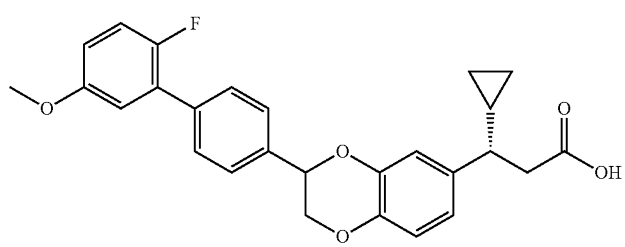 [SMILES: COc1ccc(F)c(-c2ccc(C3COc4ccc([C@@H](CC(=O)O)C5CC5)cc4O3)cc2)c1] | A | RS, 3S | 449.58 |
| 167 | 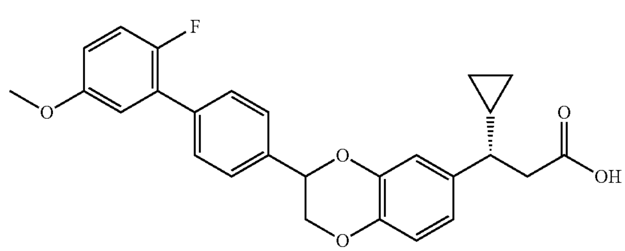 [SMILES: COc1ccc(F)c(-c2ccc(C3COc4ccc([C@@H](CC(=O)O)C5CC5)cc4O3)cc2)c1] | A | R or S, 3S | 449.59 |

-continued

| Example | Structure | Method | Stereochemistry | LC/MS: found m/z [M + 1] |
|---|---|---|---|---|
| 168 | 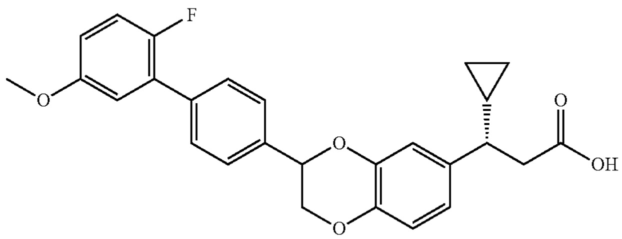 [SMILES: COc1ccc(F)c(-c2ccc(C3COc4ccc([C@@H](CC(=O)O)C5CC5)cc4O3)cc2)c1] | A | R or S, 3S | 449.58 |
| 169 | 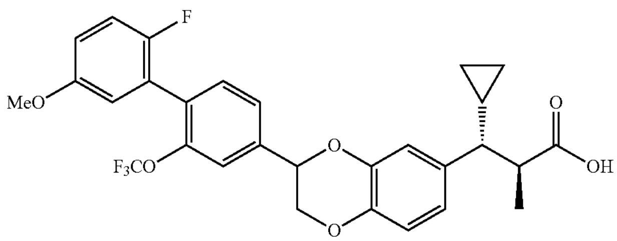 [SMILES: COc1ccc(F)c(-c2ccc(C3COc4ccc([C@H](C5CC5)[C@H](C)C(=O)O)cc4O3)cc2OC(F)(F)F)c1] | A | RS, 2S, 3R | 547.68 |
| 170 | 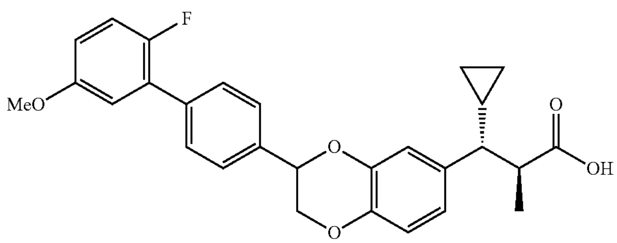 [SMILES: COc1ccc(F)c(-c2ccc(C3COc4ccc([C@H](C5CC5)[C@H](C)C(=O)O)cc4O3)cc2)c1] | A | 2S, 3R | 463.69 |
| 171 | 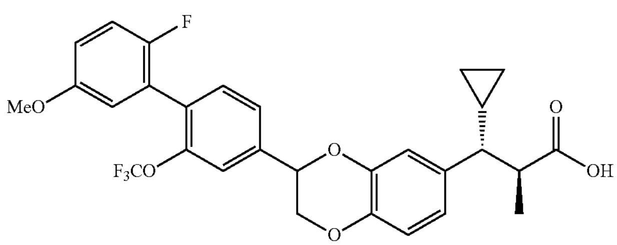 [SMILES: COc1ccc(F)c(-c2ccc(C3COc4ccc([C@H](C5CC5)[C@H](C)C(=O)O)cc4O3)cc2OC(F)(F)F)c1] | A | 2S, 3R, R or S | 547.65 |
| 172 | 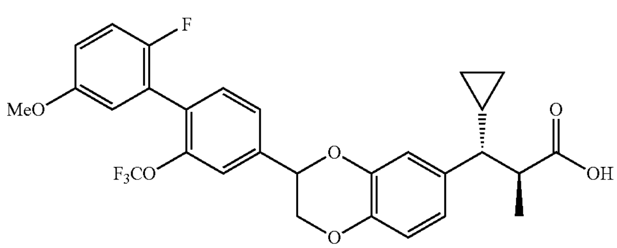 [SMILES: COc1ccc(F)c(-c2ccc(C3COc4ccc([C@H](C5CC5)[C@H](C)C(=O)O)cc4O3)cc2OC(F)(F)F)c1] | A | 2S, 3R, R or S | 547.68 |
| 173 | 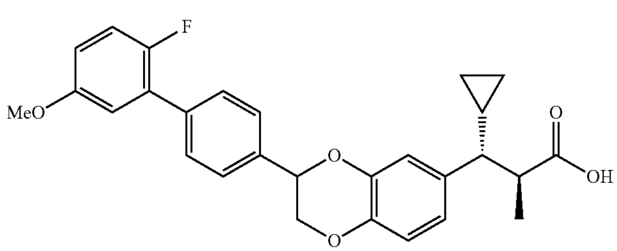 [SMILES: COc1ccc(F)c(-c2ccc(C3COc4ccc([C@H](C5CC5)[C@H](C)C(=O)O)cc4O3)cc2)c1] | A | 2S, 3R, R or S | 463.67 |

-continued

| Example | Structure | Method | Stereochemistry | LC/MS: found m/z [M + 1] |
|---|---|---|---|---|
| 174 | 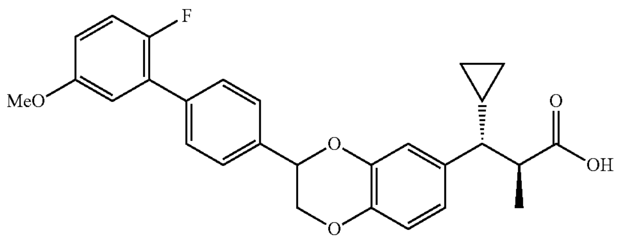 [SMILES: COc1ccc(F)c(-c2ccc(C3COc4ccc([C@H](C5CC5)[C@H](C)C(=O)O)cc4O3)cc2)c1] | A | 2S, 3R, R or S | 463.67 |
| 175 | 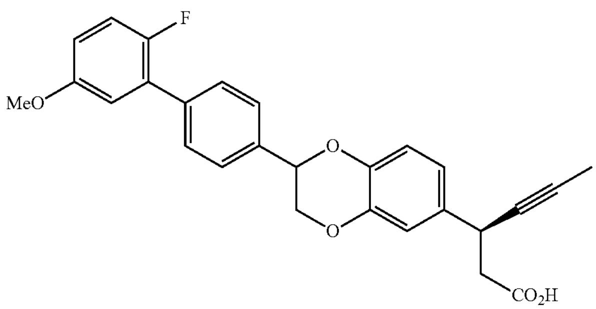 [SMILES: CC#C[C@@H](CC(=O)O)c1ccc2c(c1)OCC(c1ccc(-c3cc(OC)ccc3F)cc1)O2] | A | 3S | 447.61 |
| 176 | 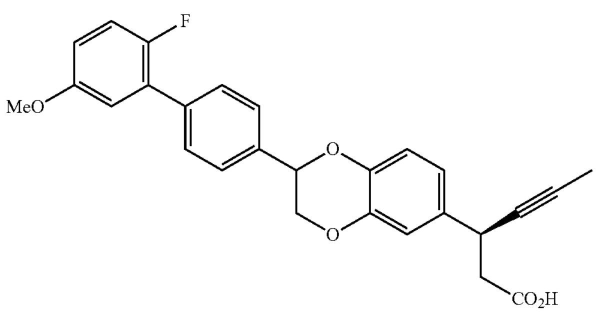 [SMILES: CC#C[C@@H](CC(=O)O)c1ccc2c(c1)OCC(c1ccc(-c3cc(OC)ccc3F)cc1)O2] | A | 3S R OR S | 447.45 |
| 177 | 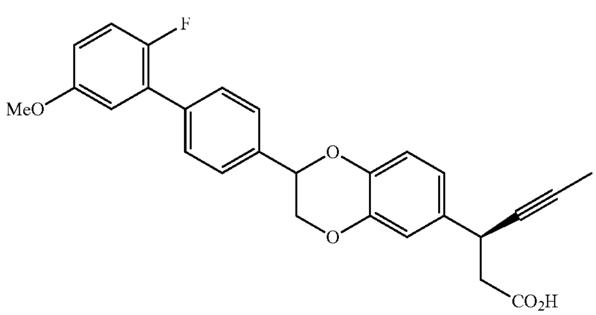 [SMILES: CC#C[C@@H](CC(=O)O)c1ccc2c(c1)OCC(c1ccc(-c3cc(OC)ccc3F)cc1)O2] | A | 3S R OR S | 447.48 |
| 178 | 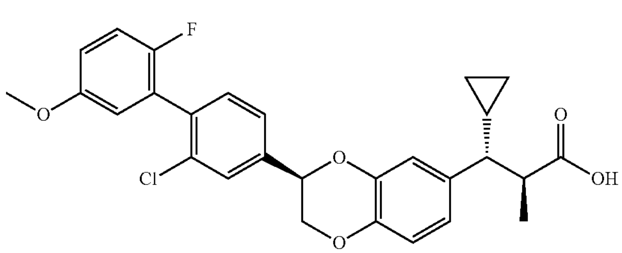 [SMILES: COc1ccc(F)c(-c2ccc([C@@H]3COc4ccc([C@H](C5CC5)[C@H](C)C(=O)O)cc4O3)cc2Cl)c1] | A | R, 2S, 3R | 497.55 |

-continued

| Example | Structure | Method | Stereochemistry | LC/MS: found m/z [M + 1] |
|---------|-----------|--------|-----------------|--------------------------|
| 179 | 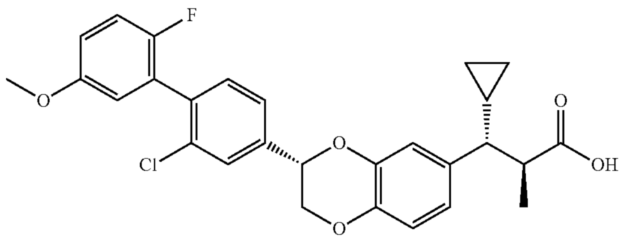 [SMILES: COc1ccc(F)c(-c2ccc([C@H]3COc4ccc([C@H](C5CC5)[C@H](C)C(=O)O)cc4O3)cc2Cl)c1] | A | S, 2S, 3R | 497.57 |
| 180 | 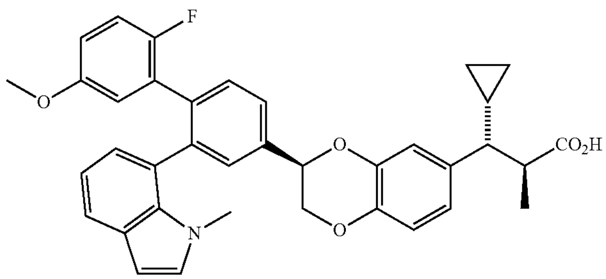 [SMILES: COc1ccc(F)c(-c2ccc([C@@H]3COc4ccc([C@H](C5CC5)[C@H](C)C(=O)O)cc4O3)cc2-c2cccc3ccn(C)c23)c1] | A | R, 2S, 3R | 592.80 |
| 181 | 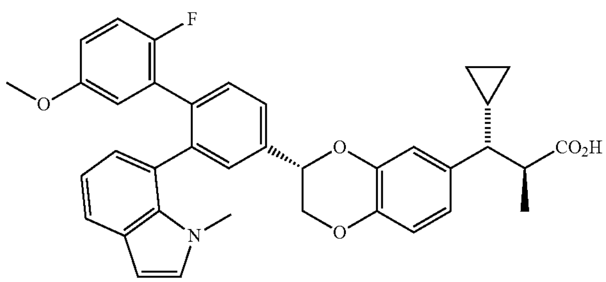 [SMILES: COc1ccc(F)c(-c2ccc([C@H]3COc4ccc([C@H](C5CC5)[C@H](C)C(=O)O)cc4O3)cc2-c2cccc3ccn(C)c23)c1] | A | R, 2S, 3R | 592.74 |
| 182 | 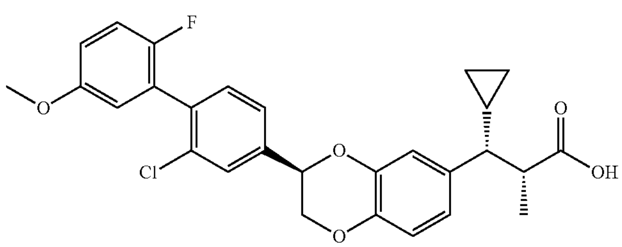 [SMILES: COc1ccc(F)c(-c2ccc([C@@H]3COc4ccc([C@H](C5CC5)[C@@H](C)C(=O)O)cc4O3)cc2Cl)c1] | A | R, 2R, 3R | 497.56 |
| 183 | 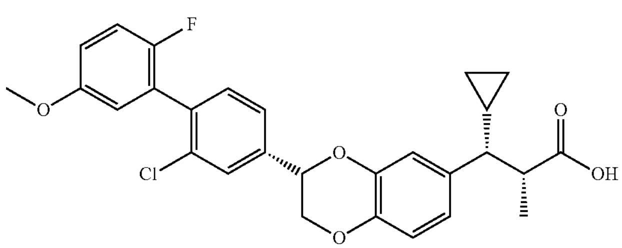 | A | S, 2R, 3R | 497.57 |
| 184 | 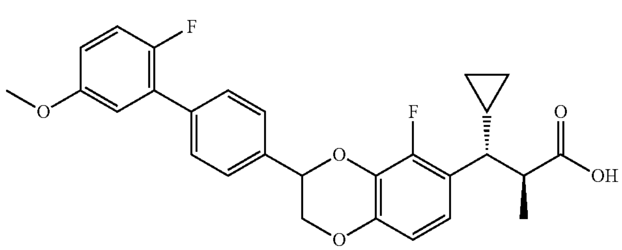 [SMILES: COc1ccc(F)c(-c2ccc(C3COc4ccc([C@H](C5CC5)[C@H](C)C(=O)O)c(F)c4O3)cc2)c1] | A | 2S, 3R | 481.55 |

| Example | Structure | Method | Stereochemistry | LC/MS: found m/z [M + 1] |
|---------|-----------|--------|-----------------|--------------------------|
| 185 | 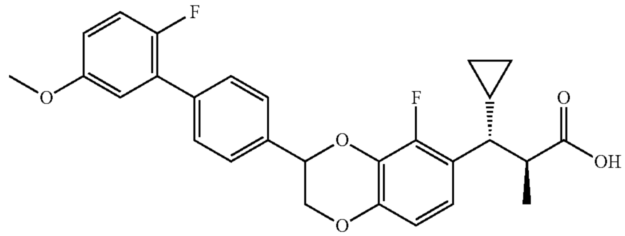 [SMILES: COc1ccc(F)c(-c2ccc(C3COc4ccc([C@H](C5CC5)[C@H](C)C(=O)O)c(F)c4O3)cc2)c1] | A | 2S, 3R, R OR S | 481.50 |
| 186 | 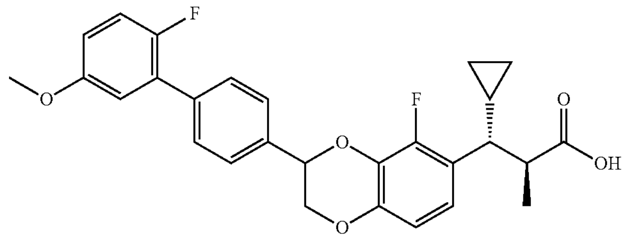 [SMILES: COc1ccc(F)c(-c2ccc(C3COc4ccc([C@H](C5CC5)[C@H](C)C(=O)O)c(F)c4O3)cc2)c1] | A | 2S, 3R, R OR S | 481.48 |

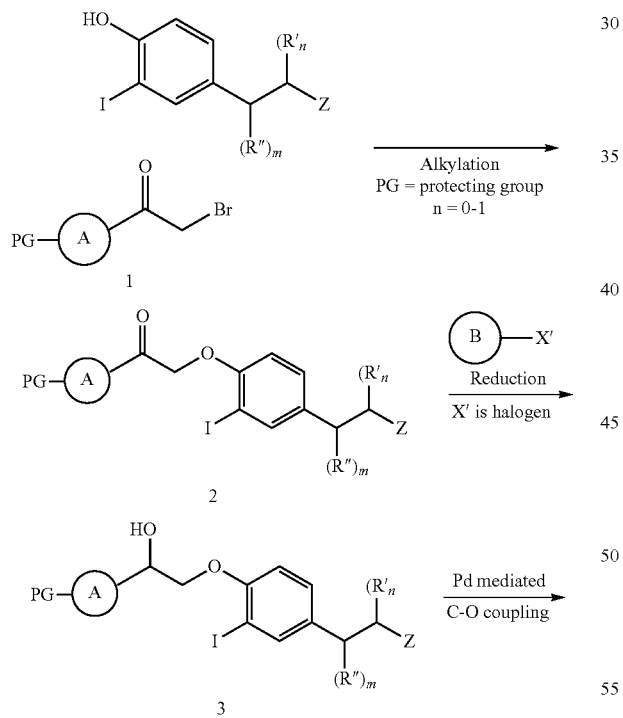

An alpha bromo-ketone such as compound 1 is alkylated with an iodophenol to provide compound 2. The ketone of compound 2 is reduced using sodium borohydride to give the corresponding alcohol 3. Subsequent C-O coupling under Pd mediated conditions gives dioxane 4. Protecting group removal of compound 4, followed by benzylation using standard benzylation conditions gives the ester of compound 5. Hydrolysis of the ester with LiOH provides the acid of compound 5.

Examples 187 and 188

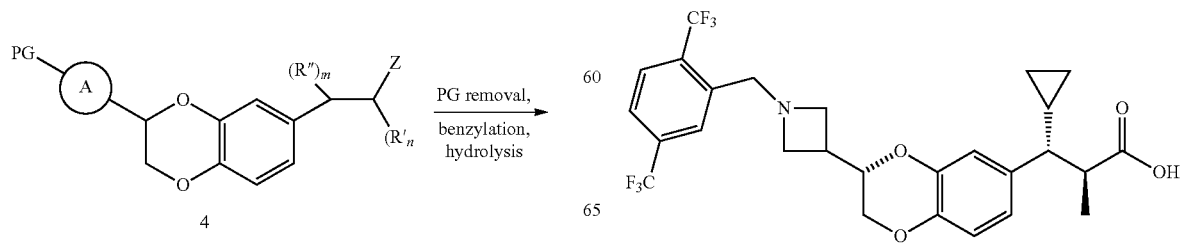

261

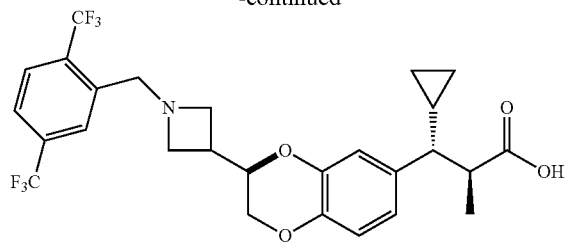

(2S,3R)-3-((R)-3-(1-(2,5-Bis(trifluoromethyl)benzyl)azetidin-3-yl)-2,3-dihydrobenzo[b][1,4]dioxin-6-yl)-3-cyclopropyl-2-methylpropanoic acid and (2S,3R)-3-((S)-3-(1-(2,5-Bis(trifluoromethyl)benzyl)azetidin-3-yl)-2,3-dihydrobenzo[b][1,4]dioxin-6-yl)-3-cyclopropyl-2-methylpropanoic acid

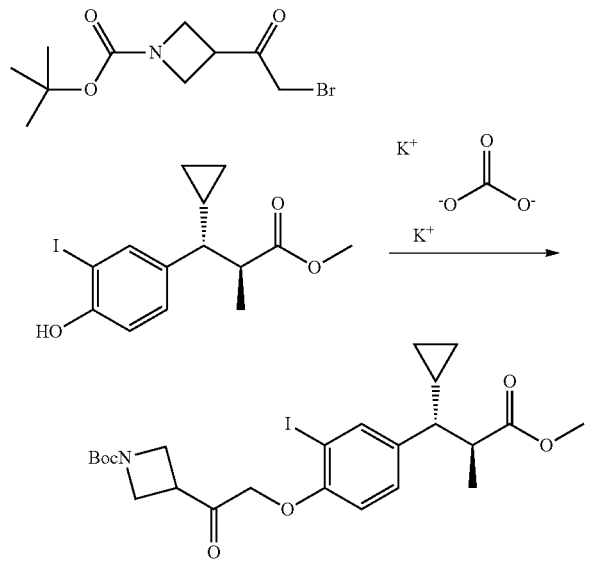

Step A: A solution of (2S,3R)-methyl 3-cyclopropyl-3-(4-hydroxy-3-iodophenyl)-2-methylpropanoate (360 mg, 0.999 mmol), K$_2$CO$_3$ (276 mg, 1.999 mmol) and tert-butyl 3-(2-bromoacetyl)azetidine-1-carboxylate (278 mg, 0.999 mmol) in acetonitrile (5 mL) was heated to 40° C. for 12 h. Then the reaction was diluted with H$_2$O, and extracted with EtOAc (3×50 mL). The combined organic extracts were washed with brine, dried over MgSO$_4$, filtered, concentrated. The resulting residue was purified by ISCO (24 g, 0-30% EtOAc/hexanes) to give tert-butyl 3-(2-(4-((1R,2S)-1-cyclopropyl-3-methoxy-2-methyl-3-oxopropyl)-2-iodophenoxy)acetyl)azetidine-1-carboxylate. LC/MS: m/e 558.37 (M+H)$^+$.

262

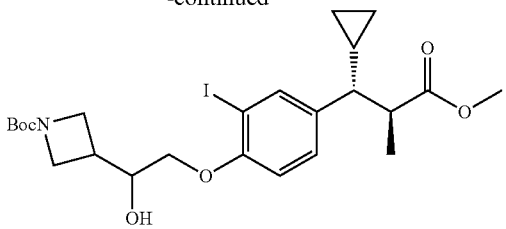

Step B: To tert-butyl 3-(2-(4-((1R,2S)-1-cyclopropyl-3-methoxy-2-methyl-3-oxopropyl)-2-iodophenoxy)acetyl)azetidine-1-carboxylate (443 mg, 0.795 mmol) in MeOH (4 mL) at rt was added NaBH$_4$ (15 mg, 0.4 mmol). The solution was stirred at rt for 1 h, then concentrated to dryness. The crude product was purified by ISCO (40 g, 0-30% EtOAc/hexanes) to give tert-butyl 3-(2-(4-((1R,2S)-1-cyclopropyl-3-methoxy-2-methyl-3-oxopropyl)-2-iodophenoxy)-1-hydroxyethyl)azetidine-1-carboxylate. LC/MS: m/e 560.41 (M+H)$^+$.

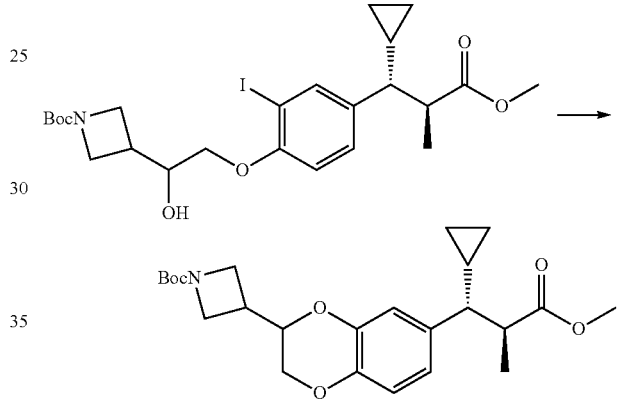

Step C: A solution of tert-butyl 3-(2-(4-((1R,2S)-1-cyclopropyl-3-methoxy-2-methyl-3-oxopropyl)-2-iodophenoxy)-1-hydroxyethyl)azetidine-1-carboxylate (248 mg, 0.4 mmol), BrettPhos Palladacycle precatalyst (35 mg, 0.04 mmol) and Cs$_2$CO$_3$ (289 mg, 0.89 mmol) in 1,4-Dioxane (2 mL) was sparged with N$_2$ for 5 minutes. The reaction was then heated to 100° C. for 12 h. Then the reaction was cooled, diluted with EtOAc, and filtered through a Celite™ pad. The filtrate was concentrated to give the crude product, which was purified by ISCO (24 g, 0-30% EtOAc:Hexanes) to give tert-butyl 3-(7-((1R,2S)-1-cyclopropyl-3-methoxy-2-methyl-3-oxopropyl)-2,3-dihydrobenzo[b][1,4]dioxin-2-yl)azetidine-1-carboxylate. LC/MS: m/e 432.45 (M+H)$^+$.

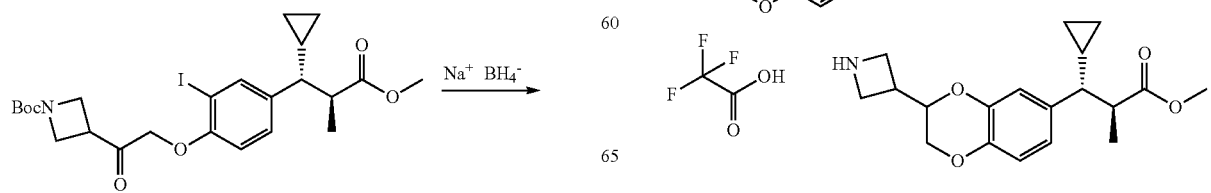

Step D: To a solution of tert-butyl 3-(7-((1R,2S)-1-cyclopropyl-3-methoxy-2-methyl-3-oxopropyl)-2,3-dihydrobenzo[b][1,4]dioxin-2-yl)azetidine-1-carboxylate (227 mg, 0.526 mmol) in DCM (5 mL) at rt was added TFA (0.2 mL, 2.63 mmol). The reaction was stirred at rt for 3 h, then concentrated to dryness by azeotroping with toluene to give (2S,3R)-methyl 3-(3-(azetidin-3-yl)-2,3-dihydrobenzo[b][1,4]dioxin-6-yl)-3-cyclopropyl-2-methylpropanoate. LC/MS: m/e 332.39 (M+H)+.

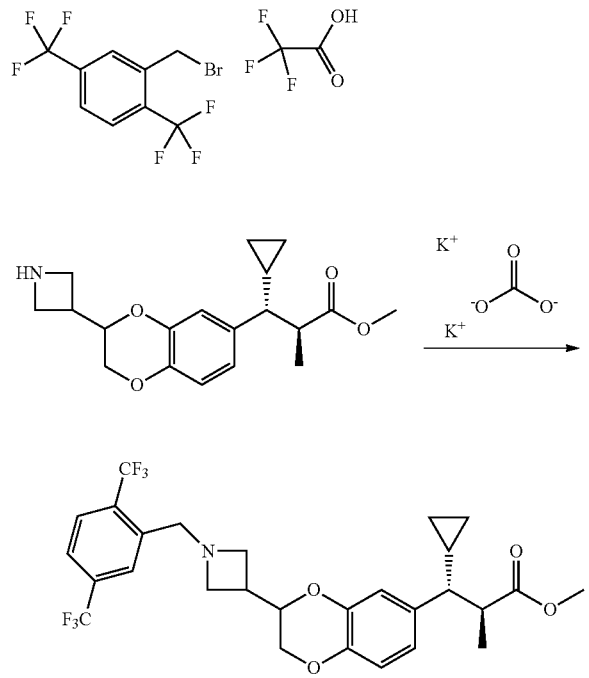

Step E: To a solution of (2S,3R)-methyl 3-(3-(azetidin-3-yl)-2,3-dihydrobenzo-[b][1,4]dioxin-6-yl)-3-cyclopropyl-2-methylpropanoate (160 mg, 0.5 mmol) in DMF (4 mL) at rt was added 2,5-bis(trifluoromethyl)benzyl bromide (160 mg, 0.521 mmol) and K₂CO₃ (288 mg, 2.1 mmol). The reaction mixture was stirred at rt for 12 h, then diluted with H₂O, and extracted with EtOAc (3×10 mL). The combined organic layers were washed with brine (3×10 mL), dried over MgSO₄, filtered, concentrated to give the crude product, which was purified by MPLC (ISCO, 24 g, 0-30% EtOAc/hexanes) to give (2S,3R)-methyl 3-(3-(1-(2,5-bis(trifluoromethyl)benzyl)azetidin-3-yl)-2,3-dihydrobenzo-[b][1,4]dioxin-6-yl)-3-cyclopropyl-2-methylpropanoate, as a mixture of diastereomers. LC/MS: m/e 558.51 (M+H)+.

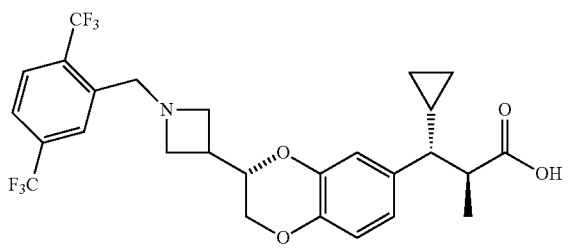

-continued

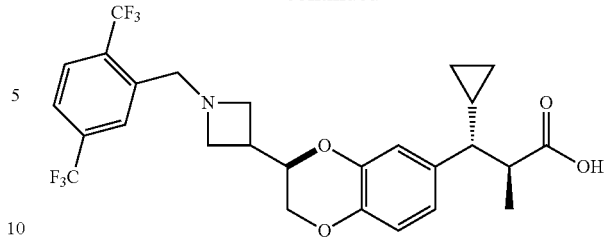

Step F: (2S,3R)-methyl 3-((S)-3-(1-(2,5-bis(trifluoromethyl)benzyl)azetidin-3-yl)-2,3-dihydrobenzo[b][1,4]dioxin-6-yl)-3-cyclopropyl-2-methylpropanoate and (2S,3R)-methyl 3-((R)-3-(1-(2,5-bis(trifluoromethyl)benzyl)azetidin-3-yl)-2,3-dihydrobenzo-[b][1,4]-dioxin-6-yl)-3-cyclopropyl-2-methylpropanoate The mixture of diastereomers of (2S,3R)-methyl 3-(3-(1-(2,5-bis(trifluoro-methyl)benzyl)azetidin-3-yl)-2,3-dihydrobenzo-[b][1,4]dioxin-6-yl)-3-cyclopropyl-2-methylpropanoate was separated by Chiral SFC (AD column, 21×250 mm, 5% MeOH+0.2% DEA/CO₂, 60 mL/min, 35° C., 100 bar, 254 nM, 20 mg/mL in MeOH) to afford the following two isomers:

Isomer 1: (Peak 1, Faster-eluting isomer)¹H NMR (500 MHz, acetone): δ (ppm) 0.02 (s, 1H); 0.22 (dt, J=9.4, 4.9 Hz, 1H); 0.32-0.28 (m, 1H); 0.55 (t, J=6.7 Hz, 1H); 0.92 (d, J=6.9 Hz, 3H); 1.06 (m, 1H); 1.84-1.90 (m, 1H), 2.75-2.90 (m, 2H); 3.30-3.45 (m, 2H); 3.55-3.60 (m, 2H); 3.70 (s, 3H); 3.86-3.91 (m, 1H); 3.95 (s, 2H); 4.35 (d, J=11.5 Hz, 1H); 4.42 (t, J=7.9 Hz, 1H); 6.72 (d, J=8.3 Hz, 1H); 6.82-6.78 (m, 2H); 7.85 (d, J=8.2 Hz, 1H); 7.98 (d, J=8.2 Hz, 1H); 8.18 (s, 1H).

Isomer 2: (Peak 2, Slower-eluting isomer)¹H NMR (500 MHz, acetone): δ (ppm) 0.01 (s, 1H); 0.23 (dt, J=9.4, 4.9 Hz, 1H); 0.33-0.29 (m, 1H); 0.56 (d, J=7.7 Hz, 1H); 0.93 (d, J=6.9 Hz, 3H); 1.06 (m, 1H); 1.84-1.90 (m, 1H); 2.75-2.90 (m, 2H); 3.30-3.45 (m, 2H); 3.55-3.60 (m, 2H); 3.71 (s, 3H); 3.86-3.91 (m, 1H); 3.96 (s, 2H); 4.36 (d, J=11.5 Hz, 1H); 4.43 (t, J=7.9 Hz, 1H); 6.72 (d, J=8.3 Hz, 1H); 6.83-6.79 (m, 2H); 7.86 (d, J=8.2 Hz, 1H); 7.99 (d, J=8.2 Hz, 1H); 8.18 (s, 1H).

Step G: To a solution of Isomer 1 (Step F, 74 mg, 0.1 mmol) in THF (0.75 ml)/MeOH (0.75 ml)/water (0.5 ml) at rt was added LiOH. The reaction was stirred at 55° C. for 12 h. Then the reaction was diluted with H₂O, acidified with 1N HCl to pH 4-5, and extracted with EtOAc (3×). The combined organic extracts were washed with brine, dried over MgSO₄, filtered, and concentrated to give a crude product, which was purified by ISCO (4 g, 0-100% EtOAc/hexanes) to give (2S,3R)-3-((S)-3-(1-(2,5-bis(trifluoromethyl)benzyl)azetidin-3-yl)-2,3-dihydrobenzo[b][1,4]dioxin-6-yl)-3-cyclopropyl-2-methylpropanoic acid. ¹H NMR (500 MHz, acetone): δ (ppm) 0.01 (m, 1H); 0.35-0.31 (m, 2H); 0.56 (d, J=8.2 Hz, 1H); 0.94 (d, J=6.9 Hz, 3H); 1.14 (m, 1H); 1.96 (m, 1H); 2.88-2.72 (m, 2H); 3.37 (dt, J=29.9, 6.6 Hz, 2H); 3.56 (q, J=8.2 Hz, 2H); 3.89-3.87 (m, 1H); 3.94 (s, 2H); 4.34 (d, J=11.5 Hz, 1H); 4.41 (t, J=7.9 Hz, 1H); 6.72 (d, J=8.4 Hz, 1H); 6.80-6.77 (m, 2H); 7.84 (d, J=8.3 Hz, 1H); 7.96 (d, J=8.2 Hz, 1H); 8.16 (s, 1H).

Step H: To a solution of Isomer 2 (Step F, 64 mg, 0.1 mmol) in THF (0.75 ml)/MeOH (0.75 ml)/water (0.5 ml) at rt was added LiOH. The reaction was stirred at 55° C. for 12 h. Then the reaction was diluted with H₂O, acidified with 1N HCl to pH 4-5, and extracted with EtOAc (3×). The combined organic extracts were washed with brine, dried over MgSO₄, filtered, and concentrated to give a crude product, which was purified by ISCO (4 g, 0-100% EtOAc/hexanes) to give (2S,3R)-3-((R)-3-(1-(2,5-bis(trifluoro-methyl)benzyl)azetidin-3-yl)-2,3-dihydrobenzo[b][1,4]dioxin-6-yl)-3-cyclopropyl-2-methylpropanoic acid. $^1$H NMR (500 MHz, Acetone-d₆): δ (ppm) 0.01 (m, 1H); 0.36-0.31 (m, 2H); 0.58-0.56 (m, 1H); 0.95 (d, J=6.9 Hz, 3H); 1.14 (m, 1H); 1.96 (m, 1H); 2.88-2.72 (m, 2H); 3.37 (dt, J=29.9, 6.6 Hz, 2H); 3.56 (q, J=8.2 Hz, 2H); 3.90-3.88 (m, 1H); 3.95 (s, 2H); 4.34 (d, J=11.5 Hz, 1H); 4.41 (t, J=7.9 Hz, 1H); 6.73 (d, J=8.4 Hz, 1H); 6.81-6.78 (m, 2H); 7.84 (d, J=8.3 Hz, 1H); 7.97 (d, J=8.2 Hz, 1H); 8.17 (s, 1H).

Example 189

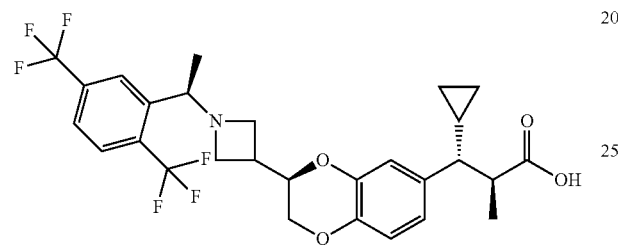

(2S,3R)-3-((R)-3-(1-((R)-1-(2,5-bis(trifluoromethyl)phenyl)ethyl]azetidin-3-yl)-2,3-dihydrobenzo[b][1,4]dioxin-6-yl)-3-cyclopropyl-2-methylpropanoic acid

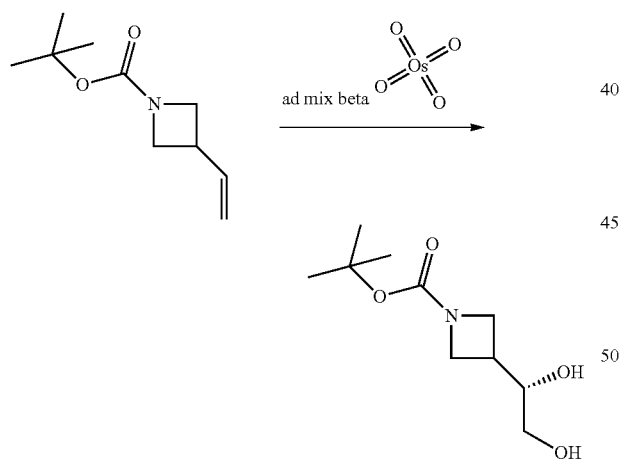

Step A: To a stirred solution of tert-butyl 3-vinylazetidine-1-carboxylate (1.75 g, 9.6 mmol) was suspended in t-BuOH (37.00 mL) and H₂O (37.00 mL) was added AD-MIX-ALPHA (13.4 g, 9.6 mmol, Sigma Aldrich) in several portions. The reaction was stirred at ambient temperature for 20 h, then diluted with H₂O, and extracted with EtOAc. The combined organic extracts were washed with brine (1×), dried over MgSO₄, filtered, and concentrated in vacuo. The resulting residue was purified by silica gel column chromatography (ISCO system, RediSep 40 g column) using a gradient of 0-100% EtOAc/Hexanes to give (S)-tert-butyl 3-(1,2-dihydroxyethyl)azetidine-1-carboxylate.

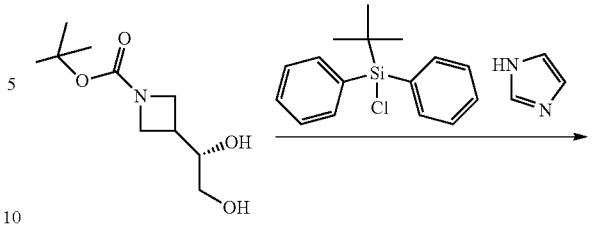

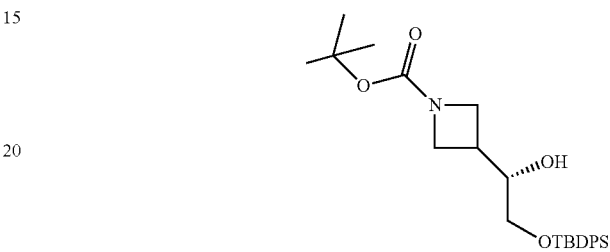

Step B: To a solution of (S)-tert-butyl 3-(1,2-dihydroxyethyl)azetidine-1-carboxylate (1.9 g, 8.8 mmol) in CH₂Cl₂ (25 mL) was added imidazole (0.6 g, 8.8 mmol) and tert-butylchlorodiphenylsilane (2.2 mL, 8.8 mmol). After stirring at ambient temperature for 20 minutes, the resulting precipitate was removed by filtration and the filtrate was concentrated in vacuo. The resulting residue was purified by silica gel column chromatography (ISCO system, RediSep 80 g column) using a gradient of 0-65% EtOAC/Hexanes as eluent to give (S)-tert-butyl 3-(2-((tert-butyldiphenylsilyl)oxy)-1-hydroxyethyl)azetidine-1-carboxylate.

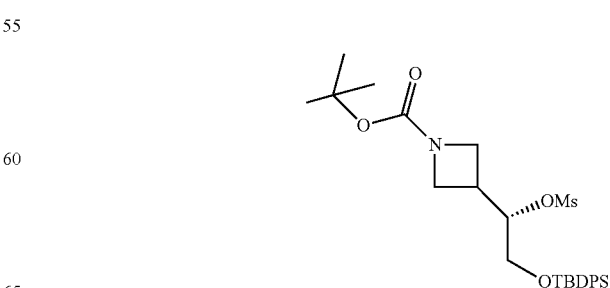

Step C: To a solution of (S)-tert-butyl 3-(2-((tert-butyldiphenylsilyl)oxy)-1-hydroxy-ethyl)azetidine-1-carboxylate (0.39 g, 0.9 mmol) in CH$_2$Cl$_2$ (5 mL) at −50° C. were added TEA (0.18 mL, 1.3 mmol) and MsCl (0.1 mL, 1.2 mmol). After 20 min, the reaction was quenched with saturated aqueous NH$_4$Cl solution and allowed to warm to rt. Then the organic layer was separated, dried over MgSO$_4$, filtered and concentrated to give (S)-tert-butyl 3-(2-((tert-butyldiphenylsilyl)oxy)-1-methanesulfonylethyl)azetidine-1-carboxylate, which was used immediately in the next step.

lethyl)azetidine-1-carboxylate (100 mg, 0.19 mmol) in DMF (2 mL) was heated to 65° C. for 12 h. Then the reaction mixture was diluted with H$_2$O, and extracted with EtOAc (3×50 mL). The combined organic layers were washed with brine, dried over MgSO$_4$, filtered, and concentrated to give the crude product, which was purified by ISCO (4 g, 0-20% EtOAc/hexanes) to give tert-butyl 3-((R)-2-((tert-butyldiphenylsilyl)oxy)-1-(5-((1R,2S)-1-cyclopropyl-3-methoxy-2-methyl-3-oxopropyl)-2-iodophenoxy)ethyl)azetidine-1-carboxylate. LC/MS: m/e 798.92 (M+H)$^+$.

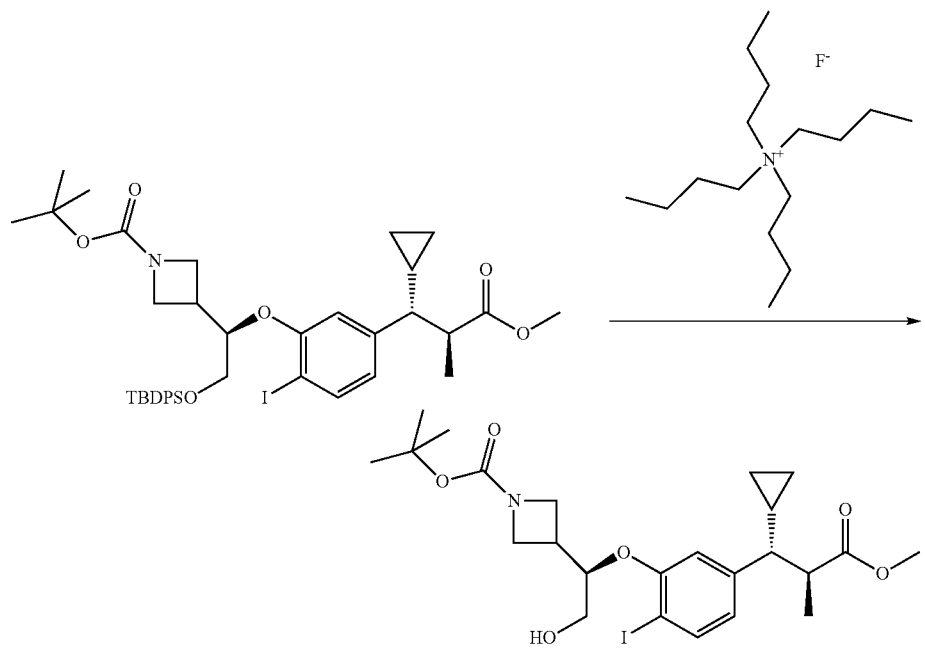

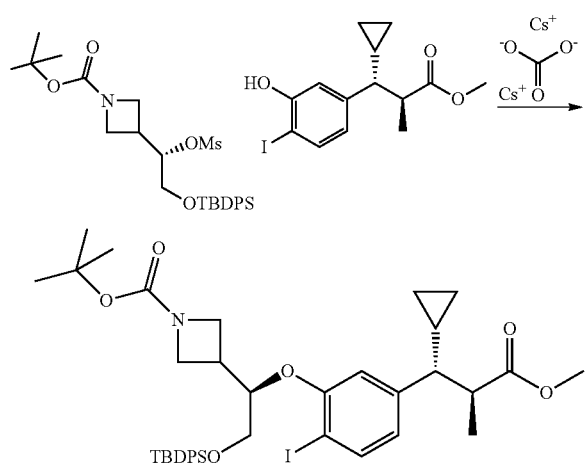

Step D: A stirred solution of (2S,3R)-methyl 3-cyclopropyl-3-(3-hydroxy-4-iodophenyl)-2-methylpropanoate (68 mg, 0.19 mmol), Cs$_2$CO$_3$ (122 mg, 0.3 mmol) and (S)-tert-butyl 3-(2-((tert-butyldiphenylsilyl)oxy)-1-methanesulfony- Step E: To a solution of tert-butyl 3-((R)-2-((tert-butyl-diphenylsilyl)oxy)-1-(5-((1R,2S)-1-cyclopropyl-3-methoxy-2-methyl-3-oxopropyl)-2-iodophenoxy)ethyl)azetidine-1-carboxylate (45 mg, 0.06 mmol) in THF (6 mL) was added dropwise TBAF (0.1 mL, 0.1 mmol, 1M in THF). The reaction was stirred for 30 min, then quenched with aqueous saturated NH$_4$Cl solution and poured into EtOAc and H$_2$O. The layers were separated, and the combined organic layers were washed with brine, dried over MgSO$_4$, filtered, and concentrated in vacuo onto silica gel. The crude product was purified by column chromatography (ISCO system, RediSep 24 g column) using a gradient of 0-30-80% EtOAc/Hexanes as eluent to provide tert-butyl 3-((R)-1-(5-((1R,2S)-1-cyclopropyl-3-methoxy-2-methyl-3-oxopropyl)-2-iodophenoxy)-2-hydroxyethyl)azetidine-1-carboxylate. LC/MS: m/e 560.72 (M+H)$^+$.

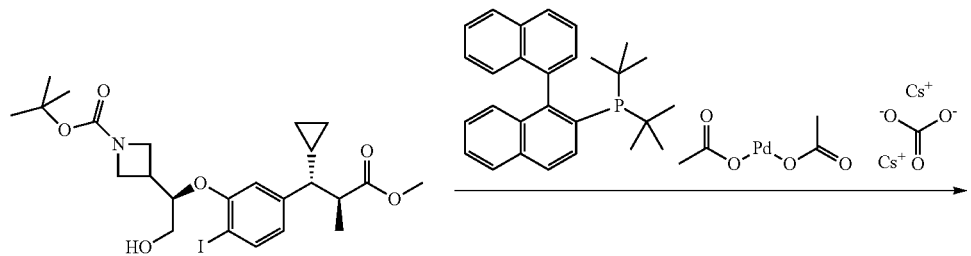

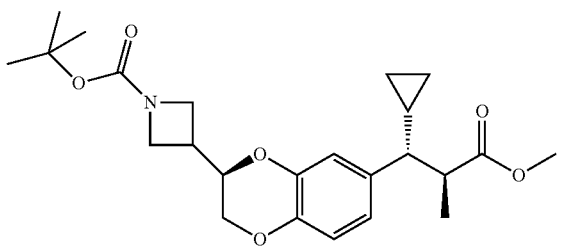

Step F: A solution of tert-butyl 3-((R)-1-(5-((1R,2S)-1-cyclopropyl-3-methoxy-2-methyl-3-oxopropyl)-2-iodophenoxy)-2-hydroxyethyl)azetidine-1-carboxylate (113 mg, 0.2 mmol), Pd(OAc)$_2$ (4.5 mg, 0.02 mmol), Trixiephos (16 mg, 0.02 mmol, Strem), and Cs$_2$CO$_3$ (132 mg, 0.4 mmol) in toluene (4 mL) was sparged with N$_2$ for 10 minutes, then heated to 50° C. under N$_2$ for 14 h. The reaction was then cooled, and diluted with EtOAc. The organic layer was separated, washed with H$_2$O and brine (2×), dried over MgSO$_4$, filtered, and concentrated in vacuo. Purification of the resulting residue by silica gel column chromatography (ISCO system, RediSep 24 g column) using a gradient of 0-30% EtOAc/Hexanes as eluent provided tert-butyl 3-((R)-7-((1R,2S)-1-cyclopropyl-3-methoxy-2-methyl-3-oxopropyl)-2,3-dihydrobenzo[b][1,4]dioxin-2-yl)azetidine-1-carboxylate. LC/MS: m/e 432.69 (M+H)$^+$.

-continued

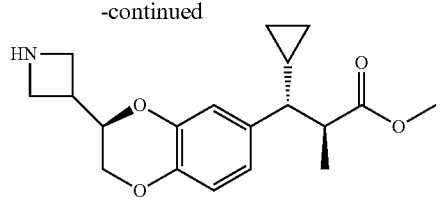

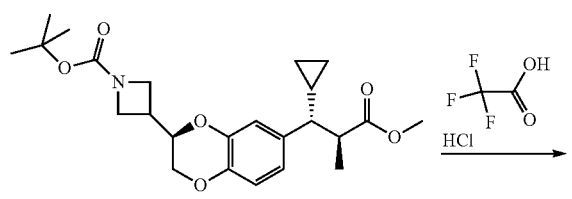

Step G: To a solution of tert-butyl 3-((R)-7-((1R,2S)-1-cyclopropyl-3-methoxy-2-methyl-3-oxopropyl)-2,3-dihydrobenzo[b][1,4]dioxin-2-yl)azetidine-1-carboxylate (120 mg, 0.3 mmol) in DCM (5 mL) at rt was added TFA (0.2 mL, 2.63 mmol). The resulting solution was stirred at rt for 3 h, then concentrated to dryness by azeotroping with toluene to give (2S,3R)-methyl 3-((R)-3-(azetidin-3-yl)-2,3-dihydrobenzo[b][1,4]dioxin-6-yl)-3-cyclopropyl-2-methylpropanoate. LC/MS: m/e 446.43 (M+H)$^+$.

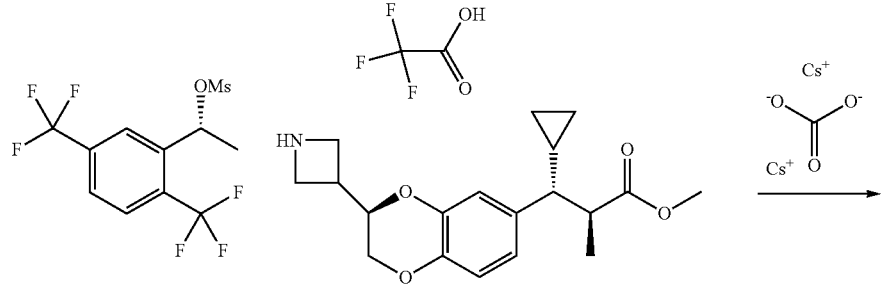

-continued

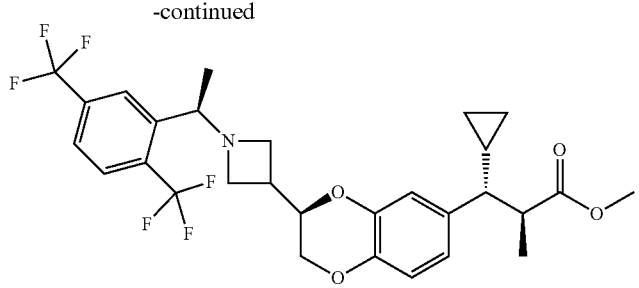

Step H: To a solution of (2S,3R)-methyl 3-((R)-3-(azetidin-3-yl)-2,3-dihydrobenzo[b][1,4]dioxin-6-yl)-3-cyclopropyl-2-methylpropanoate (114 mg, 0.3 mmol) in acetonitrile (3 mL) at rt was added (R)-1-(2,5-bis(trifluoromethyl)phenyl)ethyl methanesulfonate (114 mg, 0.4 mmol) and Cs₂CO₃ (300 mg, 0.9 mmol). The reaction was stirred at 60° C. for 12 h, then diluted with H₂O, and extracted with EtOAc (3×10 mL). The combined organic layers were washed with brine (3×10 mL), dried over MgSO₄, filtered, concentrated. The crude product was purified by MPLC (ISCO, 4 g, 0-50% EtOAc/hexanes) to give (2S,3R)-methyl 3-((R)-3-(1-((R)-1-(2,5-bis(trifluoro-methyl)phenyl)ethyl)azetidin-3-yl)-2,3-dihydrobenzo[b][1,4]dioxin-6-yl)-3-cyclopropyl-2-methylpropanoate. LC/MS: m/e 572.63 (M+H)⁺.

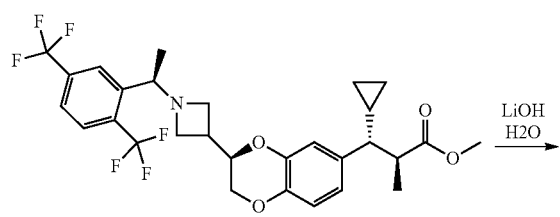

Step I: To a solution of (2S,3R)-methyl 3-((R)-3-(1-((R)-1-(2,5-bis(trifluoromethyl)-phenyl)ethyl)azetidin-3-yl)-2,3-dihydrobenzo[b][1,4]dioxin-6-yl)-3-cyclopropyl-2-methylpropanoate (84 mg, 0.1 mmol) in THF (0.75 ml)/MeOH (0.75 ml)/water (0.5 ml) at rt was added LiOH. The reaction was stirred at 55° C. for 12 h, then diluted with H₂O, and acidified with 1N HCl to pH 4-5. The reaction mixture was extracted with EtOAc (3×). The combined organic layers were washed with brine, dried over MgSO₄, filtered, and concentrated to give the crude product, which was purified by ISCO (4 g, 0-100% EtOAc/hexanes) to give (2S,3R)-3-((R)-3-(1-(2,5-bis(trifluoromethyl)benzyl)-azetidin-3-yl)-2,3-dihydrobenzo[b][1,4]dioxin-6-yl)-3-cyclopropyl-2-methylpropanoic acid. ¹H NMR (500 MHz, acetone): δ (ppm) 0.01 (m, 1H); 0.26 (m, 2H); 0.57 (m, 1H); 0.93 (d, J=6.9 Hz, 1.12 (m, 1H); 1.25-1.21 (m, 3H); 1.97 (m, 1H); 2.74 (m, 2H); 3.27-3.18 (m, 2H); 3.50-3.44 (m, 1H); 3.89-3.78 (m, 2H); 4.06 (q, J=7.1 Hz, 1H); 4.35-4.28 (m, 2H); 6.79-6.70 (m, 3H); 7.82 (t, J=7.1 Hz, 1H); 7.95 (t, J=7.8 Hz, 1H); 8.27 (s, 1H).

Example 190 was prepared in an analogous manner to Example 189, starting from the appropriate starting materials.

| Example | Structure | Method | Stereochemistry | LC/MS: found m/z [M + 1] |
|---|---|---|---|---|
| 190 | 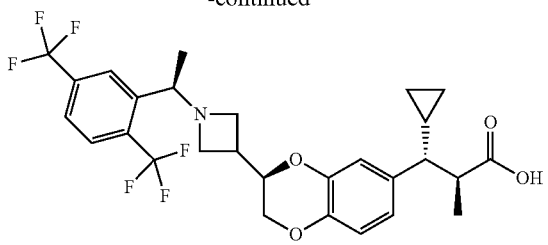 | C | S, R, 2S, 3R | 558.60 |

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells

Human and mouse GPR40 stable cell-lines were generated in CHO cells stably expressing NFAT BLA (Betalactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 μL medium/well. The cells were incubated with 20 μl/well of the assay buffer (HBSS, 0.1% BSA, 20 mM HEPES, 2.5 mM probenecid, pH 7.4) containing 8 μM fluo-4, AM, 0.08% pluronic acid at room temperature for 100 minutes. Fluorescence output was measured using FLIPR. Compounds were dissolved in DMSO and diluted to desired concentrations with assay buffer. 13.3 μL/well of compound solution was added. The compounds of the present invention, including the compounds in Examples 1-190, have $EC_{50}$ values less than 10 micromolar (μM) in the FLIPR assay described above. Preferred compounds of the present invention have $EC_{50}$ values less than 3000 nanomolar (nM) in the FLIPR assay described above. FLIPR assay $EC_{50}$ values for specific compounds are listed in Table 1.

Inositol Phosphate Turnover (IP1) Assay 1:

The assay is performed in 96-well format. HEK cells stably expressing human GPR40 are plated to be 60-80% confluent within 72 h. After 72 h, the plates are aspirated and the cells washed with inositol-free DMEM (ICN). The wash media is replaced with 150 μL of 3H-inositol labeling media (inositol-free media containing 0.4% human albumin or 0.4% mouse albumin, 1× pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 μCi/150 μL). Alternatively, the human and mouse albumin can be added after the overnight labeling step before the addition of LiCl.

The assay is typically run the next day after 18 h labeling. On the day of the assay, 5 μL of 300 mM LiCl is added to all wells and incubated at 37 degrees for 20 min. 0.75 μL of 200× compounds are added and incubated with the cells for 60 min at 37 degrees. The media is then aspirated off and the assay terminated with the addition of 60 μL 10 mM formic acid. The cells are lysed for 60 min at room temperature. 15-30 μL of lysate is mixed with 70 μL/1 mg YSi SPA beads (Amersham) in clear bottom Isoplates. The plates are shaken for 2 h at room temperature. Beads are allowed to settle and the plates are counted in the Wallac Microbeta. The compounds of the present invention, including the compounds in Examples 1-190, have $EC_{50}$ values less than 6500 nanomolar (nM) in the Inositol Phosphate Turnover (IP1) Assay 1 described above. Inositol Phosphate Turnover (IP1) Assay 1 $EC_{50}$ values for specific compounds are in Table 1.

TABLE 1

| Example No. | Stereoisomers | Human FLIPR $EC_{50}$, nM or % activation | Human IP1 Assay 1, EC50, nM |
| --- | --- | --- | --- |
| 1 | racemate | 102 | 1212 |
| 2 |  | 79% @ 10 uM | nd |
| 3 | racemate | 292 | 3635 |
| 4 | single isomer A | 38 | 544 |
| 5 | single isomer B | 85 | 1669 |
| 6 | racemate | 185 | 1698 |
| 7 | racemate | 70% @ 10 uM | nd |
| 8 | racemate | 349 | nd |
| 9 | mixture of 2 diastereomers | 1920 | nd |
| 10 | racemate | 1309 | nd |
| 11 | racemate (4 isomers) | 27 | 188 |
| 12 | single isomer A | 345 | 1654 |
| 13 | single isomer B | 10 | 36 |
| 14 | single isomer C | 944 | 3568 |
| 15 | single isomer D | 16 | 110 |
| 16 | racemate (4 isomers) | 76 | 710 |
| 17 | racemate (4 isomers) | 61 | 447 |
| 18 | racemate (4 isomers) | 1535 | nd |
| 19 | racemate (4 isomers) | 106 | 4503 |
| 20 | racemate (4 isomers) | 172 | nd |
| 21 | single isomer | 26 | 83 |
| 22 | racemate (4 isomers) | 151 | 638 |
| 23 | 2 diastereomers | 40 | 116 |
| 24 | 2 diastereomers | 57 | 58 |
| 25 | 2 diastereomers | 33 | 179 |
| 26 | mixture of 4 isomers | 244 | nd |
| 27 | mixture of 4 isomers | 52 | 726 |
| 28 | mixture of 2 diastereomers | 115 | 536 |
| 29 | mixture of 2 diastereomers | 162 | nd |
| 30 | mixture of 2 diastereomers | 128 | nd |
| 31 | mixture of 2 diastereomers | 95 | 60 |
| 32 | mixture of 2 diastereomers | 57 | 149 |
| 33 | mixture of 2 diastereomers | 114 | 1302 |
| 34 | 4 isomers | 734 | nd |
| 35 | single isomer A | 37 | 31 |
| 36 | single isomer B | 178 | nd |
| 37 | single isomer A | 38 | 47 |
| 38 | single isomer B | 83 | 1690 |
| 39 | single isomer A | 113 | nd |
| 40 | single isomer B | 255 | nd |
| 41 | single isomer A | 64 | 175 |
| 42 | single isomer B | 74 | 1222 |
| 43 | racemate (4 isomers) | 2036 | nd |
| 44 | racemate (4 isomers) | 69 | 6057 |
| 45 | racemate (4 isomers) | 12.5% @ 10 μM | nd |
| 46 | racemate (4 isomers) | 41% @ 10 μM | nd |
| 47 | racemate (4 isomers) | 61% @ 10 μM | nd |
| 48 | racemate | 12 | 1017 |
| 49 | mixture of 2 diastereomers | 45 | 450 |
| 50 | mixture of 2 diastereomers | 9 | 877 |
| 51 | mixture of 2 diastereomers | 105 | 1202 |
| 52 | mixture of 2 diastereomers | 17 | 248 |
| 53 | single isomer A | 2138 | nd |
| 54 | single isomer B | 1090 | nd |
| 55 | mixture of 2 diastereomers | 247 | nd |
| 56 | mixture of 2 diastereomers | 117 | 1912 |

TABLE 1-continued

| Example No. | Stereoisomers | Human FLIPR EC$_{50}$, nM or % activation | Human IP1 Assay 1, EC50, nM |
|---|---|---|---|
| 57 | mixture of 2 diastereomers | 1047 | nd |
| 58 | mixture of 2 diastereomers | 1036 | nd |
| 59 | mixture of 2 diastereomers | 51 | 2519 |

"nd" is not determined.

Inositol Phosphate Turnover (IP1) Assay 2:

The assay is performed in 384-well format. HEK cells stably expressing human GPR40 are plated at 15,000 cells per well in growth medium (DMEM/10% fetal calf serum). Cell plates are then incubated 16 hours at 37 degrees in a 5% CO2 incubator.

Measurement of Inositol Phosphate Turnover (IP1) is performed using the CisBio IP-One kit (Part number 62IPA-PEB). After the 16 hour incubation, the cells are washed with HEPES buffer and 10 ul of stimulation buffer (prepared as described in the kit) is added to each well. In a separate plate, compounds are diluted in DMSO (400-fold over the final concentration in the assay well) and 25 nl is acoustically transferred to the appropriate well in the assay cell plate. The plates are then incubated for 60 minutes at 37 degrees. 10 ul of detection buffer (also prepared as described in the IP-One kit) is added to each well and the plates are incubated for 60 minutes in the dark. The plates are then read in a Perkin Elmer EnVision or equivalent reader able to measure FRET. Fluorescent ratio of emission at 665 and 620 nm is then converted to IP1 concentration by back calculating from an IP1 standard curve prepared at the time of the assay.

The compounds of the present invention, including the compounds in Examples 1-190, have EC$_{50}$ values less than 6500 nanomolar (nM) in the Inositol Phosphate Turnover (IP1) Assay 2 described above. Inositol Phosphate Turnover (IP1) Assay 2 EC$_{50}$ values for specific compounds are listed in Tables 2 and 3.

TABLE 2

| Example No. | Human IP1 (nM) | Isomer* |
|---|---|---|
| 60 | 25 | Mixture of 4 Diastereomers |
| 61 | 36 | Isomer A |
| 62 | 18 | Isomer B |
| 63 | 3.3 | Isomer A |
| 64 | 1.1 | Isomer B |
| 65 | 51 | Isomer C |
| 66 | 53 | Isomer D |
| 67 | 21 | Isomer A |
| 68 | 1.9 | Isomer B |
| 69 | 391 | Mixture of 2 Diastereomers |
| 70 | 934 | Mixture of 2 Diastereomers |
| 71 | 11 | Mixture of 2 Diastereomers |
| 72 | 116 | Mixture of 2 Diastereomers |
| 73 | 1198 | Mixture of 2 Diastereomers |
| 74 | 19 | Mixture of 2 Diastereomers |
| 75 | 304 | Mixture of 2 Diastereomers |
| 76 | 650 | Mixture of 2 Diastereomers |
| 77 | 920 | Mixture of 2 Diastereomers |
| 78 | 1700 | Mixture of 2 Diastereomers |
| 79 | 22 | Mixture of 2 Diastereomers |
| 80 | 130 | Mixture of 2 Diastereomers |
| 81 | 165 | Mixture of 2 Diastereomers |
| 82 | 54 | Mixture of 2 Diastereomers |
| 83 | nd | Mixture of 2 Diastereomers |
| 84 | 1520 | Mixture of 2 Diastereomers |
| 85 | nd | Mixture of 2 Diastereomers |
| 86 | 363 | Mixture of 2 Diastereomers |
| 87 | 1393 | Mixture of 2 Diastereomers |
| 88 | 6.5 | Mixture of 2 Diastereomers |
| 89 | nd | Mixture of 2 Diastereomers |
| 90 | 10.6 | Mixture of 2 Diastereomers |
| 91 | 3.6 | Mixture of 2 Diastereomers |
| 92 | 19 | Mixture of 2 Diastereomers |
| 93 | 488 | Mixture of 2 Diastereomers |
| 94 | nd | Mixture of 2 Diastereomers |
| 95 | 218 | Mixture of 2 diastereomers |
| 96 | 14 | Mixture of 2 diastereomers |
| 97a | 0.9 | Isomer A |
| 97b | 30 | Isomer B |
| 97c | 2.9 | Isomer C |
| 97d | 43 | Isomer D |
| 98 | 84 | Mixture of 2 diastereomers |
| 99 | 29 | Mixture of 2 diastereomers |
| 100 | 32 | Mixture of 2 diastereomers |
| 101a | 662 | Isomer A |
| 101b | 704 | Isomer B |
| 101c | 58 | Isomer C |
| 101d | 90 | Isomer D |
| 102 | 66 | Mixture of 2 diastereomers |
| 103 | 6.2 | Mixture of 2 diastereomers |
| 104 | 16 | Mixture of 2 diastereomers |
| 105a | 0.82 | Isomer A |
| 105b | 0.79 | Isomer B |
| 106 | nd | Mixture of 2 diastereomers |
| 107 | 132 | Mixture of 2 diastereomers |
| 108a | 263 | Isomer A |
| 108b | 5.8 | Isomer B |
| 109a | 0.17 | Isomer A |
| 109b | 1.2 | Isomer B |
| 110a | 6.8 | Isomer A |
| 110b | 1.6 | Isomer B |
| 111a | 6.0 | Isomer A |
| 111b | 25 | Isomer B |
| 112a | 0.17 | Isomer A |
| 112b | 0.92 | Isomer B |
| 113a | 3.9 | Isomer A |
| 113b | 14 | Isomer B |
| 114 | 8.8 | Mixture of 2 diastereomers |
| 115a | 4.2 | Isomer A |
| 115b | 17.4 | Isomer B |
| 116 | 17 | Mixture of 2 diastereomers |
| 117a | 0.89 | Isomer A |
| 117b | 0.17 | Isomer B |
| 118a | 1.6 | Isomer A |
| 118b | 5.9 | Isomer B |
| 119a | 4.1 | Isomer A |
| 119b | 7.8 | Isomer B |
| 120a | 4.4 | Isomer A |
| 120b | 1.9 | Isomer B |
| 121 | 11 | Mixture of 2 diastereomers |
| 122a | 88 | Isomer A |
| 122b | 244 | Isomer B |
| 124a | 51 | Isomer A |
| 124b | 70 | Isomer B |
| 125a | 7.3 | Isomer A |
| 125b | 8.6 | Isomer B |
| 125c | 235 | Isomer C |
| 125d | 256 | Isomer D |
| 126 | 14.1 | Mixture of 4 Diastereomers |
| 127 | 41.5 | Mixture of 4 Diastereomers |
| 128 | 3.2 | Mixture of 2 Diastereomers |
| 129 | 0.5 | Mixture of 2 Diastereomers |
| 130 | 0.9 | Mixture of 4 diastereomers |
| 131 | 1.7 | Mixture of 2 diastereomers |
| 132 | 18 | mixture of 2 diastereomers |
| 133 | 1.2 | Mixture of 2 Diastereomers |
| 135a | 0.8 | Isomer A |
| 135b | 21 | Isomer B |
| 135c | 2.8 | Isomer C |
| 135d | 44 | Isomer D |
| 136 | 217 | Mixture of 4 diastereomers |
| 137 | 454 | Mixture of 4 diastereomers |

TABLE 2-continued

| Example No. | Human IP1 (nM) | Isomer* |
|---|---|---|
| 138 | 1204 | Isomer A |
| 139 | 116 | Isomer B |
| 140 | 1233 | Isomer C |
| 141 | 354 | Isomer D |
| 142 | 13 | Isomer AA |
| 143 | 252 | Isomer AB |
| 144 | 1423 | Isomer BA |
| 145 | 77 | Isomer BB |
| 146 | 270 | Isomer CA |
| 147a | 9.0 | Isomer CB |
| 147b | 3178 | Isomer DA |
| 147c | 138 | Isomer DB |
| 148 | 398 | Isomer A |
| 149 | 41 | Isomer B |
| 150 | 660 | Isomer C |
| 151 | 79 | Isomer D |
| 152 | 774 | Isomer AA |
| 153 | 22 | Isomer AB |
| 154 | 86 | Isomer BA |
| 155 | 1.0 | Isomer BB |
| 156 | 209 | Isomer CA |
| 157 | 90 | Isomer CB |
| 158 | 132 | Isomer DA |
| 159 | 1.8 | Isomer DB |

*Isomer A = first eluting peak from chiral column;
Isomer B = second eluting peak from chiral column;
Isomer C = third eluting peak from chiral column;
Isomer D = fourth eluting peak from chiral column,
"nd" is not determined

TABLE 3

| Example No. | Human IP1 activity (nM) |
|---|---|
| 160 | 1.6 |
| 161 | 2.2 |
| 162 | 8.2 |
| 163 | 2.1 |
| 164 | 8.2 |
| 165 | 2.6 |
| 166 | 18.8 |
| 167 | 31 |
| 168 | 120 |
| 169 | 9.5 |
| 170 | 0.17 |
| 171 | 2.6 |
| 172 | 6.9 |
| 173 | 1.8 |
| 174 | 0.5 |
| 175 | 220 |
| 176 | 774 |
| 177 | 870 |
| 178 | 10.6 |
| 179 | 16.3 |
| 180 | 4.8 |
| 181 | 8.3 |
| 182 | nd |
| 183 | 99.6 |
| 184 | 1.6 |
| 185 | 2.0 |
| 186 | 7.9 |
| 187 | 1280 |
| 188 | 5.2 |
| 189 | 13.3 |
| 190 | 20.3 |

"nd" is not determined

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

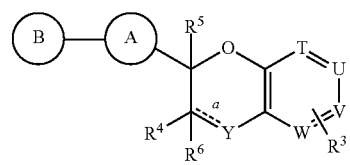

or a pharmaceutically acceptable salt thereof; wherein "a" is a single bond;
T is selected from the group consisting of:
  (1) CH,
  (2) N, and
  (3) N-oxide;
U is selected from the group consisting of:
  (1) $CR^1$,
  (2) N, and
  (3) N-oxide;
V is selected from the group consisting of:
  (1) $CR^2$,
  (2) N, and
  (3) N-oxide;
W is selected from the group consisting of:
  (1) CH,
  (2) N, and
  (3) N-oxide,
provided that no more than two of T, U, V and W are selected from N and N-oxide, further provided that if both T and W are N or N-oxide, then $R^3$ is absent, and further provided that both U and V are not N or N-oxide;

Y is selected from the group consisting of:
(1) oxygen,
(2) sulfur,
(3) —$CR^gR^g$,
(4) C=O,
(5) —$C(R^g)OC_{1-6}$alkyl,
(6) —$CF_2$, and
(7) —$NR^c$;

A is selected from the group consisting of:
(1) aryl,
(2) heteroaryl,
(3) $C_{3-6}$cycloalkyl, and
(4) $C_{2-5}$cycloheteroalkyl,
wherein A is unsubstituted or substituted with one to five substituents selected from $R^a$;

B is selected from the group consisting of:
(1) aryl,
(2) aryl-$C_{1-10}$ alkyl-,
(3) $C_{3-6}$cycloalkyl,
(4) $C_{3-6}$cycloalkyl-$C_{1-10}$alkyl,
(5) $C_{3-6}$cycloalkyl-$C_{1-10}$alkyl-O—,
(6) $C_{2-5}$cycloheteroalkyl,
(7) $C_{3-6}$cycloheteroalkyl-$C_{1-10}$alkyl-,
(8) $C_{3-6}$cycloheteroalkyl-$C_{1-10}$alkyl-O—,
(9) heteroaryl, and
(10) heteroaryl-$C_{1-10}$ alkyl-;
wherein B is unsubstituted or substituted with one to five substituents selected from $R^b$;

$R^1$ and $R^2$ are each independently selected from:
(1) hydrogen, and
(2) —$C_{1-6}$alkyl,
wherein each alkyl is unsubstituted or substituted with one to three substituents selected from $R^L$, and wherein one of $R^1$ and $R^2$ is substituted with a substituent selected from $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents selected from $R^L$, and wherein one of $R^1$ and $R^2$ is substituted with a substituent selected from $R^7$;

$R^3$ is hydrogen;
$R^4$ is hydrogen;
$R^5$ is hydrogen;
$R^6$ is hydrogen;
$R^7$ is —$CO_2R^8$;
$R^8$ is selected from the group consisting of:
(1) hydrogen,
(2) —$C_{1-6}$alkyl,
(3) —$C_{3-6}$cycloalkyl, and
(4) aryl-$C_{1-6}$alkyl,
wherein each alkyl, cycloalkyl and aryl is unsubstituted or substituted with one to three substituents selected from $R^j$;

$R^a$ is selected from the group consisting of:
(1) —$C_{1-6}$alkyl,
(2) halogen,
(3) —$OR^e$,
(4) —$NR^cS(O)_nR^e$,
(5) —$S(O)_nR^e$,
(6) —$S(O)_nNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) aryl,
(20) heteroaryl,
(21) $C_{3-6}$cycloalkyl,
(22) —$C_{3-6}$cycloalkenyl, and
(23) —$C_{2-5}$cycloheteroalkyl,
wherein each alkyl, cycloalkyl, cycloalkenyl, cycloheteroalkyl, aryl and heteroaryl is unsubstituted or substituted with —$C_{1-6}$alkyl, halogen, —O—$C_{1-6}$alkyl and —$CF_3$;

$R^b$ is independently selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)_pOC_{1-10}$alkyl,
(10) —$O(CH_2)_pOC_{3-6}$cycloalkyl,
(11) —$O(CH_2)_pC_{3-6}$cycloalkyl-$C_{1-10}$alkyl-,
(12) —$O(CH_2)_pC_{2-5}$cycloheteroalkyl,
(13) —$O(CH_2)_pC_{2-5}$cycloheteroalkyl-$C_{1-10}$alkyl-,
(14) —O-aryl,
(15) —O-heteroaryl,
(16) —O-aryl-$C_{1-10}$alkyl-,
(17) —O-heteroaryl-$C_{1-10}$alkyl-,
(18) —$O(CH_2)_pNR^cS(O)_mR^e$,
(19) —$O(CH_2)_pS(O)_mR^e$,
(20) —$O(CH_2)_pS(O)_mNR^cR^d$,
(21) —$O(CH_2)_pNR^cR^d$,
(22) —$C(O)R^e$,
(23) —$OC(O)R^e$,
(24) —$CO_2R^e$,
(25) —$C(O)NR^cR^d$,
(26) —$NR^cC(O)R^e$,
(27) —$NR^cC(O)OR^e$,
(28) —$NR^cC(O)NR^cR^d$,
(29) —$O(CH_2)_pO—C_{3-6}$cycloalkyl,
(30) —$O(CH_2)_pO—C_{2-5}$cycloheteroalkyl,
(31) —$OCF_3$,
(32) —$OCHF_2$,
(33) —$(CH_2)_pC_{3-6}$cycloalkyl,
(34) —$(CH_2)_pC_{2-5}$cycloheteroalkyl,
(35) aryl,
(36) heteroaryl,
(37) aryl-$C_{1-10}$alkyl-, and
(38) heteroaryl-$C_{1-10}$alkyl-,
wherein each CH, $CH_2$, alkyl, alkenyl, cycloalkyl, cycloheteroalkyl, aryl and heteroaryl is unsubstituted or substituted with —$C_{1-6}$alkyl, halogen, —O—$C_{1-6}$alkyl and —$CF_3$;

$R^c$ and $R^d$ are each independently selected from the group consisting of:
(1) hydrogen,
(2) $C_{1-10}$alkyl, (3) $C_{2-10}$alkenyl,
(4) $C_{3-6}$cycloalkyl,
(5) $C_{3-6}$ cycloalkyl-$C_{1-10}$alkyl-,
(6) $C_{2-5}$cycloheteroalkyl,
(7) $C_{2-5}$cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents independently selected from $R^f$,
or $R^c$ and $R^d$ together with the atom(s) to which they are attached form a $C_{2-5}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$;
each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) aryl-$C_{1-10}$alkyl-,
(10) heteroaryl, and
(11) heteroaryl-$C_{1-10}$alkyl-,
wherein each alkyl, alkenyl, cycloalkyl, cycloheteroalkyl, aryl and heteroaryl is unsubstituted or substituted with one to three substituents selected from $R^h$;
each $R^f$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;
each $R^g$ is selected from the group consisting of:
(1) hydrogen,
(2) —$C(O)R^e$, and
(3) —$C_{1-10}$alkyl,
wherein each alkyl is unsubstituted or substituted with one to five halogens;
each $R^h$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each alkyl is unsubstituted or substituted with one to three substituents independently selected from: —OH, halogen, $C_{1-6}$alkyl, cyano and $S(O)_2C_{1-6}$alkyl;

$R^j$ is independently selected from the group consisting of:
(1) —$C_{1-6}$alkyl,
(2) —$OR^e$,
(3) —$NR^cS(O)_mR^e$,
(4) halogen,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;
each $R^L$ is independently selected from the group consisting of:
(1) —$CO_2C_{1-6}$alkyl,
(2) —$C_{1-10}$alkyl,
(3) —$C_{2-10}$ alkenyl,
(4) —$C_{2-10}$alkynyl,
(5) —$C_{3-6}$cycloalkyl,
(6) —$C_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with 1-4 substituents selected from $C_{1-6}$alkyl, halogen, and —$OC_{1-6}$alkyl;
each n is independently selected from: 0, 1 or 2;
each m is independently selected from: 0, 1 or 2; and
each p is independently selected from: 0, 1, 2, 3, 4, 5 or 6.

2. The compound according to claim 1 wherein T is CH; U is $CR^1$; V is $CR^2$; and W is CH, N or N-oxide; or a pharmaceutically acceptable salt thereof.

3. The compound according to claim 2 wherein T is CH; U is $CR^1$; V is $CR^2$; and W is CH; or a pharmaceutically acceptable salt thereof.

4. The compound according to claim 2 wherein T is CH; U is $CR^1$; V is $CR^2$; and W is N; or a pharmaceutically acceptable salt thereof.

5. The compound according to claim 1 wherein Y is selected from the group consisting of:
(1) —$CR^gR^g$,
(2) C=O,
(3) —$C(R^g)OC_{1-6}$alkyl,
(4) —$CF_2$, and
(5) —$NR^c$:
or a pharmaceutically acceptable salt thereof.

6. The compound according to claim 1 wherein Y is selected from the group consisting of: —$CR^gR^g$; or a pharmaceutically acceptable salt thereof.

7. The compound according to claim 1 wherein A is selected from the group consisting of:
(1) aryl, and
(2) heteroaryl,
wherein each aryl and heteroaryl is unsubstituted or substituted with one to five substituents selected from $R^a$; or a pharmaceutically acceptable salt thereof.

8. The compound according to claim 1 wherein B is selected from the group consisting of:
(1) aryl, and
(2) heteroaryl,
wherein each aryl and heteroaryl is unsubstituted or substituted with one to five substituents selected from $R^b$; or a pharmaceutically acceptable salt thereof.

9. The compound according to claim 1 wherein $R^1$ and $R^2$ are selected from:
(1) —$C_{1-6}$ alkyl, and
(2) hydrogen,
wherein each alkyl is unsubstituted or substituted with one to three substituents selected from $R^L$, and wherein each alkyl is substituted with a substituent selected from $R^7$, provided that one of $R^1$ and $R^2$ is —$C_{1-6}$alkyl and the other of $R^1$ and $R^2$ is hydrogen;
or a pharmaceutically acceptable salt thereof.

10. The compound according to claim 1 wherein $R^1$ and $R^2$ are each independently selected from:
(1) hydrogen, and
(2) —$C_{1-6}$alkyl,
wherein each alkyl is unsubstituted or substituted with one to three substituents selected from $R^L$, and wherein one of $R^1$ and $R^2$ is substituted with a substituent selected from $R^7$;
or a pharmaceutically acceptable salt thereof.

11. The compound according to claim 1 wherein $R^1$ is selected from: —$C_{1-6}$ alkyl, wherein each alkyl is unsubstituted or substituted with one to three substituents selected-from $R^L$, and wherein $R^1$ is substituted with a substituent selected from $R^7$; and
$R^2$ is-hydrogen;
or a pharmaceutically acceptable salt thereof.

12. The compound according to claim 1 wherein $R^2$ is selected from: —$C_{1-6}$ alkyl, wherein each alkyl is unsubstituted or substituted with one to three substituents selected from $R^L$, and wherein $R^2$ is substituted with a substituent selected from $R^7$; and
$R^1$ is hydrogen;
or a pharmaceutically acceptable salt thereof.

13. The compound according to claim 1 wherein $R^8$ is hydrogen; or a pharmaceutically acceptable salt thereof.

14. The compound according to claim 1 of structural Formula Ik:

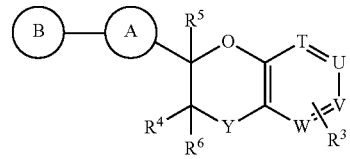

wherein
T is selected from the group consisting of:
(1) CH, and
(2) N;
U is selected from the group consisting of:
(1) $CR^1$, and
(2) N;
V is selected from the group consisting of:
(1) $CR^2$, and
(2) N;
W is selected from the group consisting of:
(1) CH, and
(2) N,
provided that no more than two of T, U, V and W are selected from N, further provided that if both T and W are N, then $R^3$ is absent, and further provided that both U and V are not N;
Y is selected from the group consisting of:
(1) —$CR^gR^g$,
(2) C=O,
(3) —$C(R^g)OC_{1-6}$ alkyl, and
(4) —$CF_2$;
A is selected from the group consisting of:
(1) aryl,
(2) hetero aryl,
(3) $C_{3-6}$ cycloalkyl, and
(4) $C_{2-5}$cycloheteroalkyl,
wherein A is unsubstituted or substituted with one to five substituents selected from $R^a$;
$R^7$ is —$CO_2R^8$; and
$R^8$ is selected from the group consisting of:
(1) hydrogen, and
(2) —$C_{1-6}$alkyl,
wherein each alkyl is unsubstituted or substituted with one to three substituents selected from $R^j$;
or a pharmaceutically acceptable salt thereof.

15. The compound according to claim 1 of structural Formula Ik:

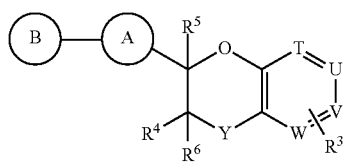

wherein
T is CH or N;
U is $CR^1$;
V is $CR^2$;
W is CH or N,
provided that T and W are both CH or one of T and W is N;
Y is selected from the group consisting of:
(1) —$CR^gR^g$,
(2) C=O, and
(3) —$CF_2$;
A is selected from the group consisting of:
(1) aryl,
(2) heteroaryl,
(3) $C_{3-6}$ cycloalkyl, and
(4) $C_{2-5}$ cycloheteroalkyl,
wherein each aryl, heteroaryl, cycloalkyl and cycloheteroalkyl is unsubstituted or substituted with one to five substituents selected from $R^a$;
$R^7$ is —$CO_2R^8$; and
$R^8$ is hydrogen;
or a pharmaceutically acceptable salt thereof.

16. The compound according to claim 1 wherein
"a" is a single bond;
T is CH;
U is $CR^1$;
V is $CR^2$;
W is CH, N or N-oxide;
Y is selected from the group consisting of:
(1) —$CR^gR^g$,
(2) C=O,
(3) —$C(R^g)OC_{1-6}$alkyl, (4) —CF$_2$, and
(5) —NR$^c$;
A is selected from the group consisting of:
  (1) aryl, and
  (2) heteroaryl,
wherein each aryl and heteroaryl is unsubstituted or substituted with one to five substituents selected from R$^a$;
R$^3$ is hydrogen;
R$^4$ is hydrogen;
R$^5$ is hydrogen;
R$^6$ is hydrogen;
R$^7$ is —CO$_2$R$^8$; and
R$^8$ is hydrogen;
or a pharmaceutically acceptable salt thereof.

17. The compound according to claim 1 wherein
"a" is a single bond;
T is CH;
U is CR$^1$;
V is CR$^2$;
W is CH;
Y is selected from the group consisting of: —CR$^g$R$^g$;
A is selected from the group consisting of:
  (1) aryl, and
  (2) heteroaryl,
wherein each aryl and heteroaryl is unsubstituted or substituted with one to five substituents selected from R$^a$;
B is selected from the group consisting of:
  (1) aryl, and
  (2) heteroaryl,
wherein each aryl and heteroaryl is unsubstituted or substituted with one to five substituents selected from R$^b$;
R$^1$ and R$^2$ are each independently selected from:
  (1) hydrogen, and
  (2) —C$_{1-6}$alkyl,
wherein each alkyl is unsubstituted or substituted with one to three substituents selected from R$^L$, and wherein one of R$^1$ and R$^2$ is substituted with a substituent selected from R$^7$;
R$^3$ is hydrogen;
R$^4$ is hydrogen;
R$^5$ is hydrogen;
R$^6$ is hydrogen;
R$^7$ is —CO$_2$R$^8$; and
R$^8$ is hydrogen;
or a pharmaceutically acceptable salt thereof.

18. A compound selected from:

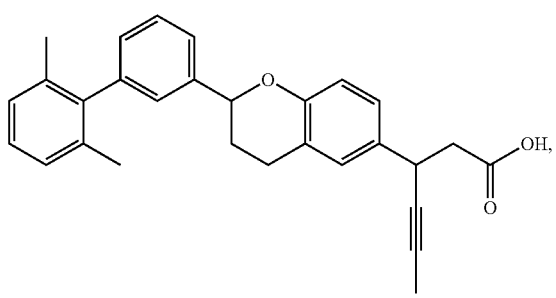

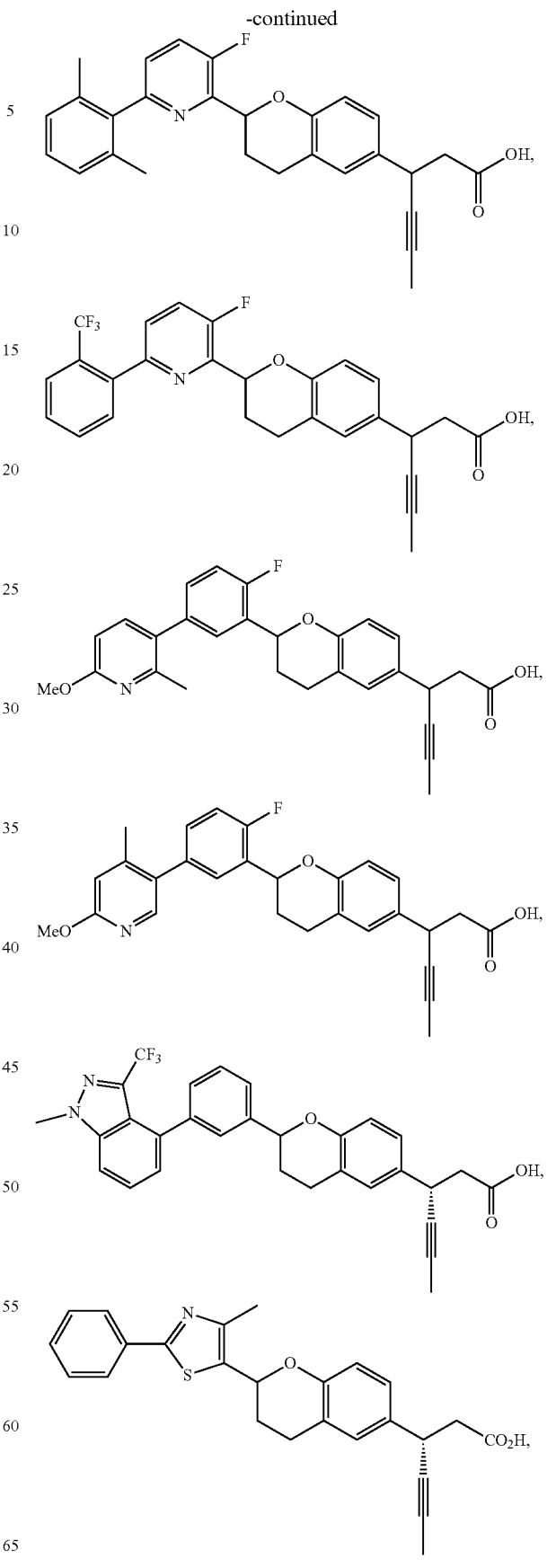

and

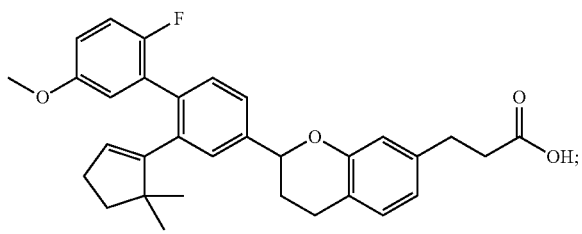

or a pharmaceutically acceptable salt thereof.

19. The compound according to claim 1 of structural Formula Ik:

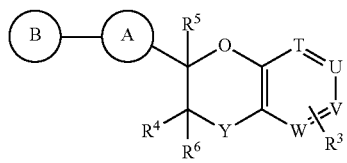

wherein
T is selected from the group consisting of:
  (1) CH, and
  (2) N;
U is selected from the group consisting of:
  (1) $CR^1$, and
  (2) N;
V is selected from the group consisting of:
  (1) $CR^2$, and
  (2) N;
W is selected from the group consisting of:
  (1) CH, and
  (2) N,
provided that no more than two of T, U, V and W are selected from N, further provided that if both T and W are N, then $R^3$ is absent, and further provided that both U and V are not N;
Y is oxygen;
A is selected from the group consisting of:
  (1) aryl,
  (2) heteroaryl,
  (3) $C_{3-6}$ cycloalkyl, and
  (4) $C_{2-5}$ cycloheteroalkyl,
wherein A is unsubstituted or substituted with one to five substituents selected from $R^a$;
B is selected from the group consisting of:
  (1) aryl,
  (2) aryl-$C_{1-10}$ alkyl-,
  (3) $C_{3-6}$ cycloalkyl,
  (4) $C_{3-6}$ cycloalkyl-$C_{1-10}$alkyl-,
  (5) $C_{3-6}$ cycloalkyl-$C_{1-10}$alkyl-O—,
  (6) $C_{2-5}$ cycloheteroalkyl,
  (7) $C_{3-6}$ cycloheteroalkyl-$C_{1-10}$alkyl-,
  (8) $C_{3-6}$ cycloheteroalkyl-$C_{1-10}$alkyl-O—,
  (9) heteroaryl, and
  (10) heteroaryl-$C_{1-10}$ alkyl-;
wherein B is unsubstituted or substituted with one to five substituents selected from $R^b$;
$R^7$ is —$CO_2R^8$;
$R^8$ is selected from the group consisting of:
  (1) hydrogen, and
  (2) —$C_{1-6}$alkyl, wherein each alkyl is unsubstituted or substituted with one to three substituents selected from $R^j$;
or a pharmaceutically acceptable salt thereof.

20. The compound according to claim 1 of structural Formula Ik:

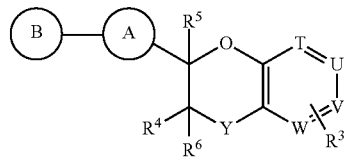

wherein
T is CH;
U is $CR^1$;
V is $CR^2$;
W is CH;
Y is oxygen;
A is selected from the group consisting of:
  (1) aryl,
  (2) heteroaryl, and
  (3) $C_{2-5}$ cycloheteroalkyl,
wherein each aryl, heteroaryl and cycloheteroalkyl is unsubstituted or substituted with one to five substituents selected from $R^a$;
B is selected from the group consisting of:
  (1) aryl, and
  (2) aryl-$C_{1-10}$alkyl-,
wherein each alkyl and aryl is unsubstituted or substituted with one to five substituents selected from $R^b$;
$R^1$ and $R^2$ are selected from:
  (1) —$C_{1-6}$ alkyl, and
  (2) hydrogen,
wherein each alkyl is unsubstituted or substituted with one to three substituents selected from $R^L$, and wherein each alkyl is substituted with a substituent selected from $R^7$, provided that one of $R^1$ and $R^2$ is —$C_{1-6}$alkyl and the other of $R^1$ and $R^2$ is hydrogen;
$R^7$ is —$CO_2R^8$;
$R^4$, $R^5$, $R^6$ and $R^8$ are hydrogen;
each $R^a$ is independently selected from the group consisting of:
  (1) —$C_{1-6}$alkyl,
  (2) halogen,
  (3) —$CF_3$,
  (4) —$OCF_3$, and
  (5) heteroaryl,
wherein each alkyl and heteroaryl is unsubstituted or substituted with —$C_{1-6}$alkyl, halogen, —O—$C_{1-6}$ alkyl and —$CF_3$;
each $R^b$ is independently selected from the group consisting of:
  (1) —$C_{1-10}$alkyl,
  (2) —$CF_3$,
  (3) halogen, and
  (4) —$OC_{1-10}$alkyl,
wherein each alkyl is unsubstituted or substituted with —$C_{1-6}$alkyl, halogen, —O—$C_{1-6}$alkyl and —$CF_3$; and
each $R^L$ is independently selected from the group consisting of:
  (1) —$C_{1-10}$alkyl,
  (2) —$C_{2-10}$alkynyl, and
  (3) —$C_{3-6}$ cycloalkyl, wherein each alkyl, alkynyl, and cycloalkyl is unsubstituted or substituted with 1-4 substituents selected from $C_{1-6}$alkyl, halogen, and —$OC_{1-6}$alkyl;
or a pharmaceutically acceptable salt thereof.

21. A pharmaceutical composition comprising a compound of claim 1, or a pharmaceutically acceptable salt thereof, and a pharmaceutically acceptable carrier.

22. A pharmaceutical composition comprising
(1) a compound of claim 1, or a pharmaceutically acceptable salt thereof;
(2) one or more compounds selected from the group consisting of:
  (a) PPAR gamma agonists and partial agonists;
  (b) biguanides;
  (c) protein tyrosine phosphatase-1B (PTP-1B) inhibitors;
  (d) dipeptidyl peptidase IV (DP-IV) inhibitors;
  (e) insulin or an insulin mimetic;
  (f) sulfonylureas;
  (g) α-glucosidase inhibitors;
  (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (viii) phenolic anti-oxidants;
  (i) PPARα/γ dual agonists,
  (j) PPARδ agonists,
  (k) antiobesity compounds,
  (l) ileal bile acid transporter inhibitors;
  (m) anti-inflammatory agents;
  (n) glucagon receptor antagonists;
  (o) GLP-1;
  (p) GIP-1;
  (q) GLP-1 analogs;
  (r) HSD-1 inhibitors;
  (s) SGLT-2 inhibitors; and
  (t) SGLT-1/SGLT-2 inhibitors; and
(3) a pharmaceutically acceptable carrier.

23. A pharmaceutical composition comprising a compound according to claim 1, or a pharmaceutically acceptable salt thereof, and a compound selected from simvastatin, ezetimibe and sitagliptin; and a pharmaceutically acceptable carrier.

* * * * *